(12) United States Patent
Xu et al.

(10) Patent No.: US 10,562,902 B2
(45) Date of Patent: Feb. 18, 2020

(54) IRAK4 INHIBITOR AND USE THEREOF

(71) Applicant: BEIJING HANMI PHARMACEUTICAL CO., LTD., Beijing (CN)

(72) Inventors: Jiangcheng Xu, Beijing (CN); Qinguan Cai, Beijing (CN); Mi Young Cha, Beijing (CN); Maengsup Kim, Beijing (CN)

(73) Assignee: Beijing Hanmi Pharmaceutical Co., Ltd., Beijing (CN)

( * ) Notice: Subject to any disclaimer, the term of this patent is extended or adjusted under 35 U.S.C. 154(b) by 0 days.

(21) Appl. No.: 15/751,782

(22) PCT Filed: Aug. 12, 2016

(86) PCT No.: PCT/CN2016/094857
§ 371 (c)(1),
(2) Date: Feb. 9, 2018

(87) PCT Pub. No.: WO2017/025064
PCT Pub. Date: Feb. 16, 2017

(65) Prior Publication Data
US 2018/0244677 A1    Aug. 30, 2018

(30) Foreign Application Priority Data
Aug. 13, 2015  (CN) .......................... 2015 1 0497741

(51) Int. Cl.
| C07D 487/04 | (2006.01) |
| A61P 35/00 | (2006.01) |
| A61K 31/519 | (2006.01) |
| A61K 31/5377 | (2006.01) |
| A61K 31/541 | (2006.01) |
| A61K 45/06 | (2006.01) |
| C07D 519/00 | (2006.01) |

(52) U.S. Cl.
CPC .......... *C07D 487/04* (2013.01); *A61K 31/519* (2013.01); *A61K 31/5377* (2013.01); *A61K 31/541* (2013.01); *A61K 45/06* (2013.01); *A61P 35/00* (2018.01); *C07D 519/00* (2013.01)

(58) Field of Classification Search
CPC .................................................. C07D 487/04
USPC ....................................................... 544/280
See application file for complete search history.

(56) References Cited

U.S. PATENT DOCUMENTS

| 6,040,310 | A | 3/2000 | Dow et al. |
| 7,511,040 | B2 | 3/2009 | Belanger et al. |
| 8,227,601 | B2 | 7/2012 | Girardet et al. |
| 8,258,144 | B2 | 9/2012 | Song et al. |
| 8,889,684 | B2 | 11/2014 | Stadtmueller |
| 2009/0124802 | A1* | 5/2009 | Girardet .............. C07D 473/30 544/280 |
| 2014/0018361 | A1 | 1/2014 | Harriman et al. |
| 2014/0194417 | A1 | 7/2014 | Greenwood et al. |
| 2015/0094305 | A1 | 4/2015 | Romero et al. |
| 2016/0229865 | A1 | 8/2016 | Liu et al. |

FOREIGN PATENT DOCUMENTS

| CN | 101233135 A | 7/2008 |
| CN | 103476773 A | 12/2013 |
| JP | H11130774 A | 5/1999 |
| JP | 2008540454 A | 11/2008 |
| JP | 2010509328 A | 3/2010 |
| JP | 2011518219 A | 6/2011 |
| JP | 2014504622 A | 2/2014 |
| KR | 20140014149 A | 2/2014 |
| WO | 2004043367 A2 | 5/2004 |
| WO | 2006122003 A2 | 11/2006 |
| WO | 2010111406 A2 | 9/2010 |
| WO | 2012129258 A1 | 9/2012 |
| WO | 2013130461 A1 | 9/2013 |
| WO | 2014011911 A2 | 1/2014 |
| WO | 2014113429 A2 | 7/2014 |
| WO | 2014135473 A1 | 9/2014 |
| WO | 2015039612 A1 | 3/2015 |
| WO | 2015048281 A1 | 4/2015 |
| WO | 2016010886 A1 | 1/2016 |

OTHER PUBLICATIONS

King, Med. Chem: Principle and Practice (1994), pp. 206-208.*
Powers et al., "Discovery and initial SAR of inhibitors of interleukin-1 receptor-associated kinase-4," Bioorganic & Medicinal Chemistry Letters (2006); 16:2842-2845.

(Continued)

*Primary Examiner* — Taofiq A Solola
(74) *Attorney, Agent, or Firm* — Fox Rothschild LLP

(57) ABSTRACT

Disclosed are a compound related to inhibiting the activity of an IRAK4 kinase, a pharmaceutical composition thereof, a use thereof in preparing drugs, a method in which same is used for inhibiting the activity of the IRAK4 kinase and a method in which same is used for treating and/or preventing IRAK4 kinase mediated diseases or conditions in mammals (especially humans). The compound has a structural formula I.

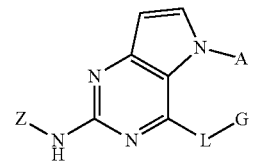

Formula I

6 Claims, No Drawings

(56) References Cited

OTHER PUBLICATIONS

Katayama et al., "DNA damaging agent-induced autophagy produces a cytoprotective adenosine triphosphate surge in malignant glioma cells," Cell Death and Differentiation (2007); 14:548-558.
Cheung-Ong et al., "DNA-Damaging Agents in Cancer Chemotheraphy: Serendipity and Chemical Biology," Chemistry & Biology (2013); 20:648-659.

* cited by examiner

IRAK4 INHIBITOR AND USE THEREOF

TECHNOLOGY FILED

The invention relates to the field of medicine, in particular to IRAK4 inhibitors and use thereof.

BACKGROUND ART

Toll/IL-1 receptor family members are important regulatory factors of inflammation and host resistance. The Toll-like receptor (TLR) family identifies molecular patterns from pathogens such as bacteria, fungi, parasites and viruses (for review, see Kawai, T., et al. 2010, Nature Immunol. 77: 373-384). Ligands binding to receptors can induce dimerization of adapter molecules, and can recruit the adapter molecules into conserved cytoplasmic motifs called Toll/IL-1 receptor (TIR) domains in the receptor. Except TLR3, all TLRs recruited adapter molecules are myeloid differentiation factor 88 (MyD88). The IL-I receptor family also contains a TIR domain and likewise recruits MyD88 upon binding to ligands (for review, see Sims, J. E. et al., 2010, Nature Rev. Immunol. 10: 89-102).

Human interleukin receptor-associated kinase (IRAK) family members belong to serine/threonine kinases that are recruited by the receptor through interaction with MyD88. The IRAK family consists of four members. Evidence has shown that IRAK4 plays a crucial and non-redundant role in initiating signals that are transduced by MyD88-dependent TLR and IL-1R family members. Structural data confirm that IRAK4 directly interacts with MyD88 and subsequently recruits IRAK1 or IRAK2 to the receptor complex to transduce the signal downstream (Lin, S. et al, 2010, Nature 465: 885-890). IRAK4 directly phosphorylates IRAK1, to transduce the signal to the downstream E3 ubiquitin ligase TRAF6, resulting in the activation of the serine/threonine kinase TAK1 followed by activation of the NF-κB pathway and the MAPK cascade (Flannery, S. et al, 2010, Biochem. Pharmacol. 80: 1981-1991). Tests revealed that a subset of human patients lacked IRAK4 expression (Picard, C. et al, 2003, Science 299: 2076-2079) and that cells obtained from these patients made no response to all TLR (except TLR3) agonists and IL-1 family members (including IL-1β and IL-18) (Ku, C. et al, 2007, J. Exp. Med. 204: 2407-2422). Deficiency of IRAK4 in mice results in severe blockade of IL-1, IL-18 and all TLRs (except TLR3) dependent responses (Suzuki, N. et al, 2002, Nature 416: 750-754). In contrast, deficiency of IRAK1 (Thomas, J. A. et al, 1999, J. Immunol. 163: 978-984; Swantek, J. L. et al, 2000, J. Immunol. 164: 4301-4306) or IRAK2 (Wan, Y. et al, 2009, J. Biol. Chem. 284: 10367-10375) results in only partially blocked signaling. Moreover, IRAK4 is the only family member in the IRAK family that has been demonstrated its kinase activity to be essential for initiating signaling. Replacing the wild-type IRAK4 in the mouse genome with a kinase-inactive mutant (KDKI) can block all signals transduced by MyD88-dependent receptors, including IL-1, IL-18 and all TLRs (except TLR3) (Koziczak-Holbro, M. et al, 2007, J. Biol. Chem. 282: 13552-13560; Kawagoe, T. et al, 2007, J. Exp. Med. 204: 1013-1024; and Fraczek, J. et al, 2008, J. Biol. Chem. 283: 31697-31705).

Compared with wild mice, mice having IRAK4 kinase-inactive mutant (KDKI) exhibited a dramatic reduction in the severity of diseases in models of multiple sclerosis (Staschke, K. A. et al, 2009, J. Immunol. 183: 568-577), rheumatoid arthritis (Koziczak-Holbro, M. et al, 2009, Arthritis Rheum. 60: 1661-1671), atherosclerosis (Kim, T. W. et al, 2011, J. Immunol. 186: 2871-2880; and Rekhter, M. et al, 2008, Bioch. Bioph. Res. Comm. 367: 642-648) and myocardial infarction (Maekawa, Y. et al, 2009, Circulation 120: 1401-1414). As mentioned above, IRAK4 inhibitors can block all MyD88-dependent signaling. MyD88-dependent TLRs have been demonstrated to be responsible for the following conditions: multiple sclerosis, rheumatoid arthritis, cardiovascular disease, metabolic syndrome, sepsis, systemic lupus erythematosus, inflammatory bowel disease including Crohn's disease and ulcerative colitis, autoimmune uveitis, asthma, allergies, type I diabetes and rejection after organ transplantation (Keogh, B. et al, 2011, Trends Pharmacol. Sci. 32: 435-442; Mann, D. L. 2011, Circ. Res. 108: 1133-1145; Goldstein, D. R. et al, 2005, J. Heart Lung Transpl. 24: 1721-1729; and Cario, E., 2010, Inflamm. Bowel Dis. 16: 1583-1597). In diffuse large B-cell lymphomas, tumor cells harboring oncogenic MyD88 mutations have been identified as being sensitive to IRAK4 inhibition (Ngo, V. et al, 2011, Nature 470: 115-121). Genome-wide sequencing also confirmed that MyD88 mutations are associated with chronic lymphocytic leukemia, suggesting the possibility of IRAK4 inhibitors for use in the treatment of leukemia (Puente, X. S. et al, 2011, Nature 475: 101-105).

In addition to blocking the signals transduced by the TLR pathway, IRAK4 inhibitors can also block the signals transduced by IL-1 and IL-1 family. Regulation of IL-1 has been demonstrated to be effective in a variety of diseases including gout, gouty arthritis, type 2 diabetes, auto-inflammatory disease, tumor necrosis factor receptor-associated periodic syndrome, familial Mediterranean fever, adult onset still's disease, systemic onset juvenile idiopathic arthritis, stroke, graft versus host disease, asymptomatic multiple myeloma, recurrent pericarditis, osteoarthritis, emphysema, and so on (Dinarello, C. A., 2011, Eur. J. Immunol. 41: 1203-1217; and Couillin, I. et al, 2009. J. Immunol. 183: 8195-8202). Blocking the IL-1 receptor improves cognitive deficits, reduces Tau proteinopathy, and reduces oligomeric forms of the amyloid-β protein in a mouse model of Alzheimer's disease (Kitazawa, M. et al, 2011, J. Immunol. 187: 6539-6549). IL-1 has also been demonstrated to be a key link in adaptive immunity that drives differentiation of effector T cell subsets Th17 (Chung, Y. et al, 2009, Immunity 30: 576-587). Therefore, IRAK4 inhibitors are predicted to exert their effects on Th17 cell-related diseases including multiple sclerosis, psoriasis, inflammatory bowel disease, autoimmune uveitis, rheumatoid arthritis, and so on (Wilke, C. M. et al, 2011, Trends Immunol. 32: 603-611).

Considering that patients can benefit from therapies that modulate protein kinases in many situations, there is an urgent need to provide new compounds that modulate protein kinases such as IRAK4 and methods of using these compounds, thereby providing a plenty of therapeutic benefits to a wide variety of patients.

SUMMARY OF INVENTION

It is an object of the invention to provide a new class of amino-substituted pyrimidopyrrole compounds which are potent inhibitors of the protein kinase IRAK4.

In one aspect, the invention provides a compound which has a structural formula I (which is hereinafter sometimes referred to as compound of Formula I):

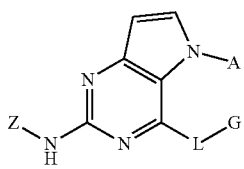

Formula I wherein:

A is aryl or heteroaryl, optionally substituted with one or more $R^1$ groups;

L is O, S, or $NR^2$;

G is alkyl, cycloalkyl, heterocyclyl, aryl, or heteroaryl, optionally substituted with one or more $R^3$ groups;

Z is aryl or heteroaryl, optionally substituted with one or more $R^4$ groups;

each $R^1$ is independently alkyl, cycloalkyl, heterocyclyl, hydroxy, halogen, haloalkyl, hydroxyalkyl, alkyloxyalkyl, heterocyclylalkyl, aminoalkyl, alkylaminoalkyl, dialkylaminoalkyl, alkyloxy, amino, alkylamino, dialkylamino, carboxy, or alkylsulfonyl;

$R^2$ is hydrogen or alkyl;

each $R^3$ is independently hydroxy, oxo, alkyl, cycloalkyl, heterocyclyl, aryl, heteroaryl, hydroxyalkyl, alkyloxy, cycloalkyloxy, heterocyclyloxy, alkylacylamino, alkylcarbonyl, cycloalkylcarbonyl, heterocyclylcarbonyl, or alkylaminoacyl;

each $R^4$ is independently alkyl, cyano, cycloalkyl, heterocyclyl, aryl, heteroaryl, oxo, haloalkyl, hydroxyalkyl, alkyloxyalkyl, heterocyclylalkyl, heterocyclylcarbonyl, or $R^{4a}R^{4b}NC(\!=\!\!O)\!-\!$;

each of $R^{4a}$ and $R^{4b}$ is independently hydrogen, alkyl, haloalkyl, cycloalkyl, hydroxyalkyl, alkyloxyalkyl, heterocyclylalkyl, heteroarylalkyl, heterocyclyl, aryl, or heteroaryl;

wherein said cycloalkyl, heterocyclyl, aryl or heteroaryl, in $R^1$, $R^3$, $R^4$, $R^{4a}$ and $R^{4b}$, as an independent group or a part of a group, is optionally substituted with one or more substituents independently selected from the group consisting of alkyl and oxo; and wherein said heterocyclyl and said heteroaryl contain one or more heteroatoms selected from the group consisting of nitrogen, oxygen and sulfur, or a stereoisomer, tautomer, solvate, or a pharmaceutically acceptable salt thereof.

Another aspect of the invention relates to a pharmaceutical composition comprising a compound of Formula I according to the invention or a stereoisomer, tautomer, solvate, or a pharmaceutically acceptable salt thereof, and a pharmaceutically acceptable excipient. In a further embodiment, the pharmaceutical composition according to the invention may further comprise one or more active agents selected from the group consisting of immunosuppressants, glucocorticoids, nonsteroidal anti-inflammatory drugs, vinca alkaloids, paclitaxel, DNA damaging agents, Bcl-2 inhibitors, BTK inhibitors, JAK inhibitors, Hsp90 inhibitors, ALK inhibitors, Flt3 inhibitors, PI3K inhibitors and SYK inhibitors.

Another aspect of the invention relates to use of a compound of Formula I according to the invention, or a stereoisomer, tautomer, solvate, or a pharmaceutically acceptable salt thereof, in the manufacture of a medicament for inhibiting the activity of IRAK4.

Another aspect of the invention relates to use of a compound of Formula I according to the invention, or a stereoisomer, tautomer, solvate, or a pharmaceutically acceptable salt thereof, in the manufacture of a medicament for the prevention or treatment of IRAK4-mediated diseases.

Another aspect of the invention relates to use of a pharmaceutical composition according to the invention in the manufacture of a medicament for inhibiting the activity of IRAK4, wherein the pharmaceutical composition comprises a compound of Formula I according to the invention or a stereoisomer, tautomer, solvate, or a pharmaceutically acceptable salt thereof, and a pharmaceutically acceptable excipient. In a further embodiment, the pharmaceutical composition of the invention may further comprise one or more active agents selected from the group consisting of immunosuppressants, glucocorticoids, nonsteroidal anti-inflammatory drugs, vinca alkaloids, paclitaxel, DNA damaging agents, Bcl-2 inhibitors, BTK inhibitors, JAK inhibitors, Hsp90 inhibitors, ALK inhibitors, Flt3 inhibitors, PI3K inhibitors and SYK inhibitors.

Another aspect of the invention relates to use of a pharmaceutical composition according to the invention in the manufacture of a medicament for the prevention or treatment of IRAK4-mediated diseases, wherein the pharmaceutical composition comprises a compound of Formula I according to the invention or a stereoisomer, tautomer, solvate, or a pharmaceutically acceptable salt thereof, and a pharmaceutically acceptable excipient. In a further embodiment, the pharmaceutical composition of the invention may further comprise one or more active agents selected from the group consisting of immunosuppressants, glucocorticoids, nonsteroidal anti-inflammatory drugs, vinca alkaloids, paclitaxel, DNA damaging agents, Bcl-2 inhibitors, BTK inhibitors, JAK inhibitors, Hsp90 inhibitors, ALK inhibitors, Flt3 inhibitors, PI3K inhibitors and SYK inhibitors.

Another aspect of the invention relates to a compound of Formula I according to the invention, or a stereoisomer, tautomer, solvate, or a pharmaceutically acceptable salt thereof, or a pharmaceutical composition comprising a compound of Formula I according to the invention or a stereoisomer, tautomer, solvate, or a pharmaceutically acceptable salt thereof, for use in the inhibition of the activity of IRAK4.

Another aspect of the invention relates to a compound of Formula I according to the invention, or a stereoisomer, tautomer, solvate or pharmaceutically acceptable salt thereof, or a pharmaceutical composition comprising a compound of Formula I according to the invention or a stereoisomers, tautomer, solvate, or a pharmaceutically acceptable salt thereof for use in the prevention or treatment of IRAK4-mediated diseases.

Another aspect of the invention relates to a method for inhibiting IRAK4 activity in a biological system comprising administering to the biological system a compound of Formula I according to the invention, or a stereoisomer, tautomer, solvate or pharmaceutically acceptable salt thereof, or a pharmaceutical composition comprising a compound of Formula I according to the invention, or a stereoisomer, tautomer, solvate, or a pharmaceutically acceptable salt thereof.

Another aspect of the invention relates to a method for preventing or treating IRAK4-mediated diseases comprising administering to a subject in need thereof a therapeutically effective amount of a compound of Formula I according to the invention, or a stereoisomer, tautomer, solvate, or a pharmaceutically acceptable salt thereof, or a pharmaceutical composition comprising a compound of Formula I according to the invention, or a stereoisomer, tautomer, solvate, or a pharmaceutically acceptable salt thereof.

Another aspect of the invention relates to use of a compound of Formula I according to the invention or a stereoisomer, tautomer, solvate, or a pharmaceutically acceptable salt thereof in the manufacture of a medicament for the treatment of IRAK4-mediated diseases in combination with one or more active agents selected from the group consisting of immunosuppressants, glucocorticoids, nonsteroidal anti-inflammatory drugs, vinca alkaloids, paclitaxel, DNA damaging agents, Bcl-2 inhibitors, BTK Inhibitors, JAK inhibitors, Hsp90 inhibitors, ALK inhibitors, Flt3 inhibitors, PI3K inhibitors and SYK inhibitors.

In the present application, the IRAK4-mediated diseases include autoimmune diseases, inflammatory diseases, heteroimmune conditions or diseases, thromboembolic diseases and cancers.

DETAILED DESCRIPTION OF THE EMBODIMENTS

Unless otherwise defined, all technical and scientific terms used herein have the same meanings as those commonly understood by a person having ordinary skill in the art to which the subject matters of the claims pertain.

It should be understood that both the foregoing general description and the following detailed description are exemplary and are intended for the purpose of illustration only and are not restrictive of the subject matters of the invention in any way.

All literatures or sections of literatures including but not limited to patents, patent applications, articles, books, manuals and theses as cited in the present application, are hereby incorporated by reference in their entirety.

Certain chemical groups as defined herein are preceded by the total number of carbon atoms present in the group represented by simplified notation. For example, $C_{1-6}$ alkyl refers to an alkyl group as defined hereinafter having a total of 1 to 6 carbon atoms; $C_{6-12}$ aryl refers to an aryl group as defined hereinafter having a total of 6 to 12 carbon atoms. The total number of carbon atoms in the simplified notation does not include the number of carbon atoms that may be present in the substituents of the groups.

Unless otherwise stated specifically in the specification, all combined groups (i.e., groups that are combined by two or more groups) of the invention are attached to the rest of the molecule in such a way that the lastly described group acts as the point of attachment. For example, the group "heterocyclylalkyl" refers to a heterocyclyl group attached to the rest of the molecule via an alkyl group; the group "alkyloxy" refers to an alkyl group attached to the rest of the molecule via an oxy group; and so on.

In addition to the foregoing, when used in the specification and claims of this application, the following terms have the meanings indicated below, unless otherwise specified:

"Oxo" refers to the =O group.
"Amino" refers to the —NH$_2$ group.
"Cyano" refers to the —CN group.
"Hydroxy" refers to the —OH group.
"Carbonyl" or "acyl" refers to the —C(=O)— group.
"Carboxy" refers to the —C(=O) OH group.
"Sulfonyl" refers to the —S(=O)$_2$— group.
"Aminoacyl" refers to the —C(=O)—NH$_2$ group.

In the present application, the term "halogen" refers to fluorine, chlorine, bromine and iodine, preferably fluorine.

In the present application, the term "alkyl", as an independent group or a part of a group means a straight or branched chain group consisting solely of carbon atoms and hydrogen atoms, containing no unsaturated bond and being attached to the rest of the molecule by a single bond. The alkyl group may have, for example, 1 to 18, preferably 1 to 8, more preferably 1 to 6, more preferably 1 to 4, carbon atoms. Examples of the alkyl group include, but are not limited to, methyl, ethyl, propyl, isopropyl, n-butyl, isobutyl, sec-butyl, tert-butyl, n-pentyl, n-hexyl, 2-pentyl, heptyl, 2-methylhexyl, 3-methylhexyl, octyl, nonyl, decyl, and the like, preferably methyl, ethyl, propyl, isopropyl, and butyl. The hydrogen(s) in the alkyl group may be optionally replaced with any suitable groups such as halogen, hydroxy, amino, mono-substituted amino, di-substituted amino, alkyloxy, aminoacyl, cycloalkyl, aryl, heteroaryl, heterocyclyl, or the like.

In the present application, the term "haloalkyl", as an independent group or a part of a group means an alkyl group, as defined above, substituted with one or more halogen atoms. Examples thereof include, but are not limited to, fluoromethyl, difluoromethyl, trifluoromethyl, 2-fluoroethyl, 2,2-difluoroethyl, 2,2,2-trifluoroethyl, chloromethyl, 2-chloroethyl, dichloromethyl, 1,2-dichloroethyl, 3-bromopropyl, and the like, preferably difluoromethyl, trifluoromethyl, 2-fluoroethyl, 2,2-difluoroethyl, and 2,2,2-trifluoroethyl.

In the present application, the term "hydroxyalkyl", as an independent group or a part of a group, refers to an alkyl group, as defined above, substituted with one or more hydroxyl groups. Examples thereof include, but are not limited to, hydroxymethyl, 2-hydroxyethyl, 1,2-dihydroxyethyl, 3-hydroxypropyl, 1-hydroxypropyl, 2-hydroxypropyl, 1,2-dihydroxypropyl, 4-hydroxybutyl, and the like, preferably hydroxymethyl, and 2-hydroxyethyl.

In the present application, the term "aminoalkyl", as an independent group or a part of a group, refers to an alkyl group, as defined above, substituted with one or more amino groups. Examples thereof include, but are not limited to, aminomethyl, aminoethyl, 1,2-diaminoethyl, aminopropyl, 2-aminopropyl, 2,3-diaminopropyl, and the like.

In the present application, the term "alkyloxy", as an independent group or a part of a group, refers to a group that is formed by attaching an alkyl group to an oxygen atom and may be represented by —OR$_a$, wherein R$_a$ is an alkyl group as defined above. Examples of the alkyloxy group include, but are not limited to, methoxy, ethoxy, isopropoxy, n-butoxy, isobutoxy, tert-butoxy, and the like, preferably methoxy, and ethoxy.

In the present application, the term "alkylsulfonyl", as an independent group or a part of a group, refers to a group represented by —S(=O)$_2$—R$_a$, wherein R$_a$ is an alkyl group as defined above. Examples of the alkylsulfonyl group include, but are not limited to, methylsulfonyl, ethylsulfonyl, isopropylsulfonyl, n-butylsulfonyl, isobutylsulfonyl, tert-butylsulfonyl, and the like, preferably methylsulfonyl.

In the present application, the term "alkyloxyalkyl", as an independent group or a part of a group, is an alkyl group, as defined above, substituted with an alkyloxy group as defined above. Examples of the alkyloxyalkyl group include, but are not limited to, 2-methoxyethyl, ethoxymethyl, 2-ethoxyethyl, isopropoxymethyl, n-butoxymethyl, 2-isobutoxyethyl, and the like, preferably 2-methoxyethyl.

In the present application, the term "alkylcarbonyl", as an independent group or a part of a group, refers to a —C(=O) R$_a$ group, wherein R$_a$ is an alkyl group as defined above. Examples of the alkylcarbonyl group include, but are not limited to, acetyl, isopropionyl, tert-butyryl, and the like, preferably acetyl.

In the present application, the term "alkylamino", as an independent group or a part of a group, refers to a group in which one hydrogen atom in the amino group is replaced with an alkyl group as defined above, which may be represented by the formula —NHR$_a$ wherein R$_a$ is an alkyl group as defined above. Examples of the alkylamino group include, but are not limited to, methylamino, ethylamino, propylamino, isopropylamino, butylamino, isobutylamino, tert-butylamino, and the like, preferably methylamino, ethylamino, propylamino, and isopropylamino.

In the present application, the term "alkylaminoalkyl", as an independent group or a part of a group, refers to a group of an alkyl group, as defined above, substituted with an alkylamino group as defined above. Examples of the alkylaminoalkyl group include, but are not limited to, CH$_3$—NH—CH$_2$—, C$_2$H$_5$—NH—CH$_2$—, and the like.

In the present application, the term "dialkylamino", as an independent group or a part of a group, refers to a group in which two hydrogen atoms in the amino group are each replaced with an alkyl group as defined above, which may be represented by the formula —NR$_a$R$_b$, wherein R$_a$ and R$_b$ are each independently an alkyl group as defined above and may be the same or different. Examples of the dialkylamino group include, but are not limited to, dimethylamino, diethylamino, dipropylamino, methylethylamino, and the like, preferably dimethylamino.

In the present application, the term "dialkylaminoalkyl", as an independent group or a part of another group, refers to an alkyl group, as defined above, substituted with a dialkylamino group as defined above. Examples of the dialkylaminoalkyl group include, but are not limited to, dimethylaminomethyl, diethylaminoethyl, dipropylaminoethyl, and the like.

In the present application, the term "alkylacylamino", as an independent group or a part of another group, refers to a group represented by —NHC(=O)—R$_a$, wherein R$_a$ is an alkyl group as defined above. Examples of the alkylacylamino groups include, but are not limited to, CH$_3$—C(=O)—NH—, C$_2$H$_5$—C(=O)—NH—, C$_3$H$_7$—C(=O)—NH—, (CH$_3$)$_2$CH—C(=O)—NH—, and the like, preferably CH$_3$—C(=O)—NH—.

In the present application, the term "alkylaminoacyl", as an independent group or a part of another group, refers to a group represented by —C(=O)—NHR$_a$, wherein R$_a$ is an alkyl group as defined above. Examples of the alkylaminoacyl group include, but are not limited to, CH$_3$—NH—C(=O)—, C$_2$H$_5$—NH—C(=O)—, C$_3$H$_7$—NH—C(=O)—, (CH$_3$)$_2$CH—NH—C(=O)—, and the like.

In the present application, the term "cycloalkyl", as an independent group or a part of a group, means a stable, monovalent non-aromatic monocyclic or polycyclic hydrocarbon group consisting solely of carbon atoms and hydrogen atoms, which may include a fused ring system or a bridged ring system, and which has 3 to 15 carbon atoms, preferably 3 to 10 carbon atoms, more preferably 3 to 8 carbon atoms, and most preferably 3 to 6 carbon atoms, and which is saturated or partially unsaturated and may be attached to the rest of the molecule through a single bond via any suitable carbon atom. Examples of the cycloalkyl group include, but are not limited to, cyclopropyl, cyclobutyl, cyclopentyl, cyclohexyl, cycloheptyl, cyclooctyl, 1H-indenyl, 2,3-dihydro-indenyl, 1,2,3,4-tetrahydro-naphthyl, 5,6,7,8-tetrahydro-naphthyl, 8,9-dihydro-7H-benzocyclohepten-6-yl, 6,7,8,9-tetrahydro-5H-benzocycloheptenyl, 5,6,7,8,9,10-hexahydro-benzocyclooctenyl, fluorenyl, bicyclo[2.2.1]heptyl, 7,7-dimethyl-bicyclo[2.2.1]heptyl, bicyclo[2.2.1]heptenyl, bicyclo[2.2.2]octyl, bicyclo[3.1.1]heptyl, bicyclo[3.2.1]octyl, bicyclo[2.2.2]octenyl, bicyclo[3.2.1]octenyl, adamantyl, octahydro-4,7-methylene-1H-indenyl and octahydro-2,5-methylene-pentalenyl, and the like, preferably cyclopropyl, cyclobutyl, cyclopentyl and cyclohexyl. The hydrogen(s) in the cycloalkyl group may be optionally replaced with any suitable groups such as oxo, halogen, hydroxy, amino, mono-substituted amino, di-substituted amino, alkyl, haloalkyl, alkyloxy, alkylcarbonyl, alkylcarbonylamino, carboxy, hydroxyalkyl, aminoacyl, aryl, heterocyclyl, ureido, or the like.

In the present application, the term "cycloalkyloxy", as an independent group or a part of a group, refers to a group of the formula R$_c$O— wherein R$_c$ is a cycloalkyl group as defined above. Examples of the cycloalkyloxy group include, but are not limited to, cyclopropyloxy, cyclobutyloxy, cyclopentyloxy, cyclohexyloxy, cycloheptyloxy, and the like.

In the present application, the term "cycloalkylcarbonyl", as an independent group or a part of a group, refers to a radical of the formula R$_c$—C(=O)—, wherein R$_c$ is a cycloalkyl group as defined above. Examples of the cycloalkylcarbonyl group include, but are not limited to, cyclopropylcarbonyl, cyclobutylcarbonyl, cyclopentylcarbonyl, cyclohexylcarbonyl, cycloheptylcarbonyl, and the like.

In the present application, the term "heterocyclyl", as an independent group or a part of a group, means a stable 3- to 18-membered non-aromatic cyclic group consisting of 2 to 12 carbon atoms and 1 to 6 heteroatoms selected from the group consisting of nitrogen, oxygen and sulfur. Unless otherwise stated specifically in the specification, a heterocyclyl group may be a monocyclic, bicyclic, tricyclic or polycyclic ring system which may include a fused ring system or a bridged ring system. For the purposes of the invention, heterocyclyl is preferably a stable 3- to 8-membered non-aromatic monocyclic or bicyclic group containing 1 to 3 heteroatoms selected from the group consisting of nitrogen, oxygen and sulfur, more preferably a stable 4- to 7-membered non-aromatic monocyclic group containing 1 to 3 heteroatoms selected from the group consisting of nitrogen, oxygen and sulfur, more preferably a stable 4- to 6-membered, more preferably 5- to 6-membered non-aromatic monocyclic group containing 1 to 2 heteroatoms selected from the group consisting of nitrogen, oxygen and sulfur. The nitrogen, carbon or sulfur atom in the heterocyclyl may be optionally oxidized; the nitrogen atom may be optionally quaternized; and the heterocyclyl may be partially or fully saturated. The heterocyclyl group may be attached to the rest of the molecule through a single bond via a carbon atom or a heteroatom. In a heterocyclyl group containing a fused ring, one or more of the rings can be aryl or heteroaryl, with the proviso that the point of attachment of the heterocyclyl group to the rest of the molecule is through an atom on a non-aromatic ring. Examples of the heterocyclyl group include, but are not limited to, oxetanyl, azetidinyl, pyrrolidinyl, tetrahydrofuranyl, pyranyl, tetrahydropyranyl, tetrahydrothiopyranyl, 1,1-dioxotetrahydrothiopyranyl, morpholinyl, thiomorpholinyl, 1,1-dioxothiomorpholinyl, piperazinyl, piperidinyl, oxazinyl, dioxolanyl, tetrahydroisoquinolinyl, decahydroisoquinolinyl, imidazolinyl, imidazolidinyl, quinolizinyl, thiazolidinyl, isothiazolidinyl, isooxazolidinyl, indolinyl, octahydroindolyl, octahydroisoindolyl, pyrazolidinyl, phthalimido, and the like, preferably oxetanyl, tetrahydrofuranyl, tetrahydropyranyl, tetrahydrothiopyranyl, 1,1-dioxotetrahydrothiopyranyl, morpholinyl, thiomorpholinyl, 1,1-dioxothiomorpholinyl, piperazinyl, and piperidinyl. The hydrogen atom in the heterocyclyl group may be optionally replaced with any suitable groups such as halogen, hydroxy, amino, mono-substituted amino, di-substituted amino, alkyl, haloalkyl, alkyloxy, cycloalkyl, heterocyclyl, alkylcarbonyl, aminoacyl, or the like.

In the present application, the term "heterocyclyloxy", as an independent group or a part of a group, refers to a group of the formula $R_hO—$, wherein $R_h$ is a heterocyclyl group as defined above. Examples of the heterocyclyloxy group include, but are not limited to, tetrahydrofuranyloxy, tetrahydropyranyloxy, piperidyloxy, pyrrolidinyloxy, and the like.

In the present application, the term "heterocyclylalkyl", as an independent group or a part of a group, refers to an alkyl group, as defined above, substituted with one or more heterocyclyl groups as defined above. Examples of the heterocyclylalkyl group include, but are not limited to, tetrahydrofurylalkyl, tetrahydropyranylalkyl such as tetrahydropyran-4-ylmethyl and the like, piperidinylalkyl such as 1-methylpiperidin-4-ylmethyl and the like, piperazinylalkyl, morpholinylalkyl such as morpholin-4-ylethyl, morpholin-4-ylpropyl, and the like, pyrrolidinylalkyl, and the like.

In the present application, the term "heterocyclylcarbonyl", as an independent group or a part of a group, refers to a group of the formula $R_h—C(=O)—$, wherein $R_h$ is a heterocyclyl group as defined above. Examples of the heterocyclylcarbonyl group include, but are not limited to, piperazinylcarbonyl such as 4-methyl-piperazin-1-ylcarbonyl and the like, piperidinylcarbonyl such as piperidin-1-ylcarbonyl and the like, morpholinylcarbonyl, thiomorpholinylcarbonyl, and the like.

In the present application, the term "aryl", as an independent group or a part of a group, means a system having 6 to 18, preferably 6 to 10 carbon atoms and at least one aromatic ring. For the purpose of the invention, the aryl group may be a monocyclic, bicyclic, tricyclic or polycyclic ring system which may contain a fused or bridged ring system. The aryl group is attached to the rest of the molecule through a single bond via an atom on an aromatic ring. The aryl group may be substituted at any suitable position with one or more substituents selected from the group consisting of halogen, hydroxy, amino, alkyl, cycloalkyl, haloalkyl, hydroxyalkyl, alkyloxy, heterocyclyl, aryl, heteroaryl, substituted aminoacyl, heterocyclylalkylacyl, heterocyclylcarbonyl, and the like. Examples of the aryl group include, but are not limited to, phenyl, naphthyl, anthryl, phenanthryl, and the like, preferably phenyl.

In the present application, the term "heteroaryl", as an independent group or a part of a group, means a 5-membered to 16-membered ring system group having 1 to 4 heteroatoms selected from the group consisting of nitrogen, oxygen and sulfur, and at least one aromatic ring. Unless otherwise stated specifically in the specification, the heteroaryl group may be a monocyclic, bicyclic, tricyclic or polycyclic ring system which may include a fused ring system or a bridged ring system, with the proviso that the point of attachment is an atom on an aromatic ring. The nitrogen, carbon or sulfur atom in the heteroaryl group may be optionally oxidized; and the nitrogen atom may optionally be quaternized. For the purpose of the invention, the heteroaryl group is preferably a stable 5-membered to 12-membered aromatic monocyclic or bicyclic group containing 1 to 3 heteroatoms selected from the group consisting of nitrogen, oxygen and sulfur, more preferably a stable 5-membered to 10-membered aromatic monocyclic group containing 1 to 2 heteroatoms selected from the group consisting of nitrogen, oxygen and sulfur. Examples of the heteroaryl group include, but are not limited to, thienyl, benzothienyl, furanyl, pyrrolyl, imidazolyl, benzimidazolyl, pyrazolyl, benzopyrazolyl, triazolyl, tetrazolyl, pyridinyl, pyrazinyl, triazinyl, pyrimidinyl, pyridazinyl, indolizinyl, indolyl, isoindolyl, indazolyl, isoindazolyl, purinyl, quinolinyl, isoquinolinyl, diazanaphthalenyl, naphthyridinyl, quinoxalinyl, pteridinyl, carbazolyl, carbolinyl, phenanthridinyl, phenanthrolinyl, acridinyl, phenazinyl, thiazolyl, isothiazolyl, benzothiazolyl, benzothienyl, oxazolyl, isoxazolyl, oxadiazolyl, oxatriazolyl, cinnolinyl, quinazolinyl, phenylthio, indolizinyl, phenanthrolinyl, phenoxazinyl, phenothiazinyl, 2,3-dihydro-1H-isoindolyl, benzo[1,3]dioxolyl, 2,3-dihydro-benzo[1,4]dioxinyl, 1,2,3,4-tetrahydro-pyrrolo[1,2-a]pyrizine, 4,5,6,7-tetrahydrobenzo[b]thienyl, naphthopyridinyl, imidazo[1,2-a]pyridinyl, and the like, preferably pyrrolyl, pyrazolyl, furanyl, thienyl, isoxazolyl, thiazolyl, isothiazolyl, pyridinyl, pyrimidinyl, pyridazinyl, benzothienyl, benzothiazolyl, indazolyl, 2,3-dihydro-1H-isoindolyl, benzo[1,3]dioxolyl, 2,3-dihydro-benzo[1,4]dioxinyl, and 1,2,3,4-tetrahydro-pyrrolo[1,2-a]pyrazine. The heteroaryl group may be substituted at any suitable position with one or more substituents selected from the group consisting of oxo, halogen, hydroxy, amino, alkyl, cycloalkyl, haloalkyl, hydroxyalkyl, alkyloxy, heterocyclyl, aryl, heteroaryl, substituted or unsubstituted aminoacyl, heterocyclylalkylacyl, heterocyclylcarbonyl, and the like.

In the present application, the term "optional" or "optionally" means that the subsequently described event or circumstance may or may not occur, and that the description includes instances where said event or circumstance occurs and instances in which it does not. For example, "alkyl optionally substituted with one or more halogens" means that the alkyl is unsubstituted or substituted with one or more halogens, and that the description includes both substituted and unsubstituted alkyl groups.

A "stereoisomer" refers to a compound that consists of the same atoms, bonded by the same bond, but has a different three-dimensional structure. Stereoisomers include enantiomers and diastereomers, where diastereomers include cis-trans isomers (i.e., geometric isomers) and conformational isomers. The invention will encompass various stereoisomers and mixtures thereof.

A "tautomer" refers to an isomer resulted from a proton shift from one atom of a molecule to another atom of the same molecule. All tautomeric forms of the compound of Formula I according to the invention are also intended to be embraced within the scope of the invention.

In the present application, the term "pharmaceutically acceptable salt" includes both pharmaceutically acceptable acid addition salts and pharmaceutically acceptable base addition salts.

"Pharmaceutically acceptable acid addition salts" refers to those salts which are capable of retaining the biological effectiveness of free bases without any undesirable effects, and which are formed with inorganic or organic acids. The inorganic acids include, but are not limited to, hydrochloric acid, hydrobromic acid, sulfuric acid, nitric acid, phosphoric acid, and the like; and the organic acids include, but are not limited to, formic acid, acetic acid, trifluoroacetic acid, propionic acid, caprylic acid, caproic acid, capric acid, undecylenic acid, glycolic acid, gluconic acid, lactic acid, oxalic acid, sebacic acid, adipic acid, glutaric acid, malonic acid, maleic acid, succinic acid, fumaric acid, tartaric acid, citric acid, palmitic acid, stearic acid, oleic acid, cinnamic acid, lauric acid, malic acid, glutamic acid, pyroglutamic acid, aspartic acid, benzoic acid, methanesulfonic acid, p-toluenesulfonic acid, alginic acid, ascorbic acid, salicylic acid, 4-aminosalicylic acid, naphthalene disulfonic acid, and the like. These salts can be prepared by the methods known in the art.

"Pharmaceutically acceptable base addition salts" refers to those salts which are capable of retaining the biological effectiveness of free acids without any undesirable effects. These salts are prepared by adding inorganic or organic bases to the free acids. The salts derived from inorganic bases include, but are not limited to, sodium, potassium, lithium, ammonium, calcium, magnesium, iron, zinc, copper, manganese, aluminum salts, and the like. Preferred inorganic salts are ammonium, sodium, potassium, calcium and magnesium salts. The salts derived from organic bases includes, but are not limited to, salts of primary, secondary, and tertiary amines, substituted amines including naturally occurring substituted amines, cyclic amines, and basic ion exchange resins, such as ammonia, isopropylamine, trimethylamine, diethylamine, triethylamine, tripropylamine, ethanolamine, diethanolamine, triethanolamine, dimethylethanolamine, 2-dimethylaminoethanol, 2-diethylaminoethanol, dicyclohexylamine, lysine, arginine, histidine, caffeine, choline, betaine, ethylenediamine, glucosamine, methylglucamine, theobromine, tromethamine, purine, piperazine, piperidine, N-ethylpiperidine, polyamine resins, and the like.

Depending on the number of charged functional groups and the valency of the cation or anion, the compound of the invention may contain a plurality of cations or anions.

Often, crystallization will produce a solvate of the compound of the invention. In the present application, a "solvate" refers to an aggregate comprising one or more molecules of a compound according to the invention with one or more solvent molecules. They either react with each other in a solvent or precipitate or crystallize out from a solvent. The solvent may be water, in which case the solvate is a hydrate. Alternatively, the solvent may be an organic solvent. The solvate of the compound of the invention are also within the scope of the invention.

In the present application, a "pharmaceutical composition" refers to a formulation of a compound according to the invention and a medium commonly accepted in the art for the delivery of a biologically-active compound to a mammal, e.g., a human. The medium includes a pharmaceutically acceptable excipient. The pharmaceutical composition of the present application may be a single formulation or a combination of a plurality of formulations.

In the present application, a "pharmaceutically acceptable excipient" includes, but is not limited to, any of adjuvants, carriers, excipients, glidants, sweeteners, preservatives, dyes/colorants, flavoring agents, surfactants, wetting agents, dispersing agents, suspending agents, stabilizers, isotonic agents, solvents or emulsifiers which have been approved by relevant state authorities as being acceptable for use in humans or domestic animals.

According to one aspect of the invention, the invention provides a compound which has a structural formula I:

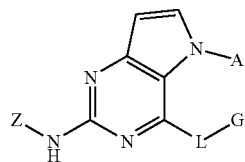

Formula I wherein:
A is aryl or heteroaryl, optionally substituted with one or more $R^1$ groups;

L is O, S, or $NR^2$;
G is alkyl, cycloalkyl, heterocyclyl, aryl, or heteroaryl, optionally substituted with one or more $R^3$ groups;
Z is aryl or heteroaryl, optionally substituted with one or more $R^4$ groups;
each $R^1$ is independently alkyl, cycloalkyl, heterocyclyl, hydroxy, halogen, haloalkyl, hydroxyalkyl, alkyloxyalkyl, heterocyclylalkyl, aminoalkyl, alkylaminoalkyl, dialkylaminoalkyl, alkyloxy, amino, alkylamino, dialkylamino, carboxy or alkylsulfonyl;
$R^2$ is hydrogen or alkyl;
each $R^3$ is independently hydroxy, oxo, alkyl, cycloalkyl, heterocyclyl, aryl, heteroaryl, hydroxyalkyl, alkyloxy, cycloalkyloxy, heterocyclyloxy, alkylacylamino, alkylcarbonyl, cycloalkylcarbonyl, heterocyclylcarbonyl, or alkylaminoacyl;
each $R^4$ is independently alkyl, cyano, cycloalkyl, heterocyclyl, aryl, heteroaryl, oxo, haloalkyl, hydroxyalkyl, alkyloxyalkyl, heterocyclylalkyl, heterocyclylcarbonyl, or $R^{4a}R^{4b}NC(\!=\!O)\!-\!$; and
each of $R^{4a}$ and $R^{4b}$ is independently hydrogen, alkyl, haloalkyl, cycloalkyl, hydroxyalkyl, alkyloxyalkyl, heterocyclylalkyl, heteroarylalkyl, heterocyclyl, aryl, or heteroaryl;
wherein said cycloalkyl, heterocyclyl, aryl, and heteroaryl, in $R^1$, $R^3$, $R^4$, $R^{4a}$ and $R^{4b}$, as an independent group or a part of a group, are optionally substituted with one or more substituents independently selected from the group consisting of alkyl and oxo; and
wherein said heterocyclyl and said heteroaryl contain one or more heteroatoms selected from the group consisting of nitrogen, oxygen and sulfur,
or a stereoisomer, tautomer, solvate, or a pharmaceutically acceptable salt thereof.

In some embodiments of the compound of Formula I, A is aryl or heteroaryl, optionally substituted with one or more $R^1$ groups as defined herein, said heteroaryl contains one, two or three heteroatoms selected from the group consisting of nitrogen, oxygen and sulfur.

In some embodiments of the compound of Formula I, A is $C_{6-12}$ aryl optionally substituted with one or more $R^1$ groups as defined herein. In some embodiments, A is phenyl optionally substituted with one or more $R^1$ groups as defined herein.

In some embodiments of the compound of Formula I, A is 5- to 12-membered heteroaryl optionally substituted with one or more $R^1$ groups as defined herein; in some embodiments, A is 5- to 10-membered heteroaryl optionally substituted with one or more $R^1$ groups as defined herein; said heteroaryl contains one, two or three heteroatoms selected from the group consisting of nitrogen, oxygen and sulfur.

In some embodiments of the compound of Formula I, A is pyrrolyl, pyrazolyl, furanyl, thienyl, pyridinyl, pyrimidinyl, pyridazinyl, indazolyl, benzo[1,3]dioxol-4 or 5-yl

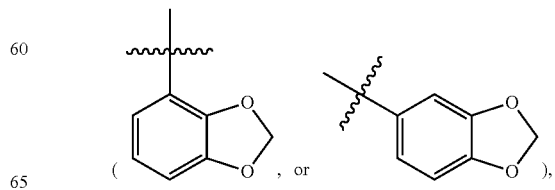

or 2,3-dihydro-benzo[1,4]dioxin-5 or 6-yl

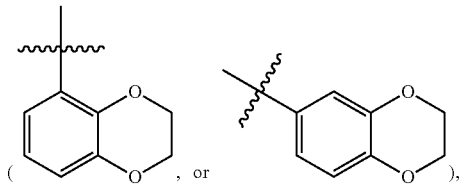 [SMILES: *c1cccc2c1OCCO2 ; *c1ccc2c(c1)OCCO2]

optionally substituted with one or more $R^1$ groups as defined herein.

In some embodiments of the compound of Formula I, A is pyrrolyl, pyrazolyl, furanyl, thienyl, pyridinyl, pyrimidinyl, pyridazinyl, benzo[1,3]dioxol-5-yl, or 2,3-dihydrobenzo[1,4]dioxin-5-yl, optionally substituted with one or more $R^1$ groups as defined herein.

In some embodiments of the compound of Formula I, A is pyrazolyl, furanyl, or pyridinyl, optionally substituted with one or more $R^1$ groups as defined herein.

In some embodiments of the compound of Formula I, each $R^1$ is independently alkyl, cycloalkyl, heterocyclyl, hydroxy, halogen, haloalkyl, hydroxyalkyl, alkyloxyalkyl, heterocyclylalkyl, aminoalkyl, alkylaminoalkyl, dialkylaminoalkyl, alkyloxy, amino, alkylamino, dialkylamino, carboxy, or alkylsulfonyl.

In some embodiments of the compound of Formula I, each $R^1$ is independently halogen, hydroxy, alkyl, haloalkyl, heterocyclyl, alkyloxyalkyl, alkyloxy, amino, dialkylamino, carboxy, or alkylsulfonyl.

In some embodiments of the compound of Formula I, each $R^1$ is independently halogen, hydroxy, alkyl, haloalkyl, alkyloxy, alkyloxyalkyl, or heterocyclyl.

In some embodiments of the compound of Formula I, each $R^1$ is independently alkyl.

In some embodiments of the compound of Formula I, A is selected from the group consisting of:

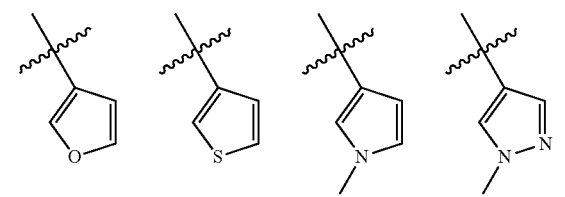

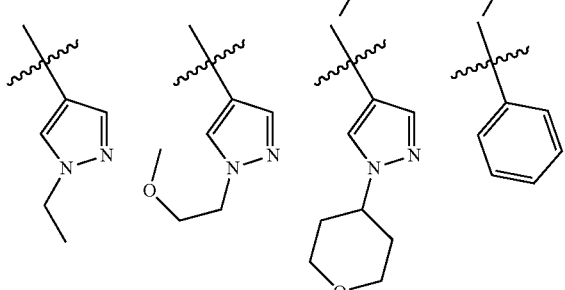

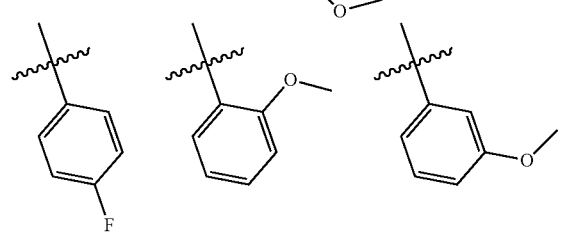

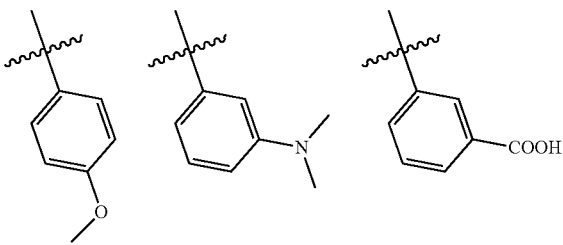

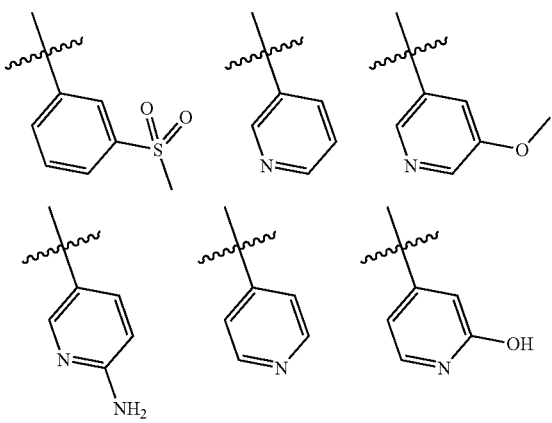

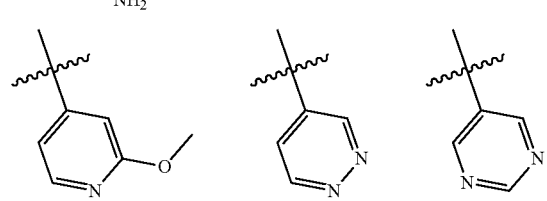

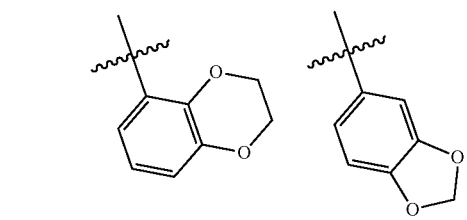

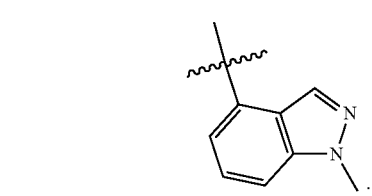

In some embodiments of the compound of Formula I, A is selected from the group consisting of:

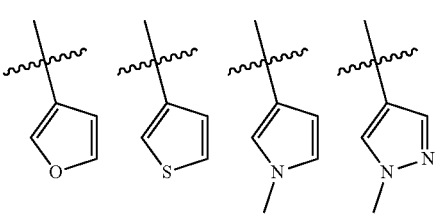

-continued

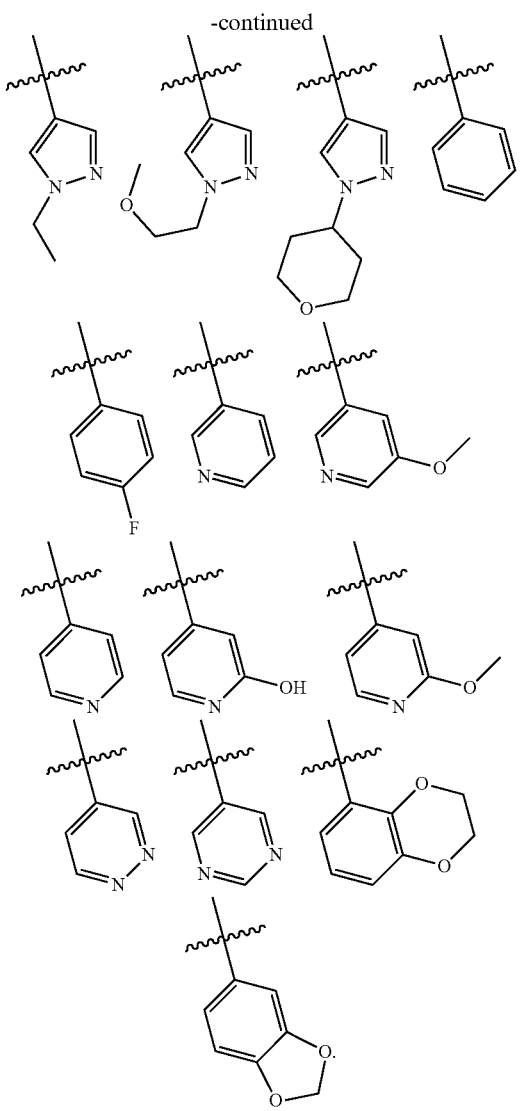

In some embodiments of the compound of Formula I, A is selected from the group consisting of:

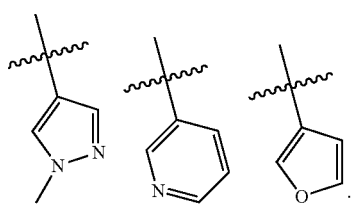

In some embodiments of the compound of Formula I, when A is phenyl, $R^1$ is not alkyloxy, dialkylamino, carboxy, and alkylsulfonyl. In some embodiments of the compound of Formula I, when A is pyridinyl, $R^1$ is not amino.

In some embodiments of the compound of Formula I, L is O. In some other embodiments, L is S. In some other embodiments, L is $NR^2$, wherein $R^2$ is hydrogen. In some other embodiments, L is $NR^2$, where $R^2$ is alkyl, preferably $C_{1-6}$ alkyl, more preferably methyl.

In some embodiments of the compound of Formula I, G is alkyl, cycloalkyl, heterocyclyl, aryl, or heteroaryl, optionally substituted with one or more $R^3$ groups as defined herein, wherein said heterocyclyl and heteroaryl contain one, two or three heteroatoms selected from the group consisting of nitrogen, oxygen and sulfur.

In some embodiments of the compound of Formula I, G is $C_{1-6}$ alkyl optionally substituted with one or more $R^3$ groups as defined herein. In some embodiments, G is methyl, ethyl, propyl, isopropyl, or butyl, optionally substituted with one or more $R^3$ groups as defined herein.

In some embodiments of the compound of Formula I, G is $C_{3-8}$ cycloalkyl, preferably $C_{3-6}$ cycloalkyl, more preferably cyclobutyl, cyclopentyl, or cyclohexyl, optionally substituted with one or more $R^3$ groups as defined herein.

In some embodiments of the compound of Formula I, G is 3- to 8-membered heterocyclyl, preferably 4- to 6-membered heterocyclyl, optionally substituted with one or more $R^3$ groups as defined herein, said heterocyclyl containing one, two or more heteroatoms selected from the group consisting of sulfur, oxygen, and nitrogen. In some embodiments, G is oxetanyl, tetrahydrofuranyl, tetrahydropyranyl, tetrahydrothiopyranyl or piperidinyl, optionally substituted with one or more $R^3$ groups as defined herein.

In some embodiments of the compound of Formula I, G is $C_{6-10}$ aryl optionally substituted with one or more $R^3$ groups as defined herein. In some embodiments, G is phenyl optionally substituted with one or more $R^3$ groups as defined herein.

In some embodiments of the compound of Formula I, G is a 5- to 6-membered heteroaryl optionally substituted with one or more $R^3$ groups as defined herein, said heteroaryl containing one, two or three heteroatoms selected from the group consisting of sulfur, oxygen and nitrogen.

In some embodiments of the compound of Formula I, G is $C_{1-6}$ alkyl, $C_{3-6}$ cycloalkyl, $C_{6-10}$ aryl or 4- to 6-membered heterocyclyl, preferably methyl, ethyl, propyl, isopropyl, butyl, cyclobutyl, cyclopentyl, cyclohexyl, oxetanyl, tetrahydrofuranyl, tetrahydropyranyl, piperidinyl, tetrahydrothiopyranyl or phenyl, optionally substituted with one or more $R^3$ groups as defined herein.

In some embodiments of the compound of Formula I, G is $C_{1-6}$ alkyl, $C_{3-6}$ cycloalkyl, or 4- to 6-membered heterocyclyl, preferably ethyl, propyl, isopropyl, butyl, cyclobutyl, cyclopentyl, cyclohexyl, oxetanyl, tetrahydrofuranyl, or tetrahydropyranyl, optionally substituted with one or more $R^3$ groups as defined herein.

In some embodiments of the compound of Formula I, each $R^3$ is independently hydroxy, oxo, alkyl, cycloalkyl, heterocyclyl, aryl, heteroaryl, hydroxyalkyl, alkyloxy, cycloalkyloxy, heterocyclyloxy, alkyloxyalkyl, alkylacylamino, alkylcarbonyl, cycloalkylcarbonyl, heterocyclylcarbonyl, or alkylaminoacyl, wherein said cycloalkyl, heterocyclyl, aryl, and heteroaryl, as an independent group or a part of a group, optionally substituted with one or more substituents independently selected from the group consisting of alkyl and oxo; and wherein said heterocyclyl and heteroaryl contain one, two or three heteroatoms selected from the group consisting of nitrogen, oxygen and sulfur.

In some embodiments of the compound of Formula I, each $R^3$ is independently hydroxyl, alkyl, heterocyclyl, hydroxyalkyl, or alkyloxy.

In some embodiments of the compound of Formula I, each $R^3$ is independently hydroxy, oxo, alkyl, heterocyclyl, heteroaryl, hydroxyalkyl, alkyloxy, alkylacylamino, alkylcarbonyl, or alkylaminoacyl, wherein said heterocyclyl and heteroaryl contain one, two or three heteroatoms selected from the group consisting of nitrogen, oxygen and sulfur and are optionally substituted with one or more substituents independently selected from the group consisting of alkyl and oxo.

In some embodiments of the compound of Formula I, each $R^3$ is independently hydroxy, oxo, $C_{1-6}$ alkyl, 5- to 6-membered heterocyclyl, 5- to 6-membered heteroaryl, hydroxy $C_{1-6}$ alkyl, $C_{1-6}$ alkyloxy, $C_{1-6}$ alkylacylamino, $C_{1-6}$ alkylcarbonyl, or $C_{1-6}$ alkylaminoacyl, wherein said 5- to 6-membered heterocyclyl and said 5- to 6-membered heteroaryl contain one, two or three heteroatoms selected from the group consisting of nitrogen, oxygen and sulfur, and are optionally substituted with one or more substituents independently selected from the group consisting of alkyl and oxo.

In some embodiments of the compound of Formula I, each $R^3$ is independently methyl, hydroxy, oxo, hydroxymethyl, methoxy, $CH_3NHC(=O)-$, $CH_3C(=O)NH-$, acetyl, tetrahydrofuranyl, piperidinyl, 1-methyl-piperidinyl, tetrahydropyranyl, morpholinyl, or pyridinyl.

In some embodiments of the compound of Formula I, G is selected from the group consisting of:

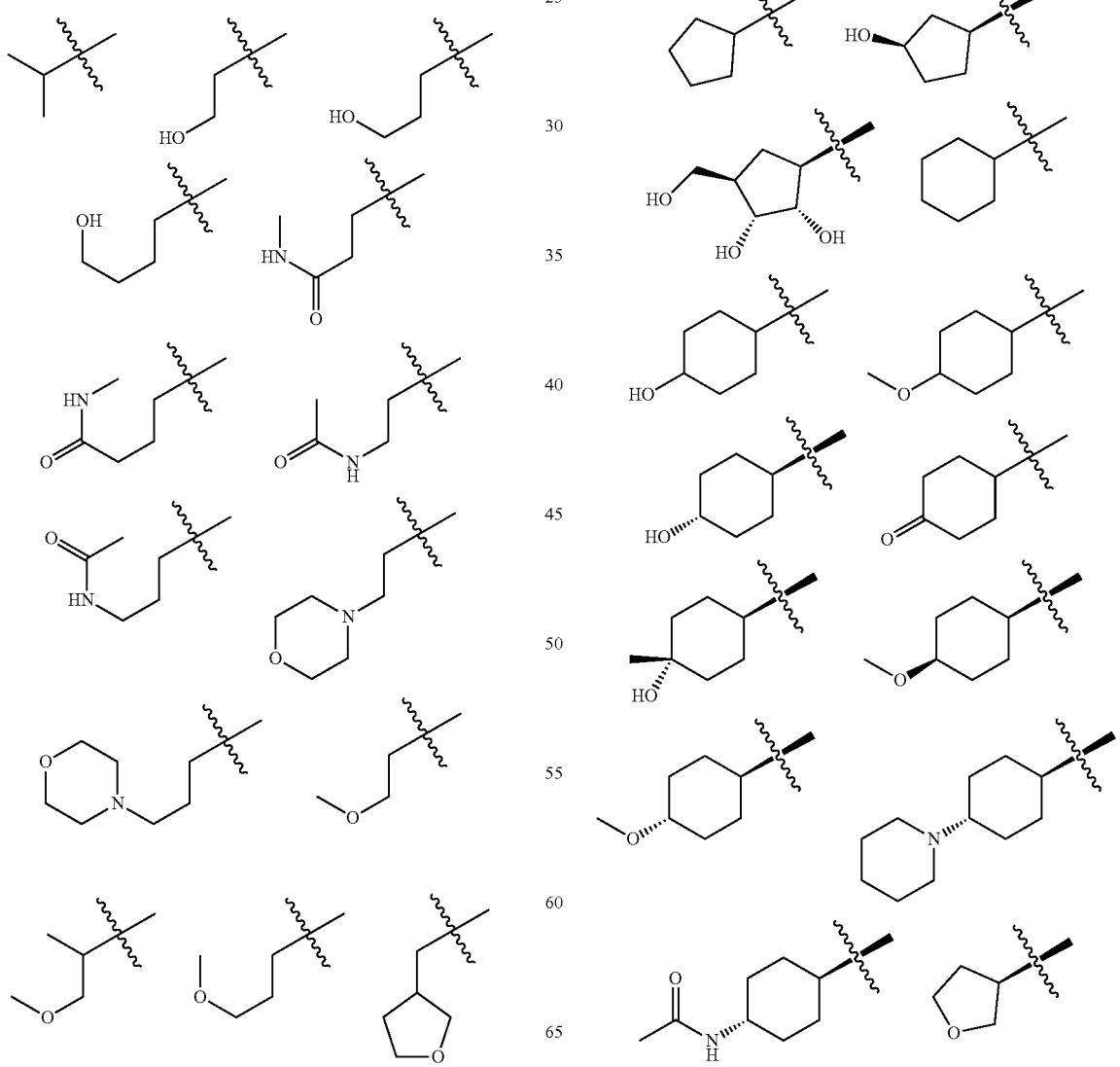

-continued

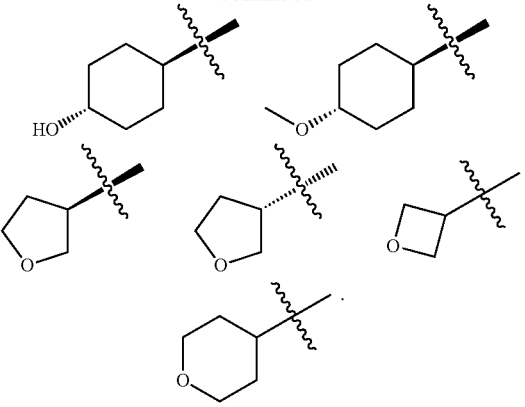

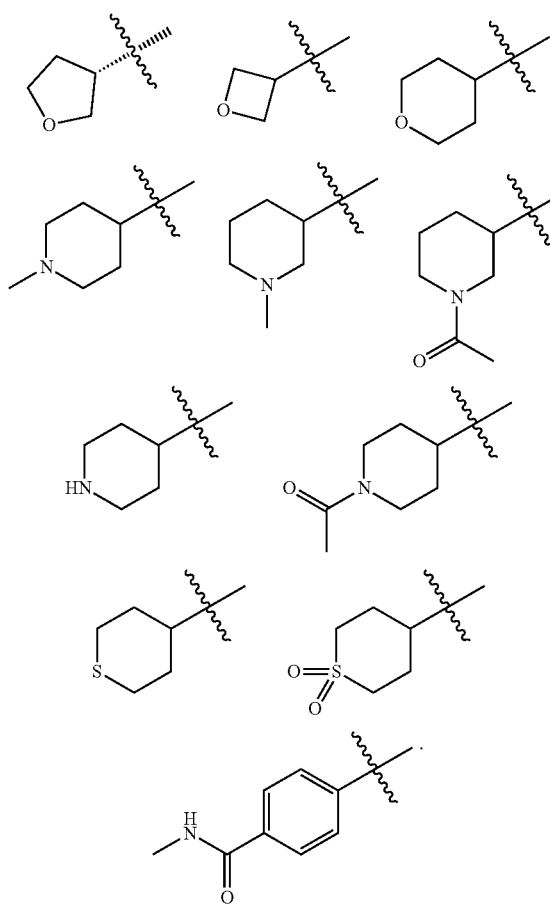

In some embodiments of the compound of Formula I, G is selected from the group consisting of:

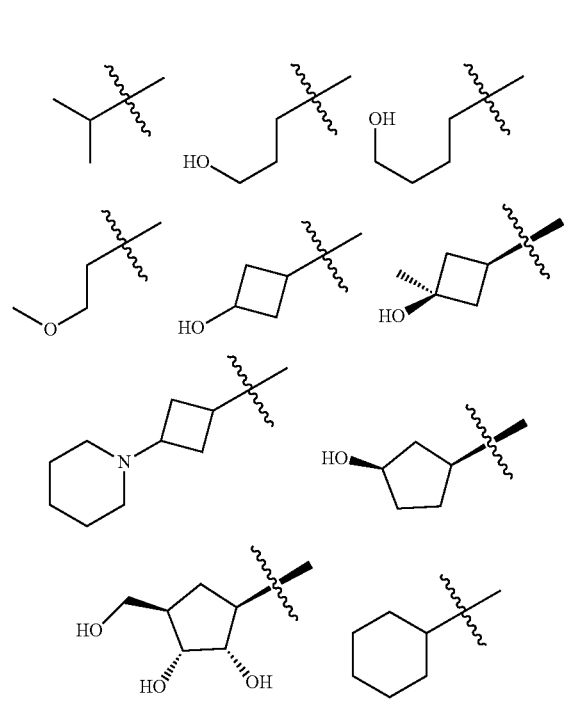

In some embodiments of the compound of Formula I, Z is aryl optionally substituted with one, two, or more $R^4$ groups as defined herein. In some embodiments of the compound of Formula I, Z is $C_{6-12}$ aryl optionally substituted with one, two, or more $R^4$ groups as defined herein. In some embodiments, Z is phenyl optionally substituted with one, two, or more $R^4$ groups as defined herein.

In some embodiments of the compound of Formula I, Z is heteroaryl, preferably 5- to 12-membered heteroaryl, more preferably 5- to 10-membered heteroaryl, optionally substituted with one, two, or more $R^4$ groups as defined herein, said heteroaryl containing one, two or three heteroatoms selected from the group consisting of nitrogen, oxygen and sulfur. In some embodiments, Z is 5- to 10-membered heteroaryl, preferably pyrrolyl, pyrazolyl, thienyl, thiazolyl, isothiazolyl, isoxazolyl, pyridinyl, benzothienyl, benzothiazolyl, indazolyl, 2,3-dihydro-1H-isoindol-4 or 5-yl

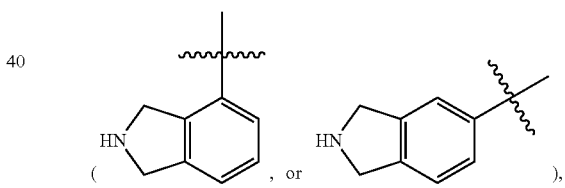

or 1,2,3,4-tetrahydro-pyrrolo[1,2-a]pyrazin-6,7, or 8-yl

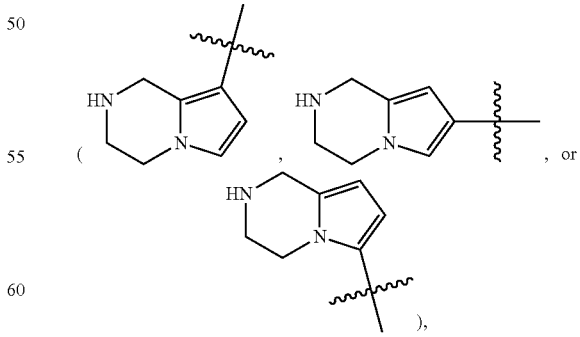

optionally substituted with one, two or more $R^4$ groups as defined herein.

In some embodiments of the compound of Formula I, Z is 5- to 10-membered heteroaryl, preferably pyrrolyl, pyrazolyl, thienyl, isothiazolyl, isoxazolyl, benzothiazolyl, indazolyl, 2,3-dihydro-1H-isoindol-5-yl

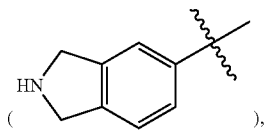

or 1,2,3,4-tetrahydro-pyrrolo [1,2-a]pyrazin-7-yl

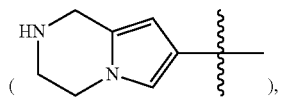

optionally substituted with one, two, or more $R^4$ groups as defined herein.

In some embodiments of the compound of Formula I, Z is 5- to 10-membered heteroaryl, preferably pyrrolyl, pyrazolyl, thienyl, isothiazolyl, indazolyl, or 2,3-dihydro-1H-isoindol-5-yl, optionally substituted with one, two, or more $R^4$ groups as defined herein.

In some embodiments of the compound of Formula I, each $R^4$ is independently alkyl, cyano, cycloalkyl, heterocyclyl, aryl, heteroaryl, oxo, haloalkyl, hydroxyalkyl, alkyloxyalkyl, heterocyclylalkyl, heterocyclylcarbonyl, or $R^{4a}R^{4b}NC(=O)$—; each of $R^{4a}$ and $R^{4b}$ is independently hydrogen, alkyl, haloalkyl, cycloalkyl, hydroxyalkyl, alkyloxyalkyl, heterocyclylalkyl, heteroarylalkyl, heterocyclyl, aryl, or heteroaryl; wherein said cycloalkyl, heterocyclyl, aryl, and heteroaryl, as an independent group or a part of a group, are optionally substituted with one or more substituents independently selected from the group consisting of oxo and alkyl, and wherein said heterocyclyl and heteroaryl contain one, two or three heteroatoms selected from the group consisting of nitrogen, oxygen and sulfur.

In some embodiments of the compound of Formula I, each $R^4$ is independently alkyl, oxo, cyano, cycloalkyl, heterocyclyl, aryl, heteroaryl, haloalkyl, hydroxyalkyl, heterocyclylcarbonyl, or $R^{4a}R^{4b}NC(=O)$—; each of $R^{4a}$ and $R^{4b}$ is independently hydrogen, alkyl, haloalkyl, cycloalkyl, alkyloxyalkyl, heterocyclylalkyl, heteroarylalkyl, or heterocyclyl; wherein said cycloalkyl, heterocyclyl, aryl, and heteroaryl, as an independent group or a part of a group, are optionally substituted with one or more substituents independently selected from the group consisting of alkyl and oxo, and wherein said heterocyclyl and said heteroaryl contain one, two or three heteroatoms selected from the group consisting of nitrogen, oxygen and sulfur.

In some embodiments of the compound of Formula I, each $R^4$ is independently alkyl, oxo, heterocyclyl, heteroaryl, haloalkyl, hydroxyalkyl, heterocyclylcarbonyl, or $R^{4a}R^{4b}NC(=O)$—; each $R^{4a}$ and $R^{4b}$ is independently hydrogen, alkyl, haloalkyl, cycloalkyl, alkyloxyalkyl, heterocyclylalkyl, heteroarylalkyl, or heterocyclyl; wherein said heterocyclyl, as an independent group or a part of a group, is optionally substituted with one or more substituents independently selected from the group consisting of oxo and alk, and wherein said heterocyclyl and heteroaryl contain one, two or three heteroatoms selected from the group consisting of nitrogen, oxygen and sulfur.

In some embodiments of the compound of Formula I, each $R^4$ is independently $C_{1-6}$ alkyl, oxo, cyano, $C_{3-6}$ cycloalkyl, 5- to 6-membered heterocyclyl, $C_{6-10}$ aryl, 5- to 6-membered heteroaryl, halo $C_{1-6}$ alkyl, hydroxyl $C_{1-6}$ alkyl, 5- to 6-membered heterocyclylcarbonyl, or $R^{4a}R^{4b}NC(=O)$—; each of $R^{4a}$ and $R^{4b}$ is independently hydrogen, $C_{1-6}$ alkyl, halo $C_{1-6}$ alkyl, $C_{3-6}$ cycloalkyl, $C_{1-6}$ alkyloxy $C_{1-6}$ alkyl, 5- to 6-membered heterocyclyl $C_{1-6}$ alkyl, 5- to 6-membered heteroaryl $C_{1-6}$ alkyl, or 5- to 6-membered heterocyclyl; wherein said $C_{3-6}$ cycloalkyl, 5- to 6-membered heterocyclyl, $C_{6-10}$ aryl, and 5- to 6-membered heteroaryl, as an independent group or a part of a group, are optionally substituted with one or more substituents independently selected from the group consisting of oxo and $C_{1-6}$ alkyl, and wherein said heterocyclyl and heteroaryl contain one, two or three heteroatoms selected from the group consisting of nitrogen, oxygen and sulfur.

In some embodiments of the compound of Formula I, each $R^4$ is independently $C_{1-6}$ alkyl, oxo, 5- to 6-membered heterocyclyl, 5- to 6-membered heteroaryl, halo $C_{1-6}$ alkyl, hydroxyl $C_{1-6}$ alkyl, 5- to 6-membered heterocyclylcarbonyl, or $R^{4a}R^{4b}NC(=O)$—; each of $R^{4a}$ and $R^{4b}$ is independently hydrogen, $C_{1-6}$ alkyl, halo $C_{1-6}$ alkyl, $C_{3-6}$ cycloalkyl, $C_{1-6}$ alkyloxy $C_{1-6}$ alkyl, 5- to 6-membered heterocyclyl $C_{1-6}$ alkyl, 5- to 6-membered heteroaryl $C_{1-6}$ alkyl, or 5- to 6-membered heterocyclyl; wherein said 5- to 6-membered heterocyclyl, as an independent group or a part of a group, is optionally substituted with one or more substituents independently selected from the group consisting of oxo and $C_{1-6}$ alkyl, and wherein said heterocyclyl and heteroaryl contain one, two or three heteroatoms selected from the group consisting of nitrogen, oxygen and sulfur.

In some embodiments of the compound of Formula I, each $R^4$ is independently oxo, cyano, methyl, 2-fluoroethyl, 2-hydroxyethyl, cyclohexyl, tetrahydropyranyl, 1-methylpiperidinyl, morpholinyl, 4-acetylmorpholinyl, phenyl, pyridinyl, $NH_2$—C(=O)—, $CH_3$—NH—C(=O)—, $C_2H_5$—NH—C(=O)—, $C_3H_6$—NH—C(=O)—, $(CH_3)_2C$—NH—C(=O)—, $(CH_3)_2N$—C(=O)—, $CH_2FCH_2$—NH—C(=O)—, $CHF_2CH_2$—NH—C(=O)—, $CF_3CH_2$—NH—C(=O)—, $CH_3OC_2H_4$—NH—C(=O)—, tetrahydropyran-4-yl-$CH_2$—NH—C(=O)—, 1-methyl-piperidin-4-yl-$CH_2$—NH—C(=O)—, thiophen-2-yl-$CH_2$—NH—C(=O)—, cyclopropyl-NH—C(=O)—, cyclohexyl-NH—C(=O)—, tetrahydrofuran-3-yl-NH—C(=O)—, 1-methyl-piperazin-4-yl-NH—C(=O)—, tetrahydropyran-4-yl-NH—C(=O)—, piperidin-1-ylcarbonyl, 4-methyl-piperazin-1-ylcarbonyl, morpholin-4-ylcarbonyl, thiomorpholin-4-ylcarbonyl, or 1,1-dioxothiomorpholin-4-ylcarbonyl.

In some embodiments of the compound of Formula I, Z is selected from the group consisting of:

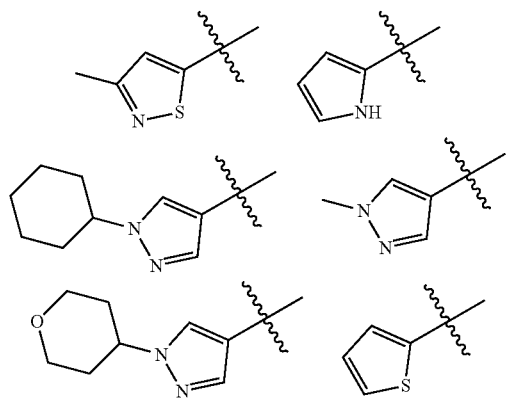

-continued
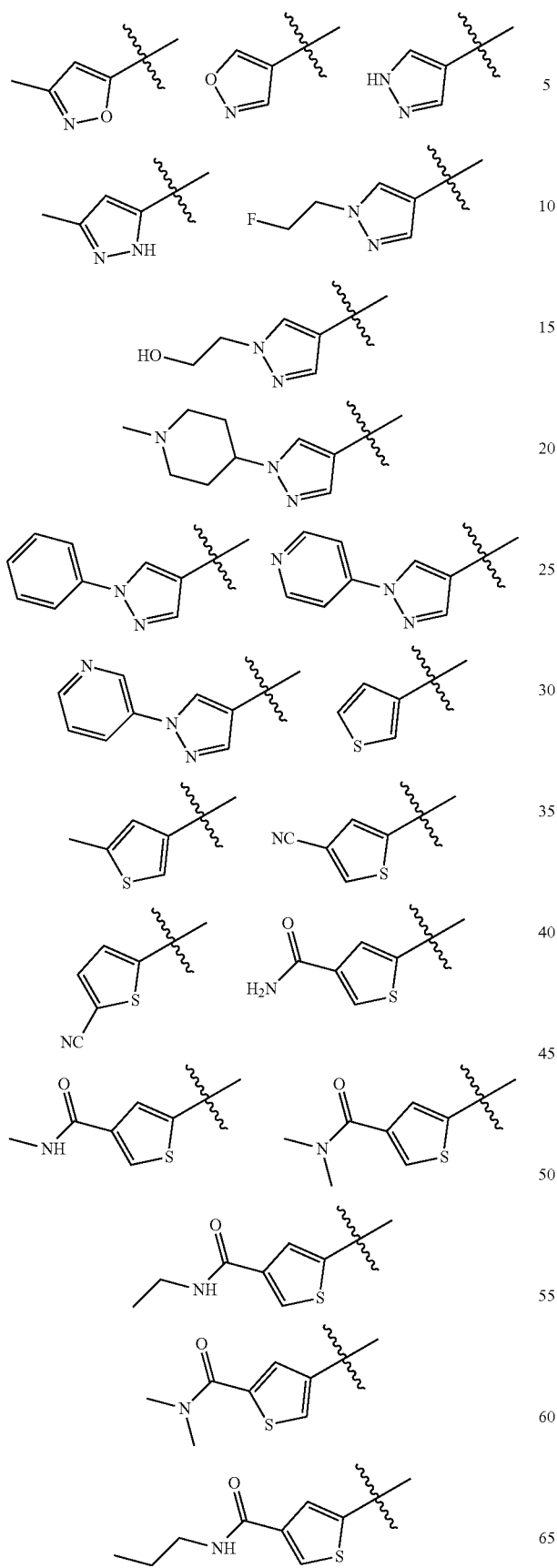
-continued
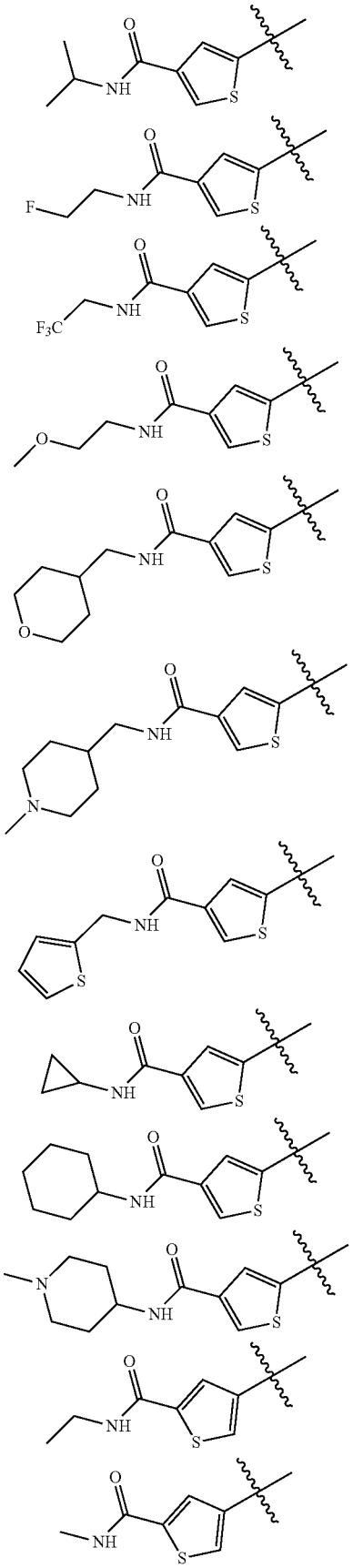

-continued
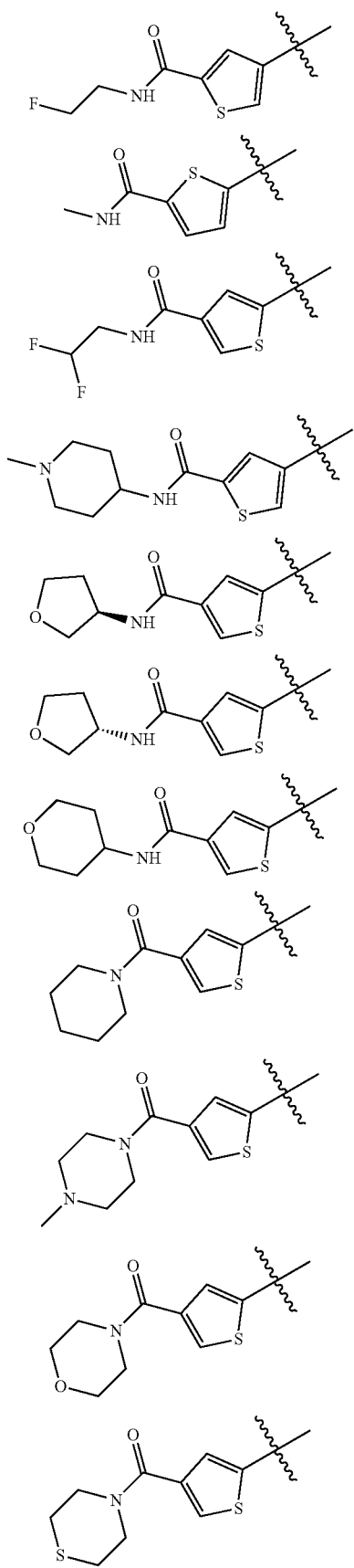
-continued
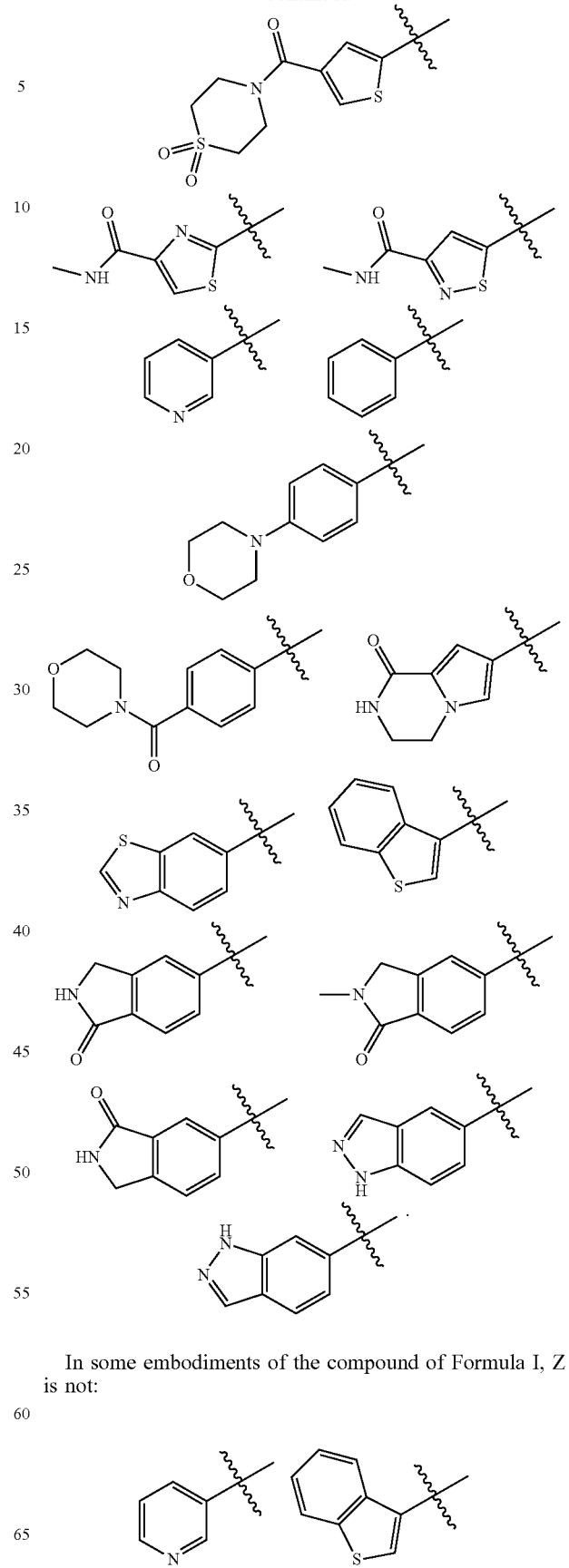
In some embodiments of the compound of Formula I, Z is not:

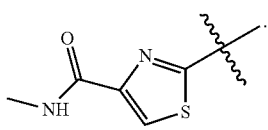
In some embodiments of the compound of Formula I, Z is selected from the group consisting of:
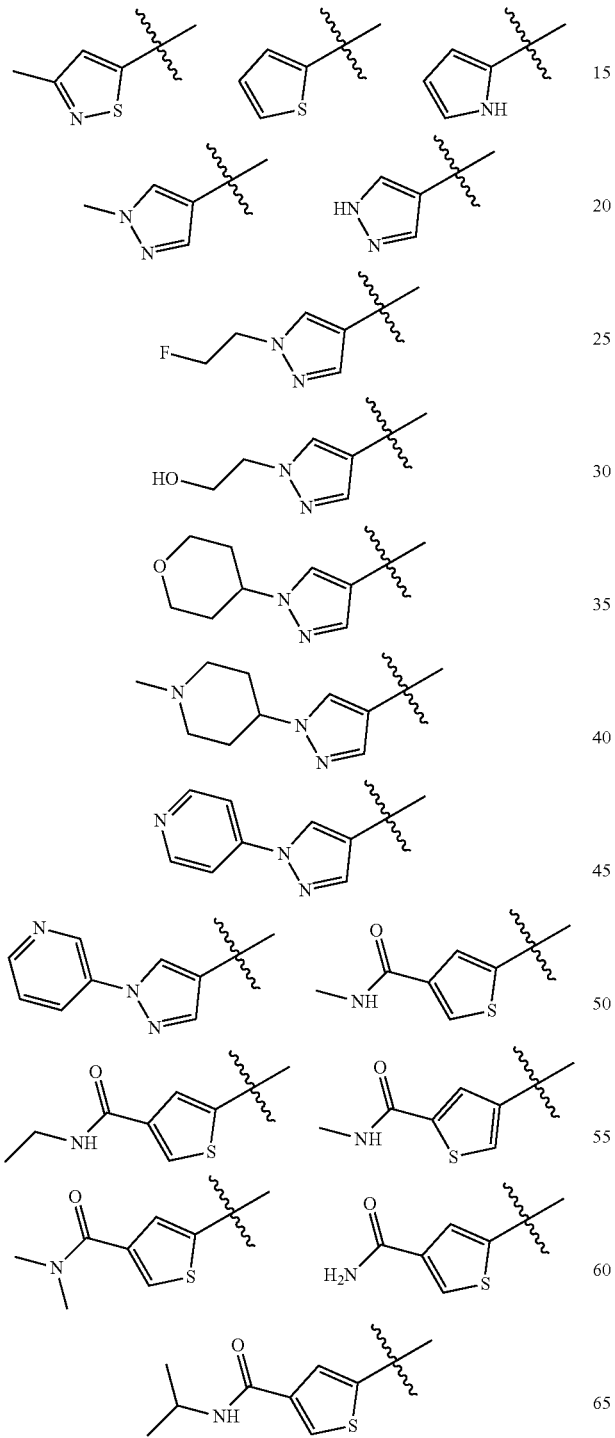
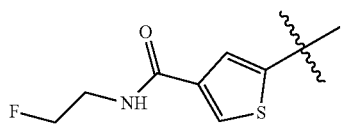
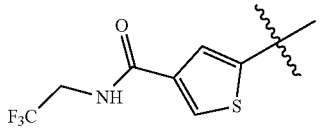
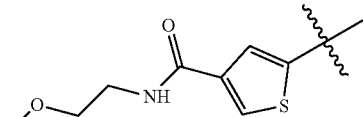
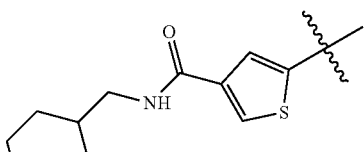
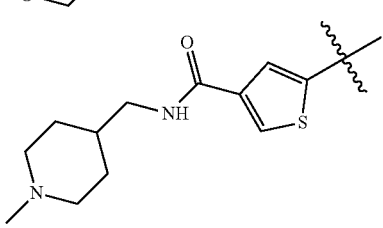
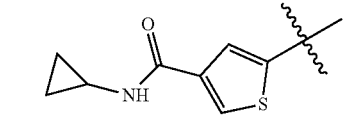
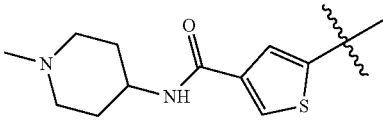
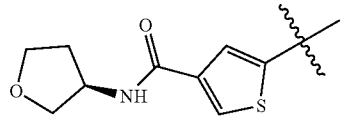
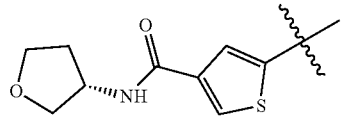
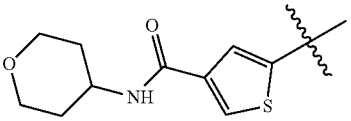
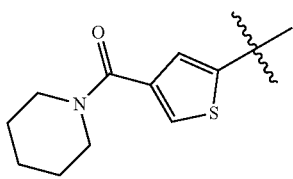

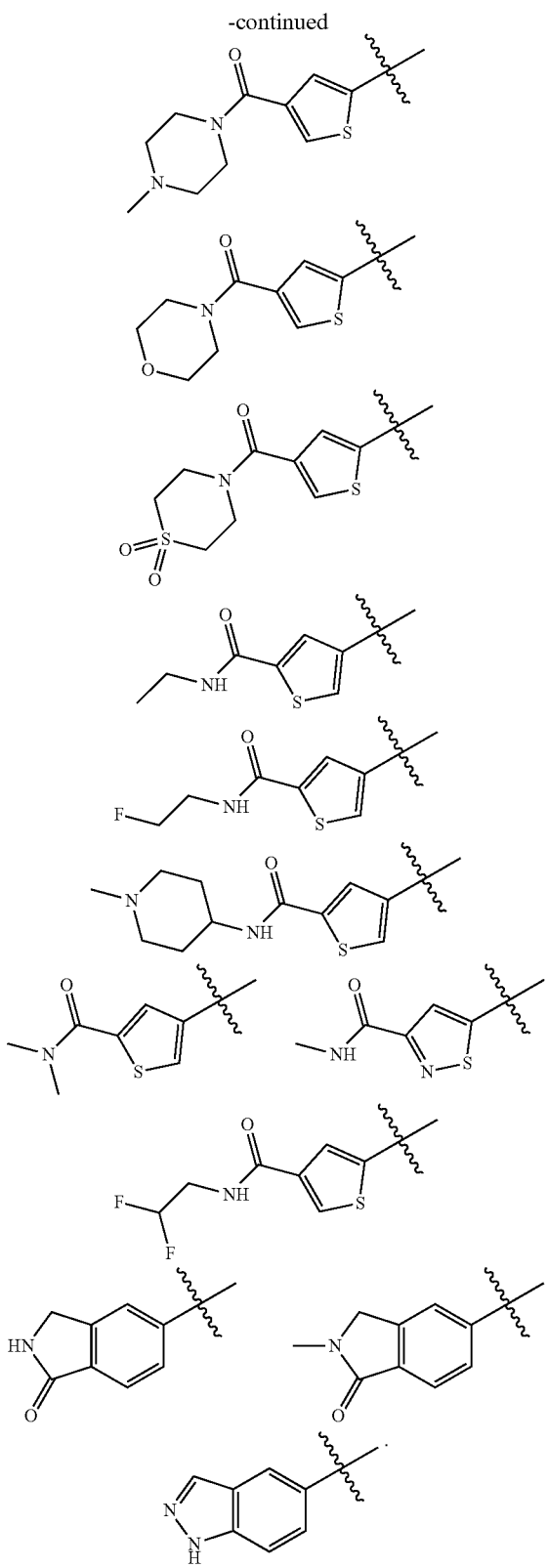

In some embodiments of the compound of Formula I, A is phenyl or 5- to 10-membered heteroaryl, optionally substituted with one or more $R^1$ groups; L is O or $NR^2$; G is alkyl, cycloalkyl, heterocyclyl, or aryl, optionally substituted with one or more $R^3$ groups; Z is phenyl or 5- to 10-membered heteroaryl, optionally substituted with one or more $R^4$ groups; each $R^1$ is independently halogen, hydroxy, alkyl, haloalkyl, heterocyclyl, alkyloxyalkyl, alkyloxy, amino, dialkylamino, carboxy, or alkylsulfonyl; $R^2$ is hydrogen or alkyl; each $R^3$ is independently hydroxy, oxo, alkyl, heterocyclyl, heteroaryl, hydroxyalkyl, alkyloxy, alkylacylamino, alkylcarbonyl, or alkylaminoacyl; each $R^4$ is independently alkyl, oxo, cyano, cycloalkyl, heterocyclyl, aryl, heteroaryl, haloalkyl, hydroxyalkyl, heterocyclylcarbonyl, or $R^{4a}R^{4b}NC(=O)-$; each of $R^{4a}$ and $R^{4b}$ is hydrogen, alkyl, haloalkyl, cycloalkyl, alkyloxyalkyl, heterocyclylalkyl, heteroarylalkyl or heterocyclyl; wherein said heterocyclyl in $R^4$, $R^{4a}$, and $R^{4b}$, as an independent group or a part of a group, is optionally substituted with one or more substituents independently selected from the group consisting of alkyl and oxo; and wherein said heterocyclyl and said heteroaryl contain one or more heteroatoms selected from the group consisting of nitrogen, oxygen and sulfur.

In some embodiments of the compound of Formula I, A is $C_{6-10}$ aryl or 5- to 10-membered heteroaryl, preferably phenyl, pyrazolyl, pyridinyl, pyrrolyl, furanyl, thienyl, pyridazinyl, pyrimidinyl, benzo[1,3]dioxol-5-yl, or 2,3-dihydro-benzo[1,4]dioxin-5-yl, optionally substituted with one or more $R^1$ groups; L is O or $NR^2$; G is alkyl, cycloalkyl, heterocyclyl, or aryl, optionally substituted with one or more $R^3$ groups; Z is $C_{6-10}$ aryl or 5- to 10-membered heteroaryl, preferably phenyl, pyrrolyl, isothiazolyl, isooxazolyl, pyrazolyl, thienyl, indazolyl, 2,3-dihydro-1H-isoindol-5-yl, benzothiazolyl, or 1,2,3,4-tetrahydro-pyrrolo[1,2-a]pyrazine-7-yl, optionally substituted with one or more $R^4$ groups; each $R^1$ is independently halogen, hydroxy, alkyl, haloalkyl, heterocyclyl, alkyloxyalkyl, or alkyloxy; $R^2$ is hydrogen or alkyl; each $R^3$ is independently hydroxy, oxo, alkyl, heterocyclyl, heteroaryl, hydroxyalkyl, alkyloxy, alkylacylamino, alkylcarbonyl, or alkylaminoacyl; each $R^4$ is independently alkyl, oxo, cyano, cycloalkyl, heterocyclyl, aryl, heteroaryl, haloalkyl, hydroxyalkyl, heterocyclylcarbonyl, or $R^{4a}R^{4b}NC(=O)-$; each of $R^{4a}$ and $R^{4b}$ is independently hydrogen, alkyl, haloalkyl, cycloalkyl, alkyloxyalkyl, heterocyclylalkyl, heteroarylalkyl, or heterocyclyl; wherein said heterocyclyl in $R^4$, $R^{4a}$ and $R^{4b}$, as an independent group or a part of a group, is optionally substituted with one or more substituents independently selected from the group consisting of alkyl and oxo; and wherein said heterocyclyl and said heteroaryl contain one or more heteroatoms selected from the group consisting of nitrogen, oxygen and sulfur.

In some embodiments of the compound of Formula I, A is $C_{6-10}$ aryl or 5- to 6-membered heteroaryl, preferably phenyl, pyrazolyl, furanyl, or pyridinyl, optionally substituted with one or more $R^1$ groups; L is O or $NR^2$; G is alkyl, cycloalkyl, or heterocyclyl, optionally substituted with one or more $R^3$ groups; Z is 5-10 membered heteroaryl, preferably pyrrolyl, pyrazolyl, thienyl, isothiazolyl, indazolyl, or 2,3-dihydro-1H-isoindol-5-yl, optionally substituted with one or more $R^4$ groups; Each $R^1$ is independently alkyl; $R^2$ is hydrogen; each $R^3$ is independently hydroxy, alkyl, heterocyclyl, hydroxyalkyl, or alkyloxy; each $R^4$ is independently alkyl, oxo, heterocyclyl, aryl, heteroaryl, haloalkyl, hydroxyalkyl, heterocyclylcarbonyl, or $R^{4a}R^{4b}NC(=O)-$; each of $R^{4a}$ and $R^{4b}$ is independently hydrogen, alkyl, haloalkyl, cycloalkyl, alkyloxyalkyl, heterocyclylalkyl, or heterocyclyl; wherein said heterocyclyl in $R^4$, $R^{4a}$ and $R^{4b}$, as an independent group or a part of a group, is optionally substituted with one or more substituents independently selected from the group consisting of alkyl and oxo; and wherein said heterocyclic and said heteroaryl contains one or two heteroatoms selected from the group consisting of nitrogen, oxygen and sulfur.
In some embodiments, the compound of Formula I according to the invention is selected from the group consisting of:
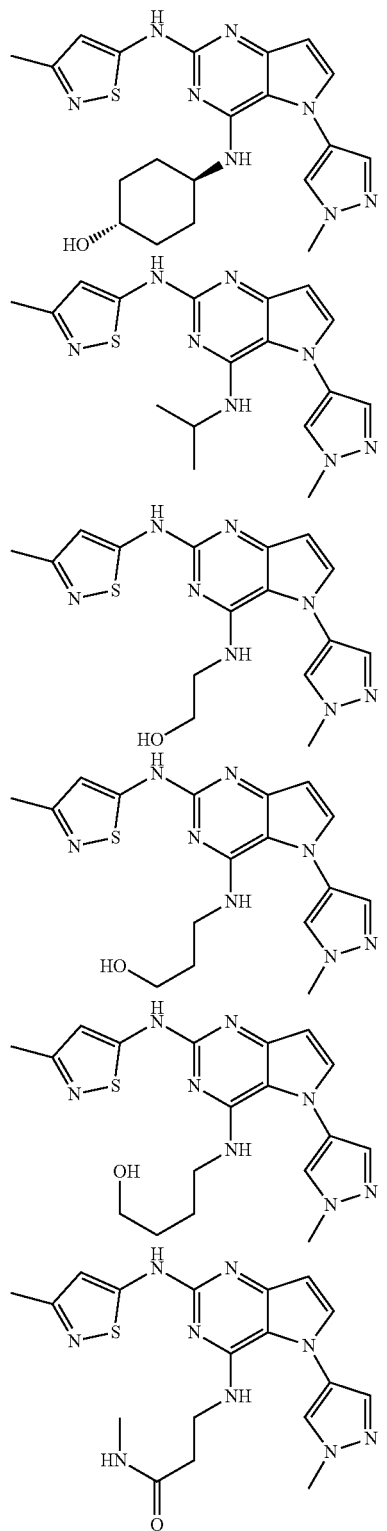
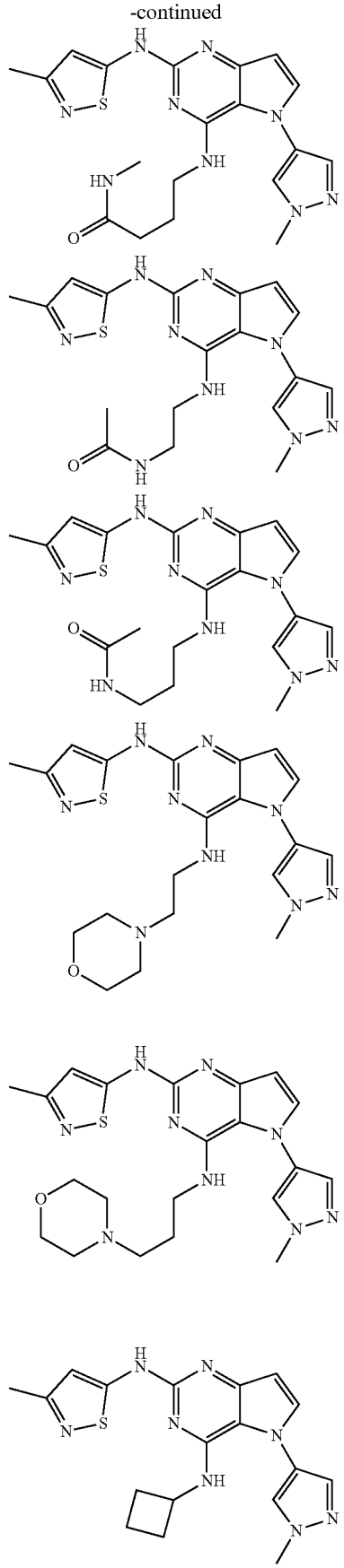

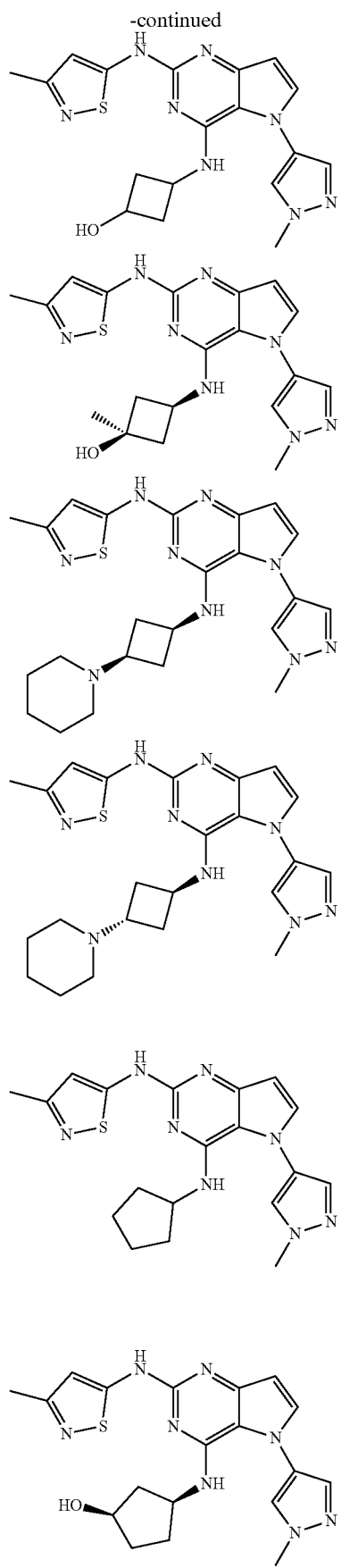
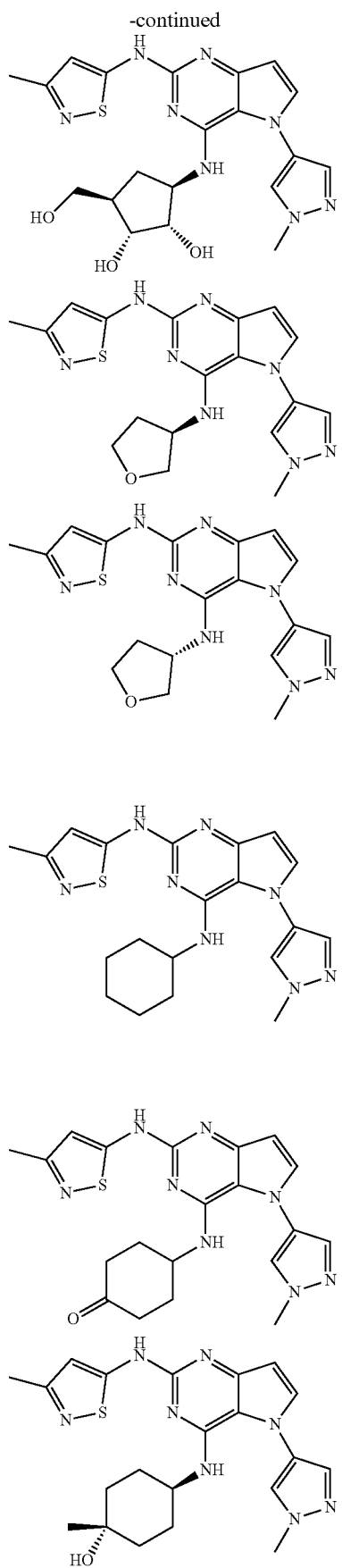

35
-continued
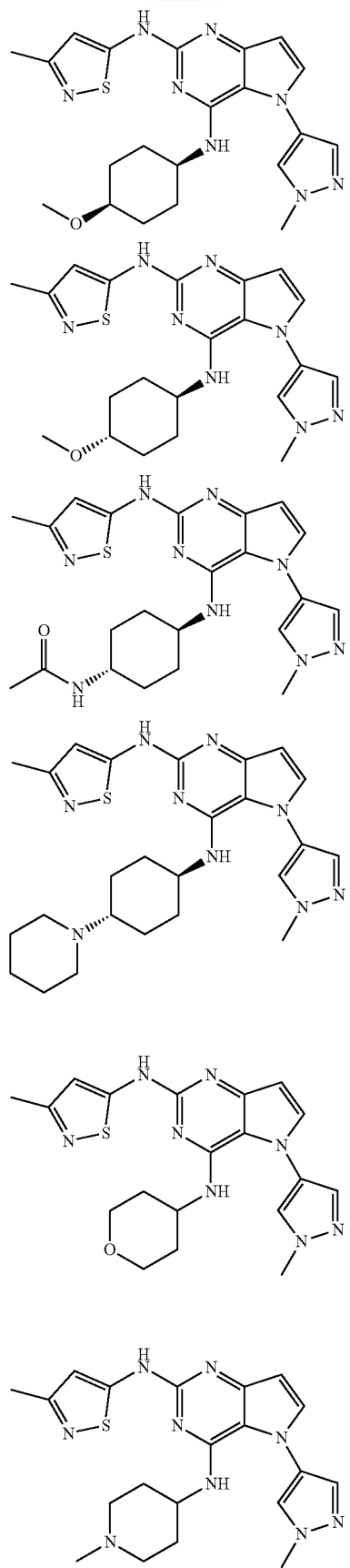
36
-continued
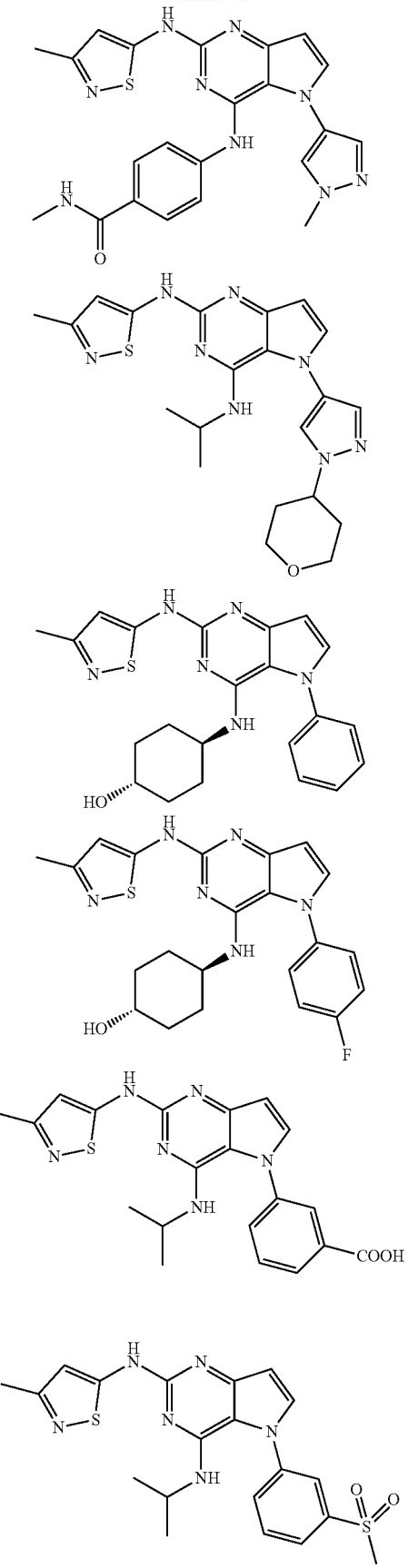

-continued
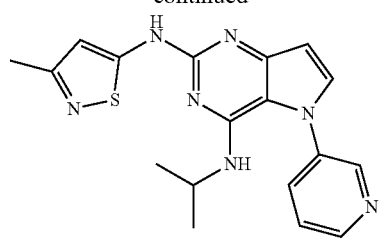
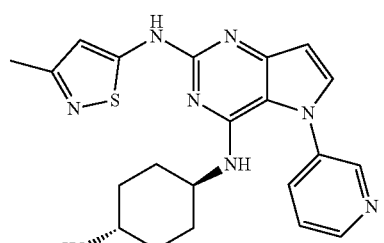
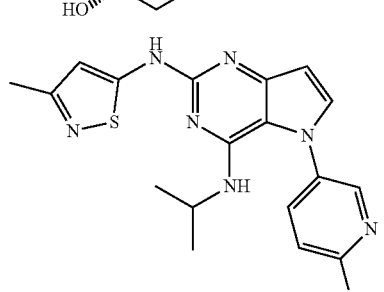
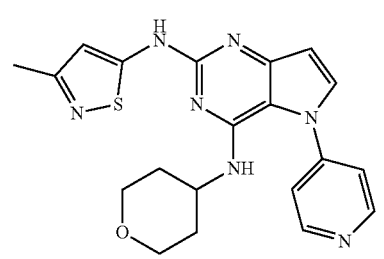
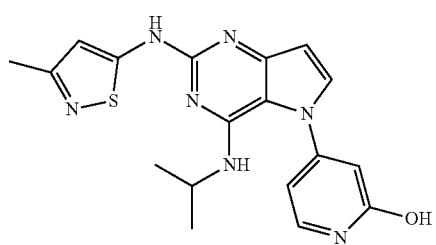
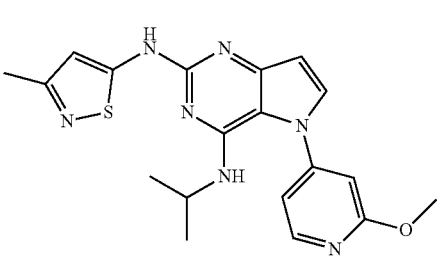
-continued
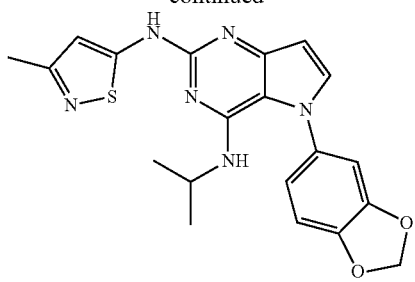
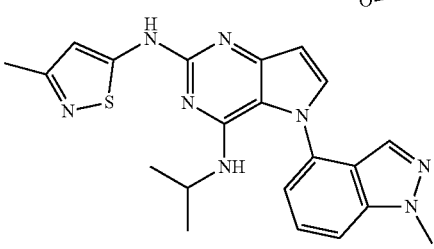
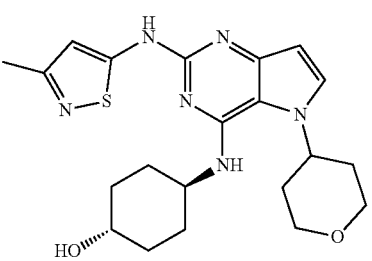
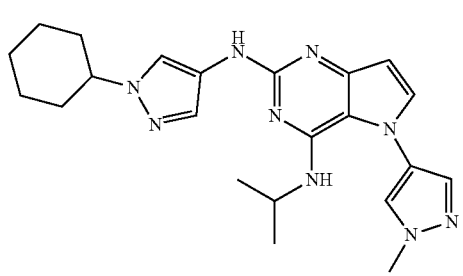
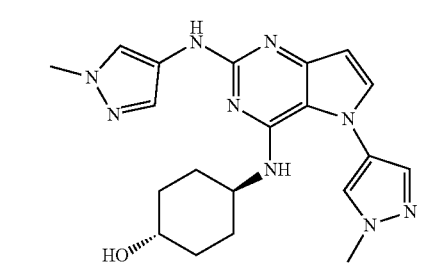
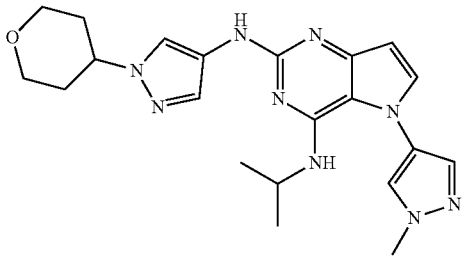

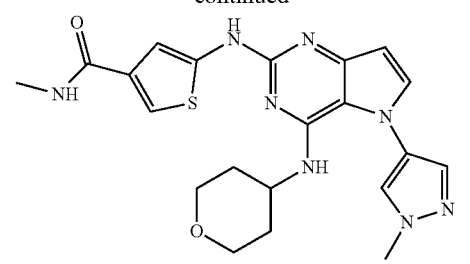
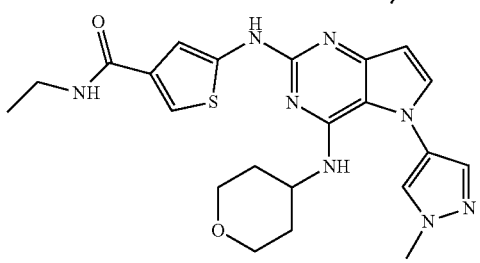
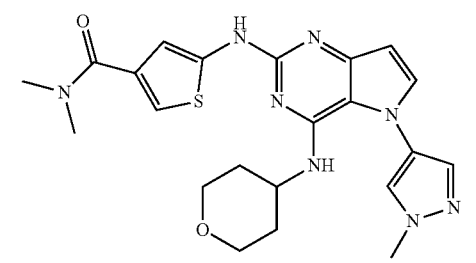
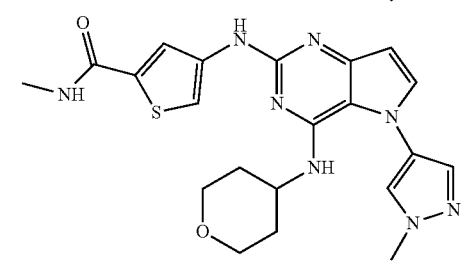
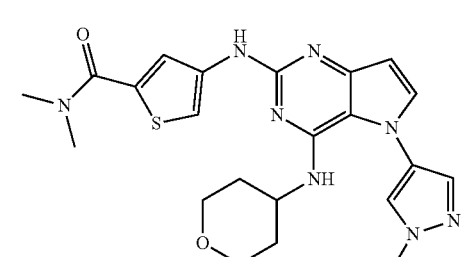
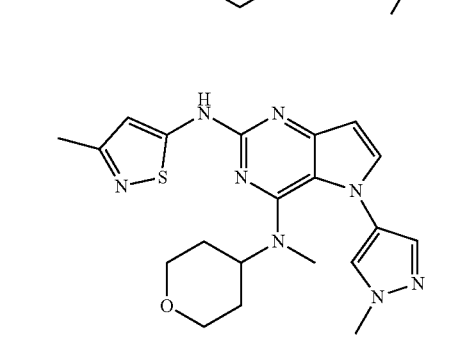
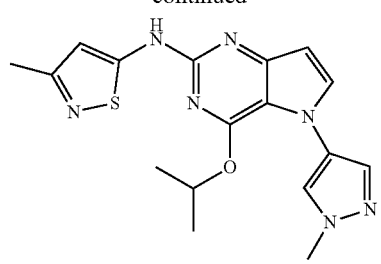
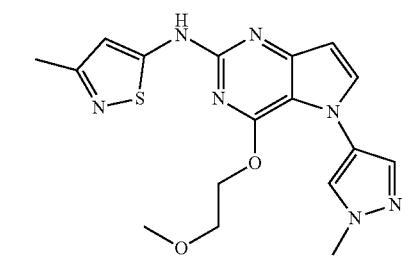
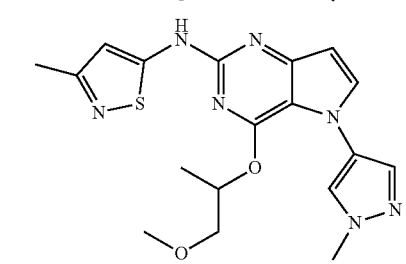
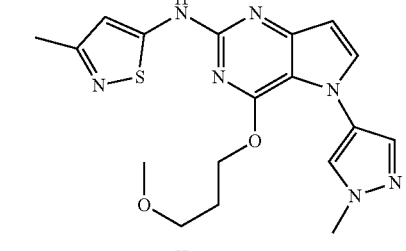
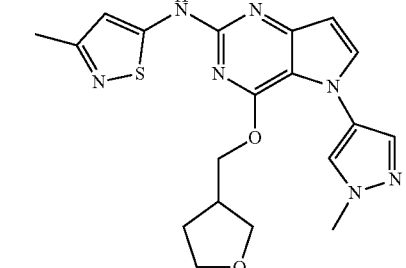
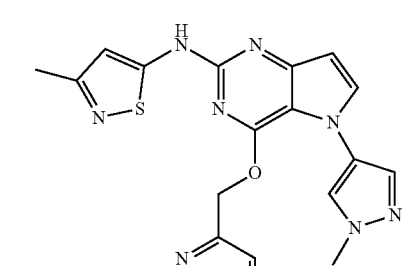

41
-continued
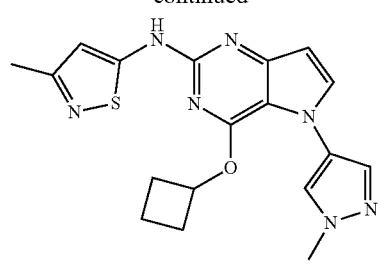
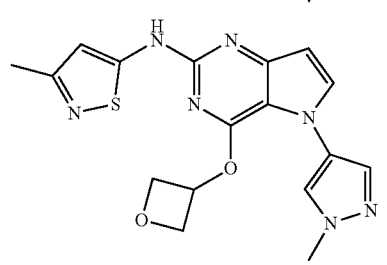
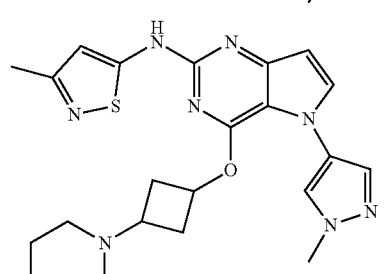
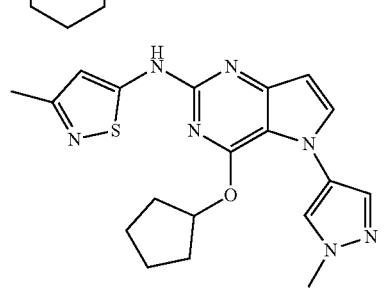
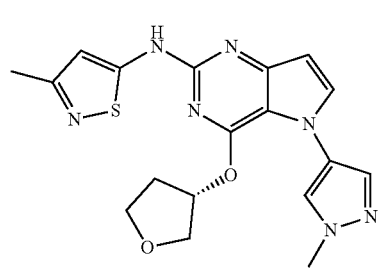
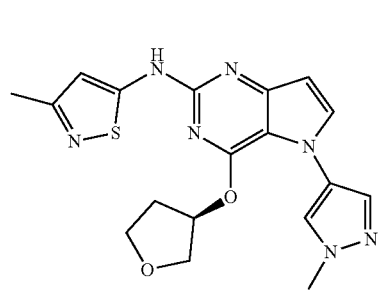
42
-continued
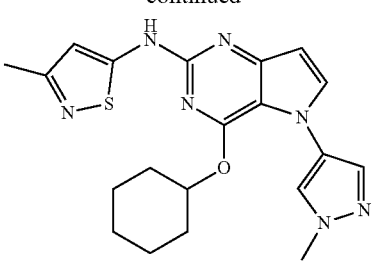
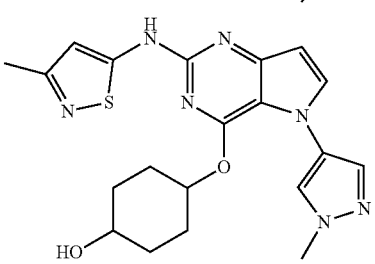
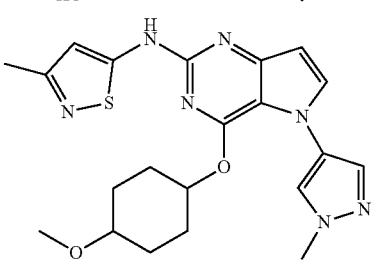
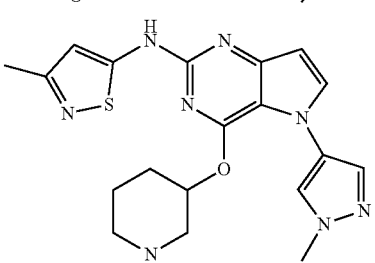
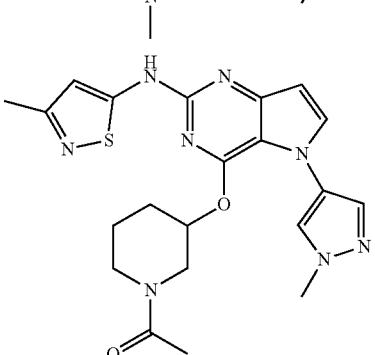
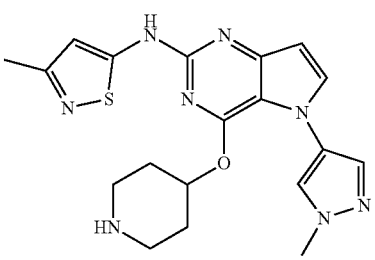

43
-continued
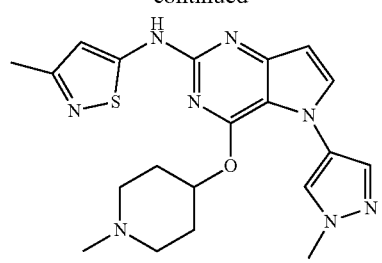
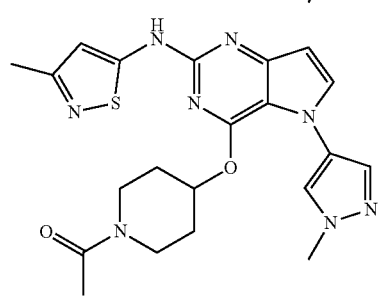
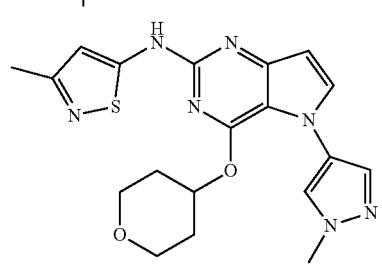
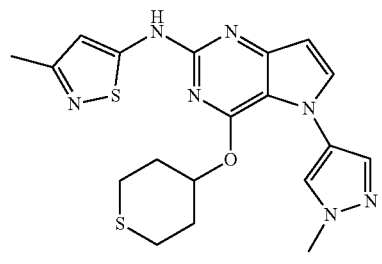
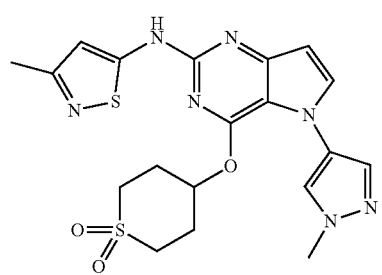
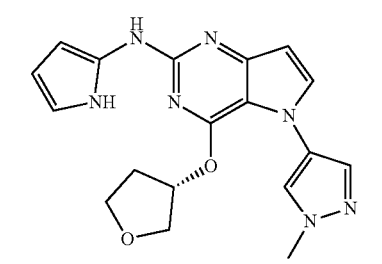
44
-continued
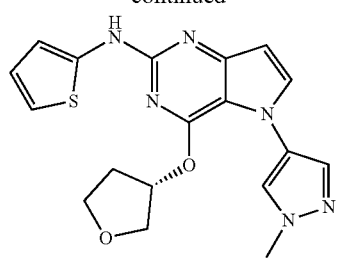
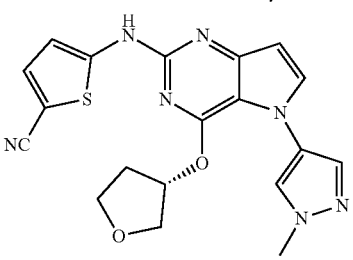
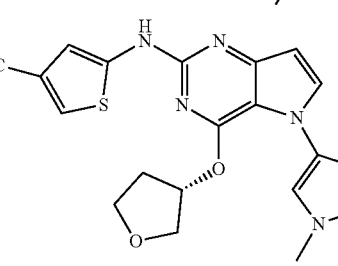
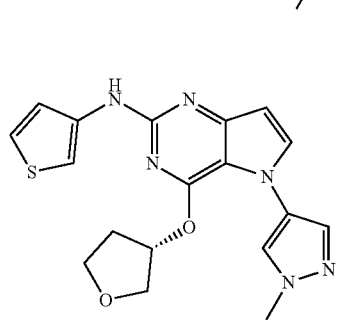
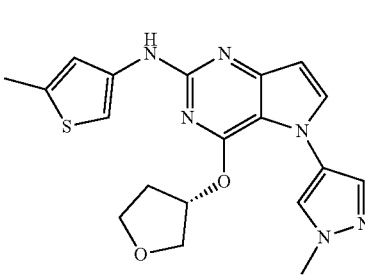
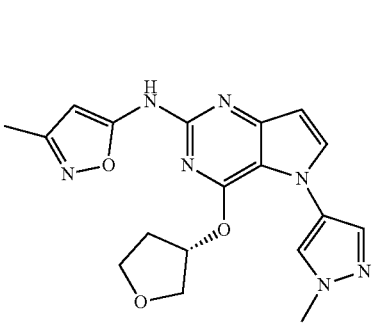

45
-continued
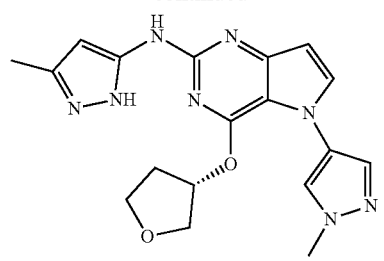
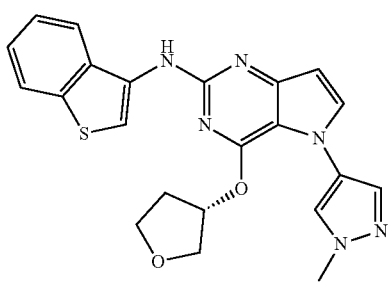
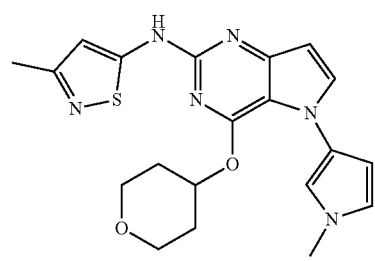
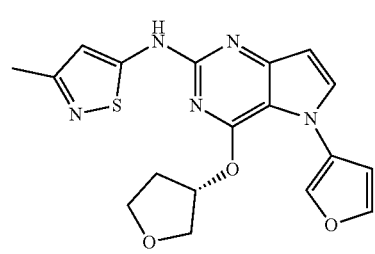
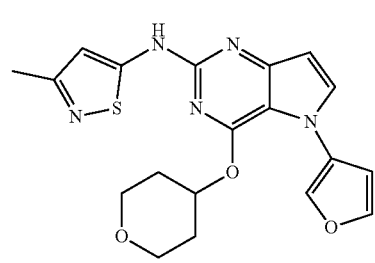
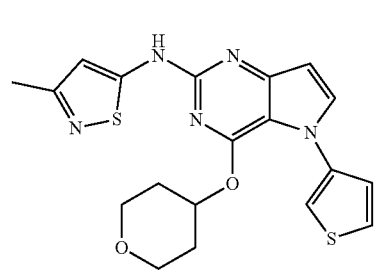
46
-continued
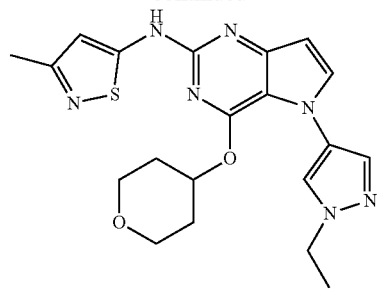
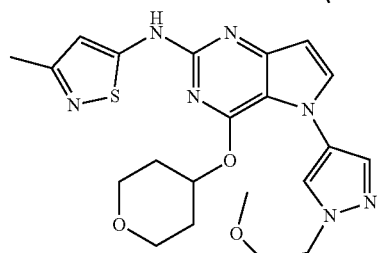
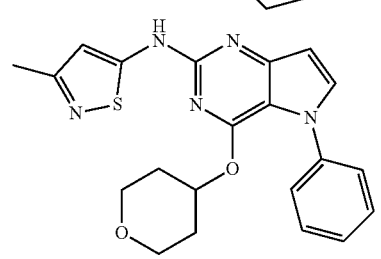
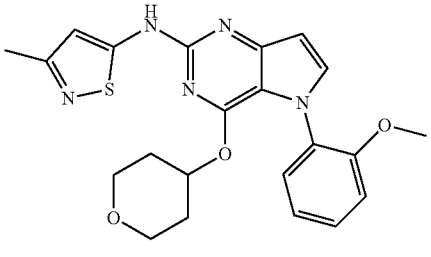
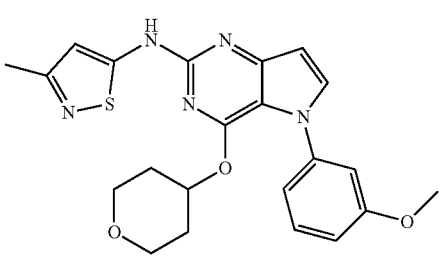
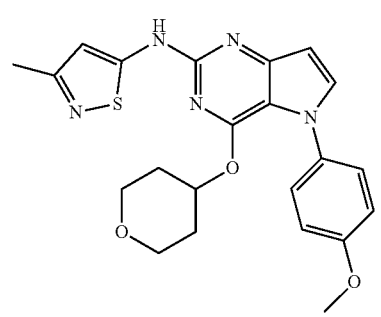

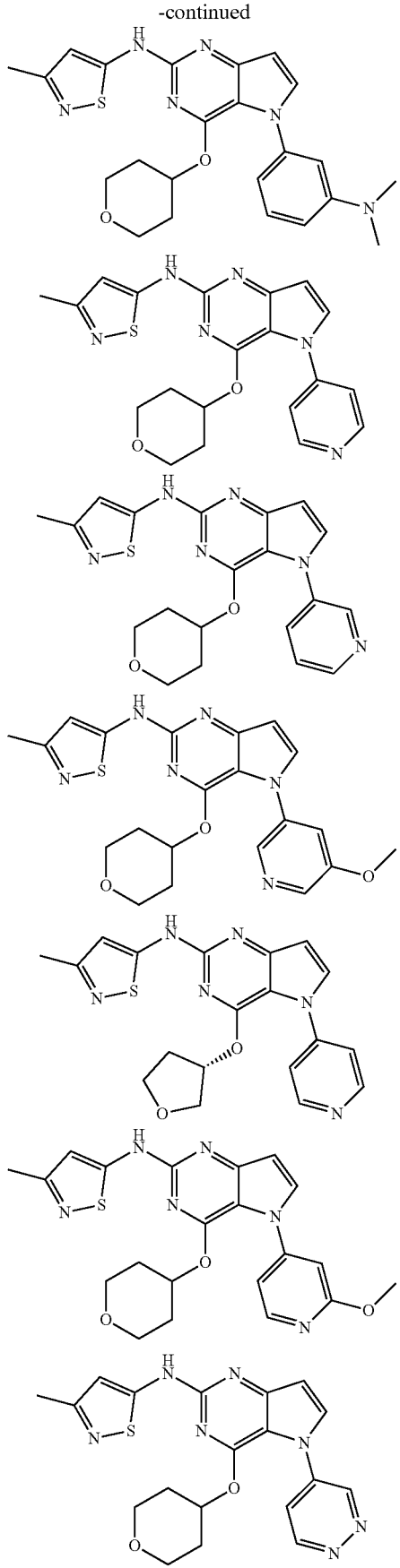
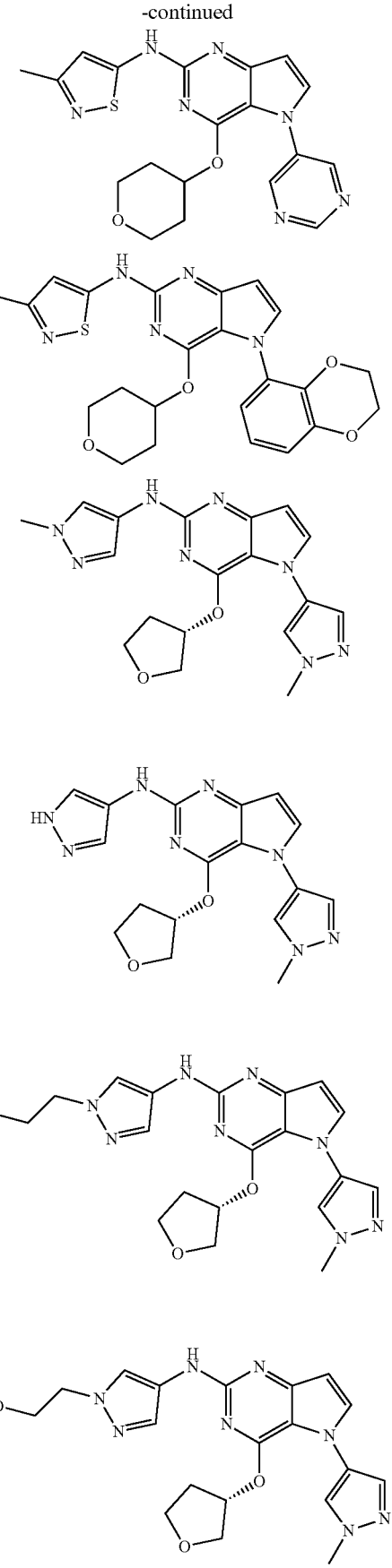

-continued
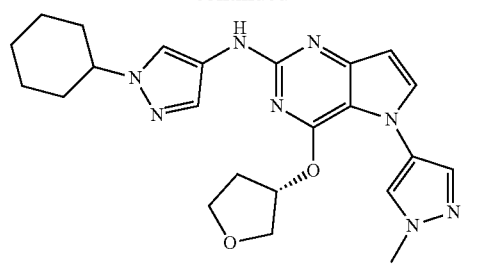
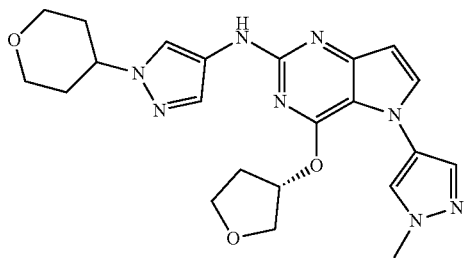
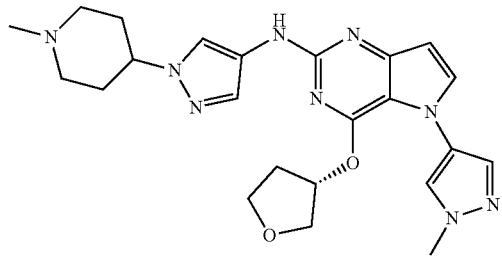
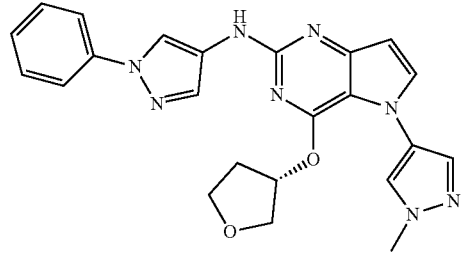
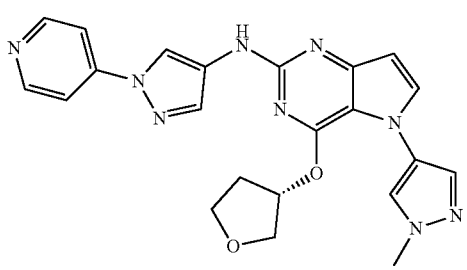
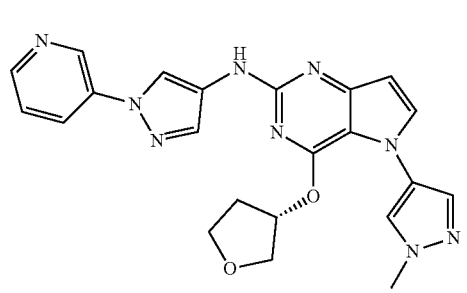
-continued
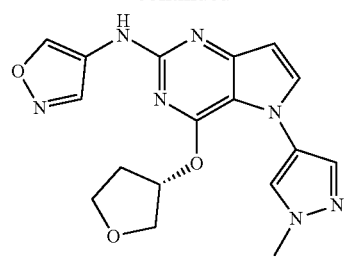
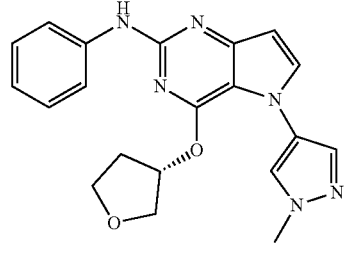
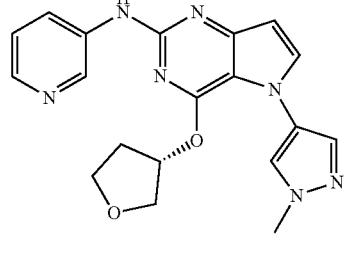
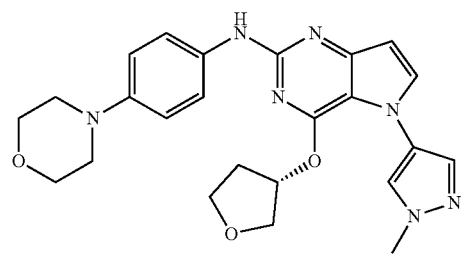
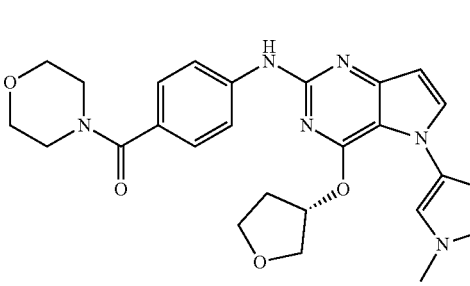
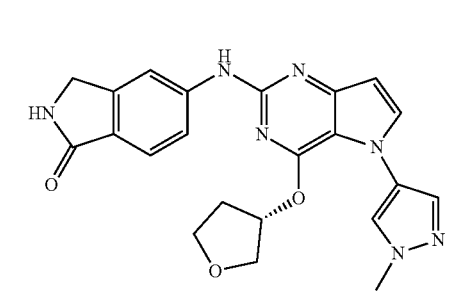

51
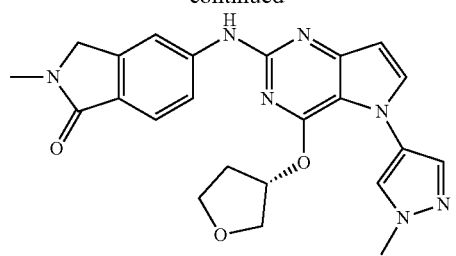
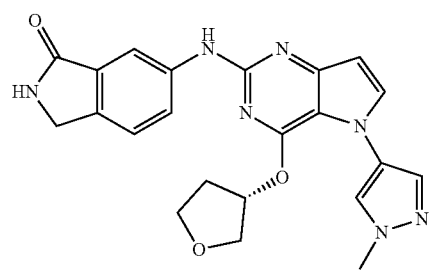
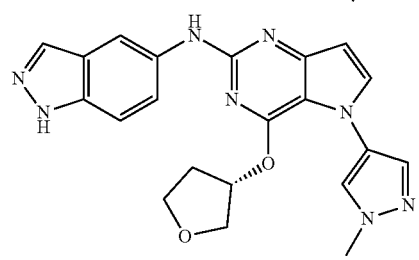
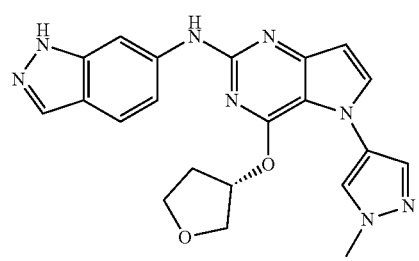
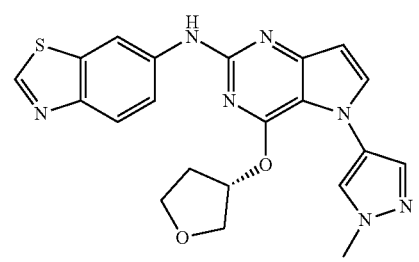
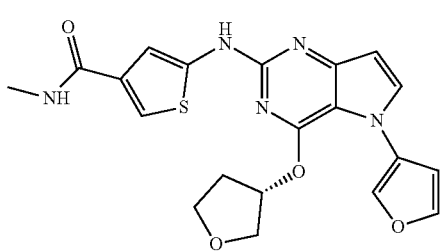
52
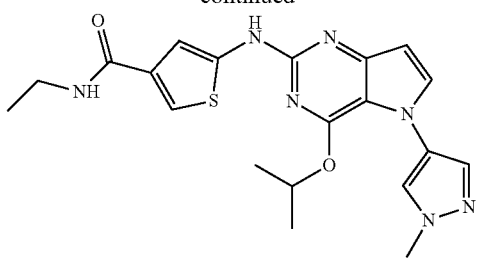
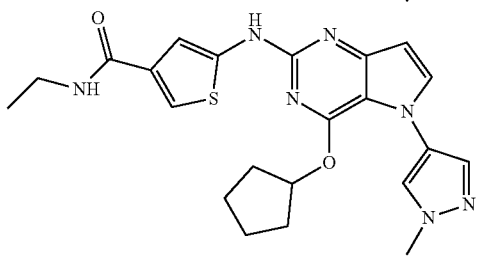
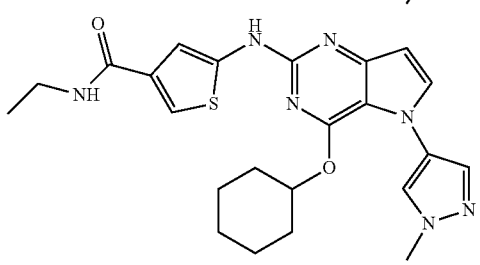
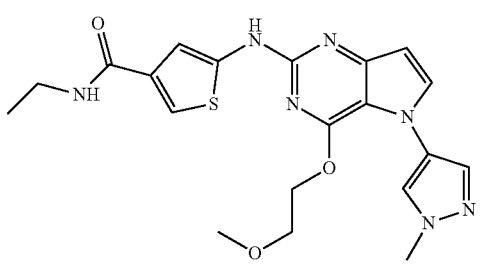
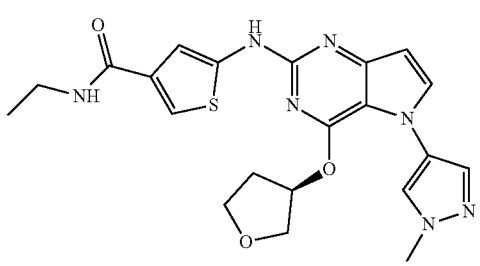
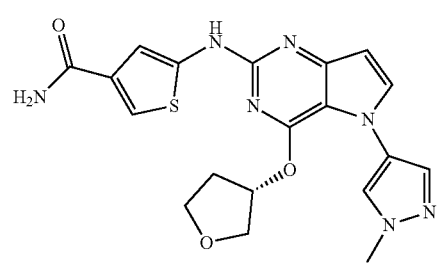

53
-continued
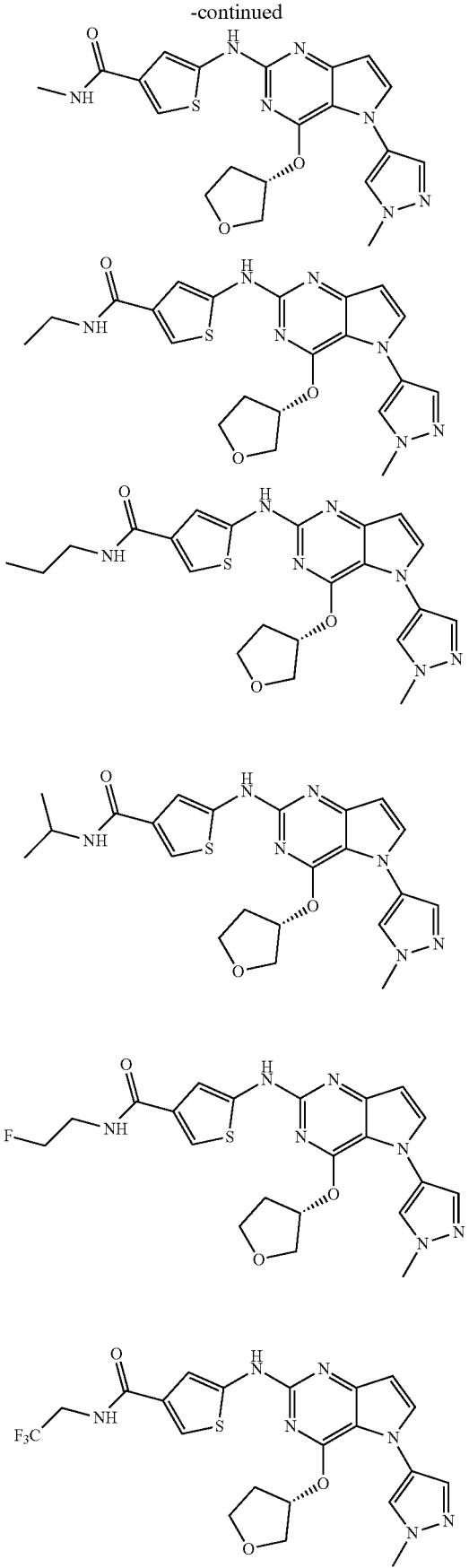
54
-continued
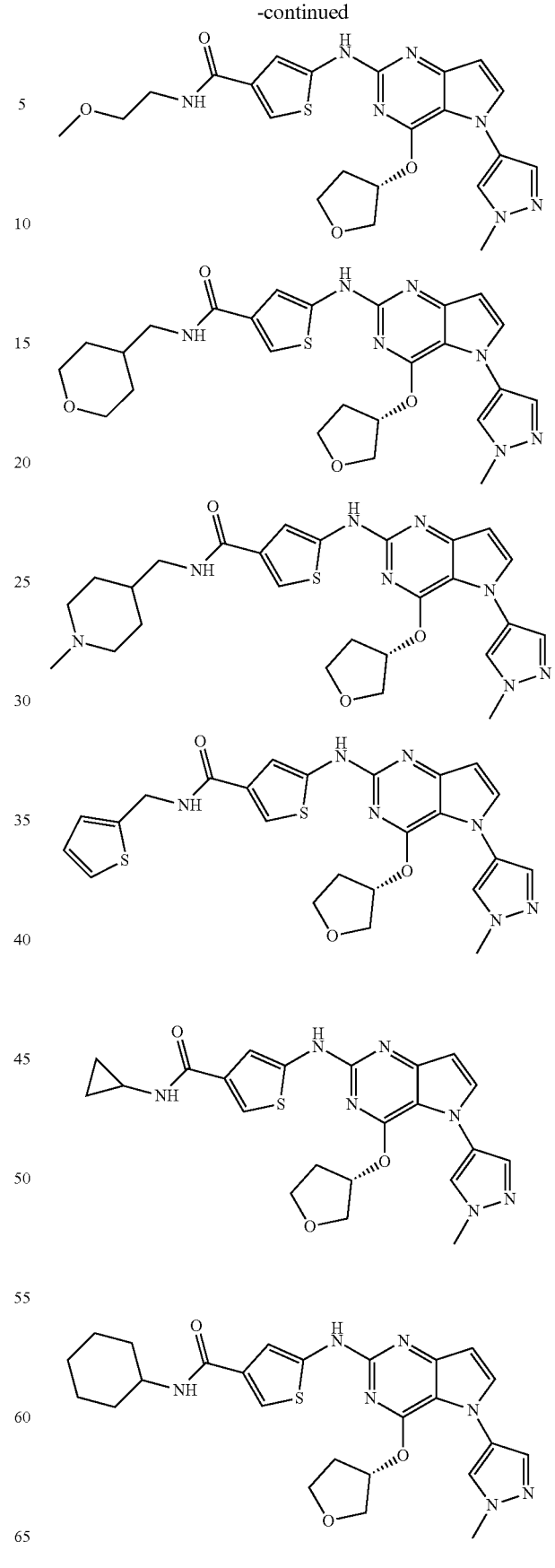

55
-continued
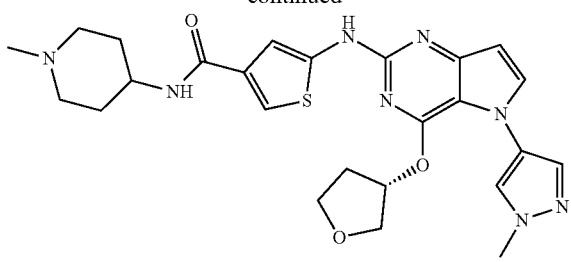
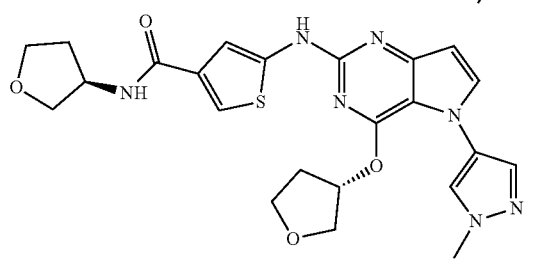
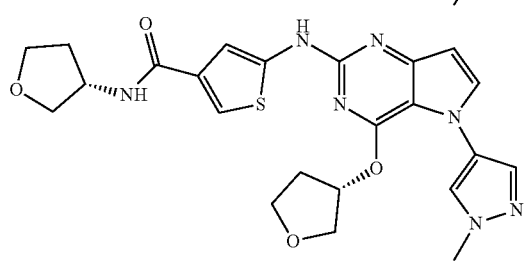
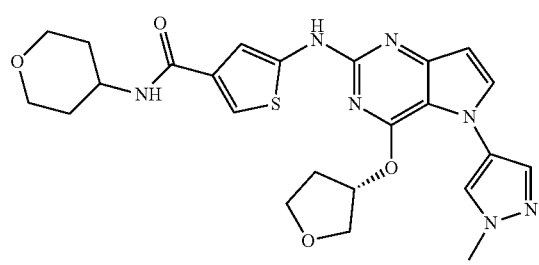
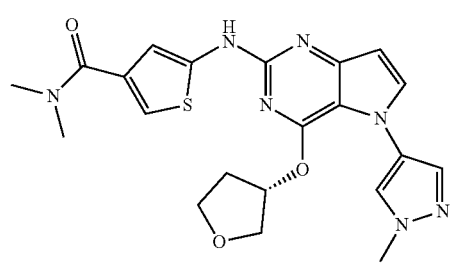
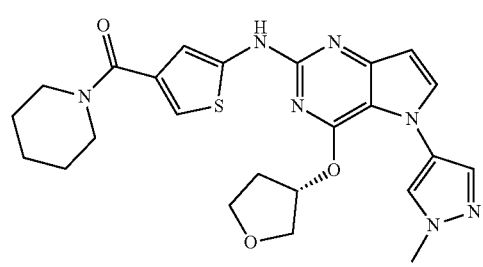
56
-continued
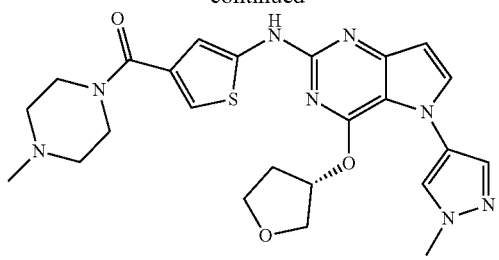
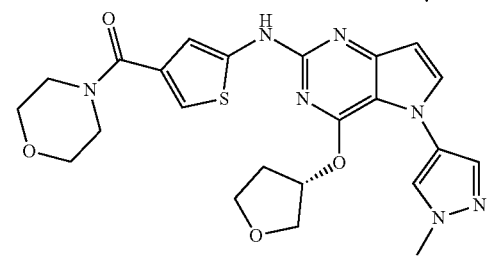
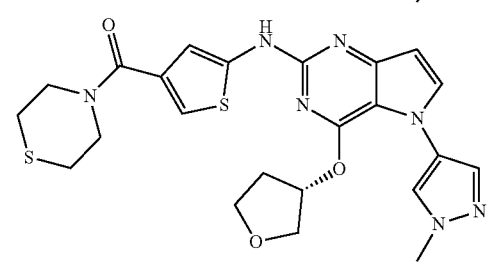
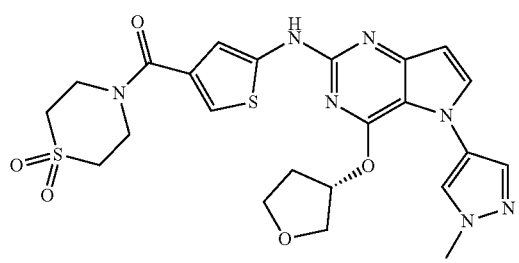
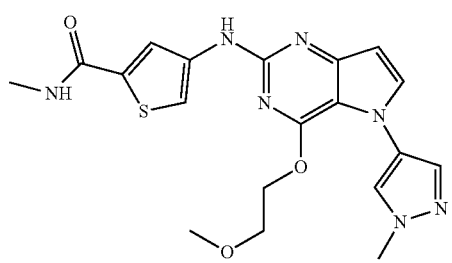
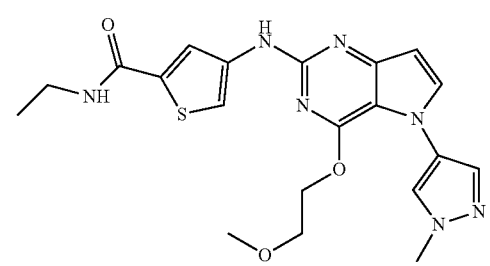

57
-continued
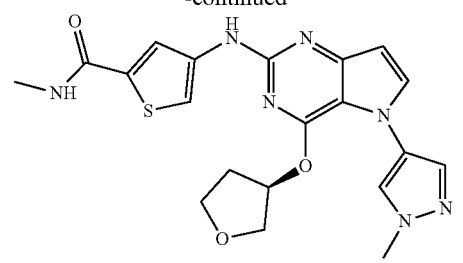
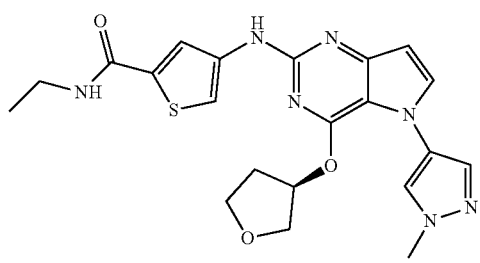
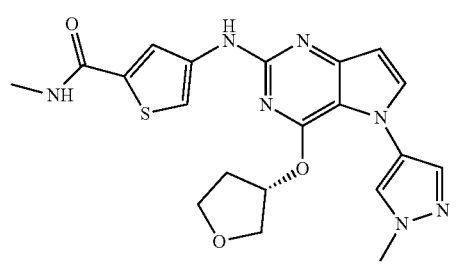
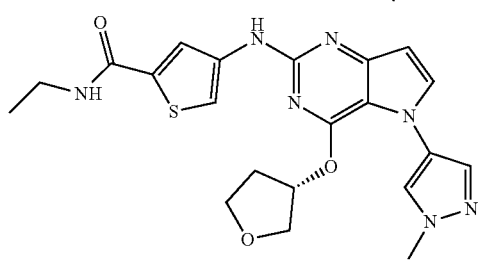
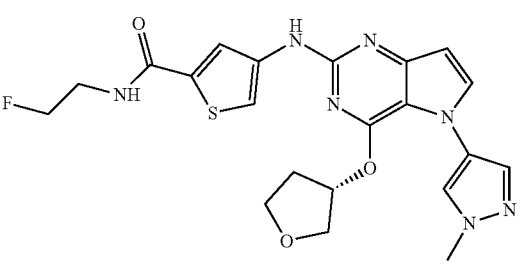
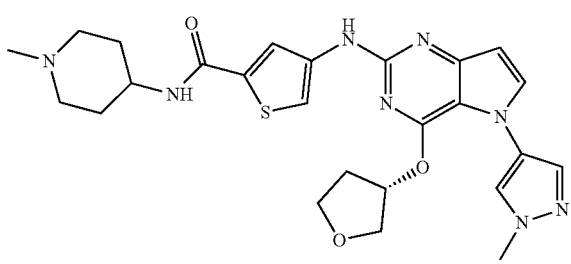
58
-continued
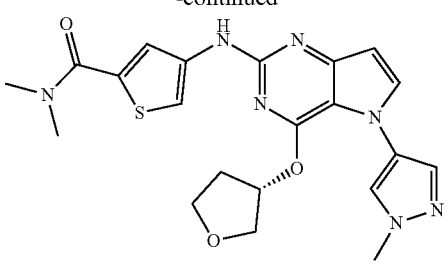
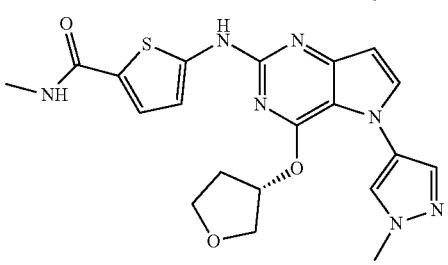
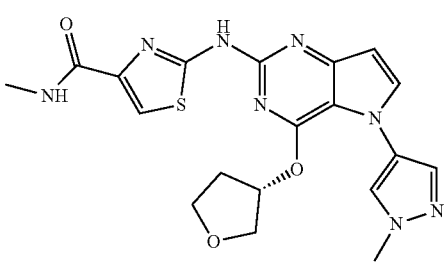
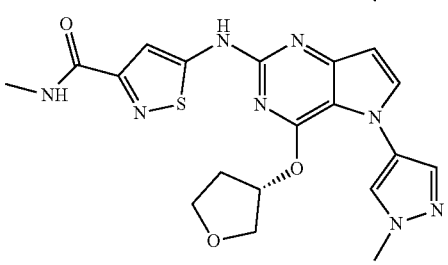
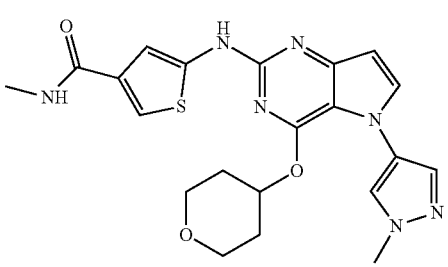
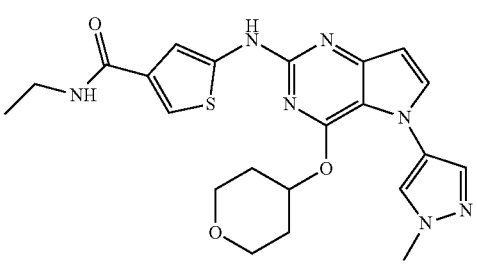

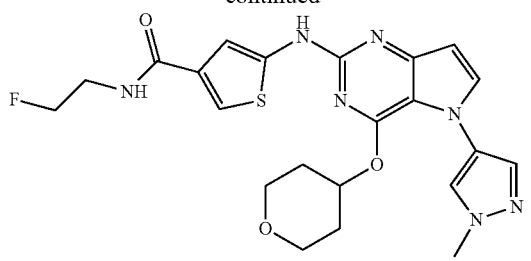
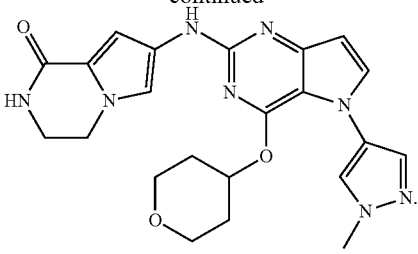
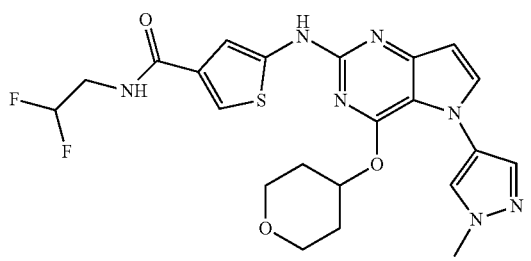
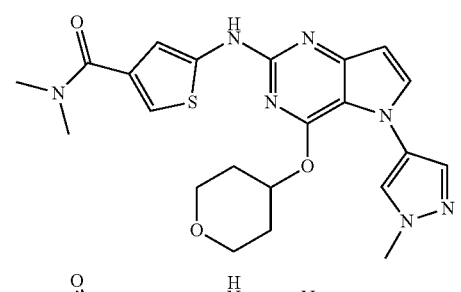
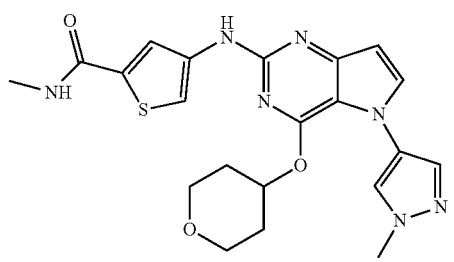
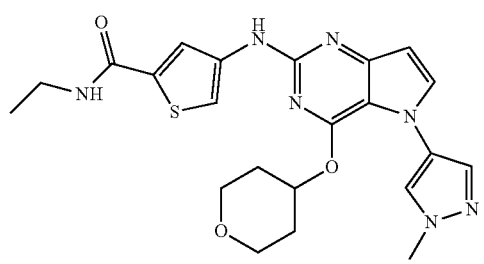
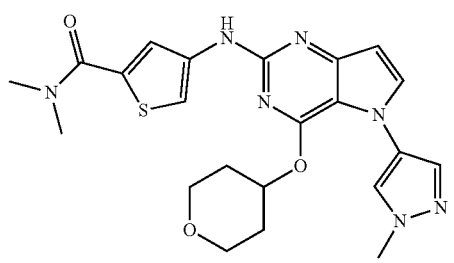

Another aspect of the invention relates to a pharmaceutical composition comprising one or more compounds of Formula I according to the invention, or a stereoisomer, tautomer, solvate, or pharmaceutically acceptable salt thereof, and a pharmaceutically acceptable excipient.

The pharmaceutical composition of the invention may be formulated as solid, semi-solid, liquid or gaseous formulations such as tablets, capsules, powders, granules, ointments, solutions, suppositories, injections, inhalations, gels, microspheres, and aerosols.

The pharmaceutical composition of the invention may be prepared by a method well known in the pharmaceutical field. For example, a pharmaceutical composition intended for administration by injection may be prepared by combining a compound of Formula I of the invention, or a pharmaceutically acceptable salt or prodrug thereof, with sterilized distilled water, so as to form a solution. A surfactant may be added to facilitate the formation of a homogeneous solution or suspension. Actual methods of preparing a pharmaceutical composition are known to those skilled in the art, for example, see *The Science and Practice of Pharmacy*, $20^{th}$ Edition (Philadelphia College of Pharmacy and Science, 2000).

Routes of administration of the pharmaceutical composition of the invention include, but are not limited to, oral, topical, transdermal, intramuscular, intravenous, inhalation, parenteral, sublingual, rectal, vaginal and intranasal. For example, dosage forms suitable for oral administration include capsules, tablets, granules, syrups, and the like. The compound of Formula I according to the invention contained in these formulations may be solid powders or granules; solutions or suspensions in aqueous or non-aqueous liquids; water-in-oil or oil-in-water emulsions; or the like. The above dosage forms may be prepared from the active compound with one or more carriers or excipients by conventional pharmacological methods. The above carriers are required to be compatible with the active compound or other excipients. Commonly used non-toxic carriers for solid formulations include, but are not limited to, mannitol, lactose, starch, magnesium stearate, cellulose, dextrose, sucrose, and the like. Carriers for liquid formulations include, but are not limited to, water, physiological saline, aqueous dextrose, ethylene glycol, polyethylene glycols, and the like. The active compound may form a solution or a suspension with the above carriers. The specific mode of administration and dosage form depend on the physicochemical properties of the compound itself and the severity of the disease to be treated, etc. The specific route of administration can be determined by those skilled in the art based on the above factors in combination with his or her own knowledge. See, for example, Li Jun, "Clinical Pharmacology", People's Medical Publishing House, 2008.06; Ding Yufeng, Discussion on Clinical Dosage Form factors and Drug Rational use in Hospital, *Herald of Medicine*, 26(5), 2007; Howard C. Ansel, Loyd V. Allen, Jr., Nicholas G. Popovich ed., Jiang Zhiqiang translated, "Pharmaceutical Dosage Forms and Drug Delivery System", China Medical Science Press, 2003.05.

The compounds of Formula I according to the invention or the pharmaceutical composition comprising the compound of Formula I according to the invention may be used in association or combination with one or more other active agents. The active agents which may be combined with the compound of Formula I according to the invention or with the pharmaceutical composition comprising a compound of Formula I according to the invention include, but are not limited to, immunosuppressants, glucocorticoids, nonsteroidal anti-inflammatory drugs, vinca alkaloids, paclitaxel, DNA damaging agents, Bcl-2 inhibitors, BTK inhibitors, JAK inhibitors, Hsp90 inhibitors, ALK inhibitors, Flt3 inhibitors, PI3K inhibitors and SYK inhibitors.

Another aspect of the invention relates to use of a compound of Formula I according to the invention, or a stereoisomer, tautomer, solvate or a pharmaceutically acceptable salt thereof, in the manufacture of a medicament for inhibiting the activity of IRAK4.

Another aspect of the invention relates to use of a pharmaceutical composition comprising a compound of Formula I according to the invention, or a stereoisomer, tautomer, solvate or a pharmaceutically acceptable salt thereof, in the manufacture of a medicament for inhibiting the activity of IRAK4.

Another aspect of the invention relates to use of a pharmaceutical composition comprising a compound of Formula I according to the invention, or a stereoisomer, tautomer, solvate or pharmaceutically acceptable salt thereof, in the manufacture of a medicament for the prevention or treatment of IRAK4-mediated diseases.

Another aspect of the invention relates to use of a pharmaceutical composition comprising a compound of Formula I according to the invention, or a stereoisomer, tautomer, solvate or pharmaceutically acceptable salt thereof, in the manufacture of a medicament for the prevention or treatment of IRAK4-mediated diseases.

Another aspect of the invention relates to a method of inhibiting IRAK4 activity in a biological system comprising administering to the biological system a compound of Formula I according to the invention, or a stereoisomer, tautomer, solvate, or a pharmaceutically acceptable salt or a pharmaceutical composition comprising a compound of Formula I according to the invention, or a stereoisomer, tautomer, solvate, or a pharmaceutically acceptable salt thereof. In some embodiments, the biological system is an enzyme, a cell, or a mammal. Examples of the mammal include, but are not limited to, humans; non-human primates (e.g., chimpanzees and other apes and monkey species); farm animals such as cattles, horses, sheep, goats, and pigs; domestic animals such as rabbits, dogs and cats; laboratory animals, including rodents, such as rats, mice and guinea pigs; and the like.

Another aspect of the invention relates to a method of inhibiting IRAK4 activity in a mammal, especially in a human, comprising administering to the mammal, especially the human, in need thereof, a therapeutically effective amount of a compound of Formula I according to the invention or a stereoisomer, tautomer, solvate, or a pharmaceutically acceptable salt thereof, or a pharmaceutical composition comprising a compound of Formula I according to the invention, or a stereoisomer, tautomer, solvate, or a pharmaceutically acceptable salt thereof.

Another aspect of the invention relates to a method of preventing or treating IRAK4-mediated diseases comprising administering to a mammal, especially a human, in need thereof, a therapeutically effective amount of a compound of Formula I according to the invention or a stereoisomer, tautomer, solvate, or a pharmaceutically acceptable salt thereof, or a pharmaceutical composition comprising a compound of Formula I according to the invention, or a stereoisomer, tautomer, solvate, or a pharmaceutically acceptable salt thereof.

Another aspect of the invention relates to use of a compound of Formula I according to the invention or a stereoisomer, tautomer, solvate, or a pharmaceutically acceptable salt thereof in the manufacture of a medicament for the treatment of IRAK4-mediated diseases in combination with one or more active agents selected from the group consisting of immunosuppressants, glucocorticoids, nonsteroidal anti-inflammatory drugs, vinca alkaloids, paclitaxel, DNA damaging agents, Bcl-2 inhibitors, BTK Inhibitors, JAK inhibitors, Hsp90 inhibitors, ALK inhibitors, Flt3 inhibitors, PI3K inhibitors and SYK inhibitors.

In the present application, among the immunosuppressive agents as mentioned, examples of azathioprine drugs include, but are not limited to, 6-mercaptopurine, Azathioprine, and the like; examples of cyclosporine drugs include, but are not limited to, Cyclosporine, Tacrolimus, and the like; examples of biological agents include, but are not limited to, antilymphocyte globulin, antithymocyte globulin, anti-Tac monoclonal antibody, Basiliximab, and the like.

Examples of glucocorticoids include, but are not limited to, Hydrocortisone, Dexamethasone, Betamethasone, Prednisone, Methylprednisolone, and the like.

Examples of nonsteroidal anti-inflammatory drugs include, but are not limited to, Aspirin, Acetaminophen, Ibuprofen, Diclofenac, Aceclofenac, Rofecoxib, Celecoxib, and the like.

Examples of vinca alkaloids include, but are not limited to, Vinblastine, Vincristine, Vinorelbine, and the like.

Among the DNA damaging agents as mentioned, examples of nitrogen mustards include, but are not limited to, Mechlorethamine, Cyclophosphamide, Ifosfamide, and the like; examples of nitrosoureas include, but are not limited to, Carmustine, Lomustine, Semustine, Nimustine, and the like.

Examples of Bcl-2 inhibitors include, but are not limited to, Navitoclax, Obatoclax Mesylate, and the like.

Examples of BTK inhibitors include, but are not limited to, Ibrutinib, HM71224, and the like.

Examples of JAK inhibitors include, but are not limited to, Ruxolitinib, Cerdulatinib, Tofacitinib, Baricitinib, and the like.

Examples of Hsp90 (heat shock protein 90) inhibitors include, but are not limited to, 17-AAG, 17-DMAG, Luminespib, Ganetespib, and the like.

Examples of ALK inhibitors include, but are not limited to, Crizotinib, Ceritinib, Alectinib, and the like.

Examples of Flt3 inhibitors include, but are not limited to, Dovitinib, Quizartinib, Tandutinib, and the like.

Examples of PI3K inhibitors include, but are not limited to, LY294002, Dactolisib, Pictilisib, Idelalisib, Buparlisib, and the like.

Examples of SYK inhibitors include, but are not limited to, Fostamatinib, R406, Entospletinib, Piceatannol, and the like.

In the present application, the IRAK4-mediated diseases as mentioned include autoimmune diseases, inflammatory diseases, heteroimmune conditions or diseases, thromboembolic diseases, cancers, and the like. The autoimmune diseases and inflammatory diseases include rheumatoid arthritis, osteoarthritis, juvenile arthritis, chronic obstructive pulmonary disease, multiple sclerosis, systemic lupus erythematosus, psoriasis, psoriatic arthritis, Crohn's disease, ulcerative colitis, irritable bowel syndrome, and the like. The cancers include B-cell chronic lymphocytic leukemia, acute lymphocytic leukemia, non-Hodgkin's lymphoma, Hodgkin's lymphoma, acute myeloid leukemia, diffuse large B-cell lymphoma, multiple myeloma, mantle cell lymphoma, small lymphocytic lymphoma, Waldenstrom macroglobulinemia, and the like.

The composition of the invention is formulated, dosed and administered in a manner conforming to the guidelines of medical practices. A "therapeutically effective amount" of a compound of the invention refers to an amount of the compound of the invention that is sufficient to effectively treat a disease or disorder in a mammal (e.g., a human) when the compound of the invention is administered to the mammal, e.g., the human. The amount of a compound of the invention which constitutes a "therapeutically effective amount" depends on the particular compound employed, the particular disorder to be treated, the cause of the disorder, the target of the drug, the severity of the disease, the mode of administration and the age, body weight, general condition of the mammal being treated, and the like, but may be determined conventionally by those skilled in the art based on his or her own knowledge and the disclosure of the present application. Typically, the dosage for parenteral administration may be 1 to 200 mg/kg, and the dosage for oral administration may be 1 to 1000 mg/kg.

The ranges of the effective dosages provided herein are not intended to limit the scope of the invention, but rather represent the preferred ranges of dosages. However, the most preferred dosage will be tailored to the individual subjects, as is understood and determinable by those skilled in the art (see, for example, Berkow et. al. eds., The Merck Manual, 16$^{th}$ edition, Merck Company, Rahway, N.J., 1992).

Preparation of the Compound of the Invention

The following reaction scheme illustrates the methods for preparing the compound of the invention.

It will be understood by those skilled in the art that in the description herein, combinations of substituents are permissible only if such combinations of the substituents results in a stable compound.

It will also be appreciated by those skilled in the art that in the methods described below, the functional group(s) of an intermediate compound may need to be protected by a suitable protecting group "PG". Such functional groups include hydroxyl, amino, mercapto and carboxyl groups. Suitable protecting groups for hydroxyl group include trialkylsilyl or diarylalkylsilyl groups (e.g., tert-butyldimethylsilyl, tert-butyldiphenylsilyl or trimethylsilyl), tetrahydropyranyl, benzyl, and the like. Suitable protecting groups for amino, amidino and guanidine groups include tert-butoxycarbonyl, benzyloxycarbonyl, and the like. Suitable protecting groups for mercapto group include —C(=O)—R" wherein R" is alkyl, aryl or arylalkyl, p-methoxybenzyl, trityl, or the like. Suitable protecting groups for carboxyl group include alkyl, aryl or arylalkyl esters, and the like.

Protecting groups may be introduced and removed in accordance with standard techniques, which are known to those skilled in the art and as described herein.

The use of protecting groups is described in detail in Greene, T. W. And P. G. M. Wuts, Protective Groups in Organic Synthesis, (1999), 4$^{th}$ Ed., Wiley. The protecting group may also be a polymeric resin.

The compound of Formula I according to the invention may be prepared according to the following reaction scheme:

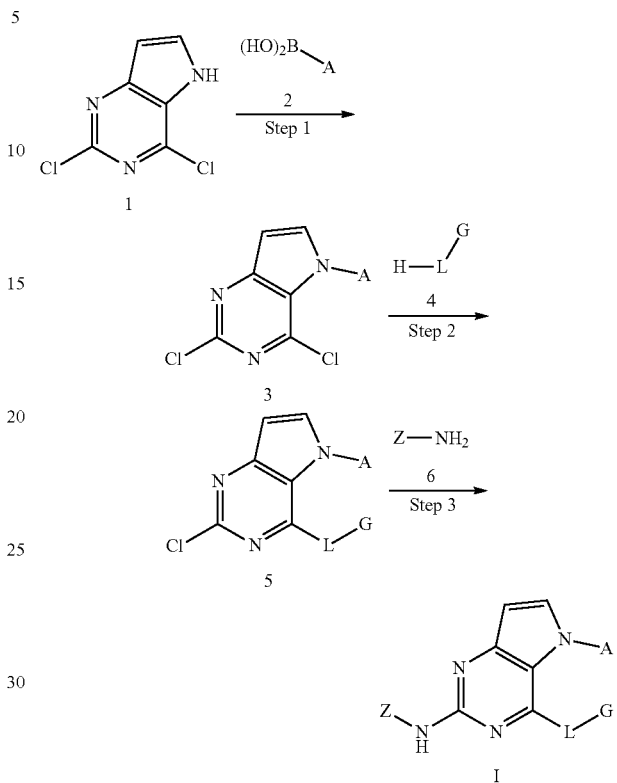

Wherein: the groups A, Z, L, and G in each formula are all defined as those in Formula I above.

The above reaction scheme includes the followings steps:

Step 1: Coupling a Compound of Formula 1 with a Compound of Formula 2 to Prepare a Compound of Formula 3

In this step, the reaction is carried out in the presence of a copper catalyst, and the copper catalyst that may be used in the invention is selected from the group consisting of copper acetate, copper sulfate, copper chloride, and the like. The base that may be used under this condition is selected from the group consisting of triethylamine, pyridine, 4-dimethylaminopyridine, and the like. The reaction temperature is from 80° C. to 160° C. The solvent used in the reaction may be selected from the group consisting of dimethylsulfoxide, 1,4-dioxane, N,N-dimethylformamide, toluene, ethanol, isopropanol, butanol, 2-butanol, and water.

Step 2: Subjecting the Compound of Formula 3 to a Substitution Reaction with a Compound of Formula 4 to Prepare a Compound of Formula 5

This step is preferably carried out in the presence of a base. The base used in the reaction may be organic bases such as triethylamine, N,N-diisopropylethylamine and pyridine. The base used in the reaction may also be inorganic bases such as sodium carbonate, potassium carbonate, sodium hydroxide and sodium hydride. The reaction may also be carried out in the presence of an acid or under a neutral condition. The acid used in the reaction may be selected from the group consisting of hydrochloric acid, trifluoroacetic acid, hydrogen chloride in 1,4-dioxane, acetic acid, sulfuric acid, and the like. The reaction temperature is from −80° C. to 160° C. The solvent used in the reaction may be selected from the group consisting of 1,4-dioxane, tetrahydrofuran, dichloromethane, toluene, methanol, ethanol, isopropanol, n-butanol, dimethylsulfoxide, N-methylpyrrolidone, and the like.

Step 3: Subjecting the Compound of Formula 5 to a Substitution Reaction with a Compound of Formula 6 to Prepare a Corresponding Compound of Formula I In this step, the reaction may be carried out in the presence of an acid or under a neutral condition. The acid used in the reaction may be selected from the group consisting of hydrochloric acid, trifluoroacetic acid, hydrogen chloride in 1,4-dioxane, acetic acid, sulfuric acid, and the like. The reaction may also be carried out in the presence of a base. The base used in the reaction may be strong bases such as sodium hydroxide, sodium tert-butoxide and sodium hydride. The reaction may also be carried out in the presence of a palladium catalyst. The palladium catalyst that may be used in the invention is selected from the group consisting of bis(triphenylphosphine)palladium dichloride (Pd(PPh$_3$)$_2$Cl$_2$), tris(dibenzylidenepropanone)dipalladium (Pd$_2$(dba)$_3$), tetra(triphenylphosphine)palladium (Pd(PPh$_3$)$_4$), palladium acetate (Pd(OAc)$_2$), [1,1'-bis(diphenylphosphino)ferrocene]palladium dichloride (Pd(dppf)Cl$_2$) and palladium chloride (PdCl$_2$). The base that may be used under this condition is preferably an inorganic base such as sodium carbonate, potassium carbonate, potassium phosphate, cesium carbonate, and the like. The reaction temperature is from 80° C. to 160° C. The solvent used in the reaction may be 1,4-dioxane, toluene, ethanol, isopropanol, n-butanol, 2-butanol, water, or a mixture thereof.

It will be appreciated by those skilled in the art that the above reaction scheme and preparation processes are only for a purpose of simple and clear illustration, and are not intended to be limiting; and that the compound of Formula I according to the invention may also be obtained by analogous methods as described above by selection of appropriate starting materials, which may be commercially available or be obtainable by using a method well-known in the art.

EXAMPLES

The experiments, synthetic methods, and intermediates involved, as described below, are illustrative of the invention and are not intended to limit the scope of the invention.

The starting materials used in the experiments of the invention are either purchased from reagent suppliers or prepared from known starting materials by a method well known in the art. Unless otherwise indicated, the examples herein use the following conditions:

The unit of temperature is degrees Celsius (° C.); and room temperature is defined as 18-25° C.;

The organic solvent is dried over anhydrous magnesium sulphate or anhydrous sodium sulphate, and spin dried using a rotary evaporator under reduced pressure at an elevated temperature (e.g., 15 mmHg, 30° C.);

200-300 Mesh silica gel is used as a carrier in the separation by flash column chromatography; and TLC represents thin layer chromatography;

Typically, the progress of a reaction is monitored by TLC or LC-MS;

The final product is identified by nuclear magnetic resonance (Bruker AVANCE 300, 300 MHz) and LC-MS (Bruker esquine 6000, Agilent 1200 series).

Example 1

Preparation of trans-4-[2-(3-methylisothiazol-5-ylamino)-5-(1-methyl-1H-pyrazol-4-yl)-5H-pyrrolo[3,2-d]pyrimidin-4-ylamino]cyclohexanol

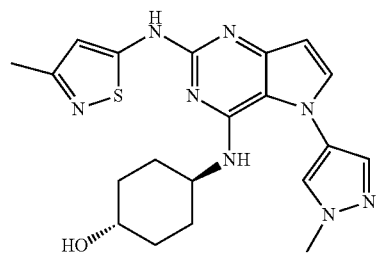 [SMILES: Cc1cc(Nc2nc(N[C@H]3CC[C@H](O)CC3)c3c(ccn3-c3cnn(C)c3)n2)sn1]

Step 1: Preparation of 2,4-dichloro-5-(1-methyl-1H-pyrazol-4-yl)-5H-pyrrolo[3,2-d]pyrimidine

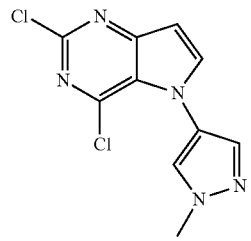

2,4-Dichloro-5H-pyrrolo[3,2-d]pyrimidine (376 mg, 2 mmol), 1-methyl-4-(4,4,5,5-tetramethyl-1,3,2-dioxaborolan-2-yl)-1H-pyrazole (832 mg, 4 mmol), anhydrous copper acetate (363 mg, 2 mmol), and pyridine (158 mg, 2 mmol) were added into dimethylsulfoxide (10 mL). The reaction liquid was heated to 110° C. and stirred overnight. The reaction liquid was naturally cooled down to room temperature, followed by adding ethyl acetate (50 mL). The insolubles were removed by filtration. The filtrate was washed with water (40 mL×2), dried over anhydrous sodium sulfate, and concentrated under reduced pressure. The residue was beaten in a mixed solution of n-hexane/ethyl acetate (2/1, 30 mL), and filtered to give 150 mg of a pale yellow solid. Yield: 28.0%. MS (ESI, m/z): [M+H]$^+$: 267.9.

Step 2: Preparation of trans-4-[2-chloro-5-(1-methyl-1H-pyrazol-4-yl)-5H-pyrrolo[3,2-d]pyrimidin-4-ylamino]cyclohexanol

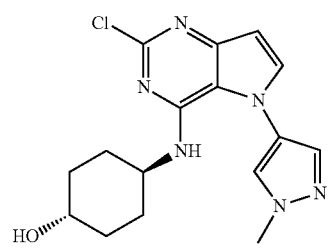 [SMILES: Cn1cc(-n2ccc3nc(Cl)nc(N[C@H]4CC[C@H](O)CC4)c32)cn1]

2,4-Dichloro-5-(1-methyl-1H-pyrazol-4-yl)-5H-pyrrolo[3,2-d]pyrimidine (150 mg, 0.56 mmol), trans-4-aminocyclohexanol (129 mg, 1.12 mmol), and N,N-diisopropylethylamine (217 mg, 1.68 mmol) were added into n-butanol (10 mL). The reaction liquid was refluxed for 3 hours, naturally cooled down to room temperature, diluted with ethyl acetate (15 mL), and washed with water (10 mL×2). The organic phase was dried over anhydrous sodium sulfate, concentrated under reduced pressure, beaten in a mixed solution of n-hexane/ethyl acetate (2/1, 30 mL), and filtered to give 110 mg of a brown solid. Yield: 56.6%. MS (ESI, m/z): [M+H]⁺: 347.0.

Step 3: Preparation of trans-4-[2-(3-methylisothiazol-5-ylamino)-5-(1-methyl-1H-pyrazol-4-yl)-5H-pyrrolo[3,2-d]pyrimidin-4-ylamino]cyclohexanol The product obtained in Step 2 (35 mg, 0.1 mmol), 3-methylisothiazol-5-ylamine hydrochloride (23 mg, 0.15 mmol), cesium carbonate (130 mg, 0.4 mmol), 4,5-bis(diphenylphosphino)-9,9-dimethylxanthene (9 mg, 0.015 mmol), and tris(dibenzylidenepropanone)dipalladium (9 mg, 0.01 mmol) were dissolved in 1,4-dioxane/water (20/1, 1.5 mL). The reaction liquid was reacted under microwave condition at 100° C. for 1 hour. The reaction liquid was cooled down to room temperature, concentrated under reduced pressure, and separated by flash column chromatography (eluent: dichloromethane:methanol=10:1) to give 3 mg of a pale yellow solid. Yield: 7.1%. MS (ESI, m/z): [M+H]⁻: 425.1; ¹H-NMR (300 MHz, CD₃OD) δ: 8.03 (s, 1H), 7.73 (s, 1H), 7.24 (d, 1H, J=3.0 Hz), 6.57 (s, 1H), 6.37 (d, 1H, J=3.0 Hz), 4.17-4.25 (m, 1H), 4.01 (s, 3H), 3.53-3.62 (m, 1H), 2.33 (s, 3H), 2.13-2.18 (m, 2H), 1.90-1.95 (m, 2H), 1.10-1.57 (m, 4H).

The following compounds (in Table 1) were prepared from similar starting materials by a synthesis method analogous to that as described in Example 1.

TABLE 1

| Examples | Structures | Characterization data |
| --- | --- | --- |
| 2 | (structure) | ¹H-NMR (300 MHz, CD₃OD) δ: 8.06 (s, 1H), 7.75 (s, 1H), 7.31-7.41 (m, 1H), 7.26-7.27 (m, 1H), 6.60 (s, 1H), 4.51-4.62 (m, 1H), 4.03 (s, 3H), 2.37 (s, 3H), 1.22 (d, 6H, J = 6.3 Hz). LC-MS (ESI, m/z): [M + H]⁺ = 369.2. |
| 3 | (structure) | ¹H-NMR (300 MHz, DMSO-d₆) δ: 10.60 (s, 1H), 8.16 (s, 1H), 7.75 (s, 1H), 7.37 (d, 1H, J = 3.0 Hz), 6.53 (s, 1H), 6.37 (d, 1H, J = 3.0 Hz), 5.45-5.50 (m, 1H), 4.75-4.80 (m, 1H), 3.91 (s, 3H), 3.52-3.65 (m, 4H), 2.24 (s, 3H). LC-MS (ESI, m/z): [M + H]⁺ = 371.3. |
| 4 | (structure) | ¹H-NMR (300 MHz, DMSO-d₆) δ: 8.17 (s, 1H), 7.75 (s, 1H), 7.53 (s, 1H), 6.75 (s, 1H), 6.49-6.50 (m, 1H), 3.92 (s, 3H), 3.47-3.51 (m, 2H), 3.16 (s, 2H), 2.34 (s, 3H), 1.71-1.75 (m, 2H). LC-MS (ESI, m/z): [M + H]⁺ = 385.3. |
| 5 | (structure) | ¹H-NMR (300 MHz, DMSO-d₆) δ: 8.20 (s, 1H), 7.77 (s, 1H), 7.57 (s, 1H), 6.79 (s, 1H), 6.51-6.52 (m, 1H), 3.93 (s, 3H), 3.60-3.68 (m, 2H), 3.39-3.43 (m, 2H), 2.35 (s, 3H), 1.46-1.62 (m, 4H). LC-MS (ESI, m/z): [M + H]⁺ = 399.3. |

TABLE 1-continued

| Examples | Structures | Characterization data |
|---|---|---|
| 6 | 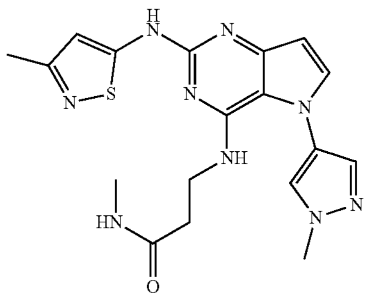 [SMILES: CNC(=O)CCNc1nc(Nc2cc(C)ns2)nc2ccn(-c3cnn(C)c3)c12] | ¹H-NMR (300 MHz, CDCl₃) δ: 7.75 (s, 1H), 7.65 (s, 1H), 7.15 (d, 1H, J = 3.0 Hz), 7.09 (s, 1H), 6.54 (d, 1H, J = 3.0 Hz), 4.11 (s, 3H), 3.99 (s, 2H), 2.81 (s, 3H), 2.52-2.58 (m, 2H), 2.40-2.42 (m, 3H).<br>LC-MS (ESI, m/z): [M + H]⁺ = 412.3. |
| 7 | 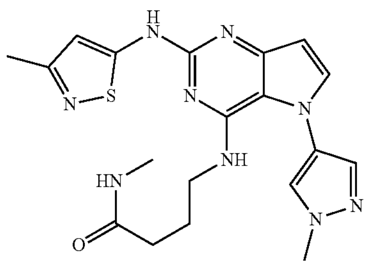 [SMILES: CNC(=O)CCCNc1nc(Nc2cc(C)ns2)nc2ccn(-c3cnn(C)c3)c12] | ¹H-NMR (300 MHz, DMSO-d₆) δ: 8.18 (s, 1H), 7.56 (s, 1H), 7.53 (s, 1H), 6.77 (s, 1H), 6.50-6.51 (m, 1H), 3.93 (s, 3H), 3.60 (s, 2H), 2.53 (s, 3H), 2.36 (s, 3H), 2.10-2.15 (m, 2H), 1.78-1.83 (m, 2H).<br>LC-MS (ESI, m/z): [M + H]⁺ = 426.2. |
| 8 | 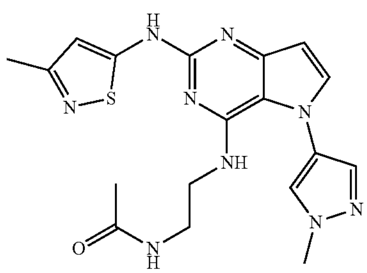 [SMILES: CC(=O)NCCNc1nc(Nc2cc(C)ns2)nc2ccn(-c3cnn(C)c3)c12] | ¹H-NMR (300 MHz, CDCl₃) δ: 7.85 (s, 1H), 7.71 (s, 1H), 6.99 (s, 1H), 6.65 (d, 1H, J = 3.0 Hz), 6.43 (s, 1H), 4.11 (s, 3H), 3.84-3.87 (m, 2H), 3.56 (s, 2H), 2.61 (s, 3H), 2.04 (s, 3H).<br>LC-MS (ESI, m/z): [M + H]⁺ = 412.2. |
| 9 | 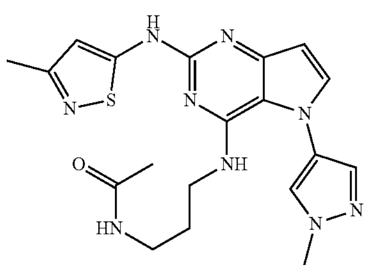 [SMILES: CC(=O)NCCCNc1nc(Nc2cc(C)ns2)nc2ccn(-c3cnn(C)c3)c12] | ¹H-NMR (300 MHz, CDCl₃) δ: 7.82 (s, 1H), 7.69 (s, 1H), 6.97 (s, 1H), 6.63 (d, 1H, J = 3.0 Hz), 6.50 (s, 1H), 4.06 (s, 3H), 3.73-3.75 (m, 2H), 3.28-3.29 (m, 2H), 2.65 (s, 3H), 2.05 (s, 3H), 1.91 (s, 2H).<br>LC-MS (ESI, m/z): [M + H]⁺ = 426.3. |
| 10 | 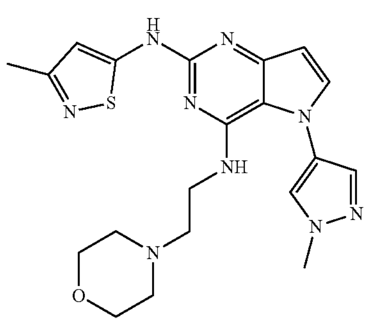 [SMILES: Cc1cc(Nc2nc(NCCN3CCOCC3)c3c(ccn3-c3cnn(C)c3)n2)sn1] | ¹H-NMR (300 MHz, CD₃OD) δ: 8.01 (s, 1H), 7.71 (s, 1H), 7.18 (d, 1H, J = 3.3 Hz), 6.54 (s, 1H), 6.35 (d, 1H, J = 3.0 Hz), 3.99 (s, 3H), 3.61-3.70 (m, 6H), 2.53-2.57 (m, 2H), 2.38-2.40 (m, 4H), 2.31 (s, 3H).<br>LC-MS (ESI, m/z): [M + H]⁺ = 440.4. |

TABLE 1-continued

| Examples | Structures | Characterization data |
|---|---|---|
| 11 | 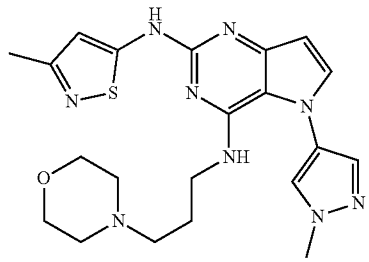 [SMILES: Cc1cc(Nc2nc(NCCCN3CCOCC3)c3c(ccn3-c3cnn(C)c3)n2)sn1] | ¹H-NMR (300 MHz, DMSO-d₆) δ: 9.94 (s, 1H), 8.20 (s, 1H), 7.79 (s, 1H), 7.55 (s, 1H), 6.75 (s, 1H), 6.51-6.52 (m, 1H), 3.96-4.00 (m, 2H), 3.93 (s, 3H), 3.60-3.68 (m, 4H), 3.41-3.45 (m, 2H), 3.12-3.17 (m, 4H), 2.35 (s, 3H), 2.03-2.06 (m, 2H). LC-MS (ESI, m/z): [M + H]⁺ = 454.4. |
| 12 | 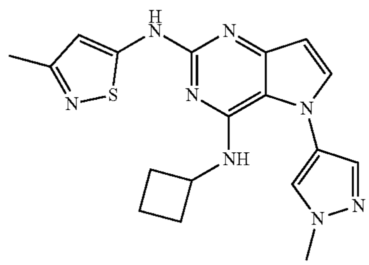 [SMILES: Cc1cc(Nc2nc(NC3CCC3)c3c(ccn3-c3cnn(C)c3)n2)sn1] | ¹H-NMR (300 MHz, DMSO-d₆) δ: 8.21 (s, 1H), 7.80 (s, 1H), 7.56 (s, 1H), 6.77 (s, 1H), 6.52 (d, 1H, J = 2.7 Hz), 4.59-4.87 (m, 1H), 3.95 (s, 3H), 2.32-2.41 (m, 5H), 1.85-1.91 (m, 2H), 1.71-1.74 (m, 2H). LC-MS (ESI, m/z): [M + H]⁺ = 381.2. |
| 13 | 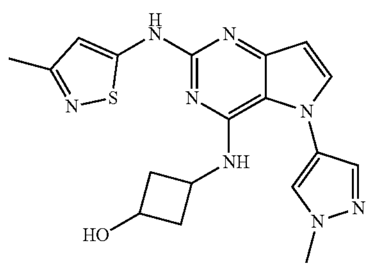 [SMILES: Cc1cc(Nc2nc(NC3CC(O)C3)c3c(ccn3-c3cnn(C)c3)n2)sn1] | ¹H-NMR (300 MHz, DMSO-d₆) δ: 10.58 (s, 1H), 8.21 (s, 1H), 7.79 (s, 1H), 7.39 (d, 1H, J = 3.0 Hz), 6.53 (s, 1H), 6.38 (d, 1H, J = 3.0 Hz), 4.10-4.24 (m, 1H), 3.95 (s, 3H), 3.84-3.91 (m, 1H), 2.67-2.73 (m, 2H), 2.25 (s, 3H), 1.55-1.65 (m, 2H). LC-MS (ESI, m/z): [M + H]⁺ = 397.1. |
| 14 | 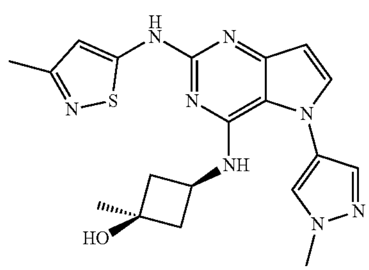 [SMILES: Cc1cc(Nc2nc(N[C@H]3C[C@@](C)(O)C3)c3c(ccn3-c3cnn(C)c3)n2)sn1] | ¹H-NMR (300 MHz, CD₃OD) δ: 8.04 (s, 1H), 7.75 (s, 1H), 7.26 (d, 1H, J = 3.3 Hz), 6.57 (s, 1H), 6.39 (d, 1H, J = 3.0 Hz), 4.43-4.53 (m, 1H), 4.02 (s, 3H), 2.57-2.64 (m, 2H), 2.33 (s, 3H), 1.79-1.86 (m, 2H). LC-MS (ESI, m/z): [M + H]⁺ = 411.2. |
| 15 | 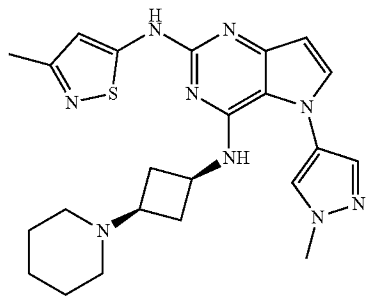 [SMILES: Cc1cc(Nc2nc(N[C@H]3C[C@@H](N4CCCCC4)C3)c3c(ccn3-c3cnn(C)c3)n2)sn1] | ¹H-NMR (300 MHz, DMSO-d₆) δ: 9.78 (s, 1H), 8.17 (s, 1H), 7.73 (s, 1H), 7.53 (s, 1H), 6.69 (s, 1H), 6.48 (s, 1H), 3.48 (s, 1H), 3.27 (d, 2H, J = 11.1 Hz), 2.65-2.72 (m, 4H), 2.31 (s, 3H), 2.22 (s, 3H), 1.74-1.78 (m, 2H), 1.16-1.34 (m, 7H). LC-MS (ESI, m/z): [M + H]⁺ = 464.3. |

TABLE 1-continued

| Examples | Structures | Characterization data |
|---|---|---|
| 16 | 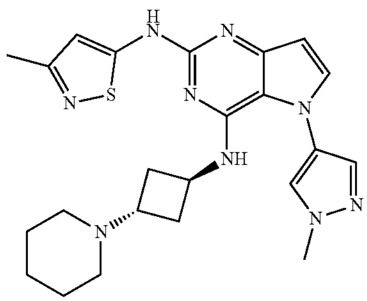 [SMILES: Cc1cc(Nc2nc(N[C@H]3C[C@H](N4CCCCC4)C3)c3c(ccn3-c3cnn(C)c3)n2)sn1] | ¹H-NMR (300 MHz, DMSO-d₆) δ: 9.72 (s, 1H), 8.11 (s, 1H), 7.71 (s, 1H), 7.50 (s, 1H), 6.68 (s, 1H), 6.44 (s, 1H), 3.92 (s, 3H), 3.48 (s, 1H), 3.26 (d, 2H, J = 11.1 Hz), 2.64-2.70 (m, 4H), 2.18 (s, 3H), 1.72-1.77 (m, 2H), 1.10-1.26 (m, 7H).<br>LC-MS (ESI, m/z): [M + H]⁺ = 464.3. |
| 17 | 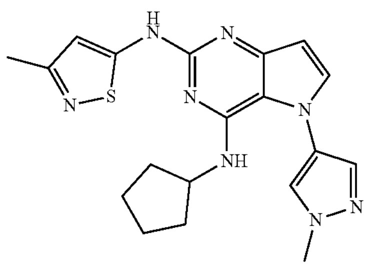 [SMILES: Cc1cc(Nc2nc(NC3CCCC3)c3c(ccn3-c3cnn(C)c3)n2)sn1] | ¹H-NMR (300 MHz, DMSO-d₆) δ: 8.26 (s, 1H), 7.82 (s, 1H), 7.54 (s, 1H), 6.74 (s, 1H), 6.51 (d, 1H, J = 3.0 Hz), 4.58 (s, 1H), 3.95 (s, 3H), 2.35 (s, 3H), 1.96-2.00 (m, 2H), 1.38-1.66 (m, 6H).<br>LC-MS (ESI, m/z): [M + H]⁺ = 395.2. |
| 18 | 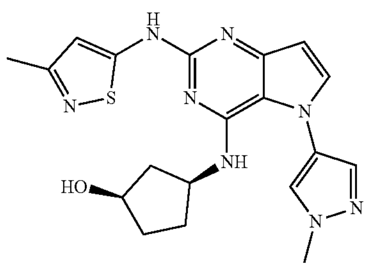 [SMILES: Cc1cc(Nc2nc(N[C@H]3CC[C@@H](O)C3)c3c(ccn3-c3cnn(C)c3)n2)sn1] | ¹H-NMR (300 MHz, DMSO-d₆) δ: 10.66 (s, 1H), 8.11 (s, 1H), 7.70 (s, 1H), 7.35 (d, 1H, J = 3.0 Hz), 6.54 (s, 1H), 6.35 (s, 1H, J = 3.0 Hz), 4.55 (s, 1H), 4.18 (s, 1H), 3.89 (s, 3H), 2.25 (s, 3H), 1.88-1.99 (m, 2H), 1.44-1.76 (m, 4H).<br>LC-MS (ESI, m/z): [M + H]⁺ = 411.0. |
| 19 | 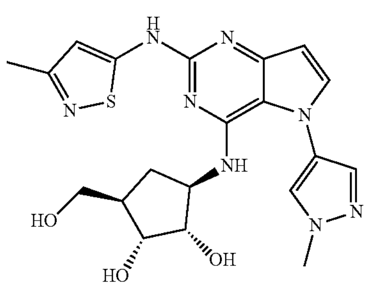 [SMILES: Cc1cc(Nc2nc(N[C@@H]3C[C@H](CO)[C@@H](O)[C@H]3O)c3c(ccn3-c3cnn(C)c3)n2)sn1] | ¹H-NMR (300 MHz, CD₃OD) δ: 8.08 (s, 1H), 7.79 (s, 1H), 7.47 (s, 1H), 6.82 (s, 1H), 6.58 (d, 1H, J = 2.7 Hz), 4.90-5.00 (m, 1H), 4.03 (s, 3H), 3.85 (t, 1H, J = 4.8 Hz), 3.78 (t, 1H, J = 5.1 Hz), 3.52-3.60 (m, 2H), 2.52-2.68 (m, 1H), 2.47 (s, 3H), 2.10-2.23 (m, 1H), 1.15-1.30 (m, 1H).<br>LC-MS (ESI, m/z): [M + H]⁺ = 457.3. |
| 20 | 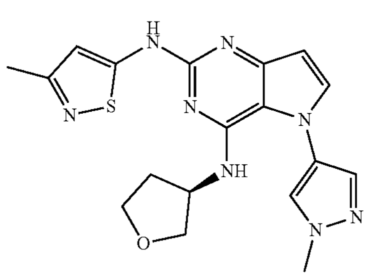 [SMILES: Cc1cc(Nc2nc(N[C@@H]3CCOC3)c3c(ccn3-c3cnn(C)c3)n2)sn1] | ¹H-NMR (300 MHz, DMSO-d₆) δ: 8.22 (s, 1H), 7.80 (s, 1H), 7.58 (d, 1H, J = 2.7 Hz), 6.77 (s, 1H), 6.54 (d, 1H, J = 2.7 Hz), 4.67-4.89 (m, 1H), 3.86-3.93 (m, 5H), 3.73-3.79 (m, 2H), 2.32 (s, 3H), 2.26-2.30 (m, 1H), 1.76-1.78 (m, 1H).<br>LC-MS (ESI, m/z): [M + H]⁺ = 397.2. |

TABLE 1-continued

| Examples | Structures | Characterization data |
|---|---|---|
| 21 | 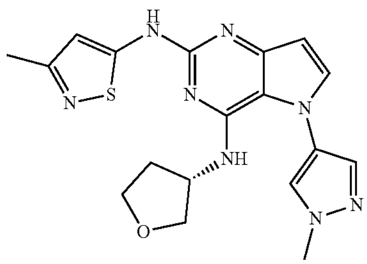 [SMILES: Cc1cc(Nc2nc(N[C@H]3CCOC3)c3c(ccn3-c3cnn(C)c3)n2)sn1] | ¹H-NMR (300 MHz, DMSO-d₆) δ: 8.21 (s, 1H), 7.80 (s, 1H), 7.57 (d, 1H, J = 2.7 Hz), 6.76 (s, 1H), 6.54 (d, 1H, J = 2.7 Hz), 4.67-4.89 (m, 1H), 3.86-3.93 (m, 5H), 3.72-3.78 (m, 2H), 2.37 (s, 3H), 2.25-2.32 (m, 1H), 1.75-1.77 (m, 1H).<br>LC-MS (ESI, m/z): [M + H]⁺ = 397.2. |
| 22 | 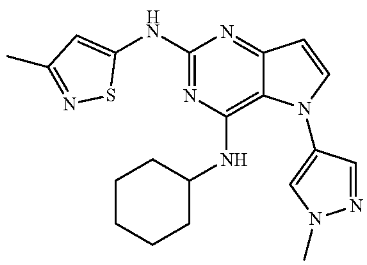 [SMILES: Cc1cc(Nc2nc(NC3CCCCC3)c3c(ccn3-c3cnn(C)c3)n2)sn1] | ¹H-NMR (300 MHz, DMSO-d₆) δ: 8.25 (s, 1H), 7.82 (s, 1H), 7.56 (s, 1H), 6.77 (s, 1H), 6.51 (d, 1H, J = 3.0 Hz), 4.12-4.29 (m, 1H), 3.94 (s, 3H), 2.34 (s, 3H), 1.82-1.97 (m, 2H), 1.22-1.52 (m, 8H).<br>LC-MS (ESI, m/z): [M + H]⁺ = 409.3. |
| 23 | 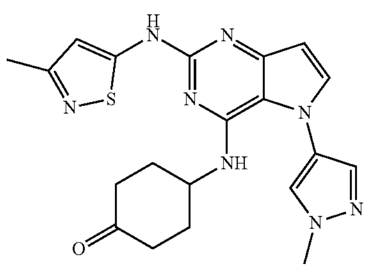 [SMILES: Cc1cc(Nc2nc(NC3CCC(=O)CC3)c3c(ccn3-c3cnn(C)c3)n2)sn1] | ¹H-NMR (300 MHz, CD₃OD) δ: 8.04 (s, 1H), 7.73 (s, 1H), 7.26 (d, 1H, J = 3.3 Hz), 6.58 (s, 1H), 6.39 (d, 1H, J = 3.3 Hz), 2.53-2.68 (m, 2H), 2.19-2.37 (m, 6H), 1.68-1.82 (m, 3H), 1.27 (s, 3H).<br>LC-MS (ESI, m/z): [M + H]⁺ = 423.2. |
| 24 | 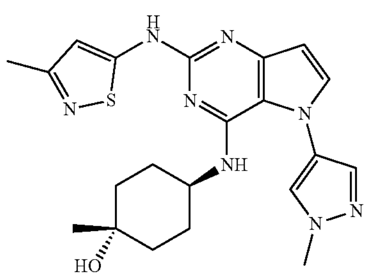 [SMILES: Cc1cc(Nc2nc(N[C@H]3CC[C@](C)(O)CC3)c3c(ccn3-c3cnn(C)c3)n2)sn1] | ¹H-NMR (300 MHz, CD₃OD) δ: 8.09 (s, 1H), 7.78 (s, 1H), 7.25 (d, 1H, J = 3.0 Hz), 6.57 (s, 1H), 6.39 (d, 1H, J = 3.0 Hz), 4.59 (s, 1H), 4.02 (s, 3H), 3.54-3.56 (m, 1H), 2.33 (s, 3H), 2.02-2.09 (m, 3H), 1.57-1.64 (m, 5H), 1.16-1.27 (m, 3H).<br>LC-MS (ESI, m/z): [M + H]⁺ = 439.3. |
| 25 | 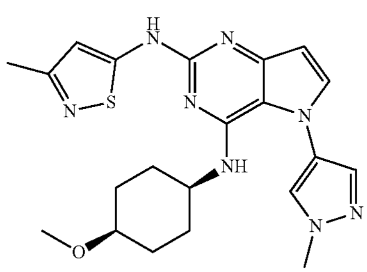 [SMILES: CO[C@H]1CC[C@@H](Nc2nc(Nc3cc(C)ns3)nc3ccn(-c4cnn(C)c4)c23)CC1] | ¹H-NMR (300 MHz, CD₃OD) δ: 8.17 (s, 1H), 7.83 (s, 1H), 7.48 (d, 1H, J = 3.0 Hz), 6.83 (s, 1H), 6.56 (d, 1H, J = 3.0 Hz), 4.44 (s, 1H), 4.04 (s, 3H), 3.38 (s, 1H), 3.33 (s, 3H), 2.42 (s, 3H), 2.53 (s, 3H), 1.12-1.81 (m, 8H).<br>LC-MS (ESI, m/z): [M + H]⁺ = 439.2. |
| 26 | 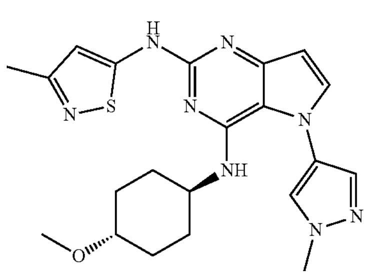 [SMILES: CO[C@H]1CC[C@H](Nc2nc(Nc3cc(C)ns3)nc3ccn(-c4cnn(C)c4)c23)CC1] | ¹H-NMR (300 MHz, DMSO-d₆) δ: 8.23 (s, 1H), 7.81 (s, 1H), 7.54 (d, 1H, J = 2.7 Hz), 6.73 (s, 1H), 6.48-6.49 (m, 1H), 4.14-4.17 (m, 1H), 3.94 (s, 3H), 3.25 (s, 3H), 3.13-3.18 (m, 1H), 2.34 (s, 3H), 1.88-2.08 (m, 4H), 1.20-1.35 (m, 4H).<br>LC-MS (ESI, m/z): [M + H]⁺ = 439.2. |

TABLE 1-continued

| Examples | Structures | Characterization data |
| --- | --- | --- |
| 27 | 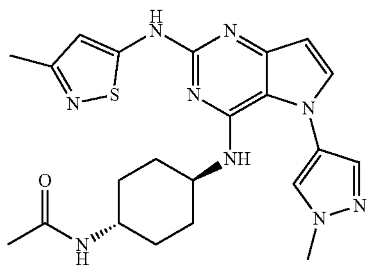 [SMILES: CC(=O)N[C@H]1CC[C@H](Nc2nc(Nc3cc(C)ns3)nc3ccn(-c4cnn(C)c4)c23)CC1] | ¹H-NMR (300 MHz, DMSO-d₆) δ: 8.23 (s, 1H), 7.80 (s, 2H), 7.58 (s, 1H), 6.77 (s, 1H), 6.50-6.51 (m, 1H), 3.95 (s, 3H), 3.47-3.55 (m, 2H), 2.35 (s, 3H), 1.99-2.06 (m, 2H), 1.80-1.90 (m, 2H), 1.79 (s, 3H), 1.24-1.34 (m, 4H). LC-MS (ESI, m/z): [M + H]⁺ = 466.2. |
| 28 | 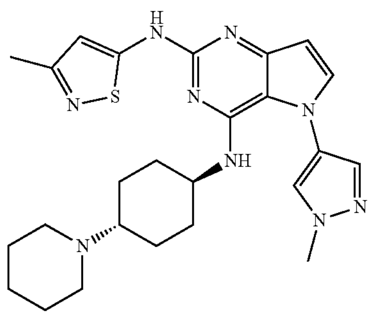 [SMILES: Cc1cc(Nc2nc(N[C@H]3CC[C@H](N4CCCCC4)CC3)c3c(ccn3-c3cnn(C)c3)n2)sn1] | ¹H-NMR (300 MHz, CD₃OD) δ: 8.05 (s, 1H), 7.71 (s, 1H), 7.27 (d, 1H, J = 3.0 Hz), 6.60 (s, 1H), 6.38 (d, 1H, J = 3.0 Hz), 4.18-4.25 (m, 1H), 4.02 (s, 3H), 3.04-3.11 (m, 4H), 2.29-2.34 (m, 4H), 2.15-2.18 (m, 2H), 1.64-1.85 (m, 9H). LC-MS (ESI, m/z): [M + H]⁺ = 492.4. |
| 29 | 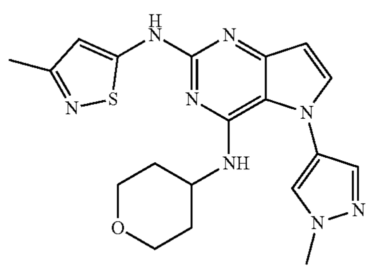 [SMILES: Cc1cc(Nc2nc(NC3CCOCC3)c3c(ccn3-c3cnn(C)c3)n2)sn1] | ¹H-NMR (300 MHz, DMSO-d₆) δ: 8.24 (s, 1H), 7.81 (s, 1H), 7.54-7.55 (m, 1H), 6.72 (s, 1H), 6.50-6.51 (m, 1H), 3.95 (s, 3H), 3.76-3.80 (m, 4H), 3.43-3.55 (m, 1H), 2.35 (s, 3H), 1.93-1.96 (m, 2H), 1.44-1.50 (m, 2H). LC-MS (ESI, m/z): [M + H]⁺ = 411.2. |
| 30 | 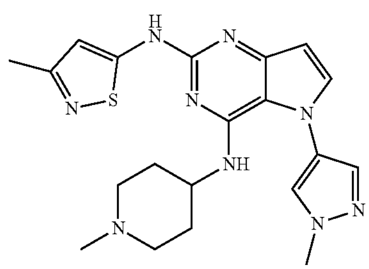 [SMILES: Cc1cc(Nc2nc(NC3CCN(C)CC3)c3c(ccn3-c3cnn(C)c3)n2)sn1] | ¹H-NMR (300 MHz, CDCl₃) δ: 8.16 (s, 1H), 7.83 (s, 1H), 7.55 (d, 1H, J = 2.7 Hz), 6.91 (s, 1H), 6.66 (d, 1H, J = 3.0 Hz), 4.45-4.70 (m, 1H), 4.08 (s, 3H), 3.63-3.77 (m, 2H), 3.20-3.33 (m, 2H), 2.98 (s, 3H), 2.52 (s, 3H), 2.40-2.51 (m, 2H), 1.70-1.90 (m, 2H). LC-MS (ESI, m/z): [M + H]⁺ = 424.2. |
| 31 | 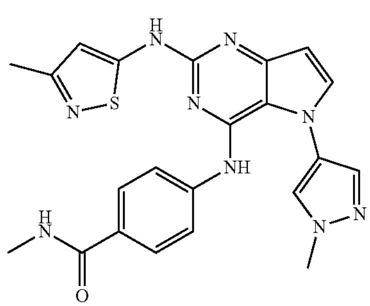 [SMILES: CNC(=O)c1ccc(Nc2nc(Nc3cc(C)ns3)nc3ccn(-c4cnn(C)c4)c23)cc1] | ¹H-NMR (300 MHz, DMSO-d₆) δ: 11.45 (s, 1H), 8.32 (d, 1H, J = 4.8 Hz), 8.26 (s, 1H), 7.81-7.85 (m, 3H), 7.63 (d, 1H, J = 3.0 Hz), 7.55-7.58 (m, 3H), 6.71 (s, 1H), 6.63 (d, 1H, J = 3.0 Hz), 3.95 (s, 3H), 2.70-2.88 (m, 3H), 2.36 (s, 3H). LC-MS (ESI, m/z): [M + H]⁺ = 460.1. |

TABLE 1-continued

| Examples | Structures | Characterization data |
|---|---|---|
| 32 | 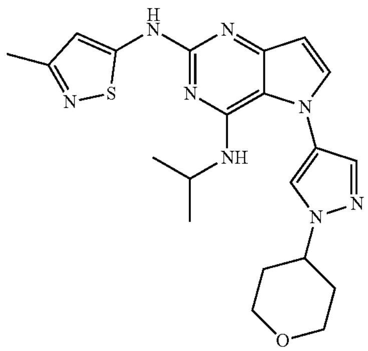 [SMILES: Cc1cc(Nc2nc(NC(C)C)c3c(ccn3-c3cnn(C4CCOCC4)c3)n2)sn1] | $^1$H-NMR (300 MHz, CD$_3$OD) δ: 8.27 (s, 1H), 7.86 (s, 1H), 7.49 (s, 1H), 6.86 (s, 1H), 6.57 (d, 1H, J = 2.7 Hz), 4.54-4.59 (m, 1H), 4.08-4.12 (m, 2H), 3.57-3.66 (m, 2H), 2.43 (s, 3H), 2.11-2.15 (m, 4H), 1.24-1.31 (m, 6H). <br> LC-MS (ESI, m/z): [M + H]$^+$ = 439.3. |
| 33 | 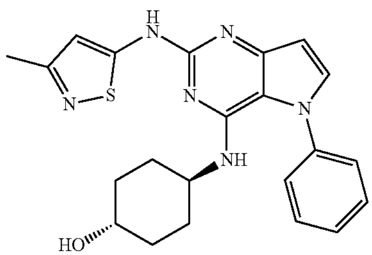 [SMILES: Cc1cc(Nc2nc(N[C@H]3CC[C@H](O)CC3)c3c(ccn3-c3ccccc3)n2)sn1] | $^1$H-NMR (300 MHz, DMSO-d$_6$) δ: 10.66 (s, 1H), 7.48-7.63 (m, 6H), 6.42-6.55 (m, 2H), 4.51-4.65 (m, 2H), 4.00-4.19 (m, 1H), 2.26 (s, 3H), 1.90-2.00 (m, 2H), 1.68-1.80 (m, 2H). <br> LC-MS (ESI, m/z): [M + H]$^+$ = 421.1. |
| 34 | 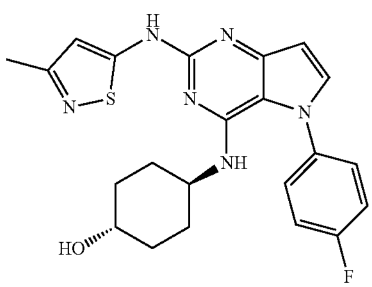 [SMILES: Cc1cc(Nc2nc(N[C@H]3CC[C@H](O)CC3)c3c(ccn3-c3ccc(F)cc3)n2)sn1] | $^1$H-NMR (300 MHz, CD$_3$OD) δ: 7.39-7.43 (m, 2H), 7.23-7.29 (m, 3H), 6.49 (s, 1H), 6.34-6.36 (m, 1H), 4.12-4.16 (m, 1H), 3.40-3.56 (m, 2H), 2.24 (s, 3H), 2.00-2.04 (m, 2H), 1.80-1.83 (m, 2H), 1.33-1.44 (m, 2H), 0.94-1.06 (m, 2H). <br> LC-MS (ESI, m/z): [M + H]$^+$ = 439.1. |
| 35 | 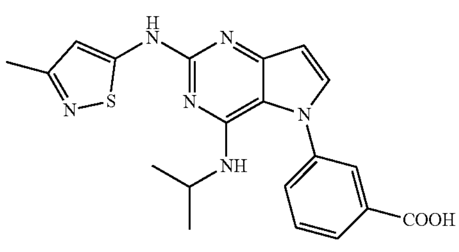 [SMILES: Cc1cc(Nc2nc(NC(C)C)c3c(ccn3-c3cccc(C(=O)O)c3)n2)sn1] | $^1$H-NMR (300 MHz, DMSO-d$_6$) δ: 10.67 (s, 1H), 7.99 (d, 1H, J = 7.5 Hz), 7.86 (s, 1H), 7.71-7.74 (m, 3H), 6.55 (s, 1H), 6.49 (s, 1H), 2.26 (s, 3H), 1.11 (d, 6H, J = 3.3 Hz). <br> LC-MS (ESI, m/z): [M + H]$^+$ = 409.3. |
| 36 | 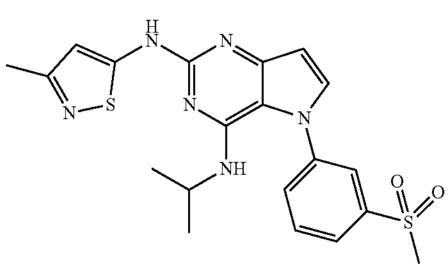 [SMILES: Cc1cc(Nc2nc(NC(C)C)c3c(ccn3-c3cccc(S(C)(=O)=O)c3)n2)sn1] | $^1$H-NMR (300 MHz, CD$_3$OD) δ: 7.99-8.05 (m, 2H), 7.78-7.87 (m, 2H), 7.56 (s, 1H), 6.53-6.61 (m, 2H), 4.61-4.63 (m, 1H), 3.21 (s, 3H), 2.33 (s, 3H), 1.21 (d, 6H, J = 6.3 Hz). <br> LC-MS (ESI, m/z): [M + H]$^+$ = 443.3. |

TABLE 1-continued

| Examples | Structures | Characterization data |
|---|---|---|
| 37 | 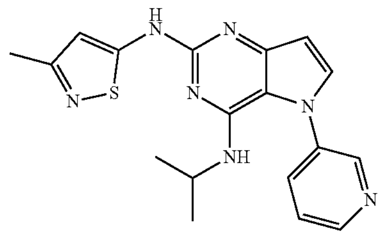 [SMILES: Cc1cc(Nc2nc(NC(C)C)c3c(ccn3-c3cccnc3)n2)sn1] | ¹H-NMR (300 MHz, CDCl₃) δ: 8.02 (d, 1H, J = 15.3 Hz), 8.08 (d, 1H, J = 8.1 Hz), 7.70-7.83 (m, 2H), 6.89 (s, 1H), 6.76 (d, 1H, J = 3.3 Hz), 4.65-4.80 (m, 1H), 2.51 (s, 3H), 1.30 (d, 6H, J = 6.6 Hz). LC-MS (ESI, m/z): [M + H]⁺ = 366.2. |
| 38 | 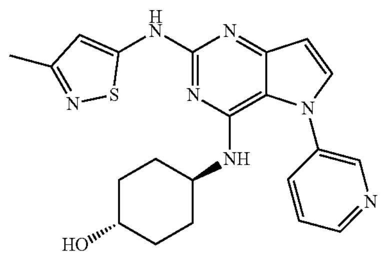 [SMILES: Cc1cc(Nc2nc(N[C@H]3CC[C@H](O)CC3)c3c(ccn3-c3cccnc3)n2)sn1] | ¹H-NMR (300 MHz, DMSO-d₆) δ: 10.67 (s, 1H), 8.73 (d, 1H, J= 2.4 Hz), 8.62 (dd, 1H, J = 1.2 Hz, J = 4.8 Hz), 7.80-7.83 (m, 1H), 7.70 (d, 1H, J = 3.3 Hz), 7.55-7.59 (m, 1H), 7.30-7.43 (m, 2H), 6.55 (s, 1H), 6.49 (d, 1H, J = 2.7 Hz), 5.13 (s, 1H), 4.56-4.58 (m, 1H), 4.43-4.47 (m, 1H), 4.15 (s, 1H), 3.38-3.40 (m, 2H), 2.26 (s, 3H), 1.78-1.99 (m, 4H). LC-MS (ESI, m/z): [M + H]⁺ = 422.1. |
| 39 | 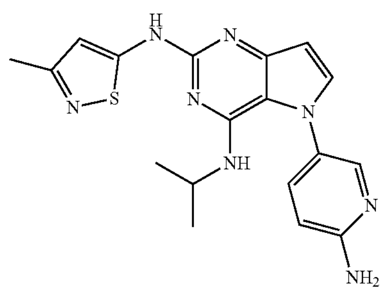 [SMILES: Cc1cc(Nc2nc(NC(C)C)c3c(ccn3-c3ccc(N)nc3)n2)sn1] | ¹H-NMR (300 MHz, CD₃OD) δ: 8.04 (s, 1H), 7.54-7.58 (m, 1H), 7.30-7.31 (m, 1H), 6.73 (d, 1H, J = 9.0 Hz), 6.58 (s, 1H), 6.41-6.42 (m, 1H), 4.54-4.59 (m, 1H), 2.33 (s, 3H), 1.19 (d, 6H, J = 6.3 Hz). LC-MS (ESI, m/z): [M + H]⁺ = 381.2. |
| 40 | 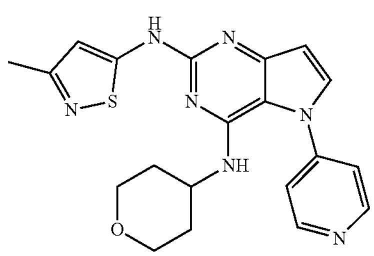 [SMILES: Cc1cc(Nc2nc(NC3CCOCC3)c3c(ccn3-c3ccncc3)n2)sn1] | ¹H-NMR (300 MHz, CD₃OD) δ: 8.83 (dd, 2H, J = 1.2 Hz, J = 5.1 Hz), 7.95 (d, 1H, J = 3.3 Hz), 7.80 (d, 2H, J = 6.6 Hz), 6.83 (s, 2H), 4.50-4.75 (m, 1H), 3.99 (d, 2H, J = 9.6 Hz), 3.60 (t, 2H, J = 11.4 Hz), 2.49 (s, 3H), 2.08 (d, 2H, J = 12.3 Hz), 1.54-1.67 (m, 2H). LC-MS (ESI, m/z): [M + H]⁺ = 408.2. |
| 41 | 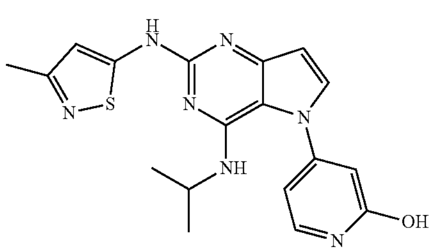 [SMILES: Cc1cc(Nc2nc(NC(C)C)c3c(ccn3-c3ccnc(O)c3)n2)sn1] | ¹H-NMR (300 MHz, CD₃OD) δ: 7.80 (s, 1H), 7.66 (d, 1H, J = 7.2 Hz), 6.70 (s, 1H), 6.64 (d, 1H, J = 6.9 Hz), 6.39 (s, 1H), 2.45 (s, 3H), 1.34 (d, 6H, J = 4.5 Hz). LC-MS (ESI, m/z): [M + H]⁺ = 382.3. |
| 42 | 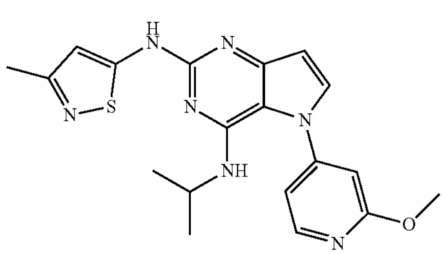 | ¹H-NMR (300 MHz, CDCl₃) δ: 8.31 (d, 1H, J = 4.5 Hz), 7.26 (s, 1H), 6.93 (s, 1H), 6.71 (s, 1H), 6.42-6.52 (m, 2H), 4.75-4.77 (m, 1H), 4.47-4.49 (m, 1H), 4.03 (s, 3H), 2.29 (s, 3H), 1.25 (s, 6H). LC-MS (ESI, m/z): [M + H]⁺ = 396.3. |

TABLE 1-continued

| Examples | Structures | Characterization data |
|---|---|---|
| 43 | 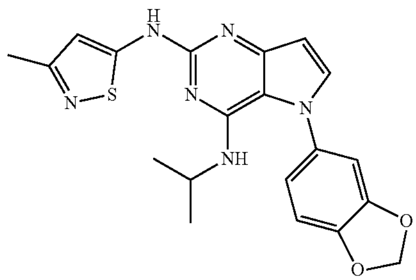 [SMILES: Cc1cc(Nc2nc(NC(C)C)c3c(ccn3-c3ccc4c(c3)OCO4)n2)sn1] | $^1$H-NMR (300 MHz, CD$_3$OD) δ: 7.39-7.43 (m, 2H), 7.10 (d, 1H, J = 7.2 Hz), 6.81-6.87 (m, 2H), 6.49 (s, 1H), 5.83 (s, 1H), 4.12-4.16 (m, 1H), 2.34 (s, 3H), 1.01-1.08 (m, 6H).<br>LC-MS (ESI, m/z): [M + H]$^+$ = 409.3. |
| 44 | 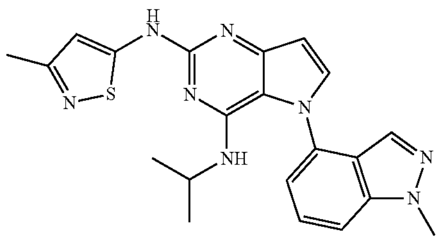 | $^1$H-NMR (300 MHz, CD$_3$OD) δ: 7.93 (s, 1H), 7.85-7.88 (m, 1H), 7.78 (d, 1H, J = 2.7 Hz), 7.65-7.70 (m, 1H), 7.34 (d, 1H, J = 7.2 Hz), 6.86 (s, 1H), 6.73 (d, 1H, J = 3.3 Hz), 4.54 (s, 1H), 4.21 (s, 3H), 2.46 (s, 3H), 0.91-0.99 (m, 6H).<br>LC-MS (ESI, m/z): [M + H]$^+$ =419.1. |

Example 45

Preparation of N$^2$-(1-cyclohexyl-1H-pyrazol-4-yl)-N$^4$-isopropyl-5-(1-methyl-1H-pyrazol-4-yl)-5H-pyrrolo[3,2-d]pyrimidin-2,4-diamine

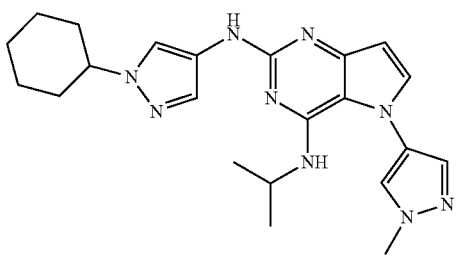 [SMILES: CC(C)Nc1nc(Nc2cnn(C3CCCCC3)c2)nc2ccn(-c3cnn(C)c3)c12]

Step 1: Preparation of 2,4-dichloro-5-(1-methyl-1H-pyrazol-4-yl)-5H-pyrrolo[3,2-d]pyrimidine

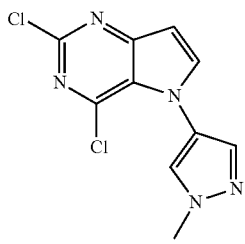 [SMILES: Cn1cc(-n2ccc3nc(Cl)nc(Cl)c32)cn1]

2,4-Dichloro-5H-pyrrolo[3,2-d]pyrimidine (376 mg, 2 mmol), 1-methyl-4-(4,4,5,5-tetramethyl-1,3,2-dioxaborolan-2-yl)-1H-pyrazole (832 mg, 4 mmol), anhydrous copper acetate (363 mg, 2 mmol), and pyridine (158 mg, 2 mmol) were added into dimethylsulfoxide (10 mL). The reaction liquid was heated to 110° C. and stirred overnight. The reaction liquid was naturally cooled down to room temperature, followed by adding ethyl acetate (50 mL). The insolubles were removed by filtration. The filtrate was washed with water (40 mL×2), dried over anhydrous sodium sulfate, and concentrated under reduced pressure. The reaction mixture was beaten in a mixed solution of n-hexane/ethyl acetate (2/1, 30 mL), and filtered to give 150 mg of a pale yellow solid. Yield: 28.0%. MS (ESI, m/z): [M+H]$^+$: 267.9.

Step 2: Preparation of [2-chloro-5-(1-methyl-1H-pyrazol-4-yl)-5H-pyrrolo[3,2-d]pyrimidin-4-yl]isopropylamine

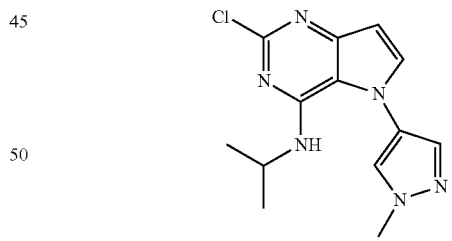

2,4-Dichloro-5-(1-methyl-1H-pyrazol-4-yl)-5H-pyrrolo[3,2-d]pyrimidine (150 mg, 0.56 mmol), isopropylamine (59 mg, 1 mmol) and N,N-diisopropylethylamine (217 mg, 1.68 mmol) were added into ethanol (10 mL). The reaction liquid was refluxed for 3 hours, naturally cooled down to room temperature, concentrated, diluted with ethyl acetate (15 mL), and washed with water (10 mL×2). The organic phase was dried over anhydrous sodium sulfate, and concentrated under reduced pressure to give 150 mg of a yellow solid. Yield: 92.4%. MS (ESI, m/z): [M+H]$^+$: 291.3.

Step 3: Preparation of 1-cyclohexyl-1H-pyrazol-4-ylamine

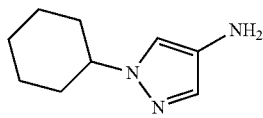 [SMILES: Nc1cnn(C2CCCCC2)c1]

4-Nitro-1H-pyrazole (220 mg, 2 mmol), bromocyclohexane (650 mg, 4 mmol), and potassium carbonate (276 mg, 2 mmol) were added into N,N-dimethylformamide (5 mL), and stirred overnight at room temperature. The reaction liquid was diluted with water (50 mL), and extracted with ethyl acetate (20 mL×3). The organic phase was collected, concentrated, and separated by flash column chromatography (eluent: n-hexane:ethyl acetate=2:1) to give 190 mg of a pale yellow solid. The resulting solid was dissolved in ethanol (10 mL), added with 10% palladium on carbon (10 mg), and stirred under hydrogen atmosphere for two hours, followed by filtration and concentration to give 160 mg of a pale yellow solid. Yield: 50%. MS (ESI, m/z): [M+H]$^+$: 166.3.

Step 4: Preparation of N$^2$-(1-cyclohexyl-1H-pyrazol-4-yl)-N$^4$-isopropyl-5-(1-methyl-1H-pyrazol-4-yl)-5H-pyrrolo[3,2-d]pyrimidin-2,4-diamine The product obtained in Step 2 (30 mg, 0.1 mmol), the product obtained in Step 3 (30 mg, 0.18 mmol) and 2 drops of trifluoroacetic acid were added into isopropanol (2 mL), and reacted under microwave at 100° C. for 1 hour. The reaction liquid was cooled down to room temperature, and concentrated. The mixture was purified by preparative liquid chromatography to give 10 mg of a white solid. Yield: 23.8%. MS (ESI, m/z): [M+H]$^+$: 420.3; $^1$H-NMR (300 MHz, CD$_3$OD) δ: 8.16 (s, 1H), 7.95 (s, 1H), 7.83 (s, 1H), 7.68 (s, 1H), 7.41 (d, 1H, J=3.0 Hz), 6.46 (d, 1H, J=3.0 Hz), 4.40-4.50 (m, 1H), 4.13-4.30 (m, 1H), 4.07 (s, 3H), 2.14-2.30 (m, 2H), 1.90-2.05 (m, 2H), 1.78-1.88 (m, 2H), 1.50-1.60 (m, 2H), 1.38-1.45 (m, 2H), 1.26 (d, 6H, J=6.6 Hz).

The following compounds (in Table 2) were prepared from similar starting materials by a synthesis method analogous to that as described in Example 45.

TABLE 2

| Examples | Structures | Characterization data |
| --- | --- | --- |
| 46 | 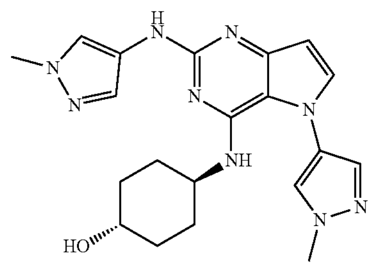 [SMILES: Cn1cc(Nc2nc(N[C@H]3CC[C@H](O)CC3)c3c(ccn3-c3cnn(C)c3)n2)cn1] | $^1$H-NMR (300 MHz, CD$_3$OD) δ: 8.11 (s, 1H), 7.85 (s, 1H), 7.77 (s, 1H), 7.60 (s, 1H), 7.35 (d, 1H, J = 3.0 Hz), 6.40 (d, 1H, J = 3.3 Hz), 4.05-4.11 (m, 1H), 4.02 (s, 3H), 3.93 (s, 3H), 3.53-3.55 (m, 1H), 2.04-2.08 (m, 2H), 1.88-1.92 (m, 2H), 1.20-1.46 (m, 4H). LC-MS (ESI, m/z): [M + H]$^+$ = 408.3. |
| 47 | 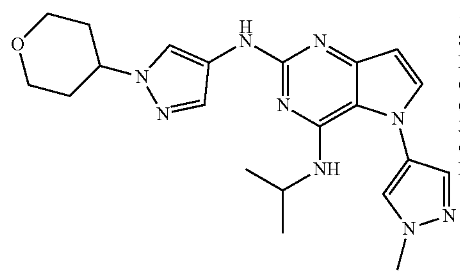 | $^1$H-NMR (300 MHz, CD$_3$OD) δ: 8.18 (s, 1H), 8.01 (s, 1H), 7.83 (s, 1H), 7.85 (d, 1H, J = 0.6 Hz), 7.72 (s, 1H), 7.44 (d, 1H, J = 3.3 Hz), 6.48 (d, 1H, J = 3.0 Hz), 4.40-4.60 (m, 2H), 4.15 (dt, 2H, J = 3.3 Hz, J = 11.4 Hz), 4.09 (s, 3H), 3.60-3.72 (m, 2H), 2.10-2.20 (m, 2H), 1.28 (d, 6H, J = 6.6 Hz). LC-MS (ESI, m/z): [M + H]$^+$ = 422.3. |

Example 48

Preparation of 5-{5-(1-methyl-1H-pyrazol-4-yl)-4-[methyl-(tetrahydropyran-4-yl)amino]-5H-pyrrolo[3,2-d]pyrimidin-2-ylamino}thiophene-3-carboxylic acid methylamide

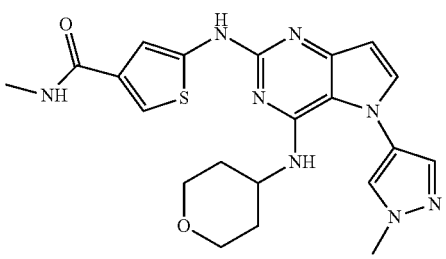 [SMILES: CNC(=O)c1csc(Nc2nc(NC3CCOCC3)c3c(ccn3-c3cnn(C)c3)n2)c1]

Step 1: Preparation of 2,4-dichloro-5-(1-methyl-1H-pyrazol-4-yl)-5H-pyrrolo[3,2-d]pyrimidine

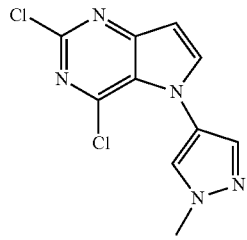 [SMILES: Cn1cc(-n2ccc3nc(Cl)nc(Cl)c32)cn1]

2,4-Dichloro-5H-pyrrolo[3,2-d]pyrimidine (376 mg, 2 mmol), 1-methyl-4-(4,4,5,5-tetramethyl-1,3,2-dioxaborolan-2-yl)-1H-pyrazole (832 mg, 4 mmol), anhydrous copper acetate (363 mg, 2 mmol), and pyridine (158 mg, 2 mmol) were added into dimethylsulfoxide (10 mL). The reaction liquid was heated to 110° C. and stirred overnight. The reaction liquid was naturally cooled down to room temperature, followed by adding ethyl acetate (50 mL). The insolubles were removed by filtration. The filtrate was washed with water (40 mL×2), dried over anhydrous sodium sulfate, and concentrated under reduced pressure. The reaction mixture was beaten in a mixed solution of n-hexane/ethyl acetate (2/1, 30 mL), and filtered to give 150 mg of a pale yellow solid. Yield: 28.0%. MS (ESI, m/z): [M+H]$^+$: 267.9.

Step 2: Preparation of [2-chloro-5-(1-methyl-1H-pyrazol-4-yl)-5H-pyrrolo[3,2-d]pyrimidin-4-yl]-(tetrahydropyran-4-yl)-amine

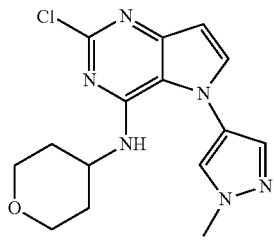

2,4-Dichloro-5-(1-methyl-1H-pyrazol-4-yl)-5H-pyrrolo[3,2-d]pyrimidine (150 mg, 0.56 mmol), tetrahydropyran-4-ylamine (113 mg, 1.12 mmol), and N,N-diisopropylethylamine (217 mg, 1.68 mmol) were added into isopropanol (10 mL). The reaction liquid was refluxed for 3 hours, naturally cooled down to room temperature, diluted with ethyl acetate (15 mL), and washed with water (10 mL×2). The organic phase was dried over anhydrous sodium sulfate, and concentrated under reduced pressure. The residue was beaten in a mixed solution of n-hexane/ethyl acetate (2/1, 30 mL), and filtered to give 120 mg of a brown solid. Yield: 64.5%. MS (ESI, m/z): [M+H]$^+$: 333.3.

Step 3: Preparation of 5-nitrothiophene-3-carboxylic acid methylamide

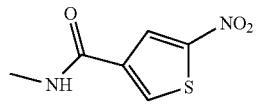

5-Nitrothiophene-3-carboxylic acid (173 mg, 1 mmol), methylamine hydrochloride (135 mg, 2 mmol), 2-(7-oxobenzotriazole)-N,N,N',N'-tetramethyluronium hexafluorophosphate (760 mg, 2 mmol), and N,N-diisopropylethylamine (387 mg, 3 mmol) were added into N,N-dimethylformamide (10 mL). The reaction liquid was stirred for 3 hours at room temperature, diluted with ethyl acetate (15 mL), and washed with water (10 mL×2). The organic phase was dried over anhydrous sodium sulfate, concentrated under reduced pressure, and separated by flash column chromatography (eluent: n-hexane:ethyl acetate=2:1) to give 150 mg of a brown solid. Yield: 80.6%. MS (ESI, m/z): [M+H]$^+$: 187.3.

Step 4: Preparation of 5-aminothiophene-3-carboxylic acid methylamide

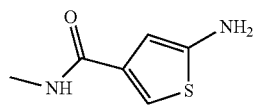

5-Nitrothiophene-3-carboxylic acid methylamide (150 mg, 0.8 mmol) and palladium on carbon (17 mg, 0.2 mmol) were added into methanol (10 mL). The reaction was carried out under hydrogen atmosphere at room temperature for 5 hours. The reaction mixture was filtered, and the filtrate was concentrated under reduced pressure to give 100 mg of a yellow solid. Yield: 80.4%. MS (ESI, m/z): [M+H]$^+$: 157.3.

Step 5: Preparation of 5-{5-(1-methyl-1H-pyrazol-4-yl)-4-[methyl-(tetrahydropyran-4-yl) amino]-5H-pyrrolo[3,2-d]pyrimidin-2-ylamino}thiophene-3-carboxylic acid methylamide The product obtained in Step 2 (100 mg, 0.3 mmol), 5-aminothiophene-3-carboxylic acid methylamide (70 mg, 0.45 mmol), and 2 drops of trifluoroacetic acid were dissolved in isopropanol (3.0 mL). The reaction liquid was reacted under microwave condition at 110° C. for 2 hours. The reaction liquid was cooled down to room temperature, concentrated under reduced pressure, and separated by flash column chromatography (eluent: dichloromethane:methanol=10:1) to give 3.5 mg of a pale yellow solid. Yield: 2.2%. MS (ESI, m/z): [M+H]$^+$: 453.3; $^1$H-NMR (300 MHz, CD$_3$OD) δ: 8.06 (s, 1H), 7.76-7.77 (m, 1H), 7.35 (d, 1H, J=1.8 Hz), 7.26 (d, 1H, J=3.0 Hz), 6.92 (d, 1H, J=1.8 Hz), 6.36 (d, 1H, J=3.0 Hz), 4.46-4.53 (m, 1H), 4.03 (s, 3H), 3.83-3.90 (m, 2H), 3.56-3.64 (m, 2H), 2.89 (s, 3H), 2.05-2.09 (m, 2H), 1.39-1.46 (m, 2H).

The following compounds (in Table 3) were prepared from similar starting materials by a synthesis method analogous to that as described in Example 48.

TABLE 3

| Examples | Structures | Characterization data |
|---|---|---|
| 49 | 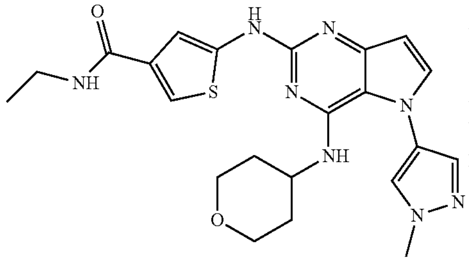 [SMILES: CCNC(=O)c1csc(Nc2nc(NC3CCOCC3)c3c(ccn3-c3cnn(C)c3)n2)c1] | ¹H-NMR (300 MHz, CD₃OD) δ: 8.15 (s, 1H), 7.83 (s, 1H), 7.71 (d, 1H, J = 1.5 Hz), 7.49 (d, 1H, J = 3.0 Hz), 7.24 (d, 1H, J = 1.8 Hz), 6.51 (d, 1H, J = 3.0 Hz), 4.48-4.59 (m, 1H), 4.04 (s, 3H), 3.84-3.91 (m, 2H), 3.54-3.62 (m, 2H), 3.36-3.43 (m, 2H), 2.00-2.10 (m, 2H), 1.47-1.60 (m, 2H), 1.23 (t, 3H, J = 7.2 Hz). LC-MS (ESI, m/z): [M + H]⁺ = 467.3. |
| 50 | 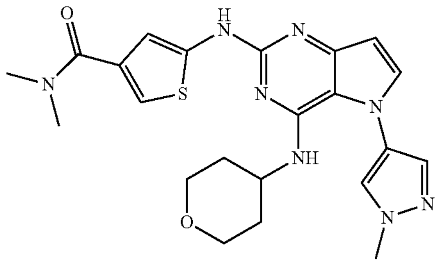 [SMILES: CN(C)C(=O)c1csc(Nc2nc(NC3CCOCC3)c3c(ccn3-c3cnn(C)c3)n2)c1] | ¹H-NMR (300 MHz, CD₃OD) δ: 8.06 (s, 1H), 7.76-7.77 (m, 1H), 7.24 (d, 1H, J = 3.3 Hz), 7.01 (d, 1H, J = 1.8 Hz), 6.70 (d, 1H, J = 1.8 Hz), 6.34 (d, 1H, J = 3.0 Hz), 4.46-4.56 (m, 1H), 4.03 (s, 3H), 3.83-3.88 (m, 2H), 3.55-3.65 (m, 2H), 3.09-3.18 (m, 6H), 2.05-2.09 (m, 2H), 1.36-1.46 (m, 2H). LC-MS (ESI, m/z): [M + H]⁺ = 467.3. |
| 51 | 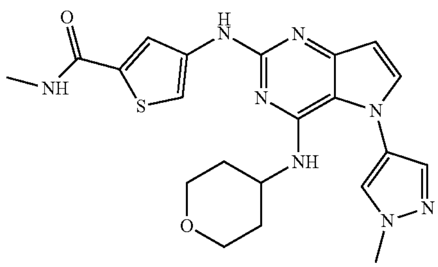 [SMILES: CNC(=O)c1cc(Nc2nc(NC3CCOCC3)c3c(ccn3-c3cnn(C)c3)n2)cs1] | ¹H-NMR (300 MHz, DMSO-d₆) δ: 10.26-10.31 (m, 1H), 8.48-8.49 (m, 1H), 8.24 (s, 1H), 7.78-7.80 (m, 2H), 7.58-7.64 (m, 2H), 6.47 (d, 1H, J = 3.0 Hz), 4.18-4.26 (m, 1H), 3.94 (s, 3H), 3.73-3.76 (m, 2H), 3.33-3.40 (m, 2H), 2.76-2.77 (m, 3H), 1.83-1.86 (m, 2H), 1.41-1.53 (m, 2H). LC-MS (ESI, m/z): [M + H]⁺ = 453.3. |
| 52 | 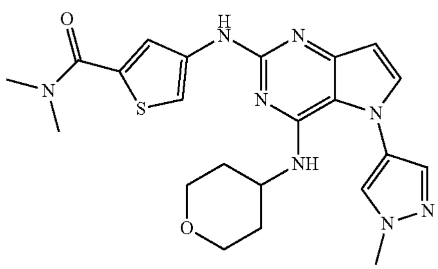 [SMILES: CN(C)C(=O)c1cc(Nc2nc(NC3CCOCC3)c3c(ccn3-c3cnn(C)c3)n2)cs1] | ¹H-NMR (300 MHz, DMSO-d₆) δ: 10.07 (s, 1H), 8.24 (s, 1H), 7.81 (s, 1H), 7.68 (s, 1H), 7.56-7.58 (m, 2H), 6.46 (d, 1H, J = 3.0 Hz), 4.15-4.22 (m, 1H), 3.94 (s, 3H), 3.72-3.76 (m, 2H), 3.35-3.42 (m, 2H), 3.11 (s, 6H), 1.84-1.87 (m, 2H), 1.45-1.48 (m, 2H). LC-MS (ESI, m/z): [M + H]⁺ = 467.3. |

Example 53

Preparation of N⁴-methyl-N²-(3-methylisothiazol-5-yl)-5-(1-methyl-1H-pyrazol-4-yl)-N⁴-(tetrahydropyran-4-yl)-5H-pyrrolo[3,2-d]pyrimidine-2,4-diamine

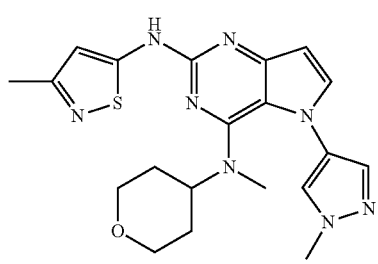 [SMILES: Cc1cc(Nc2nc(N(C)C3CCOCC3)c3c(ccn3-c3cnn(C)c3)n2)sn1]

Step 1: Preparation of 2,4-dichloro-5-(1-methyl-1H-pyrazol-4-yl)-5H-pyrrolo[3,2-d]pyrimidine

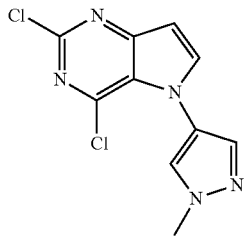 [SMILES: Cn1cc(-n2ccc3nc(Cl)nc(Cl)c32)cn1]

2,4-Dichloro-5H-pyrrolo[3,2-d]pyrimidine (376 mg, 2 mmol), 1-methyl-4-(4,4,5,5-tetramethyl-1,3,2-dioxaborolan-2-yl)-1H-pyrazole (832 mg, 4 mmol), anhydrous copper acetate (363 mg, 2 mmol), and pyridine (158 mg, 2 mmol)

were added into dimethylsulfoxide (10 mL). The reaction liquid was heated to 110° C. and stirred overnight. The reaction liquid was naturally cooled down to room temperature, followed by adding ethyl acetate (50 mL). The insolubles were removed by filtration. The filtrate was washed with water (40 mL×2), dried over anhydrous sodium sulfate, and concentrated under reduced pressure. The residue was beaten in a mixed solution of n-hexane/ethyl acetate (2/1, 30 mL), and filtered to give 150 mg of a pale yellow solid. Yield: 28.0%. MS (ESI, m/z): [M+H]$^+$: 267.9.

Step 2: Preparation of 2-chloro-5-(1-methyl-1H-pyrazol-4-yl)-5H-pyrrolo[3,2-d]pyrimidin-4-yl]-(tetrahydropyran-4-yl)-amine

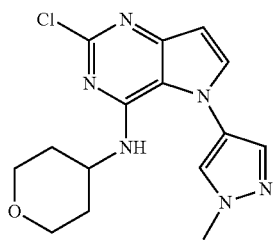 [SMILES: Cn1cc(-n2ccc3nc(Cl)nc(NC4CCOCC4)c32)cn1]

2,4-Dichloro-5-(1-methyl-1H-pyrazol-4-yl)-5H-pyrrolo[3,2-d]pyrimidine (150 mg, 0.56 mmol), tetrahydropyran-4-ylamine (113 mg, 1.12 mmol), and N,N-diisopropylethylamine (217 mg, 1.68 mmol) were added into isopropanol (10 mL). The reaction liquid was refluxed for 3 hours, naturally cooled down to room temperature, diluted with ethyl acetate (15 mL), and washed with water (10 mL×2). The organic phase was dried over anhydrous sodium sulfate, and concentrated under reduced pressure. The residue was beaten in a mixed solution of n-hexane/ethyl acetate (2/1, 30 mL), and filtered to obtain 120 mg of a brown solid. Yield: 64.5%. MS (ESI, m/z): [M+H]$^+$: 333.3.

Step 3: Preparation of [2-chloro-5-(1-methyl-1H-pyrazol-4-yl)-5H-pyrrolo[3,2-d]pyrimidin-4-yl]-methyl-(tetrahydropyran-4-yl)-amine

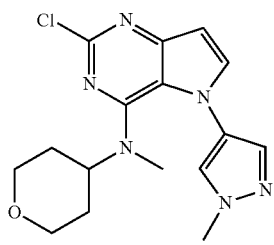 [SMILES: CN(c1nc(Cl)nc2ccn(-c3cnn(C)c3)c12)C1CCOCC1]

The product obtained in Step 2 (110 mg, 0.33 mmol) was dissolved in tetrahydrofuran (10 mL). Sodium hydride (50 mg, 0.83 mmol) was added and the mixture was stirred for fifteen minutes. Methyl iodide (141 mg, 1 mmol) was added and the mixture was stirred at room temperature for two days. The reaction was quenched with water (30 mL), and extracted with ethyl acetate (10 mL×2). The organic phase was collected and concentrated. The residue was purified by flash column chromatography (eluent: ethyl acetate:methanol=20:1) to give 60 mg of a white solid. Yield: 52.5%. MS (ESI, m/z): [M+H]$^+$: 347.3.

Step 4: Preparation of N$^4$-methyl-N$^2$-(3-methylisothiazol-5-yl)-5-(1-methyl-1H-pyrazol-4-yl)-N$^4$-(tetrahydropyran-4-yl)-5H-pyrrolo[3,2-d]pyrimidine-2,4-diamine The product of Step 3 (60 mg, 0.17 mmol), 3-methylisothiazol-5-ylamine hydrochloride (39 mg, 0.26 mmol), cesium carbonate (169 mg, 0.52 mmol), 4,5-bis(diphenylphosphino)-9,9-dimethylxanthene (9 mg, 0.015 mmol) and tris(dibenzylidenepropanone)dipalladium (9 mg, 0.01 mmol) were dissolved in 1,4-dioxane/water (20/1, 1.5 mL). The reaction liquid was reacted under microwave condition at 120° C. for 2 hours. The reaction liquid was cooled down to room temperature, concentrated under reduced pressure, and purified by preparative liquid chromatography to give 25 mg of a white solid. Yield: 34.0%. MS (ESI, m/z): [M+H]$^+$: 425.3; $^1$H-NMR (300 MHz, CD$_3$OD) δ: 7.96 (s, 1H), 7.67 (s, 1H), 7.61 (d, 1H, J=2.4 Hz), 6.82 (s, 1H), 6.67 (d, 1H, J=2.4 Hz), 3.90-4.03 (m, 3H), 3.95 (s, 3H), 3.36-3.55 (m, 2H), 2.80 (s, 3H), 2.47 (s, 3H), 1.80-1.92 (m, 2H), 1.35-1.60 (m, 2H).

Example 54

Preparation of [4-isopropoxy-5-(1-methyl-1H-pyrazol-4-yl)-5H-pyrrolo[3,2-d]pyrimidin-2-yl]-(3-methylisothiazol-5-yl)amine

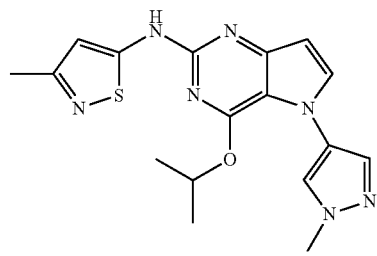 [SMILES: Cc1cc(Nc2nc(OC(C)C)c3c(ccn3-c3cnn(C)c3)n2)sn1]

Step 1: Preparation of 2,4-dichloro-5-(1-methyl-1H-pyrazol-4-yl)-5H-pyrrolo[3,2-d]pyrimidine

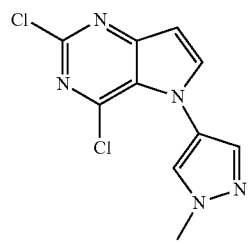 [SMILES: Cn1cc(-n2ccc3nc(Cl)nc(Cl)c32)cn1]

2,4-Dichloro-5H-pyrrolo[3,2-d]pyrimidine (376 mg, 2 mmol), 1-methyl-4-(4,4,5,5-tetramethyl-1,3,2-dioxaborolan-2-yl)-1H-pyrazole (832 mg, 4 mmol), anhydrous copper acetate (363 mg, 2 mmol), and pyridine (158 mg, 2 mmol) were added into dimethylsulfoxide (10 mL). The reaction liquid was heated to 110° C. and stirred overnight. The reaction liquid was naturally cooled down to room temperature, followed by adding ethyl acetate (50 mL). The insolubles were removed by filtration. The filtrate was washed with water (40 mL×2), dried over anhydrous sodium sulfate, and concentrated under reduced pressure. The residue was beaten in a mixed solution of n-hexane/ethyl acetate (2/1, 30 mL), and filtered to give 150 mg of a pale yellow solid. Yield: 28.0%. MS (ESI, m/z): [M+H]+: 267.9.

Step 2: Preparation of 2-chloro-4-isopropoxy-5-(1-methyl-1H-pyrazol-4-yl)-5H-pyrrolo[3,2-d]pyrimidine

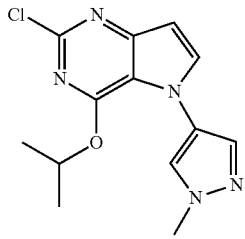 [SMILES: CC(C)Oc1nc(Cl)nc2ccn(-c3cnn(C)c3)c12]

2,4-Dichloro-5-(1-methyl-1H-pyrazol-4-yl)-5H-pyrrolo[3,2-d]pyrimidine (150 mg, 0.56 mmol) and isopropanol (67 mg, 1.12 mmol) were added into N-methylpyrrolidone (20 mL), followed by adding sodium hydride (27 mg, 1.12 mmol). The mixture was stirred at room temperature for 1 hour. The reaction was quenched with water (20 mL), and extracted with ethyl acetate (20 mL×3). The organic phase was dried over anhydrous sodium sulfate, and concentrated under reduced pressure to give 110 mg of a yellow solid. Yield: 67.5%. MS (ESI, m/z): [M+H]+: 292.2.

Step 3: Preparation of [4-isopropoxy-5-(1-methyl-1H-pyrazol-4-yl)-5H-pyrrolo[3,2-d]pyrimidin-2-yl]-(3-methylisothiazol-5-yl)amine The product obtained from Step 2 (29 mg, 0.1 mmol), 3-methylisothiazol-5-ylamine hydrochloride (23 mg, 0.15 mmol), cesium carbonate (130 mg, 0.4 mmol), 4,5-bis(diphenylphosphino)-9,9-dimethylxanthene (9 mg, 0.015 mmol), and tris(dibenzylidenepropanone)dipalladium (9 mg, 0.01 mmol) were dissolved in 1,4-dioxane/water (20/1, 1.5 mL). The reaction liquid was reacted under microwave conditions at 130° C. for 1 hour. The reaction liquid was cooled down to room temperature, concentrated under reduced pressure, and separated by flash column chromatography (eluent: dichloromethane:methanol=10:1) to give 10 mg of a pale yellow solid. Yield: 27%. MS (ESI, m/z): [M+H]+: 370.2; 1H-NMR (300 MHz, CD3OD) δ: 7.92 (s, 1H), 7.67 (s, 1H), 7.56 (d, 1H, J=3.3 Hz), 6.79 (s, 1H), 6.67 (d, 1H, J=3.0 Hz), 5.42-5.62 (m, 1H), 3.96 (s, 3H), 2.52 (s, 3H), 1.36 (d, 6H, J=6.3 Hz).

The following compounds (in Table 4) were prepared from similar starting materials by a synthesis method analogous to that as described in Example 54.

TABLE 4

| Examples | Structures | Characterization data |
|---|---|---|
| 55 | 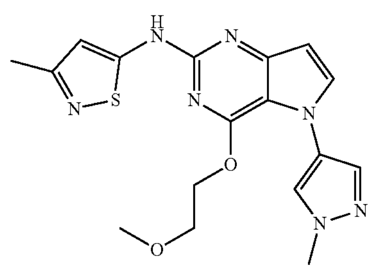 [SMILES: COCCOc1nc(Nc2cc(C)ns2)nc2ccn(-c3cnn(C)c3)c12] | 1H-NMR (300 MHz, CD3OD) δ: 7.96 (s, 1H), 7.72 (s, 1H), 7.59 (d, 1H, J = 3.0 Hz), 6.74 (s, 1H), 6.65 (d, 1H, J = 3.0 Hz), 4.62-4.65 (m, 2H), 3.96 (s, 3H), 3.70-3.73 (m, 2H), 3.39 (s, 3H), 2.49 (s, 3H). LC-MS (ESI, m/z): [M + H]+ = 386.1. |
| 56 | 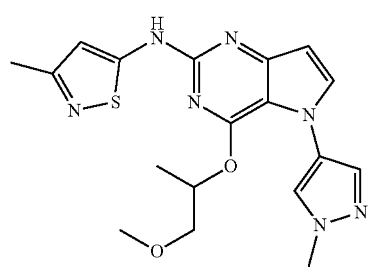 [SMILES: COCC(C)Oc1nc(Nc2cc(C)ns2)nc2ccn(-c3cnn(C)c3)c12] | 1H-NMR (300 MHz, DMSO-d6) δ: 11.28-11.91 (m, 1H), 8.04 (s, 1H), 7.70-7.72 (m, 2H), 6.71 (s, 1H), 6.61 (d, 1H, J = 2.7 Hz), 5.52-5.57 (m, 1H), 3.89 (s, 3H), 3.51-3.53 (m, 2H), 3.26 (s, 3H), 2.36 (s, 3H), 1.32 (d, 3H, J = 6.3 Hz). LC-MS (ESI, m/z): [M + H]+ = 400.2. |
| 57 | 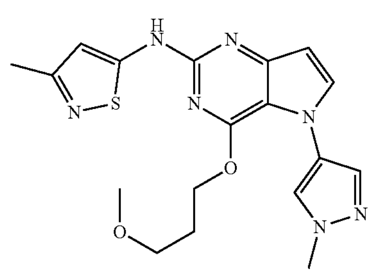 [SMILES: COCCCOc1nc(Nc2cc(C)ns2)nc2ccn(-c3cnn(C)c3)c12] | 1H-NMR (300 MHz, CD3OD) δ: 7.94 (s, 1H), 7.67 (s, 1H), 7.52 (d, 1H, J = 3.0 Hz), 6.72 (s, 1H), 6.61 (d, 1H, J = 3.0 Hz), 4.48-4.52 (m, 2H), 3.97 (s, 3H), 3.34-3.36 (m, 2H), 3.30 (s, 3H), 2.49 (s, 3H), 1.91-2.00 (m, 2H). LC-MS (ESI, m/z): [M + H]+ = 400.1. |

TABLE 4-continued

| Examples | Structures | Characterization data |
|---|---|---|
| 58 | 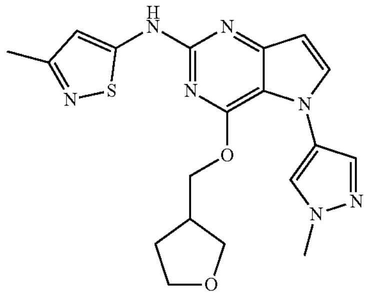 [SMILES: Cc1cc(Nc2nc(OCC3CCOC3)c3c(ccn3-c3cnn(C)c3)n2)sn1] | ¹H-NMR (300 MHz, DMSO-d₆) δ: 8.10 (s, 1H), 7.70-7.73 (m, 2H), 6.66 (s, 1H), 6.60 (s, 1H), 4.41-4.54 (m, 3H), 4.11-4.19 (m, 2H), 3.88 (s, 3H), 2.33 (s, 3H), 1.72-1.96 (m, 3H), 1.50-1.61 (m, 1H).<br>LC-MS (ESI, m/z): [M + H]⁺ = 412.0. |
| 59 | 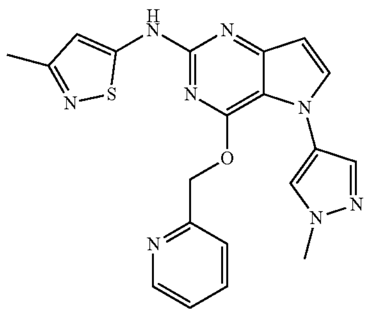 [SMILES: Cc1cc(Nc2nc(OCc3ccccn3)c3c(ccn3-c3cnn(C)c3)n2)sn1] | ¹H-NMR (300 MHz, DMSO-d₆) δ: 8.61 (d, 1H, J = 4.5 Hz), 8.09 (s, 1H), 7.84-7.90 (m, 1H), 7.73-7.74 (m, 2H), 7.38-7.42 (m, 1H), 7.20 (d, 1H, J = 7.8 Hz), 6.65-6.71 (m, 2H), 5.62 (s, 2H), 3.81 (s, 3H), 2.36 (s, 3H).<br>LC-MS (ESI, m/z): [M + H]⁺ = 419.2. |
| 60 | 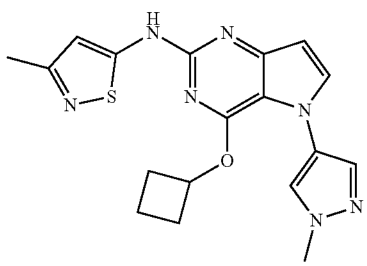 [SMILES: Cc1cc(Nc2nc(OC3CCC3)c3c(ccn3-c3cnn(C)c3)n2)sn1] | ¹H-NMR (300 MHz, CD₃OD) δ: 7.93 (s, 1H), 7.68 (s, 1H), 7.55 (d, 1H, J = 3.0 Hz), 6.75 (s, 1H), 6.64 (d, 1H, J = 3.0 Hz), 5.32-5.42 (m, 1H), 3.96 (s, 3H), 2.42-2.60 (m, 5H), 2.02-2.15 (m, 2H), 1.80-1.92 (m, 1H), 1.67-1.77 (m, 1H).<br>LC-MS (ESI, m/z): [M + H]⁺ = 382.2. |
| 61 | 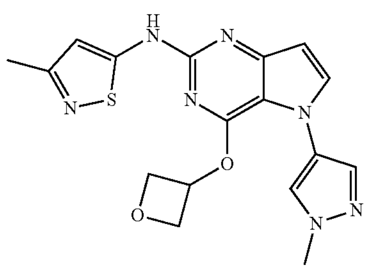 [SMILES: Cc1cc(Nc2nc(OC3COC3)c3c(ccn3-c3cnn(C)c3)n2)sn1] | ¹H-NMR (300 MHz, CD₃OD) δ: 8.04 (s, 1H), 7.79 (s, 1H), 7.64 (d, 1H, J = 3.0 Hz), 6.78 (s, 1H), 6.72 (d, 1H, J = 3.0 Hz), 5.81-5.88 (m, 1H), 5.03 (t, 2H, J = 7.2 Hz), 4.65 (t, 2H, J = 4.5 Hz), 4.00 (s, 3H), 2.51 (s, 3H).<br>LC-MS (ESI, m/z): [M + H]⁺ = 384.2. |
| 62 | 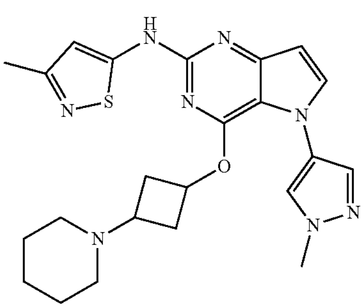 [SMILES: Cc1cc(Nc2nc(OC3CC(N4CCCCC4)C3)c3c(ccn3-c3cnn(C)c3)n2)sn1] | ¹H-NMR (300 MHz, CD₃OD) δ: 7.95 (s, 1H), 7.66 (s, 1H), 7.38-7.39 (m, 1H), 6.57 (s, 1H), 6.41-6.42 (m, 1H), 5.11-5.16 (m, 1H), 3.97 (s, 3H), 3.31 (m, 1H), 2.85-2.97 (m, 2H), 2.68 (m, 4H), 2.33 (s, 3H), 2.14-2.20 (m, 2H), 1.70 (m, 4H), 1.56 (m, 2H).<br>LC-MS (ESI, m/z): [M + H]⁺ = 465.3. |

TABLE 4-continued

| Examples | Structures | Characterization data |
|---|---|---|
| 63 | 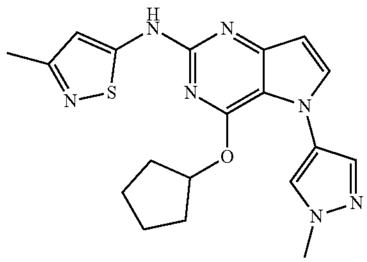 [SMILES: Cc1cc(Nc2nc(OC3CCCC3)c3c(ccn3-c3cnn(C)c3)n2)sn1] | $^1$H-NMR (300 MHz, CD$_3$OD) δ: 7.90 (s, 1H), 7.64 (s, 1H), 7.50 (d, 1H, J = 3.0 Hz), 6.72 (s, 1H), 6.61 (d, 1H, J = 3.3 Hz), 5.67-5.71 (m, 1H), 3.95 (s, 3H), 2.48 (s, 3H), 1.91-1.97 (m, 2H), 1.74-1.82 (m, 1H), 1.57-1.68 (m, 4H). LC-MS (ESI, m/z): [M + H]$^+$ = 396.3. |
| 64 | 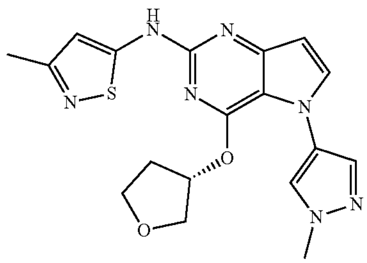 [SMILES: Cc1cc(Nc2nc(O[C@H]3CCOC3)c3c(ccn3-c3cnn(C)c3)n2)sn1] | $^1$H-NMR (300 MHz, DMSO-d$_6$) δ: 8.04 (s, 1H), 7.68-7.71 (m, 2H), 6.72 (s, 1H), 6.62 (d, 1H, J = 2.4 Hz), 5.68-5.82 (m, 1H), 3.93-3.98 (m, 1H), 3.88 (s, 3H), 3.77-3.83 (m, 2H), 3.65-3.70 (m, 1H), 2.37 (s, 3H), 2.19-2.29 (m, 1H), 1.96-2.03 (m, 1H). LC-MS (ESI, m/z): [M + H]$^+$ = 398.0. |
| 65 | 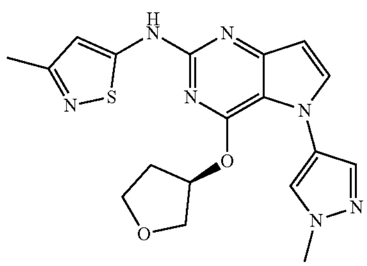 [SMILES: Cc1cc(Nc2nc(O[C@@H]3CCOC3)c3c(ccn3-c3cnn(C)c3)n2)sn1] | $^1$H-NMR (300 MHz, DMSO-d$_6$) δ: 10.95 (s, 1H), 8.04 (s, 1H), 7.65-7.68 (m, 2H), 6.62 (s, 1H), 6.53 (d, 1H, J = 3.0 Hz), 5.66-5.91 (m, 1H), 3.95-4.00 (m, 1H), 3.88 (s, 3H), 3.77-3.84 (m, 2H), 3.64-3.72 (m, 1H), 2.20-2.33 (m, 4H), 2.01-2.04 (m, 1H). LC-MS (ESI, m/z): [M + H]$^+$ = 398.2. |
| 66 | 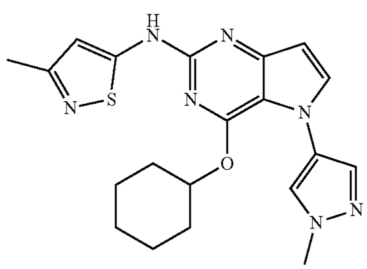 [SMILES: Cc1cc(Nc2nc(OC3CCCCC3)c3c(ccn3-c3cnn(C)c3)n2)sn1] | $^1$H-NMR (300 MHz, DMSO-d$_6$) δ: 11.42 (s, 1H), 8.05 (s, 1H), 7.63-7.67 (m, 2H), 6.68 (s, 1H), 6.56-6.57 (m, 1H), 5.33-5.36 (m, 1H), 3.88 (s, 3H), 2.34 (s, 3H), 1.89-1.90 (m, 2H), 1.36-1.56 (m, 8H). LC-MS (ESI, m/z): [M + H]$^+$ = 410.1. |
| 67 | 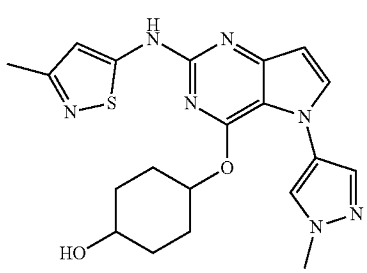 [SMILES: Cc1cc(Nc2nc(OC3CCC(O)CC3)c3c(ccn3-c3cnn(C)c3)n2)sn1] | $^1$H-NMR (300 MHz, DMSO-d$_6$) δ: 11.60-11.69 (m, 1H), 8.04-8.06 (m, 1H), 7.65-7.68 (m, 2H), 6.70 (s, 1H), 6.59 (s, 1H), 5.28-5.36 (m, 1H), 3.88-3.89 (m, 3H), 3.47-3.49 (m, 1H), 2.36 (s, 3H), 1.83-1.90 (m, 2H), 1.21-1.66 (m, 6H). LC-MS (ESI, m/z): [M + H]$^+$ = 426.2. |
| 68 | 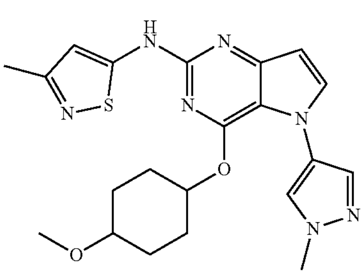 [SMILES: COC1CCC(Oc2nc(Nc3cc(C)ns3)nc3ccn(-c4cnn(C)c4)c23)CC1] | $^1$H-NMR (300 MHz, CD$_3$OD) δ: 7.95 (s, 1H), 7.70 (s, 1H), 7.54 (d, 1H, J = 3.0 Hz), 6.75 (s, 1H), 6.65 (d, 1H, J = 3.0 Hz), 5.41-5.42 (m, 1H), 3.96 (s, 3H), 3.34 (s, 3H), 2.49 (s, 3H), 2.04-2.12 (m, 2H), 1.47-1.78 (m, 7H). LC-MS (ESI, m/z): [M + H]$^+$ = 440.1. |

TABLE 4-continued

| Examples | Structures | Characterization data |
|---|---|---|
| 69 | 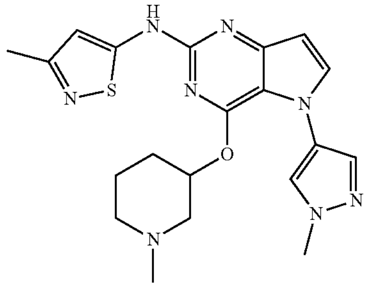 [SMILES: Cc1cc(Nc2nc(OC3CCCN(C)C3)c3c(ccn3-c3cnn(C)c3)n2)sn1] | $^1$H-NMR (300 MHz, CD$_3$OD) δ: 9.24 (s, 1H), 9.06 (s, 1H), 7.86 (d, 1H, J = 3.3 Hz), 6.88 (d, 1H, J = 3.3 Hz), 6.81 (s, 1H), 5.55-5.59 (m, 1H), 3.92 (s, 3H), 3.25-3.68 (m, 4H), 2.53 (s, 3H), 2.11 (s, 3H), 2.06-2.10 (m, 2H), 1.64-1.78 (m, 2H).<br>LC-MS (ESI, m/z): [M + H]$^+$ = 425.1. |
| 70 | 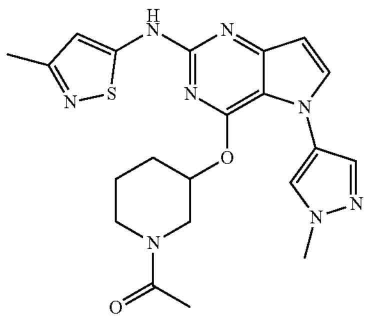 [SMILES: CC(=O)N1CCCC(Oc2nc(Nc3cc(C)ns3)nc3ccn(-c4cnn(C)c4)c23)C1] | $^1$H-NMR (300 MHz, CDCl$_3$) δ: 7.54-7.60 (m, 2H), 7.34 (dd, 1H, J = 2.7 Hz, J = 3.0 Hz), 6.95 (s, 1H), 6.66 (dd, 1H, J = 3.0 Hz, J = 3.0 Hz), 4.32-4.53 (m, 1H), 4.00 (s, 3H), 3.24-3.63 (m, 4H), 2.42 (s, 3H), 2.10 (s, 3H), 1.83-1.99 (m, 2H), 1.46-1.69 (m, 1H), 1.11-1.25 (m, 1H).<br>LC-MS (ESI, m/z): [M + H]$^+$ = 453.1. |
| 71 | 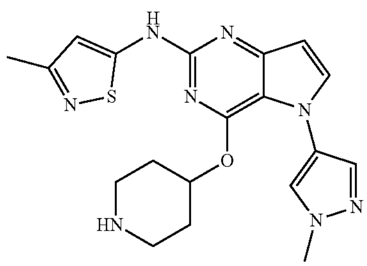 [SMILES: Cc1cc(Nc2nc(OC3CCNCC3)c3c(ccn3-c3cnn(C)c3)n2)sn1] | $^1$H-NMR (300 MHz, CD$_3$OD) δ: 8.05 (s, 1H), 7.81 (s, 1H), 7.62 (d, 1H, J = 3.0 Hz), 6.82 (s, 1H), 6.73 (d, 1H, J = 3.0 Hz), 5.68 (s, 1H), 4.02 (s, 3H), 3.23-3.33 (m, 2H), 2.88-2.97 (s, 2H), 2.54 (s, 3H), 2.53 (s, 3H), 2.12-2.24 (m, 4H).<br>LC-MS (ESI, m/z): [M + H] = 411.1. |
| 72 | 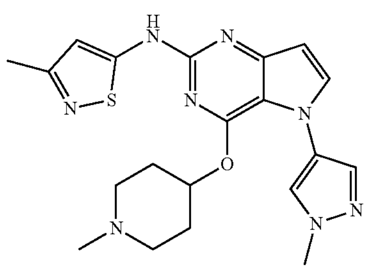 [SMILES: Cc1cc(Nc2nc(OC3CCN(C)CC3)c3c(ccn3-c3cnn(C)c3)n2)sn1] | $^1$H-NMR (300 MHz, CD$_3$OD) δ: 8.07 (s, 1H), 7.84 (s, 1H), 7.59 (d, 1H, J = 2.7 Hz), 6.81 (s, 1H), 6.71 (s, 1H), 4.03 (s, 3H), 4.00 (s, 1H), 3.40-3.44 (m, 2H), 3.31-3.33 (m, 2H), 2.95 (s, 3H), 2.53 (s, 3H), 2.12-2.29 (m, 4H).<br>LC-MS (ESI, m/z): [M + H]$^+$ = 425.1. |
| 73 | 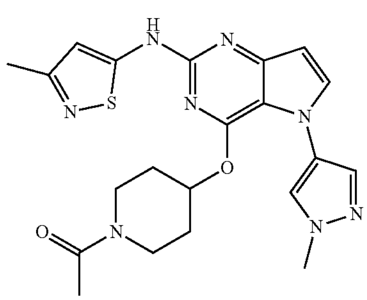 [SMILES: CC(=O)N1CCC(Oc2nc(Nc3cc(C)ns3)nc3ccn(-c4cnn(C)c4)c23)CC1] | $^1$H-NMR (300 MHz, CD$_3$OD) δ: 8.00 (s, 1H), 7.73 (s, 1H), 7.58 (d, 1H, J = 3.3 Hz), 6.79 (s, 1H), 6.70 (d, 1H, J = 3.0 Hz), 5.62-5.64 (m, 1H), 3.97 (s, 3H), 3.78-3.84 (m, 1H), 3.53-3.60 (m, 1H), 3.06-3.20 (m, 2H), 2.53 (s, 3H), 2.11 (s, 3H), 1.76-2.07 (m, 4H).<br>LC-MS (ESI, m/z): [M + H]$^+$ = 453.1. |

TABLE 4-continued

| Examples | Structures | Characterization data |
|---|---|---|
| 74 | 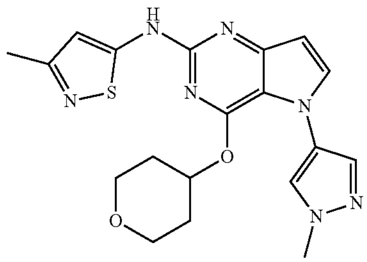 [SMILES: Cc1cc(Nc2nc(OC3CCOCC3)c3c(ccn3-c3cnn(C)c3)n2)sn1] | ¹H-NMR (300 MHz, CDCl₃) δ: 8.04 (s, 1H), 7.78 (s, 1H), 7.62 (d, 1H, J = 3.3 Hz), 6.82 (s, 1H), 6.73 (d, 1H, J = 3.0 Hz), 5.60-5.72 (m, 1H), 4.05 (s, 3H), 3.64-3.80 (m, 4H), 2.56 (s, 3H), 2.10-2.22 (m, 2H), 1.76-1.90 (m, 2H).<br>LC-MS (ESI, m/z): [M + H]⁺ = 412.1. |
| 75 | 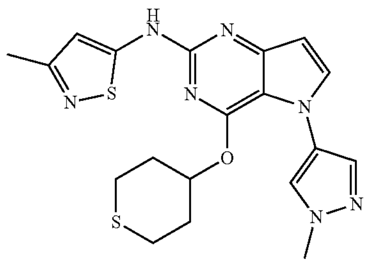 [SMILES: Cc1cc(Nc2nc(OC3CCSCC3)c3c(ccn3-c3cnn(C)c3)n2)sn1] | ¹H-NMR (300 MHz, DMSO-d₆) δ: 8.14 (s, 1H), 7.73 (s, 1H), 7.69 (d, 1H, J = 3.0 Hz), 6.71 (s, 1H), 6.62 (s, 1H), 5.46 (s, 1H), 3.91 (s, 3H), 2.54-2.50 (m, 2H), 2.44-2.49 (m, 2H), 2.37 (s, 3H), 1.92-2.13 (m, 4H).<br>LC-MS (ESI, m/z): [M + H]⁺ = 428.1. |
| 76 | 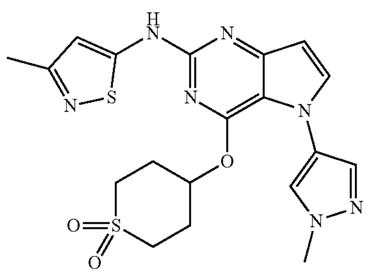 [SMILES: Cc1cc(Nc2nc(OC3CCS(=O)(=O)CC3)c3c(ccn3-c3cnn(C)c3)n2)sn1] | ¹H-NMR (300 MHz, DMSO-d₆) δ: 11.56 (s, 1H), 8.19 (s, 1H), 7.76 (s, 1H), 7.68 (d, 1H, J = 3.0 Hz), 6.69 (s, 1H), 6.62 (s, 1H), 5.55 (s, 1H), 3.90 (s, 3H), 3.04-3.08 (m, 2H), 2.64-2.74 (m, 2H), 2.35 (s, 3H), 2.26-2.30 (m, 4H).<br>LC-MS (ESI, m/z): [M + H]⁺ = 460.0. |
| 77 | 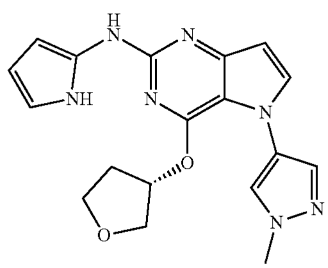 [SMILES: Cn1cc(-n2ccc3nc(Nc4ccc[nH]4)nc(O[C@H]4CCOC4)c32)cn1] | ¹H-NMR (300 MHz, DMSO-d₆) δ: 10.22 (s, 1H), 8.54 (s, 1H), 7.99 (s, 1H), 7.65 (s, 1H), 7.48 (d, 1H, J = 3.0 Hz), 7.14 (s, 1H), 6.55 (q, 1H, J = 2.4 Hz), 6.34 (d, 1H, J = 3.3 HZ), 6.07 (dd, 1H, J = 2.7 Hz, J = 2.1 Hz), 5.66-5.69 (m, 1H), 3.96 (dd, 1H, J = 4.8 Hz, J = 5.1 Hz), 3.87 (s, 3H), 3.65-3.82 (m, 3H), 2.16-2.28 (m, 1H), 1.91-2.00 (m, 1H).<br>LC-MS (ESI, m/z): [M + H]⁺ = 366.3. |
| 78 | 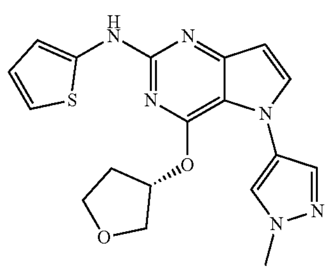 [SMILES: Cn1cc(-n2ccc3nc(Nc4cccs4)nc(O[C@H]4CCOC4)c32)cn1] | ¹H-NMR (300 MHz, CD₃OD) δ: 7.99 (s, 1H), 7.73 (s, 1H), 7.65 (d, 1H, J = 3.0 Hz), 7.17-7.19 (m, 1H), 6.96-7.02 (m, 2H), 6.55 (d, 1H, J = 3.0 Hz), 5.93-5.96 (m, 1H), 4.02-4.03 (m, 1H), 3.98 (s, 3H), 3.86-3.95 (m, 2H), 3.74-3.82 (m, 1H), 2.28-2.41 (m, 1H), 2.06-2.16 (m, 1H).<br>LC-MS (ESI, m/z): [M + H]⁺ = 383.2. |
| 79 | 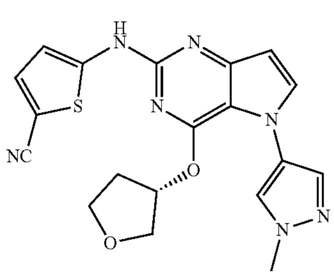 [SMILES: Cn1cc(-n2ccc3nc(Nc4ccc(C#N)s4)nc(O[C@H]4CCOC4)c32)cn1] | ¹H-NMR (300 MHz, CD₃OD) δ: 7.94 (s, 1H), 7.70 (s, 1H), 7.57 (d, 1H, J = 3.0 Hz), 7.53 (d, 1H, J = 4.2 Hz), 6.67 (d, 1H, J = 4.2 Hz), 6.57 (d, 1H, J = 3.0 Hz), 5.89-5.92 (m, 1H), 4.01-4.06 (m, 1H), 3.97 (s, 3H), 3.88-3.96 (m, 2H), 3.76-3.85 (m, 1H), 2.30-2.42 (m, 1H); 2.06-2.15 (m, 1H).<br>LC-MS (ESI, m/z): [M + H]⁺ = 408.3. |

TABLE 4-continued

| Examples | Structures | Characterization data |
|---|---|---|
| 80 | 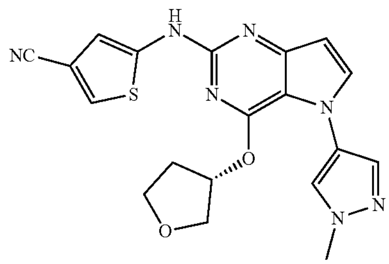 [SMILES: Cn1cc(-n2ccc3nc(Nc4cc(C#N)cs4)nc(O[C@H]4CCOC4)c32)cn1] | $^1$H-NMR (300 MHz, CD$_3$OD) δ: 7.99 (s, 1H), 7.88 (s, 1H), 7.74 (s, 1H), 7.70 (d, 1H, J = 3.0 Hz), 7.08 (s, 1H), 6.60 (d, 1H, J = 3.0 Hz), 5.96 (s, 1H), 4.00-4.05 (m, 2H), 3.95 (s, 3H), 3.88-3.93 (m, 2H), 2.29-2.43 (m, 1H), 2.09-2.20 (m, 1H).<br>LC-MS (ESI, m/z): [M + H]$^+$ = 408.2. |
| 81 | 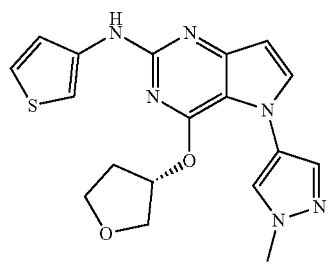 [SMILES: Cn1cc(-n2ccc3nc(Nc4ccsc4)nc(O[C@H]4CCOC4)c32)cn1] | $^1$H-NMR (300 MHz, DMSO-d$_6$) δ: 9.93 (s, 1H), 8.06 (s, 1H), 7.69 (s, 1H), 7.67 (d, 1H, J = 3.0 Hz), 7.61-7.62 (m, 1H), 7.47 (dd, 1H, J = 3.3 Hz, J = 2.4 Hz), 7.20 (dd, 1H, J = 3.3 Hz, J = 1.5 Hz), 6.49 (d, 1H, J = 3.0 Hz), 5.72 (dd, 1H, J = 4.2 Hz, J = 4.5 Hz), 3.94 (dd, 1H, J = 5.2 Hz, J = 4.5 Hz), 3.89 (s, 3H), 3.76-3.82 (m, 2H), 3.68 (dd, 1H, J = 8.4 Hz, J = 7.8 Hz), 2.18-2.30 (m, 1H), 1.96-2.04 (m, 1H).<br>LC-MS (ESI, m/z): [M + H]$^+$ = 383.2. |
| 82 | 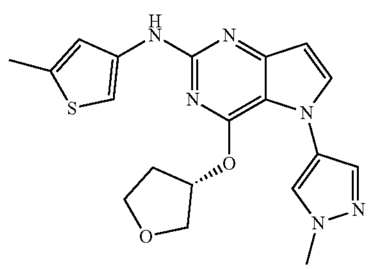 [SMILES: Cc1cc(Nc2nc(O[C@H]3CCOC3)c3c(ccn3-c3cnn(C)c3)n2)cs1] | $^1$H-NMR (300 MHz, CD$_3$OD) δ: 7.98 (s, 1H), 7.71 (s, 1H), 7.61 (d, 1H, J = 3.0 Hz), 7.24 (s, 1H), 6.88 (s, 1H), 6.53 (d, 1H, J = 3.0 Hz), 5.77-5.81 (m, 1H), 3.96 (s, 3H), 3.83-3.94 (m, 3H), 3.73-3.81 (m, 1H), 2.49 (s, 3H), 2.23-2.36 (m, 1H), 2.03-2.11 (m, 1H).<br>LC-MS (ESI, m/z): [M + H]$^+$ = 397.3. |
| 83 | 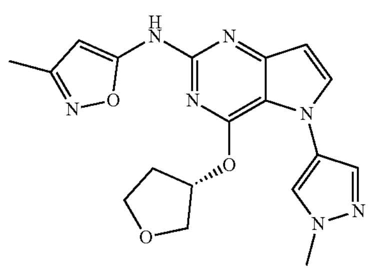 [SMILES: Cc1cc(Nc2nc(O[C@H]3CCOC3)c3c(ccn3-c3cnn(C)c3)n2)on1] | $^1$H-NMR (300 MHz, CD$_3$OD) δ: 7.98 (s, 1H), 7.72 (s, 1H), 7.67 (d, 1H, J = 3.0 Hz), 7.04 (s, 1H), 6.70 (d, 1H, J = 3.0 Hz), 5.87-5.89 (m, 1H), 3.98 (s, 3H), 3.75-3.92 (m, 4H), 2.38 (s, 3H), 3.76-3.85 (m, 1H), 2.25-2.37 (m, 1H), 2.03-2.12 (m, 1H).<br>LC-MS (ESI, m/z): [M + H]$^+$ = 382.3. |
| 84 | 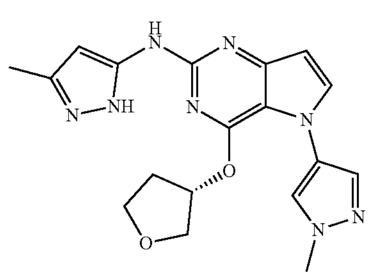 [SMILES: Cc1cc(Nc2nc(O[C@H]3CCOC3)c3c(ccn3-c3cnn(C)c3)n2)[nH]n1] | $^1$H-NMR (300 MHz, CD$_3$OD) δ: 8.01 (s, 1H), 7.73-7.74 (m, 1H), 7.67 (d, 1H, J = 3.0 Hz), 6.75 (d, 1H, J = 3.0 Hz), 5.93-5.94 (m, 1H), 5.83-5.87 (m, 1H), 3.77-4.02 (m, 7H), 2.38 (s, 3H), 2.26-2.36 (m, 1H), 2.06-2.12 (m, 1H).<br>LC-MS (ESI, m/z): [M + H]$^+$ = 381.3. |

TABLE 4-continued

| Examples | Structures | Characterization data |
|---|---|---|
| 85 | 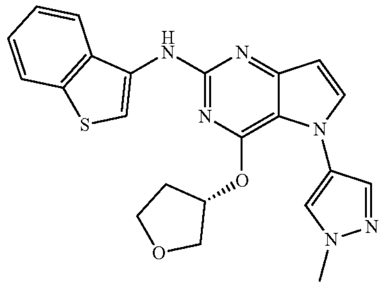 [SMILES: Cn1cc(-n2ccc3nc(Nc4csc5ccccc45)nc(O[C@H]4CCOC4)c32)cn1] | ¹H-NMR (300 MHz, DMSO-d₆) δ: 9.74-9.87 (m, 1H), 8.11-8.14 (m, 1H), 8.07 (s, 1H), 8.01 (s, 1H), 7.98 (d, 1H, J = 3.6 Hz), 7.70 (d, 1H, J = 2.1 Hz), 7.41-7.46 (m, 2H), 6.51 (d, 1H, J = 3.0 Hz), 5.68-5.76 (m, 1H), 3.89 (s, 3H), 3.87 (d, 1H, J = 4.5 Hz), 3.74-3.78 (m, 2H), 3.66-3.71 (m, 1H), 2.15-2.27 (m, 1H), 1.94-2.01 (m, 1H). LC-MS (ESI, m/z): [M + H]⁺ = 433.2. |
| 86 | 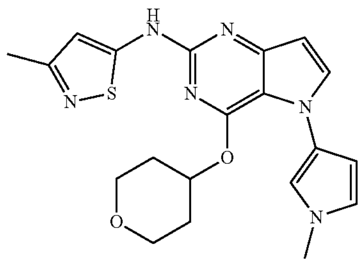 [SMILES: Cc1cc(Nc2nc(OC3CCOCC3)c3c(ccn3-c3ccn(C)c3)n2)sn1] | ¹H-NMR (300 MHz, CD₃OD) δ: 7.40 (dd, 1H, J = 3.3 Hz, J = 11.1 Hz), 6.09 (t, 1H, J = 2.1 Hz), 6.67 (t, 1H, J = 2.7 Hz), 6.58 (s, 1H), 6.42 (d, 1H, J = 3.0 Hz), 6.22 (dd, 1H, J = 2.4 Hz, J = 0.9 Hz), 5.59-5.65 (m, 1H), 3.71 (s, 3H), 3.60-3.70 (m, 4H), 2.34 (s, 3H), 2.00-2.10 (m, 2H), 1.70-1.80 (m, 2H). LC-MS (ESI, m/z): [M + H]⁺ = 411.3. |
| 87 | 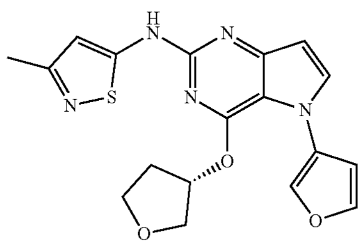 [SMILES: Cc1cc(Nc2nc(O[C@H]3CCOC3)c3c(ccn3-c3ccoc3)n2)sn1] | ¹H-NMR (300 MHz, CD₃OD) δ: 7.72 (s, 1H), 7.52 (t, 1H, J = 1.8 Hz), 7.41 (d, 1H, J = 3.0 Hz), 6.92 (s, 1H), 6.66 (d, 1H, J = 3.3 Hz), 6.63 (d, 1H, J = 0.9 Hz), 6.07-6.10 (m, 1H), 3.81-4.13 (m, 4H), 2.36-2.49 (m, 1H), 2.42 (s, 3H), 2.08-2.22 (m, 1H). LC-MS (ESI, m/z): [M + H]⁺ = 384.3. |
| 88 | 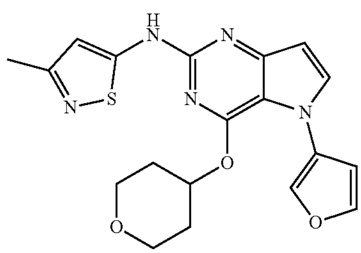 [SMILES: Cc1cc(Nc2nc(OC3CCOCC3)c3c(ccn3-c3ccoc3)n2)sn1] | ¹H-NMR (300 MHz, DMSO-d₆) δ: 10.97 (s, 1H), 8.11 (s, 1H), 7.78 (d, 1H, J = 1.5 Hz), 7.70 (d, 1H, J = 3.0 Hz), 7.21-7.42 (m, 2H), 7.10-7.13 (m, 1H) 6.90 (d, 1H, J = 1.2 Hz), 6.61 (s, 1H), 6.55 (d, 1H, J = 3.0 Hz), 4.96-5.12 (m, 1H), 3.65-3.70 (m, 2H), 3.48-3.56 (m, 2H), 2.28 (s, 3H), 2.05-2.09 (m, 2H), 1.83 (s, 1H), 1.63-1.73 (m, 2H). LC-MS (ESI, m/z): [M + H]⁺ = 398.2. |
| 89 | 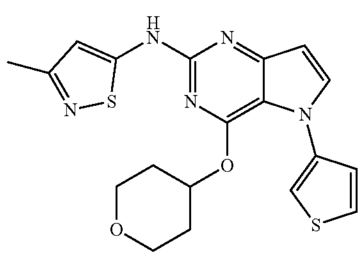 [SMILES: Cc1cc(Nc2nc(OC3CCOCC3)c3c(ccn3-c3ccsc3)n2)sn1] | ¹H-NMR (300 MHz, CD₃OD) δ: 7.46-7.48 (m, 2H), 7.39-7.41 (m, 1H), 7.17 (dd, 1H, J = 1.5 Hz, J = 5.1 Hz), 6.94 (s, 1H), 6.68 (d, 1H, J = 3.0 Hz), 5.74-5.82 (m, 1H), 3.61-3.74 (m, 4H), 2.43 (s, 3H), 2.10-2.18 (m, 2H), 1.68-1.79 (m, 2H). LC-MS (ESI, m/z): [M + H]⁺ = 414.2. |
| 90 | 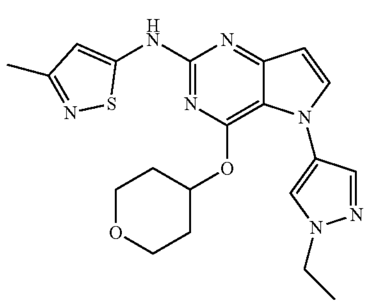 [SMILES: CCn1cc(-n2ccc3nc(Nc4cc(C)ns4)nc(OC4CCOCC4)c32)cn1] | ¹H-NMR (300 MHz, DMSO-d₆) δ: 10.94 (s, 1H), 8.14 (s, 1H), 7.72 (s, 1H), 7.64 (d, 1H, J = 3.0 Hz), 6.60 (s, 1H), 6.52 (d, 1H, J = 3.0 Hz), 5.42-5.58 (m, 1H), 4.18 (q, 1H, J = 7.2 Hz), 3.48-3.58 (m, 4H), 2.27 (s, 3H), 2.00-2.06 (m, 2H), 1.61-1.67 (m, 2H), 1.43 (t, 3H, J = 7.2 Hz). LC-MS (ESI, m/z): [M + H]⁺ = 426.1. |

TABLE 4-continued

| Examples | Structures | Characterization data |
|---|---|---|
| 91 | 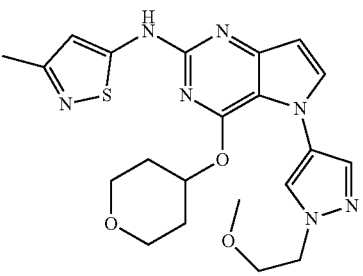 [SMILES: COCCn1cc(-n2ccc3nc(Nc4cc(C)ns4)nc(OC4CCOCC4)c32)cn1] | ¹H-NMR (300 MHz, DMSO-d₆) δ: 10.94 (s, 1H), 8.09 (s, 1H), 7.74 (s, 1H), 7.64 (d, 1H, J = 3.0 Hz), 6.60 (s, 1H), 6.52 (d, 1H, J = 3.0 Hz), 5.41-5.57 (m, 1H), 4.30 (t, 2H, J = 5.1 Hz), 3.74 (t, 2H, J = 5.1 Hz), 3.58-3.64 (m, 2H), 3.46-3.54 (m, 2H), 3.27 (s, 3H), 2.27 (s, 3H), 1.99-2.03 (m, 2H).<br>LC-MS (ESI, m/z): [M + H]⁺ = 456.0. |
| 92 | 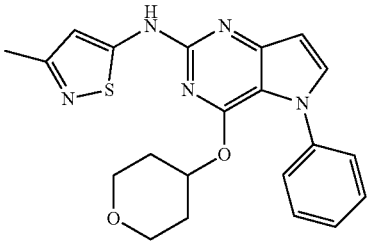 [SMILES: Cc1cc(Nc2nc(OC3CCOCC3)c3c(ccn3-c3ccccc3)n2)sn1] | ¹H-NMR (300 MHz, CD₃OD) δ: 7.69 (d, 1H, J = 3.0 Hz), 7.48-7.58 (m, 5H), 6.81 (s, 1H), 6.75 (d, 1H, J = 3.3 Hz), 5.52-5.60 (m, 1H), 3.44-3.58 (m, 4H), 2.53 (s, 3H), 1.92-2.10 (m, 2H), 1.58-1.72 (m, 2H).<br>LC-MS (ESI, m/z): [M + H]⁺ = 408.1. |
| 93 | 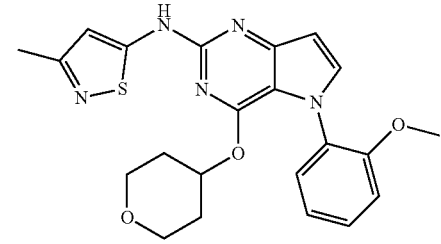 | ¹H-NMR (300 MHz, CD₃OD) δ: 7.47 (dt, 1H, J = 1.8 Hz, J = 8.1 Hz), 7.35-7.39 (m, 2H), 7.17 (d, 1H, J = 7.2 Hz), 7.07 (dt, 1H, J = 0.9 Hz, J = 7.5 Hz), 6.60 (s, 1H), 6.50 (d, 1H, J = 3.0 Hz), 5.49-5.59 (m, 1H), 3.75 (s, 3H), 3.47-3.54 (m, 2H), 3.35-3.43 (m, 2H), 2.35 (s, 3H), 1.93-2.00 (m, 2H), 1.50-1.60 (m, 2H).<br>LC-MS (ESI, m/z): [M + H]⁺ = 438.2. |
| 94 | 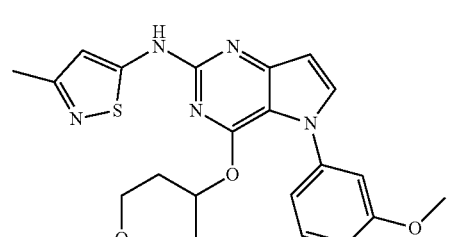 | ¹H-NMR (300 MHz, CD₃OD) δ: 7.53 (d, 1H, J = 3.0 Hz), 7.36-7.42 (m, 1H), 7.01 (d, 3H, J = 6.0 Hz), 6.60 (s, 1H), 6.52 (d, 1H, J = 3.0 Hz), 5.53-5.66 (m, 1H), 3.85 (s, 3H), 3.54 (t, 4H, J = 5.4 Hz), 2.35 (s, 3H), 1.97-2.06 (m, 2H), 1.61-1.71 (m, 2H).<br>LC-MS (ESI, m/z): [M + H]⁺ = 438.2. |
| 95 | 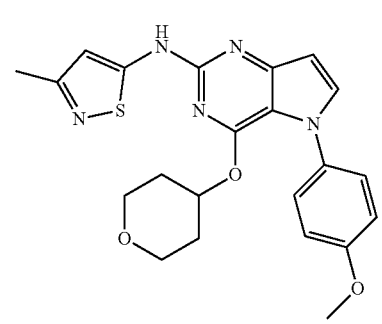 | ¹H-NMR (300 MHz, CD₃OD) δ: 7.51 (d, 1H, J = 3.0 Hz), 7.37-7.42 (m, 2H), 7.04-7.08 (m, 2H), 6.68 (s, 1H), 6.52 (d, 1H, J = 3.0 Hz), 5.57-5.63 (m, 1H), 3.88 (s, 3H), 3.52-3.61 (m, 4H), 2.37 (s, 3H), 2.00-2.10 (m, 2H), 1.62-1.72 (m, 2H).<br>LC-MS (ESI, m/z): [M + H]⁺ = 387.2. |

TABLE 4-continued

| Examples | Structures | Characterization data |
|---|---|---|
| 96 | 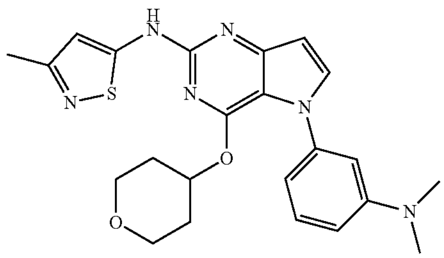 | ¹H-NMR (300 MHz, CD₃OD) δ: 7.67 (d, 1H, J = 3.3 Hz), 7.32-7.37 (m, 1H), 6.89-6.93 (m, 1H), 6.84-6.86 (m, 1H), 6.77-6.81 (m, 2H), 6.73 (d, 1H, J = 3.0 Hz), 5.55-5.59 (m, 1H), 3.46-3.53 (m, 4H), 3.01 (s, 6H), 2.55 (s, 3H), 1.93-2.03 (m, 2H), 1.61-1.71 (m, 2H). LC-MS (ESI, m/z): [M + H]⁺ = 451.2. |
| 97 | 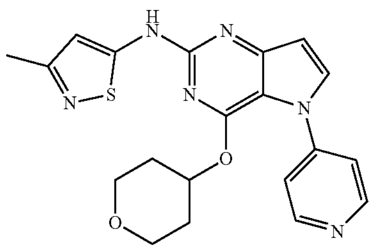 [SMILES: Cc1cc(Nc2nc(OC3CCOCC3)c3c(ccn3-c3ccncc3)n2)sn1] | ¹H-NMR (300 MHz, CD₃OD) δ: 8.84 (s, 2H), 7.90-8.05 (m, 3H), 6.93 (s, 1H), 6.82 (s, 1H), 5.52-5.72 (m, 1H), 3.68-3.82 (m, 2H), 3.50-3.66 (m, 2H), 2.52 (s, 3H), 2.08-2.22 (m, 2H), 1.66-1.86 (m, 2H). LC-MS (ESI, m/z): [M + H]⁺ = 409.1. |
| 98 | 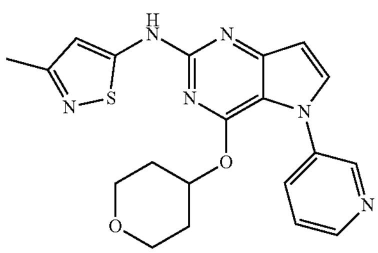 [SMILES: Cc1cc(Nc2nc(OC3CCOCC3)c3c(ccn3-c3cccnc3)n2)sn1] | ¹H-NMR (300 MHz, DMSO-d₆) δ: 11.50 (s, 1H), 8.80 (d, 1H, J = 2.4 Hz), 8.63-8.66 (m, 1H), 8.03-8.07 (m, 1H), 7.90 (d, 1H, J = 3.3 Hz), 7.58-7.63 (m, 1H), 6.69-6.72 (m, 2H), 5.49 (s, 1H), 3.62-3.68 (m, 2H), 3.30-3.38 (m, 2H), 2.34 (s, 3H), 1.95-2.00 (m, 2H), 1.48-1.59 (m, 2H). LC-MS (ESI, m/z): [M + H]⁺ = 409.1. |
| 99 | 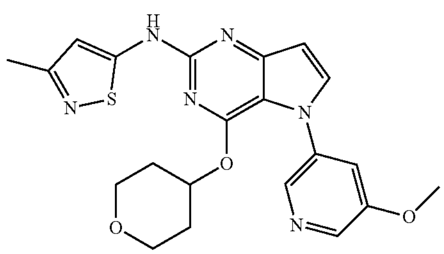 | ¹H-NMR (300 MHz, CD₃OD) δ: 8.37 (dd, 2H, J = 1.8 Hz, J = 6.9 Hz), 7.79 (d, 1H, J = 3.3 Hz), 7.65 (t, 1H, J = 2.1 Hz), 6.82 (d, 2H, J = 2.7 Hz), 5.52-5.60 (m, 1H), 3.97 (s, 3H), 3.54-3.58 (m, 4H), 2.54 (s, 3H), 2.00-2.09 (m, 2H), 1.61-1.72 (m, 2H). LC-MS (ESI, m/z): [M + H]⁺ = 439.1. |
| 100 | 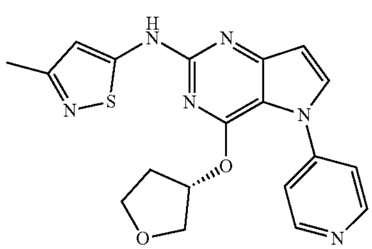 [SMILES: Cc1cc(Nc2nc(O[C@H]3CCOC3)c3c(ccn3-c3ccncc3)n2)sn1] | ¹H-NMR (300 MHz, CD₃OD) δ: 8.96 (d, 2H, J = 6.3 Hz), 8.13-8.23 (m, 3H), 7.07 (d, 1H, J = 2.7 Hz), 6.92 (s, 1H), 5.90-6.02 (m, 1H), 4.05 (d, 2H, J = 2.7 Hz), 3.90-3.95 (m, 2H), 2.62 (s, 3H), 2.38-2.50 (m, 1H), 2.17-2.25 (m, 1H). LC-MS (ESI, m/z): [M + H]⁺ = 395.2. |
| 101 | 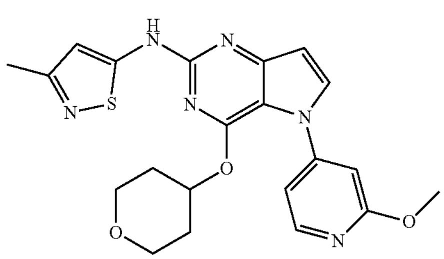 | ¹H-NMR (300 MHz, CD₃OD) δ: 8.22 (d, 1H, J = 5.7 Hz), 7.79 (d, 1H, J = 3.3 Hz), 7.11-7.14 (m, 1H), 6.91-6.92 (m, 1H), 6.77-6.78 (m, 2H), 5.52-5.59 (m, 1H), 3.97 (s, 3H), 3.52-3.68 (m, 4H), 2.52 (s, 3H), 2.01-2.10 (m, 2H), 1.66-1.75 (m, 2H). LC-MS (ESI, m/z): [M + H]⁺ = 439.3. |

| Examples | Structures | Characterization data |
|---|---|---|
| 102 | 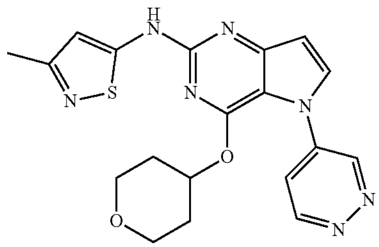 [SMILES: Cc1cc(Nc2nc(OC3CCOCC3)c3c(ccn3-c3ccnnc3)n2)sn1] | $^1$H-NMR (300 MHz, CD$_3$OD) δ: 9.54 (dd, 1H, J = 1.8 Hz, J = 2.7 Hz), 9.34 (dd, 1H, J = 1.8 Hz, J = 5.7 Hz), 7.95-7.98 (m, 2H), 6.91 (d, 1H, J = 3.0 Hz), 6.79 (s, 1H), 5.60-5.70 (m, 1H), 3.69-3.76 (m, 2H), 3.55-3.62 (m, 2H), 2.51 (s, 3H), 2.12-2.19 (m, 2H), 1.71-1.82 (m, 2H). LC-MS (ESI, m/z): [M + H]$^+$ = 410.1. |
| 103 | 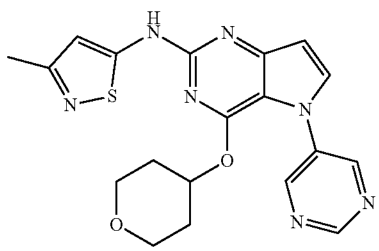 [SMILES: Cc1cc(Nc2nc(OC3CCOCC3)c3c(ccn3-c3cncnc3)n2)sn1] | $^1$H-NMR (300 MHz, CD$_3$OD) δ: 9.23 (s, 1H), 9.05 (s, 1H), 7.85 (d, 1H, J = 3.3 Hz), 6.87 (d, 1H, J = 3.3 Hz), 6.80 (s, 1H), 5.53-5.61 (m, 1H), 3.52-3.69 (m, 4H), 2.53 (s, 3H), 2.01-2.16 (m, 2H), 1.63-1.74 (m, 2H). LC-MS (ESI, m/z): [M + H]$^+$ = 410.1. |
| 104 | 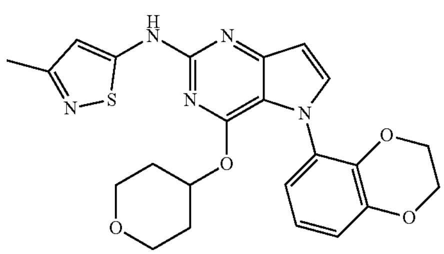 [SMILES: Cc1cc(Nc2nc(OC3CCOCC3)c3c(ccn3-c3cccc4c3OCCO4)n2)sn1] | $^1$H-NMR (300 MHz, CD$_3$OD) δ: 7.51 (d, 1H, J = 3.0 Hz), 6.93-7.03 (m, 3H), 6.78 (s, 1H), 6.69 (d, 1H, J = 3.0 Hz), 5.47-5.51 (m, 1H), 4.25-4.27 (m, 2H), 4.16-4.19 (m, 2H), 3.39-3.54 (m, 4H), 2.15 (s, 3H), 2.51 (s, 3H), 1.95-1.97 (m, 2H), 1.57-1.63 (m, 2H). LC-MS (ESI, m/z): [M + H]$^+$ = 466.2. |

Example 105

Preparation of (S)-(1-methyl-1H-pyrazol-4-yl)-[5-(1-methyl-1H-pyrazol-4-yl)-4-(tetrahydrofuran-3-yloxy)-5H-pyrrolo[3,2-d]pyrimidin-2-yl]amine

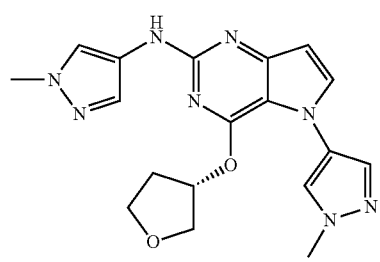 [SMILES: Cn1cc(Nc2nc(O[C@H]3CCOC3)c3c(ccn3-c3cnn(C)c3)n2)cn1]

Step 1: Preparation of 2,4-dichloro-5-(1-methyl-1H-pyrazol-4-yl)-5H-pyrrolo[3,2-d]pyrimidine

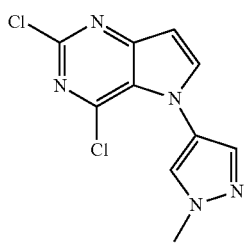 [SMILES: Cn1cc(-n2ccc3nc(Cl)nc(Cl)c32)cn1]

2,4-Dichloro-5H-pyrrolo[3,2-d]pyrimidine (376 mg, 2 mmol), 1-methyl-4-(4,4,5,5-tetramethyl-1,3,2-dioxaborolan-2-yl)-1H-pyrazole (832 mg, 4 mmol), anhydrous copper acetate (363 mg, 2 mmol), and pyridine (158 mg, 2 mmol) were added into dimethylsulfoxide (10 mL). The reaction liquid was heated to 110° C. and stirred overnight. The reaction liquid was naturally cooled down to room temperature, followed by adding ethyl acetate (50 mL). The insolubles were removed by filtration. The filtrate was washed with water (40 mL×2), dried over anhydrous sodium sulfate, and concentrated under reduced pressure. The residue was beaten in a mixed solution of n-hexane/ethyl acetate (2/1, 30 mL), and filtered to give 150 mg of a pale yellow solid. Yield: 28.0%. MS (ESI, m/z): [M+H]$^+$: 267.9.

Step 2: Preparation of (S)-2-chloro-5-(1-methyl-1H-pyrazol-4-yl)-4-(tetrahydrofuran-3-yloxy)-5H-pyrrolo[3,2-d]pyrimidine

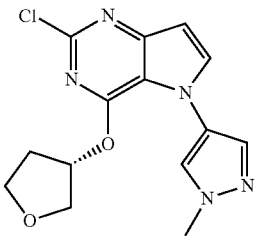 [SMILES: Cn1cc(-n2ccc3nc(Cl)nc(O[C@H]4CCOC4)c32)cn1]

2,4-Dichloro-5-(1-methyl-1H-pyrazol-4-yl)-5H-pyrrolo[3,2-d]pyrimidine (150 mg, 0.56 mmol), sodium hydroxide (45 mg, 1.12 mmol) and (S)-(+)-3-hydroxytetrahydrofuran (99 mg, 1.12 mmol) were added into dimethylsulfoxide (20 mL). The reaction liquid was stirred at room temperature for 1 hour, and quenched with water (20 mL). The mixture was extracted with ethyl acetate (20 mL×3). The organic phase was dried over anhydrous sodium sulfate and concentrated under reduced pressure to give 100 mg of a brown solid. Yield: 61.8%. MS (ESI, m/z): [M+H]$^+$: 320.2.

Step 3: Preparation of (S)-(1-methyl-1H-pyrazol-4-yl)-[5-(1-methyl-1H-pyrazol-4-yl)-4-(tetrahydrofuran-3-yloxy)-5H-pyrrolo[3,2-d]pyrimidin-2-yl] amine The product obtained in Step 2 (32 mg, 0.1 mmol), 1-methyl-1H-pyrazol-4-ylamine (15 mg, 0.15 mmol), and trifluoroacetic acid (11 mg, 0.1 mmol) were dissolved in isopropanol (1.5 mL). The reaction liquid was reacted under microwave conditions at 100° C. for 1 hour. The reaction liquid was cooled down to room temperature, concentrated under reduced pressure, and separated by flash column chromatography (eluent: dichloromethane:methanol=10:1) to give 7 mg of a pale yellow solid. Yield: 18%. MS (ESI, m/z): [M+H]$^+$: 381.3; $^1$H-NMR (300 MHz, CD$_3$OD) δ: 7.99 (s, 1H), 7.88 (s, 1H), 7.72 (s, 1H), 7.64 (s, 1H), 7.61 (d, 1H, J=3.0 Hz), 6.50 (d, 1H, J=3.0 Hz), 5.80-5.83 (m, 1H), 3.97 (s, 3H), 3.95 (s, 3H), 3.69-3.91 (m, 4H), 2.24-2.36 (m, 2H), 1.99-2.11 (m, 2H).

The following compounds (in Table 5) were prepared from similar starting materials by a synthesis method analogous to that as described in Example 105.

TABLE 5

| Examples | Structures | Characterization data |
|---|---|---|
| 106 | 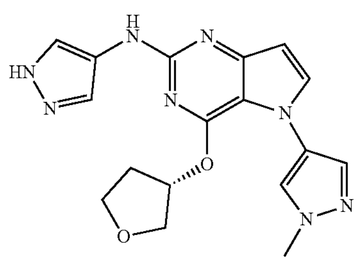 [SMILES: Cn1cc(-n2ccc3nc(Nc4cn[nH]c4)nc(O[C@H]4CCOC4)c32)cn1] | $^1$H-NMR (300 MHz, CD$_3$OD) δ: 7.88 (s, 1H), 7.80 (s, 1H), 7.66 (s, 1H), 7.36 (d, 1H, J = 3.3 Hz), 6.38 (d, 1H, J = 3.0 Hz), 5.73-5.76 (m, 1H), 3.98-4.02 (m, 1H), 3.95 (s, 3H), 3.79-3.91 (m, 3H), 2.20-2.33 (m, 1H), 2.06-2.10 (m, 1H). LC-MS (ESI, m/z): [M + H]$^+$ = 367.3. |
| 107 | 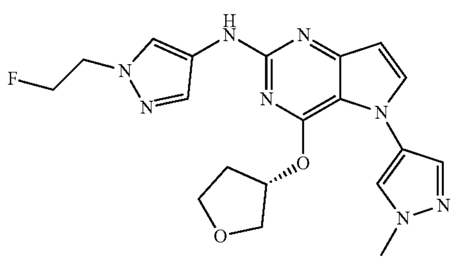 [SMILES: Cn1cc(-n2ccc3nc(Nc4cnn(CCF)c4)nc(O[C@H]4CCOC4)c32)cn1] | $^1$H-NMR (300 MHz, DMSO-d$_6$) δ: 9.78-9.84 (s, 1H), 8.00-8.07 (m, 2H), 7.62-7.69 (m, 3H), 6.47 (d, 1H, J = 3.0 Hz), 5.70-5.73 (m, 1H), 4.83-4.86 (m, 1H), 4.67-4.71 (m, 1H), 4.47-4.51 (m, 1H), 4.38-4.41 (m, 1H), 3.89-3.94 (m, 3H), 3.78-3.82 (m, 2H), 3.62-3.70 (m, 1H), 2.17-2.29 (m, 1H), 1.95-2.03 (m, 1H). LC-MS (ESI, m/z): [M + H]$^+$ = 413.3. |
| 108 | 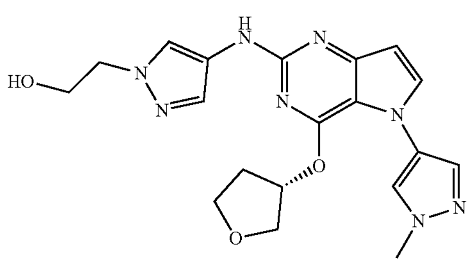 [SMILES: Cn1cc(-n2ccc3nc(Nc4cnn(CCO)c4)nc(O[C@H]4CCOC4)c32)cn1] | $^1$H-NMR (300 MHz, CD$_3$OD) δ: 7.98-8.00 (m, 2H), 7.72-7.73 (m, 1H), 7.67 (s, 1H), 7.61 (d, 1H, J = 3.3 Hz), 6.49-6.50 (m, 1H), 5.82-5.87 (m, 1H), 4.27-4.31 (m, 2H), 3.77-4.01 (m, 9H), 2.31-2.38 (m, 1H), 2.04-2.12 (m, 1H). LC-MS (ESI, m/z): [M + H]$^+$ = 411.3. |

| Examples | Structures | Characterization data |
|---|---|---|
| 109 | 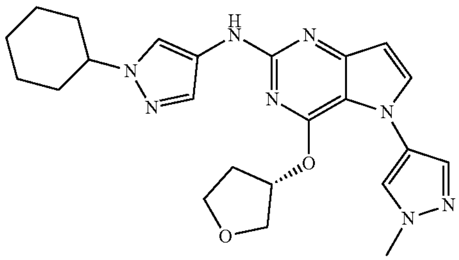 [SMILES: Cn1cc(-n2ccc3nc(Nc4cnn(C5CCCCC5)c4)nc(O[C@H]4CCOC4)c32)cn1] | $^1$H-NMR (300 MHz, CDCl$_3$) δ: 7.87 (s, 1H), 7.60-7.61 (m, 2H), 7.58 (s, 1H), 7.28 (d, 1H, J = 3.0 Hz), 6.56 (d, 1H, J = 3.0 Hz), 5.78 (s, 1H), 4.09-4.11 (m, 1H), 3.99 (s, 3H), 3.75-3.96 (m, 4H), 2.09-2.33 (m, 4H), 1.62-1.93 (m, 5H), 1.19-1.49 (m, 3H). LC-MS (ESI, m/z): [M + H]$^+$ = 449.3. |
| 110 | 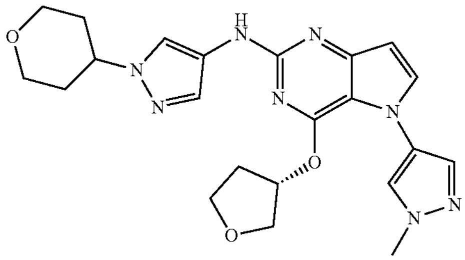 [SMILES: Cn1cc(-n2ccc3nc(Nc4cnn(C5CCOCC5)c4)nc(O[C@H]4CCOC4)c32)cn1] | $^1$H-NMR (300 MHz, CD$_3$OD) δ: 7.99 (s, 1H), 7.97 (s, 1H), 7.71 (s, 1H), 7.68 (s, 1H), 7.62 (d, 1H, J = 3.0 Hz), 6.51 (d, 1H, J = 3.0 Hz), 5.79-5.82 (m, 1H), 4.40-4.52 (m, 1H), 4.05-4.10 (m, 2H), 3.94 (s, 3H), 3.75-3.92 (m, 4H), 3.52-3.63 (m, 2H), 2.23-2.53 (m, 1H), 2.07-2.13 (m, 5H). LC-MS (ESI, m/z): [M + H]$^+$ = 451.3. |
| 111 | 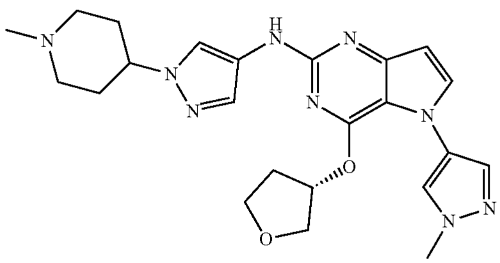 [SMILES: CN1CCC(n2cc(Nc3nc(O[C@H]4CCOC4)c4c(ccn4-c4cnn(C)c4)n3)cn2)CC1] | $^1$H-NMR (300 MHz, CD$_3$OD) δ: 7.99-8.00 (m, 2H), 7.73-7.75 (m, 2H), 7.64 (d, 1H, J = 3.0 Hz), 6.52 (d, 1H, J = 3.0 Hz), 5.82 (s, 1H), 4.50-4.70 (m, 1H), 3.98 (s, 3H), 3.85-3.96 (m, 3H), 3.69-3.82 (m, 3H), 3.54-3.56 (m, 1H), 2.96 (s, 3H), 3.21-3.32 (m, 2H), 2.27-2.41 (m, 5H), 2.05-2.13 (m, 1H). LC-MS (ESI, m/z): [M + H]$^+$ = 464.4. |
| 112 | 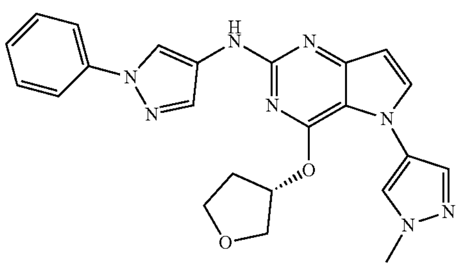 [SMILES: Cn1cc(-n2ccc3nc(Nc4cnn(-c5ccccc5)c4)nc(O[C@H]4CCOC4)c32)cn1] | $^1$H-NMR (300 MHz, DMSO-d$_6$) δ: 9.57 (s, 1H), 8.65 (s, 1H), 8.07 (s, 1H), 7.90 (s, 1H), 7.82 (d, 2H, J = 7.8 Hz), 7.71 (s, 1H), 7.67 (d, 1H, J = 3.0 Hz), 7.53 (t, 2H, J = 7.5 Hz), 7.32 (t, 1H, J = 7.5 Hz), 6.52 (d, 1H, J = 3.0 Hz), 5.72-5.78 (m, 1H), 3.92-3.99 (m, 1H), 3.90 (s, 3H), 3.78-3.84 (m, 2H), 3.66-3.74 (m, 1H), 2.20-2.32 (m, 1H), 2.01-2.05 (m, 1H). LC-MS (ESI, m/z): [M + H]$^+$ = 443.2. |
| 113 | 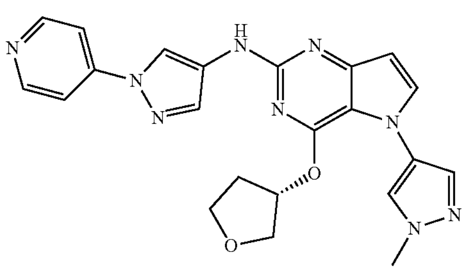 [SMILES: Cn1cc(-n2ccc3nc(Nc4cnn(-c5ccncc5)c4)nc(O[C@H]4CCOC4)c32)cn1] | $^1$H-NMR (300 MHz, DMSO-d$_6$) δ: 8.86 (s, 1H), 8.82 (d, 2H, J = 6.6 Hz), 8.34 (d, 2H, J = 6.9 Hz), 8.25 (s, 1H), 7.99 (s, 1H), 7.72 (s, 1H), 7.65 (d, 1H, J = 3.0 Hz), 6.60 (d, 1H, J = 3.3 Hz), 5.86-5.89 (m, 1H), 3.98 (s, 3H), 3.94-4.01 (m, 2H), 3.85-3.92 (m, 1H), 3.68-3.82 (m, 1H), 2.26-2.38 (m, 1H), 2.07-2.15 (m, 1H). LC-MS (ESI, m/z): [M + H]$^+$ = 444.2. |
| 114 | 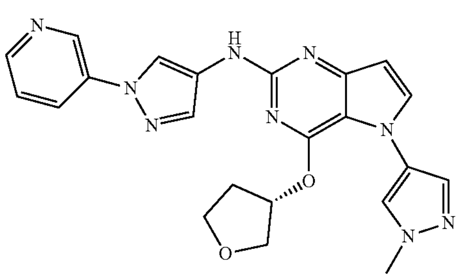 [SMILES: Cn1cc(-n2ccc3nc(Nc4cnn(-c5cccnc5)c4)nc(O[C@H]4CCOC4)c32)cn1] | $^1$H-NMR (300 MHz, DMSO-d$_6$) δ: 9.13 (s, 1H), 8.65 (s, 1H), 8.59 (d, 1H, J = 4.2 Hz), 8.41 (dd, 1H, J = 4.2 Hz, J = 1.2 Hz), 8.04 (s, 1H), 8.00 (s, 1H), 7.70-7.74 (m, 2H), 7.66 (d, 1H, J = 3.0 Hz), 6.55 (d, 1H, J = 3.3 Hz), 5.85-5.88 (m, 1H), 3.96 (s, 3H), 3.92-3.95 (m, 2H), 3.84-3.89 (m, 1H), 3.74-3.82 (m, 1H), 2.25-2.39 (m, 1H), 2.06-2.14 (m, 1H). LC-MS (ESI, m/z): [M + H]$^+$ = 444.2. |

TABLE 5-continued

| Examples | Structures | Characterization data |
|---|---|---|
| 115 | 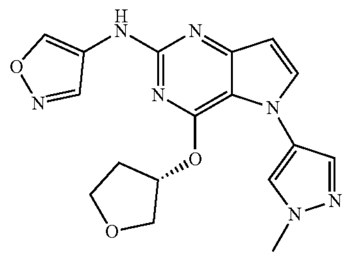 [SMILES: Cn1cc(-n2ccc3nc(Nc4cnoc4)nc(O[C@H]4CCOC4)c32)cn1] | $^1$H-NMR (300 MHz, DMSO-$d_6$) δ: 9.17 (s, 1H), 9.14 (s, 1H), 8.60 (s, 1H), 8.02 (s, 1H), 7.67 (s, 1H), 7.59 (d, 1H, J = 3.3 Hz), 6.47 (d, 1H, J = 3.3 Hz), 5.69 (dd, 1H, J = 4.5 Hz, J = 2.7 Hz), 3.90 (dd, 1H, J = 8.7 Hz, J = 4.5 Hz), 3.88 (s, 3H), 3.64-3.83 (m, 3H), 2.16-2.29 (m, 1H), 1.94-2.02 (m, 1H). LC-MS (ESI, m/z): [M + H]$^+$ = 368.3. |
| 116 | 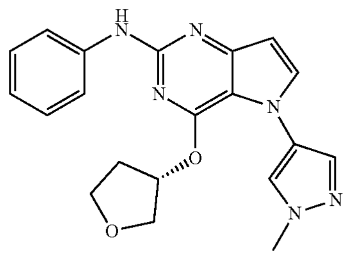 [SMILES: Cn1cc(-n2ccc3nc(Nc4ccccc4)nc(O[C@H]4CCOC4)c32)cn1] | $^1$H-NMR (300 MHz, DMSO-$d_6$) δ: 9.06 (s, 1H), 8.02 (s, 1H), 7.82 (d, 2H, J = 7.8 Hz), 7.68 (s, 1H), 7.58 (d, 1H, J = 3.0 Hz), 7.26 (t, 2H, J = 7.8 Hz), 6.87 (t, 1H, J = 7.2 Hz), 6.45 (d, 1H, J = 3.3 Hz), 3.98 (dd, 1H, J = 5.2 Hz, J = 4.5 Hz), 3.88 (s, 3H), 3.66-3.83 (m, 3H), 2.18-2.23 (m, 1H), 1.96-2.03 (m, 1H). LC-MS (ESI, m/z): [M + H]$^+$ = 377.2. |
| 117 | 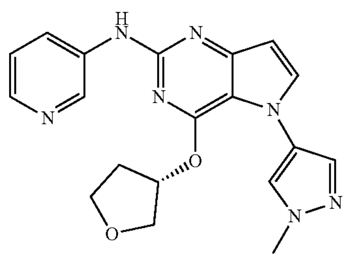 [SMILES: Cn1cc(-n2ccc3nc(Nc4cccnc4)nc(O[C@H]4CCOC4)c32)cn1] | $^1$H-NMR (300 MHz, DMSO-$d_6$) δ: 9.33 (s, 1H), 9.20 (d, 1H, J = 5.7 Hz), 8.18 (s, 1H), 8.08 (d, 1H, J = 3.0 Hz), 7.79-7.93 (m, 2H), 7.72 (d, 1H, J = 4.5 Hz), 6.98 (d, 1H, J = 3.3 Hz), 6.95 (s, 1H), 5.88-5.96 (m, 1H), 4.06 (dd, 1H, J = 5.2 Hz, J = 4.5 Hz), 3.93 (s, 3H), 3.68-3.89 (m, 3H), 2.27-2.39 (m, 1H), 1.99-2.08 (m, 1H). LC-MS (ESI, m/z): [M + H]$^+$ = 378.3. |
| 118 | 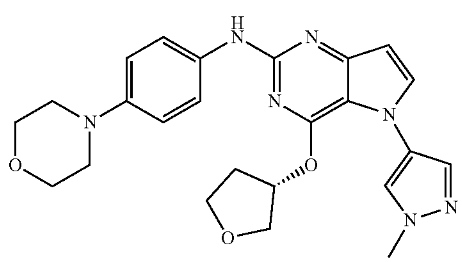 [SMILES: Cn1cc(-n2ccc3nc(Nc4ccc(N5CCOCC5)cc4)nc(O[C@H]4CCOC4)c32)cn1] | $^1$H-NMR (300 MHz, DMSO-$d_6$) δ: 8.84 (s, 1H), 8.01 (s, 1H), 7.66 (s, 2H), 7.63 (s, 1H), 7.54 (d, 1H, J = 3.0 Hz), 6.89 (d, 2H, J = 9.0 Hz), 6.40 (d, 1H, J = 3.0 Hz), 5.68 (dd, 1H, J = 1.2 Hz, J = 1.2 Hz), 3.96 (dd, 1H, J = 4.0 Hz, J = 1.8 Hz), 3.31 (s, 3H), 3.68-3.80 (m, 7H), 3.02 (t, 4H, J = 4.5 Hz), 2.17-2.26 (m, 1H), 1.96-2.00 (m, 1H). LC-MS (ESI, m/z): [M + H]$^+$ = 462.4. |
| 119 | 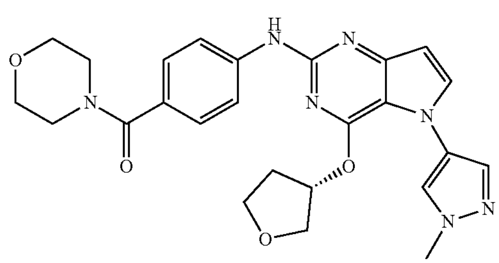 [SMILES: Cn1cc(-n2ccc3nc(Nc4ccc(C(=O)N5CCOCC5)cc4)nc(O[C@H]4CCOC4)c32)cn1] | $^1$H-NMR (300 MHz, DMSO-$d_6$) δ: 9.37 (s, 1H), 8.04 (s, 1H), 7.99 (d, 2H, J = 5.7 Hz), 7.68 (s, 1H), 7.61 (d, 1H, J = 3.0 Hz), 7.36 (d, 2H, J = 8.7 Hz), 6.49 (d, 1H, J = 3.0 Hz), 5.71-5.74 (m, 1H), 3.98 (dd, 1H, J = 4.8 Hz, J = 8.1 Hz), 3.82 (s, 3H), 3.68-3.80 (m, 3H), 3.52-3.60 (m, 8H), 2.16-2.31 (m, 1H), 1.98-2.02 (m, 1H). LC-MS (ESI, m/z): [M + H]$^+$ = 490.3. |
| 120 | 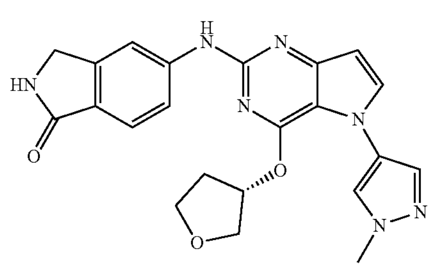 [SMILES: Cn1cc(-n2ccc3nc(Nc4ccc5c(c4)CNC5=O)nc(O[C@H]4CCOC4)c32)cn1] | $^1$H-NMR (300 MHz, DMSO-$d_6$) δ: 10.05 (s, 1H), 8.33 (s, 1H), 8.06 (s, 1H), 7.69-7.72 (m, 2H), 7.58-7.61 (m, 1H), 6.54 (d, 1H, J = 3.0 Hz), 5.69-5.72 (m, 1H), 4.36 (s, 2H), 3.65-3.96 (m, 6H), 2.18-2.30 (m, 1H), 1.97-2.05 (m, 1H). LC-MS (ESI, m/z): [M + H]$^+$ = 432.2. |

TABLE 5-continued

| Examples | Structures | Characterization data |
|---|---|---|
| 121 | 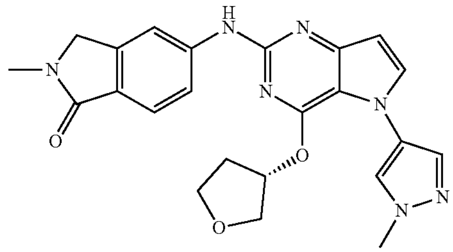 [SMILES: CN1Cc2cc(Nc3nc(O[C@H]4CCOC4)c4c(ccn4-c4cnn(C)c4)n3)ccc2C1=O] | ¹H-NMR (300 MHz, CD₃OD) δ: 8.03 (s, 1H), 7.83 (d, 1H, J = 8.1 Hz), 7.79 (s, 1H), 7.75 (s, 1H), 7.72 (d, 1H, J = 1.2 Hz), 7.63-7.66 (m, 1H), 6.61 (d, 1H, J = 3.0 Hz), 5.76-5.78 (m, 1H), 4.57 (s, 2H), 3.99 (s, 3H), 3.78-3.93 (m, 4H), 3.23 (s, 3H), 2.12-2.31 (m, 2H). LC-MS (ESI, m/z): [M + H]⁺ = 446.3. |
| 122 | 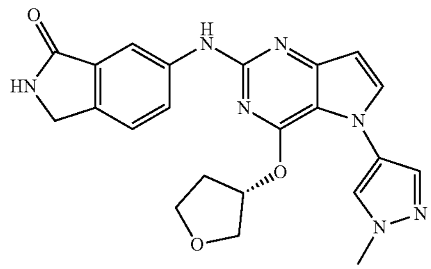 [SMILES: Cn1cc(-n2ccc3nc(Nc4ccc5c(c4)C(=O)NC5)nc(O[C@H]4CCOC4)c32)cn1] | ¹H-NMR (300 MHz, DMSO-d₆) δ: 9.99-10.18 (m, 1H), 8.54-8.61 (m, 1H), 8.19 (s, 1H), 8.07 (s, 1H), 7.71-7.78 (m, 3H), 7.51-7.53 (m, 1H), 6.53-6.54 (m, 1H), 5.67 (s, 1H), 4.33 (s, 1H), 3.96-4.01 (m, 1H), 3.89 (s, 3H), 3.65-3.84 (m, 3H), 2.21-2.34 (m, 1H), 1.98-2.05 (m, 1H). LC-MS (ESI, m/z): [M + H]⁺ = 432.2. |
| 123 | 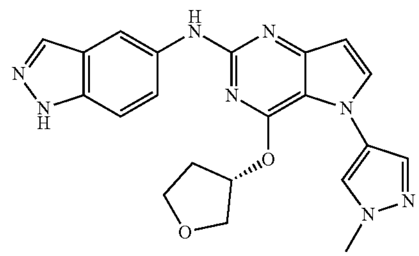 [SMILES: Cn1cc(-n2ccc3nc(Nc4ccc5[nH]ncc5c4)nc(O[C@H]4CCOC4)c32)cn1] | ¹H-NMR (300 MHz, CD₃OD) δ: 8.12-8.13 (m, 1H), 8.00 (s, 1H), 7.93-7.94 (m, 1H), 7.68-7.73 (m, 2H), 7.60-7.61 (m, 1H), 7.46-7.50 (m, 1H), 6.49 (d, 1H, J = 3.0 Hz), 5.74-5.75 (m, 1H), 3.98 (s, 3H), 3.88-3.91 (m, 2H), 3.76-3.87 (m, 2H), 2.20-2.32 (m, 1H), 2.00-2.10 (m, 1H). LC-MS (ESI, m/z): [M + H]⁺ = 417.1. |
| 124 | 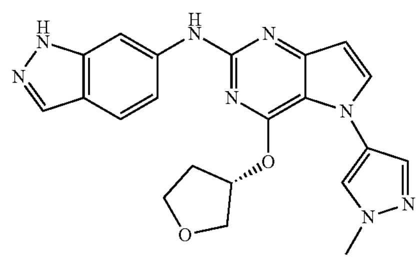 [SMILES: Cn1cc(-n2ccc3nc(Nc4ccc5cn[nH]c5c4)nc(O[C@H]4CCOC4)c32)cn1] | ¹H-NMR (300 MHz, DMSO-d₆) δ: 12.76 (s, 1H), 9.26 (s, 1H), 8.42 (s, 1H), 8.02-8.04 (m, 1H), 7.88 (s, 1H), 7.68-7.69 (m, 1H), 7.56-7.61 (m, 2H), 7.24-7.27 (m, 1H), 6.47-6.48 (m, 1H), 5.75 (s, 1H), 4.00-4.12 (m, 2H), 3.88 (s, 3H), 3.70-3.82 (m, 3H), 2.26-2.30 (m, 1H), 1.99-2.06 (m, 1H). LC-MS (ESI, m/z): [M + H]⁺ = 417.2. |
| 125 | 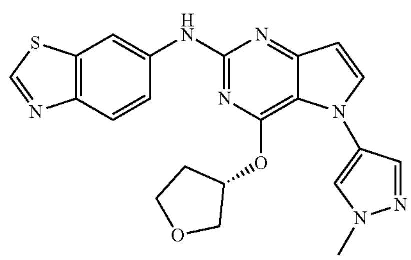 [SMILES: Cn1cc(-n2ccc3nc(Nc4ccc5ncsc5c4)nc(O[C@H]4CCOC4)c32)cn1] | ¹H-NMR (300 MHz, CD₃OD) δ: 9.27 (s, 1H), 8.34-8.35 (m, 1H), 8.13-8.16 (m, 1H), 8.00 (s, 1H), 7.64-7.73 (m, 3H), 6.55 (d, 1H, J = 3.0 Hz), 5.74-5.75 (m, 1H), 3.98 (s, 3H), 3.75-3.92 (m, 4H), 2.20-2.33 (m, 1H), 2.04-2.12 (m, 1H). LC-MS (ESI, m/z): [M + H]⁺ = 434.2. |
| 126 | 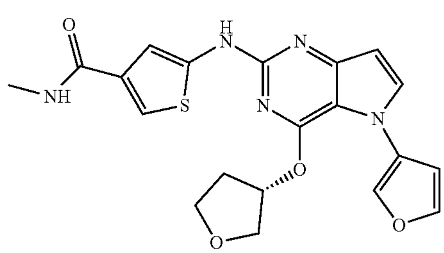 [SMILES: CNC(=O)c1csc(Nc2nc(O[C@H]3CCOC3)c3c(ccn3-c3ccoc3)n2)c1] | ¹H-NMR (300 MHz, CD₃OD) δ: 7.72 (d, 1H, J = 0.6 Hz), 7.57 (d, 1H, J = 1.5 Hz), 7.51-7.53 (m, 1H), 7.37 (d, 1H, J = 3.0 Hz), 7.06 (d, 1H, J = 1.5 Hz), 6.61-6.67 (m, 3H), 6.05-6.17 (m, 1H), 5.95-6.05 (m, 1H), 3.65-4.17 (m, 4H), 2.97 (d, 3H, J = 4.8 Hz), 2.33-2.46 (m, 1H), 2.10-2.24 (m, 1H). LC-MS (ESI, m/z): [M + H]⁺ = 426.3. |

| Examples | Structures | Characterization data |
|---|---|---|
| 127 | 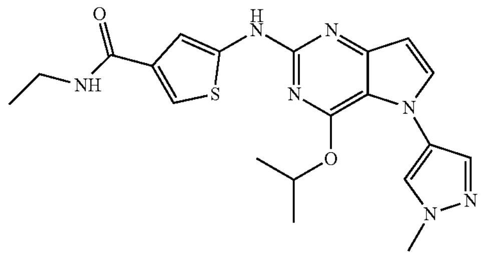 [SMILES: CCNC(=O)c1csc(Nc2nc(OC(C)C)c3c(ccn3-c3cnn(C)c3)n2)c1] | ¹H-NMR (300 MHz, CD₃OD) δ: 8.18 (s, 1H), 7.90 (s, 1H), 7.68 (s, 1H), 7.42 (d, 1H, J = 3.0 Hz), 7.36 (d, 1H, J = 1.8 Hz), 6.95 (d, 1H, J = 1.5 Hz), 6.43 (d, 1H, J = 3.3 Hz), 5.51-5.72 (m, 1H), 3.97 (s, 3H), 3.35-3.45 (m, 2H), 1.39 (d, 1H, J = 6.3 Hz), 1.23 (t, 3H, J = 7.2 Hz).<br>LC-MS (ESI, m/z): [M + H]⁺ = 426.0. |
| 128 | 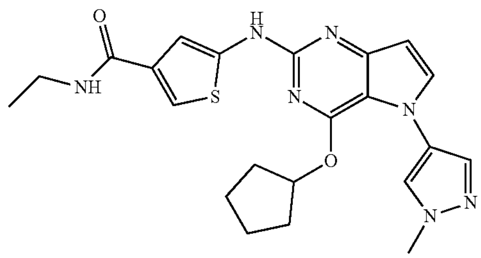 [SMILES: CCNC(=O)c1csc(Nc2nc(OC3CCCC3)c3c(ccn3-c3cnn(C)c3)n2)c1] | ¹H-NMR (300 MHz, CD₃OD) δ: 7.90 (s, 1H), 7.67 (s, 1H), 7.40 (d, 1H, J = 3.3 Hz), 7.36 (d, 1H, J = 1.8 Hz), 6.96 (d, 1H, J = 1.8 Hz), 6.43 (d, 1H, J = 3.3 Hz), 5.80-5.84 (m, 1H), 3.97 (s, 3H), 3.35-3.42 (m, 2H), 1.96-2.02 (m, 2H), 1.79-1.84 (m, 2H), 1.61-1.68 (m, 2H), 1.23 (t, 3H, J = 7.2 Hz).<br>LC-MS (ESI, m/z): [M + H]⁺ = 452.0. |
| 129 | 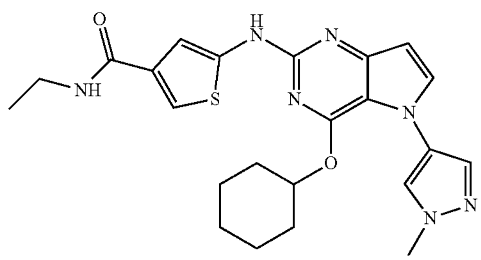 [SMILES: CCNC(=O)c1csc(Nc2nc(OC3CCCCC3)c3c(ccn3-c3cnn(C)c3)n2)c1] | ¹H-NMR (300 MHz, CD₃OD) δ: 8.17 (t, 1H, J = 5.4 Hz), 7.91 (s, 1H), 7.69 (s, 1H), 7.40 (d, 1H, J = 3.3 Hz), 7.35 (d, 1H, J = 1.8 Hz), 6.94 (d, 1H, J = 1.5 Hz), 6.43 (d, 1H, J = 3.3 Hz), 5.43-5.51 (m, 1H), 3.97 (s, 3H), 3.37-3.51 (m, 2H), 1.95-2.05 (m, 2H), 1.37-1.63 (m, 8H), 1.17-1.25 (m, 3H).<br>LC-MS (ESI, m/z): [M + H]⁺ = 466.0. |
| 130 | 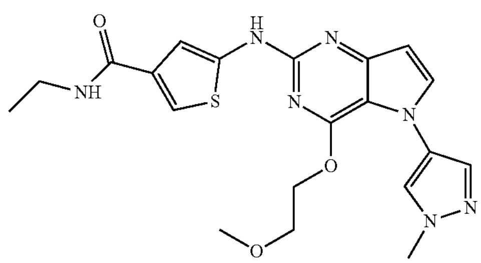 [SMILES: CCNC(=O)c1csc(Nc2nc(OCCOC)c3c(ccn3-c3cnn(C)c3)n2)c1] | ¹H-NMR (300 MHz, CD₃OD) δ: 8.18 (s, 1H), 7.59 (s, 1H), 7.74 (s, 1H), 7.47 (d, 1H, J = 3.0 Hz), 7.36 (d, 1H, J = 1.8 Hz), 6.95 (d, 1H, J = 1.8 Hz), 6.45 (d, 1H, J = 3.0 Hz), 4.69 (t, 2H, J = 4.5 Hz), 3.96 (s, 3H), 3.75 (t, 2H, J = 4.5 Hz), 3.37-3.41 (m, 5H), 1.21-1.30 (m, 3H).<br>LC-MS (ESI, m/z): [M + H]⁺ = 442.0. |
| 131 | 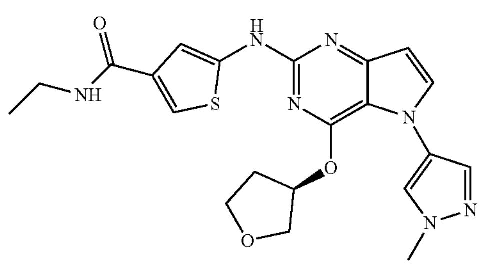 [SMILES: CCNC(=O)c1csc(Nc2nc(O[C@@H]3CCOC3)c3c(ccn3-c3cnn(C)c3)n2)c1] | ¹H-NMR (300 MHz, DMSO-d₆) δ: 8.18 (s, 1H), 7.89 (s, 1H), 7.68 (s, 1H), 7.43 (d, 1H, J = 2.7 Hz), 7.37 (s, 1H), 6.97 (s, 1H), 6.44 (d, 1H, J = 2.7 Hz), 5.89 (s, 1H), 3.77-4.13 (m, 7H), 3.73-3.40 (m, 2H), 2.03-2.38 (m, 2H), 1.30 (s, 2H), 1.23 (t, 3H, J = 7.2 Hz).<br>LC-MS (ESI, m/z): [M + H]⁺ = 454.0. |
| 132 | 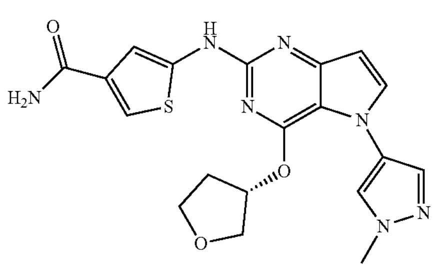 [SMILES: Cn1cc(-n2ccc3nc(Nc4cc(C(N)=O)cs4)nc(O[C@H]4CCOC4)c32)cn1] | ¹H-NMR (300 MHz, CD₃OD) δ: 7.99 (s, 1H), 7.76-7.77 (m, 1H), 7.73 (s, 1H), 7.66 (d, 1H, J = 3.0 Hz), 7.25-7.26 (m, 1H), 6.57 (d, 1H, J = 3.0 Hz), 5.94-5.97 (m, 1H), 4.01-4.07 (m, 1H), 4.00 (s, 3H), 3.87-3.94 (m, 2H), 3.75-3.83 (m, 1H), 2.26-2.42 (m, 1H), 2.07-2.15 (m, 1H).<br>LC-MS (ESI, m/z): [M + H]⁺ = 426.2. |

| Examples | Structures | Characterization data |
|---|---|---|
| 133 | 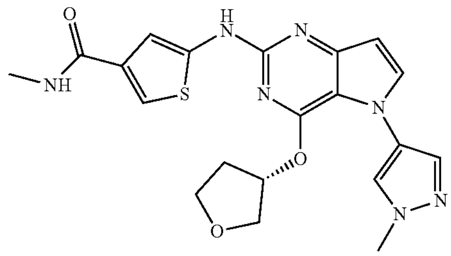 [SMILES: CNC(=O)c1csc(Nc2nc(O[C@H]3CCOC3)c3c(ccn3-c3cnn(C)c3)n2)c1] | $^1$H-NMR (300 MHz, CD$_3$OD) δ: 7.98 (s, 1H), 7.72 (s, 1H), 7.63-7.64 (m, 2H), 7.20-7.21 (m, 1H), 6.56 (d, 1H, J = 3.0 Hz), 5.93-5.96 (m, 1H), 4.03-4.06 (m, 2H), 3.97 (s, 3H), 3.81-3.96 (m, 2H), 3.74-3.80 (m, 1H), 2.89 (s, 3H), 2.30-2.42 (m, 1H), 2.06-2.16 (m, 1H). LC-MS (ESI, m/z): [M + H]$^+$ = 440.3. |
| 134 | 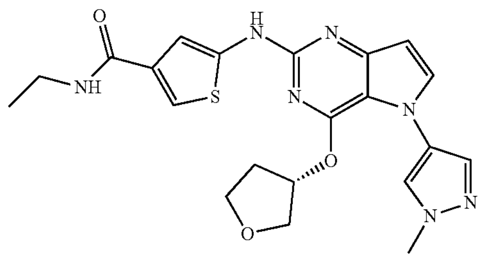 [SMILES: CCNC(=O)c1csc(Nc2nc(O[C@H]3CCOC3)c3c(ccn3-c3cnn(C)c3)n2)c1] | $^1$H-NMR (300 MHz, CD$_3$OD) δ: 7.98 (s, 1H), 7.72 (s, 1H), 7.64-7.66 (m, 2H), 7.22 (s, 1H), 6.57 (d, 1H, J = 3.3 Hz), 5.93-5.96 (m, 1H), 3.99-4.04 (m, 1H), 3.97 (s, 3H), 3.86-3.96 (m, 2H), 3.75-3.82 (m, 1H), 3.34-3.43 (m, 2H), 2.29-2.42 (m, 1H), 2.06-2.15 (m, 1H), 1.19-1.24 (m, 3H). LC-MS (ESI, m/z): [M + H]$^+$ = 454.3. |
| 135 | 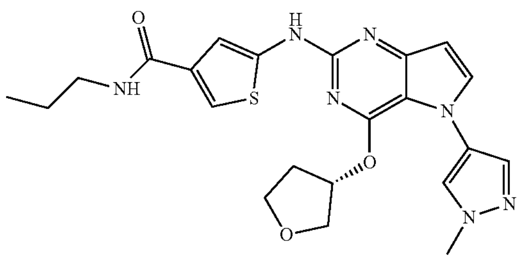 [SMILES: CCCNC(=O)c1csc(Nc2nc(O[C@H]3CCOC3)c3c(ccn3-c3cnn(C)c3)n2)c1] | $^1$H-NMR (300 MHz, CD$_3$OD) δ: 7.87-7.90 (m, 1H), 7.65-7.68 (m, 1H), 7.36-7.44 (m, 2H), 6.67-6.96 (m, 1H), 6.44-6.46 (m, 1H), 5.92 (s, 1H), 4.03-4.06 (m, 1H), 3.78-3.96 (m, 9H), 2.26-2.31 (m, 2H), 2.00-2.04 (m, 2H), 1.61-1.65 (m, 1H). LC-MS (ESI, m/z): [M + H]$^+$ = 468.3. |
| 136 | 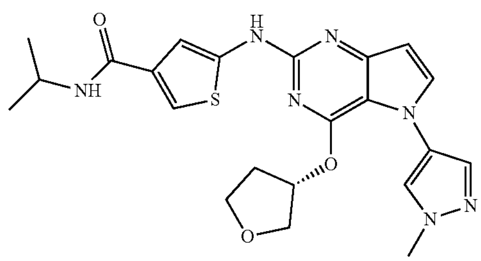 [SMILES: CC(C)NC(=O)c1csc(Nc2nc(O[C@H]3CCOC3)c3c(ccn3-c3cnn(C)c3)n2)c1] | $^1$H-NMR (300 MHz, CD$_3$OD) δ: 7.98 (s, 1H), 7.72 (s, 1H), 7.69 (s, 1H), 7.65 (d, 1H, J = 3.0 Hz), 7.24 (s, 1H), 6.57 (d, J = 3.0 Hz), 5.93-5.96 (m, 1H), 4.17-4.24 (m, 1H), 4.01-4.04 (m, 1H), 3.97 (s, 3H), 3.86-3.96 (m, 2H), 3.75-3.83 (m, 1H), 2.30-2.46 (m, 1H), 1.99-2.15 (m, 1H), 1.26 (s, 3H), 1.24 (s, 3H). LC-MS (ESI, m/z): [M + H]$^+$ = 468.2. |
| 137 | 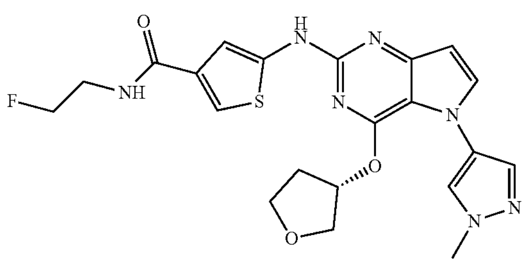 [SMILES: Cn1cc(-n2ccc3nc(Nc4cc(C(=O)NCCF)cs4)nc(O[C@H]4CCOC4)c32)cn1] | $^1$H-NMR (300 MHz, CD$_3$OD) δ: 7.98 (s, 1H), 7.71-7.73 (m, 2H), 7.63 (d, 1H, J = 3.0 Hz), 7.23-7.24 (m, 1H), 6.55 (d, 1H, J = 3.0 Hz), 5.94-5.97 (m, 1H), 4.60-4.66 (m, 2H), 4.44-4.53 (m, 2H), 3.87-4.02 (m, 7H), 3.68-3.72 (m, 2H), 3.59-3.63 (m, 2H). LC-MS (ESI, m/z): [M + H]$^+$ = 472.0. |
| 138 | 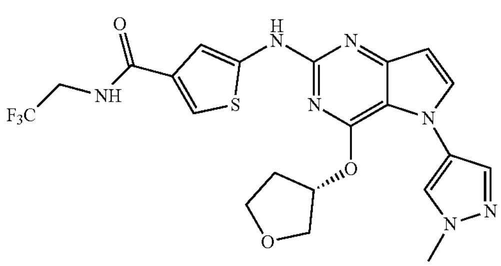 [SMILES: Cn1cc(-n2ccc3nc(Nc4cc(C(=O)NCC(F)(F)F)cs4)nc(O[C@H]4CCOC4)c32)cn1] | $^1$H-NMR (300 MHz, CD$_3$OD) δ: 7.99 (s, 1H), 7.74-7.75 (m, 2H), 7.65 (d, 1H, J = 3.3 Hz), 7.26 (s, 1H), 6.58 (d, 1H, J = 3.3 Hz), 5.95-5.98 (m, 1H), 4.02-4.13 (m, 3H), 3.99 (s, 3H), 3.85-3.96 (m, 2H), 3.76-3.83 (m, 1H), 2.32-2.44 (m, 1H), 2.11-2.17 (m, 1H). LC-MS (ESI, m/z): [M + H]$^+$ = 508.3. |

TABLE 5-continued

| Examples | Structures | Characterization data |
|---|---|---|
| 139 | 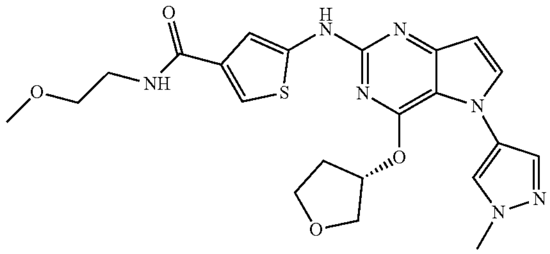 [SMILES: COCCNC(=O)c1csc(Nc2nc(O[C@H]3CCOC3)c3c(ccn3-c3cnn(C)c3)n2)c1] | ¹H-NMR (300 MHz, CD₃OD) δ: 7.99 (s, 1H), 7.73 (s, 1H), 7.70 (s, 1H), 7.64 (d, 1H, J = 3.0 Hz), 7.23 (s, 1H), 6.56 (d, 1H, J = 3.0 Hz), 5.94-5.97 (m, 1H), 4.01-4.06 (m, 2H), 3.98 (s, 3H), 3.76-3.97 (m, 2H), 3.55-3.57 (m, 4H), 3.40 (s, 3H), 2.26-2.43 (m, 1H), 2.00-2.24 (m, 1H).<br>LC-MS (ESI, m/z): [M + H]⁺ = 484.3. |
| 140 | 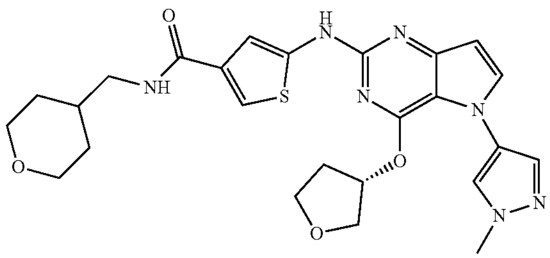 [SMILES: Cn1cc(-n2ccc3nc(Nc4cc(C(=O)NCC5CCOCC5)cs4)nc(O[C@H]4CCOC4)c32)cn1] | ¹H-NMR (300 MHz, DMSO-d₆) δ: 10.38 (s, 1H), 8.12 (d, 1H, J = 5.7 Hz), 7.97 (s, 1H), 7.61 (s, 1H), 7.57 (d, 1H, J = 3.0 Hz), 7.35 (s, 1H), 6.90 (s, 1H), 6.40 (d, 1H, J = 3.0 Hz), 5.74 (s, 1H), 3.89-3.93 (m, 1H), 3.71-3.81 (m, 1H), 3.58-3.65 (m, 1H), 3.15-3.22 (m, 1H), 3.03 (t, 2H, J = 6.3 Hz), 2.14-2.26 (m, 1H), 1.90-1.96 (m, 1H), 1.66-1.73 (m, 1H), 1.49-1.53 (m, 2H), 1.04-1.18 (m, 2H).<br>LC-MS (ESI, m/z): [M + H]⁺ = 524.2. |
| 141 | 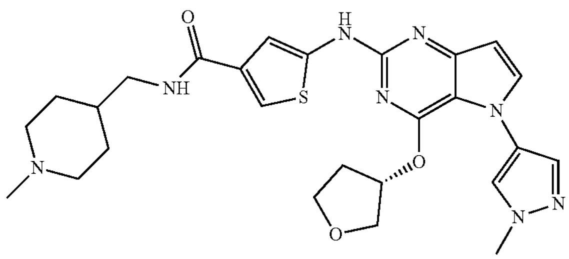 [SMILES: CN1CCC(CNC(=O)c2csc(Nc3nc(O[C@H]4CCOC4)c4c(ccn4-c4cnn(C)c4)n3)c2)CC1] | ¹H-NMR (300 MHz, DMSO-d₆) δ: 10.30 (s, 1H), 9.00 (s, 1H), 8.19 (t, 1H, J = 6.0 Hz), 7.96 (s, 1H), 7.61 (s, 1H), 7.56 (d, 1H, J = 3.0 Hz), 7.32 (d, 1H, J = 1.5 Hz), 6.87 (d, 1H, J = 1.5 Hz), 6.38 (d, 1H, J = 3.3 Hz), 5.73 (s, 1H), 3.90-3.92 (m, 2H), 3.81 (s, 3H), 3.70-3.76 (m, 2H), 3.58-3.66 (m, 2H), 3.35 (s, 2H), 3.06 (t, 2H, J = 6.0 Hz), 2.80-2.84 (m, 2H), 2.68 (d, 3H, J = 4.8 Hz), 2.13-2.22 (m, 1H), 1.91-1.96 (m, 1H), 1.76-1.80 (m, 2H), 1.60-1.73 (m, 1H), 1.22-1.33 (m, 2H).<br>LC-MS (ESI, m/z): [M + H]⁺ = 537.2. |
| 142 | 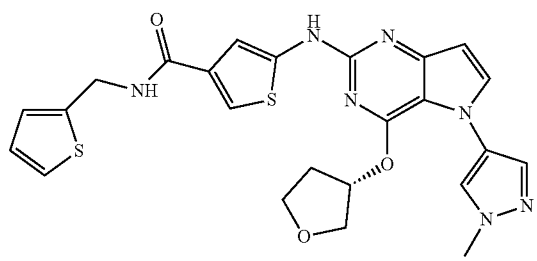 [SMILES: Cn1cc(-n2ccc3nc(Nc4cc(C(=O)NCc5cccs5)cs4)nc(O[C@H]4CCOC4)c32)cn1] | ¹H-NMR (300 MHz, CD₃OD) δ: 7.97 (s, 1H), 7.72 (s, 2H), 7.67-7.68 (m, 1H), 7.63 (d, 1H, J = 3.0 Hz), 7.28-7.30 (m, 1H), 7.22-7.23 (m, 1H), 6.94-6.97 (m, 1H), 6.55 (d, 1H, J = 3.0 Hz), 5.92-5.95 (m, 1H), 4.71 (s, 2H), 3.99-4.04 (m, 1H), 3.97 (s, 3H), 3.78-3.95 (m, 2H), 3.78-3.86 (m, 1H), 2.28-2.41 (m, 1H), 2.12-2.16 (m, 1H).<br>LC-MS (ESI, m/z): [M + H]⁺ = 522.2. |
| 143 | 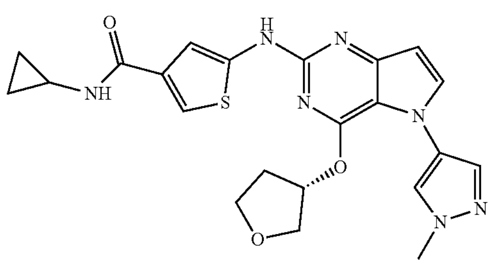 [SMILES: Cn1cc(-n2ccc3nc(Nc4cc(C(=O)NC5CC5)cs4)nc(O[C@H]4CCOC4)c32)cn1] | ¹H-NMR (300 MHz, CD₃OD) δ: 7.91 (s, 1H), 7.69 (s, 1H), 7.44 (d, 1H, J = 3.0 Hz), 7.37-7.38 (m, 1H), 6.95-6.96 (m, 1H), 6.45 (d, 1H, J = 3.0 Hz), 5.89-5.93 (m, 1H), 4.02-4.07 (m, 1H), 3.91-3.96 (m, 1H), 3.80-3.88 (m, 3H), 2.77-2.84 (m, 1H), 2.26-2.37 (m, 1H), 1.99-2.29 (m, 2H), 0.89-0.93 (m, 2H), 0.79-0.81 (m, 2H), 0.62-0.68 (m, 1H).<br>LC-MS (ESI, m/z): [M + H]⁺ = 466.3. |
| 144 | 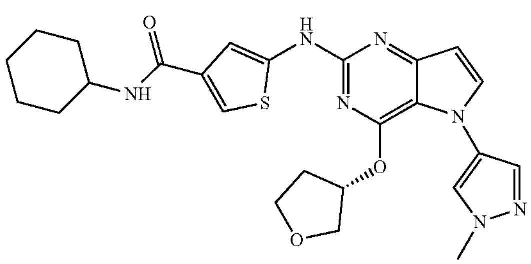 [SMILES: Cn1cc(-n2ccc3nc(Nc4cc(C(=O)NC5CCCCC5)cs4)nc(O[C@H]4CCOC4)c32)cn1] | ¹H-NMR (300 MHz, CD₃OD) δ: 7.98 (s, 1H), 7.73 (s, 1H), 7.68 (s, 1H), 7.63 (d, 1H, J = 3.0 Hz), 7.22 (s, 1H), 6.55 (d, 1H, J = 3.0 Hz), 5.95 (s, 1H), 3.99-4.06 (m, 1H), 3.98 (s, 3H), 3.87-3.96 (m, 2H), 3.76-3.84 (m, 2H), 1.81-1.97 (m, 4H), 1.25-1.46 (m, 8H).<br>LC-MS (ESI, m/z): [M + H]⁺ = 508.3. |

| Examples | Structures | Characterization data |
|---|---|---|
| 145 | 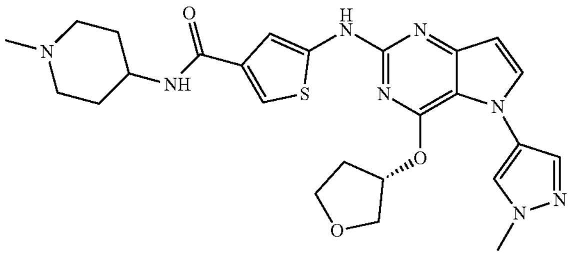 [SMILES: CN1CCC(NC(=O)c2csc(Nc3nc(O[C@H]4CCOC4)c4c(ccn4-c4cnn(C)c4)n3)c2)CC1] | ¹H-NMR (300 MHz, CD₃OD) δ: 7.97 (s, 1H), 7.72 (s, 1H), 7.66 (s, 1H), 7.63 (d, 1H, J = 3.0 Hz), 7.20 (s, 1H), 6.56 (d, 1H, J = 3.0 Hz), 5.94-5.97 (m, 1H), 4.05-4.13 (m, 1H), 4.04 (s, 3H), 3.75-3.97 (m, 4H), 3.58-3.62 (m, 2H), 3.08-3.22 (m, 2H), 2.90 (s, 3H), 2.11-2.42 (m, 4H), 1.82-2.10 (m, 2H). LC-MS (ESI, m/z): [M + H]⁺ = 523.3. |
| 146 | 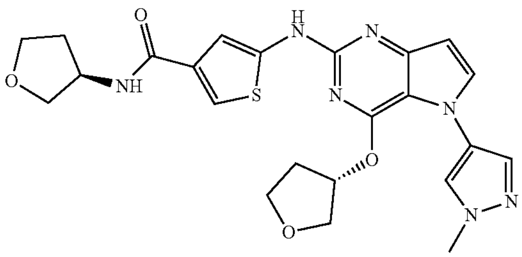 [SMILES: Cn1cc(-n2ccc3nc(Nc4cc(C(=O)N[C@@H]5CCOC5)cs4)nc(O[C@H]4CCOC4)c32)cn1] | ¹H-NMR (300 MHz, CD₃OD) δ: 7.99 (s, 1H), 7.75-7.76 (m, 1H), 7.73 (s, 1H), 7.67 (d, 1H, J = 3.0 Hz), 7.27-7.28 (m, 1H), 6.58 (d, 1H, J = 3.0 Hz), 5.95-5.98 (m, 1H), 4.53-4.60 (m, 1H), 4.01-4.06 (m, 2H), 3.98 (s, 3H), 3.56-3.97 (m, 6H), 2.23-2.43 (m, 2H), 1.97-2.16 (m, 2H). LC-MS (ESI, m/z): [M + H]⁺ = 496.3. |
| 147 | 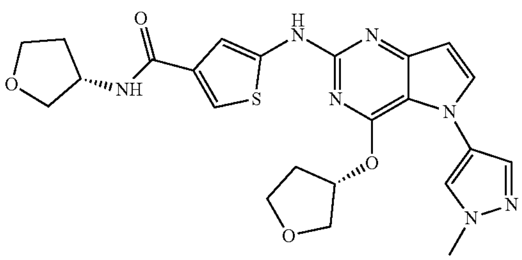 [SMILES: Cn1cc(-n2ccc3nc(Nc4cc(C(=O)N[C@H]5CCOC5)cs4)nc(O[C@H]4CCOC4)c32)cn1] | ¹H-NMR (300 MHz, CD₃OD) δ: 7.99 (s, 1H), 7.77-7.78 (m, 1H), 7.73 (s, 1H), 7.68 (d, 1H, J = 3.0 Hz), 7.28-7.29 (m, 1H), 6.58 (d, 1H, J = 3.3 Hz), 5.95-5.98 (m, 1H), 4.52-4.59 (m, 1H), 3.99-4.15 (m, 2H), 3.98 (s, 3H), 3.71-3.95 (m, 6H), 2.25-2.50 (m, 2H), 1.96-2.15 (m, 2H). LC-MS (ESI, m/z): [M + H]⁺ = 496.3. |
| 148 | 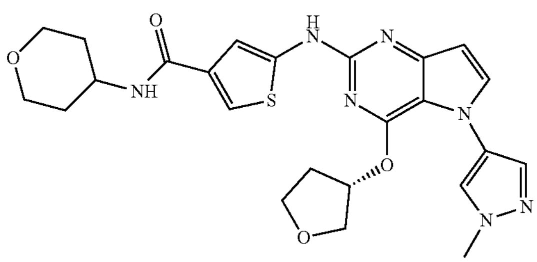 [SMILES: Cn1cc(-n2ccc3nc(Nc4cc(C(=O)NC5CCOCC5)cs4)nc(O[C@H]4CCOC4)c32)cn1] | ¹H-NMR (300 MHz, CD₃OD) δ: 7.97 (s, 1H), 7.71 (s, 1H), 7.65 (s, 1H), 7.60 (d, 1H, J = 3.0 Hz), 7.18 (s, 1H), 6.53 (d, 1H, J = 3.0 Hz), 5.95 (s, 1H), 3.98-4.03 (m, 1H), 3.98 (s, 3H), 3.76-3.96 (m, 4H), 2.13-2.41 (m, 4H), 1.61-2.08 (m, 6H). LC-MS (ESI, m/z): [M + H]⁺ = 510.3. |
| 149 | 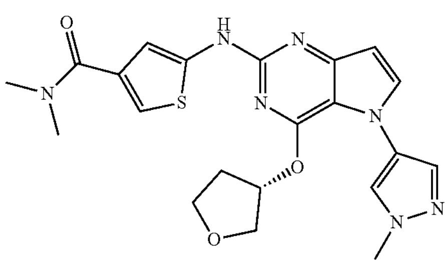 [SMILES: CN(C)C(=O)c1csc(Nc2nc(O[C@H]3CCOC3)c3c(ccn3-c3cnn(C)c3)n2)c1] | ¹H-NMR (300 MHz, CD₃OD) δ: 7.98 (s, 1H), 7.73 (s, 1H), 7.64 (d, 1H, J = 3.0 Hz), 7.34-7.35 (m, 1H), 6.99-7.00 (m, 1H), 6.56 (d, 1H, J = 3.0 Hz), 5.95-5.98 (m, 1H), 3.98-4.06 (m, 1H), 3.98 (s, 3H), 3.83-3.97 (m, 2H), 3.71-3.81 (m, 1H), 3.18 (s, 3H), 3.10 (s, 3H), 2.30-2.42 (m, 1H), 2.07-2.15 (m, 1H). LC-MS (ESI, m/z): [M + H]⁺ = 454.3. |
| 150 | 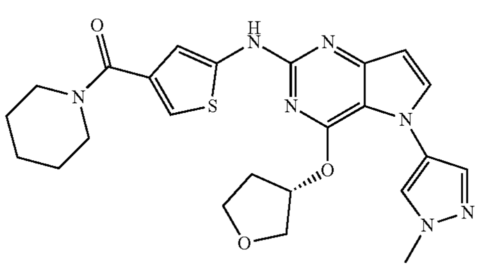 [SMILES: Cn1cc(-n2ccc3nc(Nc4cc(C(=O)N5CCCCC5)cs4)nc(O[C@H]4CCOC4)c32)cn1] | ¹H-NMR (300 MHz, CD₃OD) δ: 7.96 (s, 1H), 7.68 (s, 1H), 7.65 (d, 1H, J = 3.0 Hz), 7.29 (s, 1H), 6.96 (d, 1H, J = 1.2 Hz), 6.55 (d, 1H, J = 3.0 Hz), 5.90-6.00 (m, 1H), 3.94-3.99 (m, 1H), 3.92 (s, 3H), 3.81-3.88 (m, 1H), 3.69-3.76 (m, 1H), 3.50-3.70 (m, 4H), 2.25-2.38 (m, 1H), 2.02-2.10 (m, 1H), 1.50-1.80 (m, 6H). LC-MS (ESI, m/z): [M + H]⁺ = 494.3. |

TABLE 5-continued

| Examples | Structures | Characterization data |
|---|---|---|
| 151 | 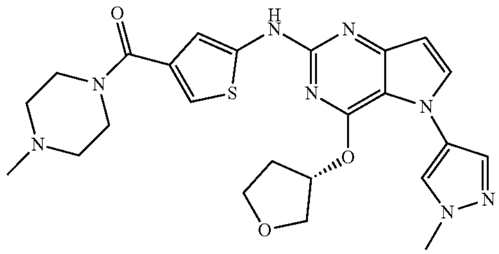 [SMILES: CN1CCN(C(=O)c2csc(Nc3nc(O[C@H]4CCOC4)c4c(ccn4-c4cnn(C)c4)n3)c2)CC1] | ¹H-NMR (300 MHz, CD₃OD) δ: 7.98 (s, 1H), 7.72 (s, 1H), 7.65 (d, 1H, J = 3.0 Hz), 7.36-7.37 (m, 1H), 6.97-6.98 (m, 1H), 6.58 (d, 1H, J = 3.0 Hz), 5.96-5.99 (m, 1H), 4.02-4.07 (m, 2H), 3.98 (s, 3H), 3.76-3.97 (m, 4H), 3.33-3.60 (m, 2H), 3.12-3.44 (m, 2H), 2.97 (s, 3H), 2.30-2.43 (m, 2H), 2.08-2.16 (m, 2H).<br>LC-MS (ESI, m/z): [M + H]⁺ = 509.3. |
| 152 | 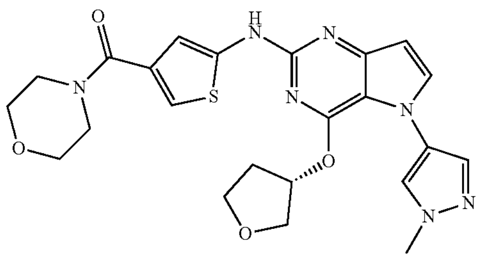 [SMILES: Cn1cc(-n2ccc3nc(Nc4cc(C(=O)N5CCOCC5)cs4)nc(O[C@H]4CCOC4)c32)cn1] | ¹H-NMR (300 MHz, CD₃OD) δ: 7.89 (s, 1H), 7.68 (s, 1H), 7.44 (d, 1H, J = 3.0 Hz), 7.02 (d, 1H, J = 1.8 Hz), 6.71 (d, 1H, J = 1.5 Hz), 6.44 (d, 1H, J = 3.3 Hz), 5.88-5.91 (m, 1H), 4.01-4.12 (m, 1H), 3.95 (s, 3H), 3.76-3.94 (m, 5H), 3.63-3.67 (m, 1H), 2.25-2.38 (m, 1H), 2.02-2.12 (m, 2H), 1.20-1.40 (m, 2H), 0.88-1.00 (m, 2H).<br>LC-MS (ESI, m/z): [M + H]⁺ = 496.3. |
| 153 | 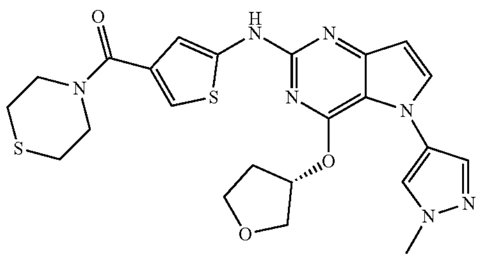 | ¹H-NMR (300 MHz, CD₃OD) δ: 7.99 (s, 1H), 7.73 (s, 1H), 7.67 (d, 1H, J = 3.1 Hz), 7.32 (s, 1H), 6.96 (s, 1H), 6.58 (d, 1H, J = 3.0 Hz), 5.96-5.99 (m, 1H), 4.01-4.05 (m, 1H), 3.98 (s, 3H), 3.87-3.93 (m, 6H), 3.75-3.83 (m, 1H), 2.69-2.74 (m, 4H), 2.30-2.41 (m, 1H), 2.07-2.15 (m, 1H).<br>LC-MS (ESI, m/z): [M + H]⁺ = 512.3. |
| 154 | 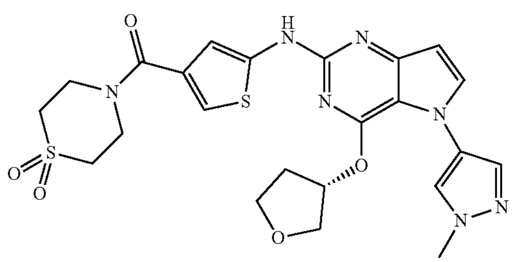 [SMILES: Cn1cc(-n2ccc3nc(Nc4cc(C(=O)N5CCS(=O)(=O)CC5)cs4)nc(O[C@H]4CCOC4)c32)cn1] | ¹H-NMR (300 MHz, CD₃OD) δ: 8.00 (s, 1H), 7.75 (s, 1H), 7.66 (d, 1H, J = 3.0 Hz), 7.41 (s, 1H), 7.01 (s, 1H), 6.59 (d, 1H, J = 3.0 Hz), 5.99-6.01 (m, 1H), 4.16-4.26 (m, 4H), 4.05-4.10 (m, 1H), 3.99 (s, 3H), 3.89-3.97 (m, 2H), 3.78-3.86 (m, 1H), 3.25-3.28 (m, 4H), 2.25-2.48 (m, 1H), 2.06-2.17 (m, 1H).<br>LC-MS (ESI, m/z): [M + H]⁺ = 544.2. |
| 155 | 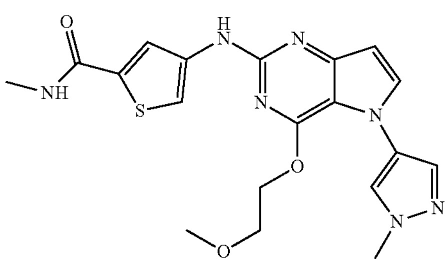 [SMILES: CNC(=O)c1cc(Nc2nc(OCCOC)c3c(ccn3-c3cnn(C)c3)n2)cs1] | ¹H-NMR (300 MHz, CD₃OD) δ: 8.05 (s, 1H), 7.75-7.78 (m, 3H), 7.71 (d, 1H, J = 3.3 Hz), 6.58 (d, 1H, J = 3.0 Hz), 4.70-4.72 (m, 2H), 3.99 (s, 3H), 3.70-3.72 (m, 2H), 3.39 (s, 3H), 2.93 (s, 3H).<br>LC-MS (ESI, m/z): [M + H]⁺ = 428.3. |
| 156 | 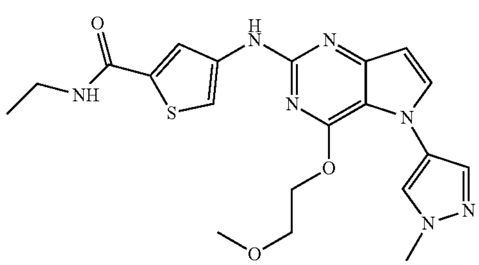 [SMILES: CCNC(=O)c1cc(Nc2nc(OCCOC)c3c(ccn3-c3cnn(C)c3)n2)cs1] | ¹H-NMR (300 MHz, CD₃OD) δ: 8.05 (s, 1H), 7.71-7.78 (m, 4H), 6.58 (d, 1H, J = 3.0 Hz), 4.69-4.72 (m, 2H), 3.99 (s, 3H), 3.38-3.43 (m, 5H), 1.24 (t, 3H, J = 7.2 Hz).<br>LC-MS (ESI, m/z): [M + H]⁺ = 442.4. |

TABLE 5-continued

| Examples | Structures | Characterization data |
|---|---|---|
| 157 | 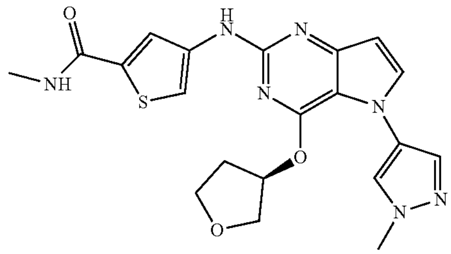 [SMILES: CNC(=O)c1cc(Nc2nc(O[C@@H]3CCOC3)c3c(ccn3-c3cnn(C)c3)n2)cs1] | $^1$H-NMR (300 MHz, CD$_3$OD) δ: 7.80 (s, 1H), 7.73 (s, 3H), 7.65 (d, 1H, J = 3.3 Hz), 6.55 (d, 1H, J = 3.0 Hz), 5.79-5.82 (m, 1H), 3.98 (s, 3H), 3.78-3.95 (m, 4H), 2.92 (s, 3H), 2.25-2.37 (m, 1H), 2.04-2.12 (m, 1H). LC-MS (ESI, m/z): [M + H]$^+$ = 440.4. |
| 158 | 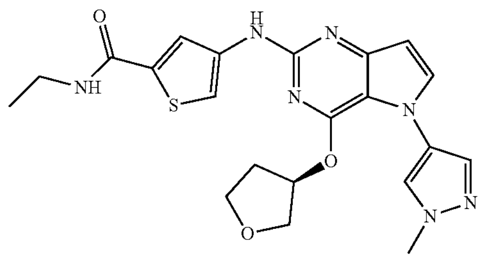 [SMILES: CCNC(=O)c1cc(Nc2nc(O[C@@H]3CCOC3)c3c(ccn3-c3cnn(C)c3)n2)cs1] | $^1$H-NMR (300 MHz, CD$_3$OD) δ: 7.99 (s, 1H), 7.72-7.76 (m, 3H), 7.63-7.64 (m, 1H), 6.54-6.55 (m, 1H), 5.80 (s, 1H), 3.78-3.98 (m, 8H), 3.40-3.42 (m, 2H), 2.27-2.34 (m, 1H), 2.05-2.10 (m, 1H), 1.21-1.26 (m, 3H). LC-MS (ESI, m/z): [M + H]$^+$ = 454.5. |
| 159 | 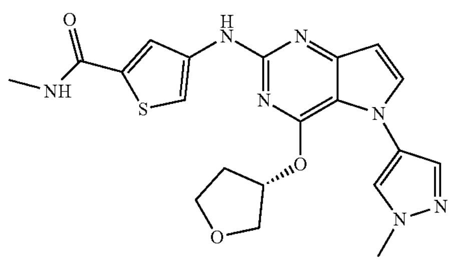 [SMILES: CNC(=O)c1cc(Nc2nc(O[C@H]3CCOC3)c3c(ccn3-c3cnn(C)c3)n2)cs1] | $^1$H-NMR (300 MHz, CD$_3$OD) δ: 7.99 (s, 1H), 7.72-7.73 (m, 3H), 7.63 (d, 1H, J = 3.3 Hz), 6.55 (d, 1H, J = 3.3 Hz), 5.79-5.82 (m, 1H), 3.98 (s, 3H), 3.75-3.95 (m, 4H), 2.92 (s, 3H), 2.25-2.37 (m, 1H), 1.99-2.12 (m, 1H). LC-MS (ESI, m/z): [M + H]$^+$ = 440.3. |
| 160 | 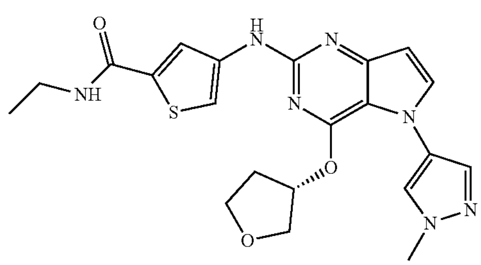 [SMILES: CCNC(=O)c1cc(Nc2nc(O[C@H]3CCOC3)c3c(ccn3-c3cnn(C)c3)n2)cs1] | $^1$H-NMR (300 MHz, DMSO-d$_6$) δ: 9.51 (s, 1H), 8.45 (t, 1H, J = 5.4 Hz), 8.03 (s, 1H), 7.68-7.74 (m, 3H), 7.58 (d, 1H, J = 3.0 Hz), 6.45 (d, 1H, J = 3.3 Hz), 5.72-5.76 (m, 1H), 3.94-3.99 (m, 1H), 3.88 (s, 3H), 3.65-3.83 (m, 3H), 3.20-3.30 (m, 2H), 2.18-2.30 (m, 1H), 1.95-2.01 (m, 1H), 1.07-1.38 (m, 3H). LC-MS (ESI, m/z): [M + H]$^+$ = 454.3. |
| 161 | 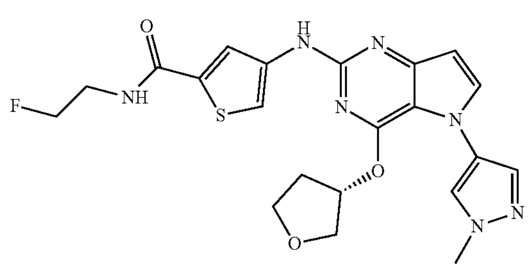 [SMILES: Cn1cc(-n2ccc3nc(Nc4csc(C(=O)NCCF)c4)nc(O[C@H]4CCOC4)c32)cn1] | $^1$H-NMR (300 MHz, DMSO-d$_6$) δ: 10.07 (s, 1H), 8.75 (s, 1H), 8.06 (s, 1H), 7.69-7.79 (m, 4H), 6.49-6.50 (m, 1H), 5.75 (s, 1H), 4.44-4.61 (m, 2H), 3.49-4.00 (m, 9H), 2.20-2.27 (m, 1H), 2.01 (s, 1H). LC-MS (ESI, m/z): [M + H]$^+$ = 472.0. |
| 162 | 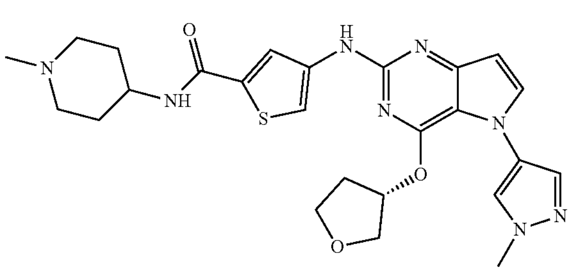 [SMILES: CN1CCC(NC(=O)c2cc(Nc3nc(O[C@H]4CCOC4)c4c(ccn4-c4cnn(C)c4)n3)cs2)CC1] | $^1$H-NMR (300 MHz, CD$_3$OD) δ: 7.97 (s, 1H), 7.75-7.78 (m, 2H), 7.70 (s, 1H), 7.64 (d, 1H, J = 3.0 Hz), 6.56 (d, 1H, J = 3.0 Hz), 5.77-5.80 (m, 1H), 4.10-4.14 (m, 1H), 4.07 (s, 3H), 3.71-3.94 (m, 4H), 3.55-3.59 (m, 2H), 3.10-3.14 (m, 2H), 2.87 (s, 3H), 1.82-2.34 (m, 6H). LC-MS (ESI, m/z): [M + H]$^+$ = 523.3. |

TABLE 5-continued

| Examples | Structures | Characterization data |
|---|---|---|
| 163 | 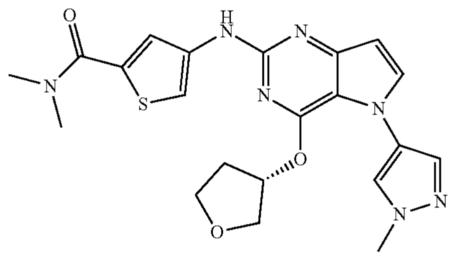 [SMILES: CN(C)C(=O)c1cc(Nc2nc(O[C@H]3CCOC3)c3c(ccn3-c3cnn(C)c3)n2)cs1] | $^1$H-NMR (300 MHz, DMSO-d$_6$) δ: 8.05 (s, 1H), 7.79-7.80 (m, 1H), 7.65-7.69 (m, 2H), 7.55-7.56 (m, 1H), 6.49 (d, 1H, J = 3.0 Hz), 5.70-5.73 (m, 1H), 3.92-3.96 (m, 1H), 3.88 (s, 3H), 3.66-3.81 (m, 4H), 3.12 (s, 6H), 2.18-2.30 (m, 1H), 1.91-2.03 (m, 1H). LC-MS (ESI, m/z): [M + H]$^+$ = 454.3. |
| 164 | 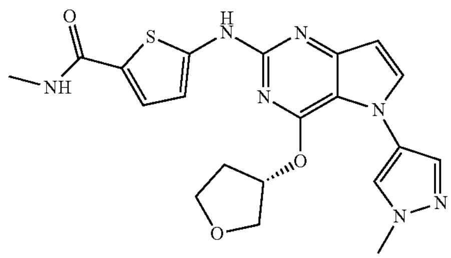 [SMILES: CNC(=O)c1ccc(Nc2nc(O[C@H]3CCOC3)c3c(ccn3-c3cnn(C)c3)n2)s1] | $^1$H-NMR (300 MHz, CD$_3$OD) δ: 7.96 (s, 1H), 7.70 (s, 1H), 7.63 (d, 1H, J = 3.0 Hz), 7.43-7.44 (m, 1H), 6.74-6.76 (m, 1H), 6.55 (d, 1H, J = 3.0 Hz), 5.99-6.02 (m, 1H), 4.03-4.53 (m, 2H), 3.95 (s, 3H), 3.74-3.92 (m, 2H), 2.86 (s, 3H), 2.35-2.52 (m, 1H), 2.06-2.15 (m, 1H). LC-MS (ESI, m/z): [M + H]$^+$ = 440.3. |
| 165 | 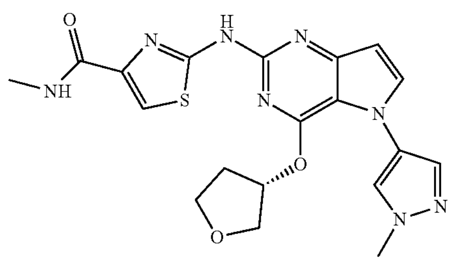 | $^1$H-NMR (300 MHz, CD$_3$OD) δ: 7.90 (s, 1H), 7.79 (s, 1H), 7.65 (s, 1H), 7.56 (d, 1H, J = 3.0 Hz), 6.46 (d, 1H, J = 3.0 Hz), 5.72 (s, 1H), 3.98 (s, 3H), 3.77-3.93 (m, 4H), 2.80 (s, 3H), 2.27-2.40 (m, 1H), 1.99-2.12 (m, 1H). LC-MS (ESI, m/z): [M + H]$^+$ = 441.2. |
| 166 | 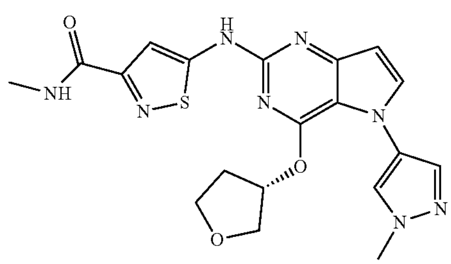 | $^1$H-NMR (300 MHz, CD$_3$OD) δ: 7.93 (s, 1H), 7.70 (s, 1H), 7.55 (d, 1H, J = 3.0 Hz), 7.26 (s, 1H), 6.57 (d, 1H, J = 3.0 Hz), 5.90 (s, 1H), 4.02-4.07 (m, 1H), 3.97 (s, 3H), 3.87-3.95 (m, 2H), 3.76-3.81 (m, 1H), 2.91 (s, 3H), 2.21-2.37 (m, 1H), 2.08-2.14 (m, 1H). LC-MS (ESI, m/z): [M + H]$^+$ = 441.3. |
| 167 | 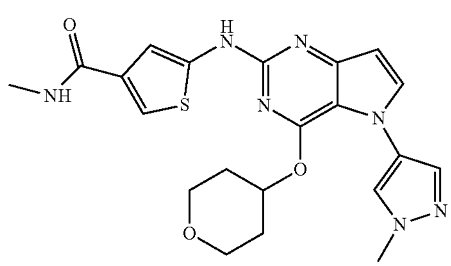 [SMILES: CNC(=O)c1csc(Nc2nc(OC3CCOCC3)c3c(ccn3-c3cnn(C)c3)n2)c1] | $^1$H-NMR (300 MHz, CD$_3$OD) δ: 7.95 (s, 1H), 7.71 (s, 1H), 7.42 (d, 1H, J = 3.0 Hz), 7.35 (s, 1H), 6.95 (s, 1H), 6.45 (d, J = 2.4 Hz), 5.65 (s, 1H), 3.98 (s, 3H), 3.64-3.67 (m, 4H), 2.90 (s, 3H), 2.08-2.14 (m, 2H), 1.75-1.80 (m, 2H). LC-MS (ESI, m/z): [M + H]$^+$ = 454.3. |
| 168 | 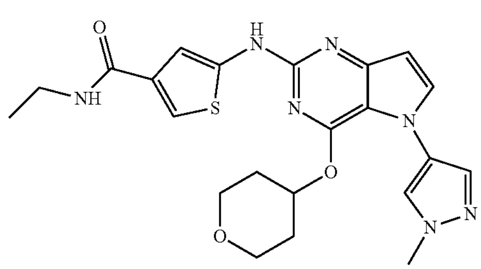 | $^1$H-NMR (300 MHz, CD$_3$OD) δ: 8.04 (s, 1H), 7.76 (s, 1H), 7.70 (d, 1H, J = 3.0 Hz), 7.65 (d, 1H, J = 3.0 Hz), 7.25 (d, 1H, J = 1.5 Hz), 6.58 (d, 1H, J = 3.0 Hz), 5.66-5.73 (m, 1H), 4.00 (s, 3H), 3.64 (t, 4H, J = 5.4 Hz), 3.33-3.50 (m, 2H), 2.00-2.20 (m, 2H), 1.70-1.90 (m, 2H), 1.23 (t, 3H, J = 7.2 Hz). LC-MS (ESI, m/z): [M + H]$^+$ = 468.3. |

TABLE 5-continued

| Examples | Structures | Characterization data |
|---|---|---|
| 169 | 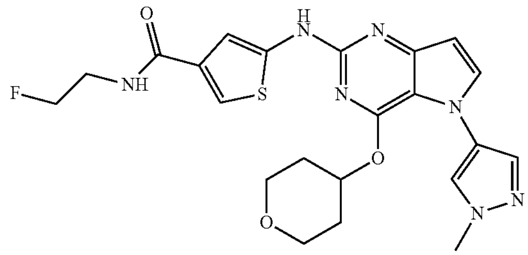 [SMILES: Cn1cc(-n2ccc3nc(Nc4cc(C(=O)NCCF)cs4)nc(OC4CCOCC4)c32)cn1] | $^1$H-NMR (300 MHz, CD$_3$OD) δ: 7.95 (s, 1H), 7.71 (s, 1H), 7.41-7.43 (m, 2H), 6.97-6.98 (m, 1H), 6.45-6.46 (m, 1H), 5.61-5.68 (m, 1H), 4.60-4.65 (m, 2H), 4.46-4.49 (m, 2H), 3.98 (s, 3H), 3.58-3.71 (m, 8H), 2.06-2.16 (m, 2H), 1.74-1.80 (m, 2H). LC-MS (ESI, m/z): [M + H]$^+$ = 486.0. |
| 170 | 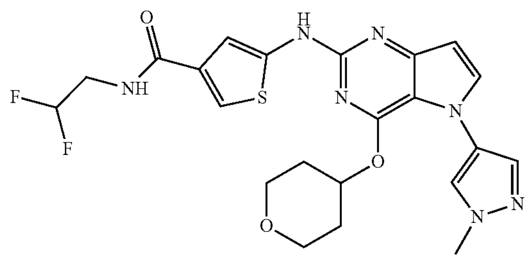 [SMILES: Cn1cc(-n2ccc3nc(Nc4cc(C(=O)NCC(F)F)cs4)nc(OC4CCOCC4)c32)cn1] | $^1$H-NMR (300 MHz, CD$_3$OD) δ: 7.58-7.62 (m, 2H), 7.33-7.34 (m, 1H), 7.24-7.26 (m, 1H), 6.84-6.85 (m, 1H), 6.49 (d, 1H, J = 3.0 Hz), 6.13-6.19 (m, 1H), 5.56-5.64 (m, 1H), 3.99 (s, 3H), 3.59-3.84 (m, 7H), 2.04-2.13 (m, 2H), 1.72-1.82 (m, 2H). LC-MS (ESI, m/z): [M + H]$^+$ = 504.0. |
| 171 | 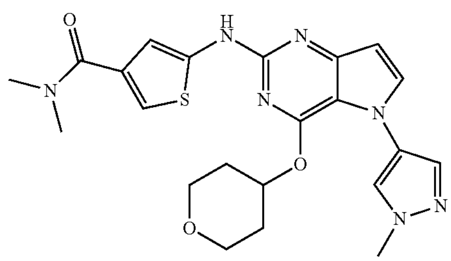 [SMILES: CN(C)C(=O)c1csc(Nc2nc(OC3CCOCC3)c3c(ccn3-c3cnn(C)c3)n2)c1] | $^1$H-NMR (300 MHz, CD$_3$OD) δ: 7.95 (s, 1H), 7.72 (s, 1H), 7.43 (d, 1H, J = 3.3 Hz), 7.03 (d, 1H, J = 1.8 Hz), 6.74 (d, 1H, J = 1.8 Hz), 6.45 (d, 1H, J = 3.0 Hz), 5.64-5.69 (m, 1H), 3.98 (s, 3H), 3.60-3.72 (m, 4H), 3.10 (s, 3H), 3.19 (s, 3H), 2.07-2.16 (m, 2H), 1.72-1.82 (m, 2H). LC-MS (ESI, m/z): [M + H]$^+$ = 468.1. |
| 172 | 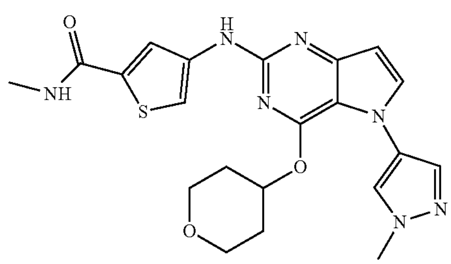 [SMILES: CNC(=O)c1cc(Nc2nc(OC3CCOCC3)c3c(ccn3-c3cnn(C)c3)n2)cs1] | $^1$H-NMR (300 MHz, CD$_3$OD) δ: 8.05 (s, 1H), 7.75-7.76 (m, 2H), 7.68 (d, 1H, J = 1.5 Hz), 7.64 (d, 1H, J = 3.0 Hz), 6.56 (d, 1H, J = 3.0 Hz), 5.52-5.56 (m, 1H), 4.00 (s, 3H), 3.55-3.66 (m, 4H), 2.93 (s, 3H), 2.02-2.11 (m, 2H), 1.70-1.80 (m, 2H). LC-MS (ESI, m/z): [M + H]$^+$ = 454.3. |
| 173 | 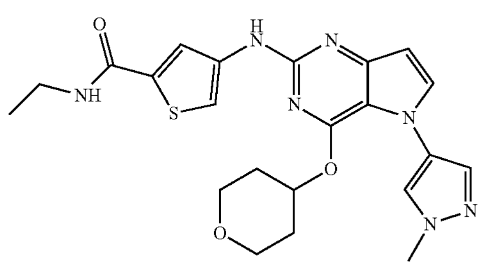 [SMILES: CCNC(=O)c1cc(Nc2nc(OC3CCOCC3)c3c(ccn3-c3cnn(C)c3)n2)cs1] | $^1$H-NMR (300 MHz, CD$_3$OD) δ: 7.95 (s, 1H), 7.73 (d, 1H, J = 1.5 Hz), 7.71 (s, 1H), 7.39 (d, 1H, J = 3.3 Hz), 6.45 (d, 1H, J = 3.0 Hz), 5.50-5.54 (m, 1H), 3.98 (s, 3H), 3.58-3.71 (m, 4H), 3.37-3.44 (m, 2H), 2.03-2.11 (m, 2H), 1.71-1.80 (m, 2H), 1.24 (t, 3H, J = 7.2 Hz). LC-MS (ESI, m/z): [M + H]$^+$ = 468.3. |
| 174 | 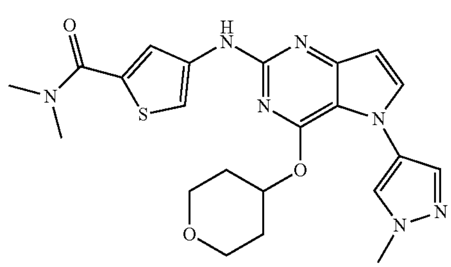 [SMILES: CN(C)C(=O)c1cc(Nc2nc(OC3CCOCC3)c3c(ccn3-c3cnn(C)c3)n2)cs1] | $^1$H-NMR (300 MHz, CD$_3$OD) δ: 7.95 (s, 1H), 7.71-7.74 (m, 2H), 7.55 (d, 1H, J = 1.5 Hz), 7.39 (d, 1H, J = 3.3 Hz), 6.44 (d, 1H, J = 3.3 Hz), 5.51-5.53 (m, 1H), 3.98 (s, 3H), 3.61-3.68 (m, 4H), 3.25 (s, 6H), 2.04-2.11 (m, 2H), 1.72-1.78 (m, 2H). LC-MS (ESI, m/z): [M + H]$^+$ = 468.3. |

| Examples | Structures | Characterization data |
|---|---|---|
| 175 | 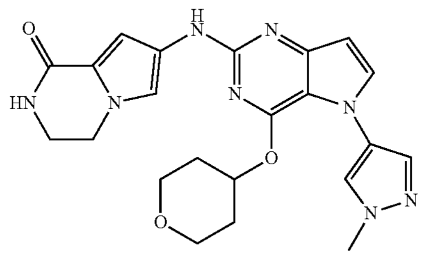 [SMILES: Cn1cc(-n2ccc3nc(Nc4cc5n(c4)CCNC5=O)nc(OC4CCOCC4)c32)cn1] | $^1$H-NMR (300 MHz, CD$_3$OD) δ: 8.04 (s, 1H), 7.75 (s, 1H), 7.59 (d, 1H, J = 3.0 Hz), 7.18-7.19 (m, 1H), 6.88-6.92 (m, 1H), 6.50 (d, 1H, J = 3.0 Hz), 5.57-5.61 (m, 1H), 4.12-4.25 (m, 2H), 3.99 (s, 3H), 3.69-3.73 (m, 7H), 2.03-2.13 (m, 2H), 1.71-1.81 (m, 2H). LC-MS (ESI, m/z): [M + H]$^+$ = 449.1. |

Evaluation of Biological Activity

Test Example 1

IRAK4 Kinase Activity Inhibition Assay

IRAK4 kinase (purchased from Life Technologies, Cat. No.: PR5612U) was diluted to 2 folds of the final concentration (the final concentration is 0.76 ng/4) with reaction buffer (40 mM Tris-HCl, pH 7.5; 20 mM MgCl$_2$; 0.1 mg/mL BSA; 1 mM DTT), and added to a 384-well plate at 5 μL/well. The test drugs were 10-fold serial diluted from 10 μM to set six concentration points and added to the test wells of the 384-well plate at 2.5 μL/well. After incubation for 10 min at 25° C., 10 μM of ATP and 0.1 μg/μL of an enzyme reaction substrate, myelin basic protein MBP (purchased from Signal Chem, Cat. No.: M42-51N) were added at 2.5 μL/well, and reacted at 25° C. for 60 minutes. After the reaction was completed, the kinase activity assay was performed using the ADP-Glo™ kinase assay kit (purchased from Promega, Cat. No.: V9102) according to the manufacture's instruction, i.e., 10 μL of ADP-Glo reaction reagent was first added and reacted at 25° C. for 40 minutes, 10 μL of the reaction mixture was taken and mixed with 10 μL of ADP-Glo detection reagent, and reacted at 25° C. for 30 minutes. The kinase activity was then detected, and the IC$_{50}$ values of the test drugs were calculated. The results were shown in Table 6.

Table 6 shows the activity of selected compounds of the invention in the IRAK4 activity inhibition assay, wherein the symbol "+++" indicates that the compound has an IC$_{50}$ of ≤0.1 μM; the symbol "++" indicates that the compound has an IC$_{50}$ of 0.1 μM<IC$_{50}$≤1 μM; and the symbol "+" indicates that the compound has an IC$_{50}$ of 1 μM<IC$_{50}$≤10 μM.

TABLE 6

Results from the IRAK4 activity inhibition assay

| Compounds | IC$_{50}$ |
|---|---|
| 1 | +++ |
| 2 | +++ |
| 3 | ++ |
| 4 | +++ |
| 5 | +++ |
| 6 | ++ |
| 7 | ++ |
| 8 | ++ |
| 9 | ++ |
| 10 | ++ |
| 11 | ++ |
| 12 | ++ |
| 13 | +++ |
| 14 | +++ |
| 15 | ++ |
| 16 | ++ |
| 17 | ++ |
| 18 | +++ |
| 19 | +++ |
| 20 | ++ |
| 21 | ++ |
| 22 | ++ |
| 23 | ++ |
| 24 | ++ |
| 25 | ++ |
| 26 | +++ |
| 27 | ++ |
| 28 | ++ |
| 29 | +++ |
| 30 | ++ |
| 31 | ++ |
| 32 | ++ |
| 33 | ++ |
| 34 | ++ |
| 35 | + |
| 36 | + |
| 37 | ++ |
| 38 | +++ |
| 39 | + |
| 40 | ++ |
| 41 | ++ |
| 42 | ++ |
| 43 | ++ |
| 44 | + |
| 45 | ++ |
| 46 | ++ |
| 47 | ++ |
| 48 | +++ |
| 49 | +++ |
| 50 | ++ |
| 51 | +++ |
| 52 | ++ |
| 53 | ++ |
| 54 | +++ |
| 55 | +++ |
| 56 | ++ |
| 57 | ++ |
| 58 | ++ |
| 59 | ++ |
| 60 | ++ |
| 61 | +++ |
| 62 | +++ |
| 63 | ++ |
| 64 | +++ |
| 65 | +++ |
| 66 | +++ |
| 67 | ++ |
| 68 | ++ |
| 69 | ++ |
| 70 | ++ |

TABLE 6-continued

Results from the IRAK4 activity inhibition assay

| Compounds | IC$_{50}$ |
|---|---|
| 71 | ++ |
| 72 | ++ |
| 73 | ++ |
| 74 | +++ |
| 75 | ++ |
| 76 | ++ |
| 77 | +++ |
| 78 | +++ |
| 79 | ++ |
| 80 | ++ |
| 81 | ++ |
| 82 | ++ |
| 83 | ++ |
| 84 | ++ |
| 85 | + |
| 86 | ++ |
| 87 | +++ |
| 88 | ++ |
| 89 | ++ |
| 90 | ++ |
| 91 | ++ |
| 92 | ++ |
| 93 | + |
| 94 | + |
| 95 | + |
| 96 | + |
| 97 | ++ |
| 98 | ++ |
| 99 | ++ |
| 100 | ++ |
| 101 | ++ |
| 102 | ++ |
| 103 | ++ |
| 104 | ++ |
| 105 | +++ |
| 106 | +++ |
| 107 | +++ |
| 108 | +++ |
| 109 | ++ |
| 110 | +++ |
| 111 | +++ |
| 112 | ++ |
| 113 | +++ |
| 114 | +++ |
| 115 | ++ |
| 116 | ++ |
| 117 | + |
| 118 | ++ |
| 119 | ++ |
| 120 | +++ |
| 121 | +++ |
| 122 | ++ |
| 123 | +++ |
| 124 | ++ |
| 125 | ++ |
| 126 | +++ |
| 127 | +++ |
| 128 | ++ |
| 129 | ++ |
| 130 | +++ |
| 131 | +++ |
| 132 | +++ |
| 133 | +++ |
| 134 | +++ |
| 135 | ++ |
| 136 | +++ |
| 137 | +++ |
| 138 | +++ |
| 139 | +++ |
| 140 | +++ |
| 141 | +++ |
| 142 | ++ |
| 143 | +++ |
| 144 | ++ |
| 145 | +++ |
| 146 | +++ |

TABLE 6-continued

Results from the IRAK4 activity inhibition assay

| Compounds | IC$_{50}$ |
|---|---|
| 147 | +++ |
| 148 | +++ |
| 149 | +++ |
| 150 | +++ |
| 151 | +++ |
| 152 | +++ |
| 153 | ++ |
| 154 | +++ |
| 155 | +++ |
| 156 | +++ |
| 157 | +++ |
| 158 | +++ |
| 159 | +++ |
| 160 | +++ |
| 161 | +++ |
| 162 | +++ |
| 163 | +++ |
| 164 | ++ |
| 165 | + |
| 166 | +++ |
| 167 | +++ |
| 168 | +++ |
| 169 | +++ |
| 170 | +++ |
| 171 | +++ |
| 172 | +++ |
| 173 | +++ |
| 174 | ++ |
| 175 | ++ |

Test Example 2

TMD-8 Cell Growth Inhibition Assay

The compound of Example 64 and the compound of Example 74 of the invention were tested in TMD-8 cell growth inhibition assay. TMD-8 cells (available from Korea Hanmi Research Center) were cultured in RMPI-1640 medium (purchased from Gibco, Cat. No.: 22440) containing 10% fetal bovine serum (purchased from Gibco, Cat. No.: 10099-141). The TMD-8 cells in logarithmic growth phase were seeded in a 96-well plate at 20,000 cells/well/100 μL, and RMPI-1640 medium (100 μL) was added into blank control wells. The test samples were diluted with RMPI-1640 medium to 2 folds of the final concentration (10-fold dilutions starting from 10 μM, setting 6 drug concentrations, and testing in replicate wells at each concentration). The diluted test samples were added to test wells seeded with cells at 100 μL/well, and RMPI-1640 medium (100 μL) was separately added to the positive control and the blank control wells. The 96-well plate was placed in the incubator and reacted at 37° C., 5% CO$_2$ for 96 hours. After the reaction was completed, the 96-well plate was taken from the incubator and to each well was added CCK-8 (100 μL) (purchased from DOJINDO, Cat. No.: CK04-11). Then the 96-well plate was put back to the incubator and incubated for another 2 hours. The light absorbance was measured at 450 nm and the compound of Example 64 was calculated to have an IC$_{50}$ value of 184 nM and the compound of Example 74 was calculated to have an IC$_{50}$ value of 479 nM.

Test Example 3

LP S-Induced TNF-α Secretion Assay in THP-1 Cells

The compound of Example 133 and the compound of Example 134 of the invention were tested in LPS-induced TNF-α secretion assay in THP-1 cells. Human THP-1 cells (purchased from ATCC, Cat. No.: TIB-202) were cultured in RPMI-1640 medium (purchased from Gibco, Cat. No.: 22440) containing 10% fetal bovine serum (purchased from Gibco, Cat. No.: 10099-141) and 0.05 mM of 2-mercaptoethanol (purchased from Gibco, Cat. No.: 21985). The THP-1 cells in logarithmic growth phase were seeded in a 96-well plate at $2\times10^5$ cells/well/100 μL. The test samples were diluted with RMPI-1640 medium to 4 folds of the final concentration (5-fold dilutions starting from 10 μM, setting 6 drug concentrations, and testing in replicate wells at each concentration). The diluted test samples were added to the test wells seeded with cells at 50 μL/well, and RMPI-1640 medium (50 μL) was separately added to positive control and negative control wells. The 96-well plate was placed in the incubator at 37° C., 5% $CO_2$ and pre-incubated for 2 hours. The 96-well plate was taken out, and 400 ng/mL of LPS (50 μL) (purchased from Sigma, Cat. No.: L6529-1MG) was added to each well of the test wells and the positive control wells, and RMPI-1640 medium (50 μL) was added to the negative control wells. After incubation in the incubator at 37° C., 5% $CO_2$ for 24 hours, the cell culture supernatant was taken and determined for the content of TNF-α in the supernatant using a human TNF-α ELISA kit (purchased from DKW, Cat. No.: 12-1720-096). The compound of Example 133 was calculated to have an $IC_{50}$ value of 161 nM and the compound of Example 134 was calculated to have an $IC_{50}$ value of 311 nM.

What is claimed is:

1. A compound selected from the group consisting of:

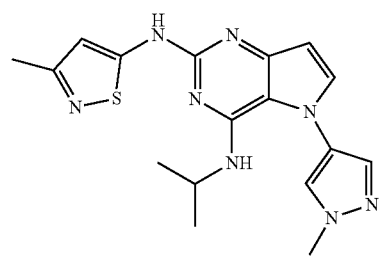

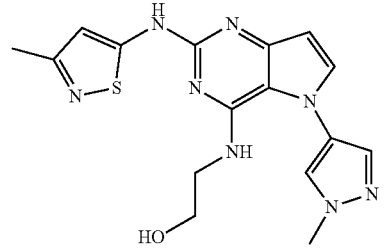

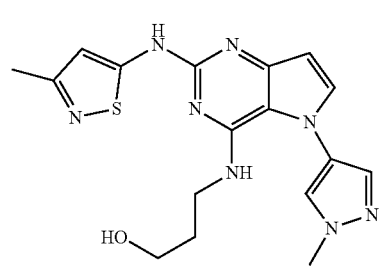

-continued

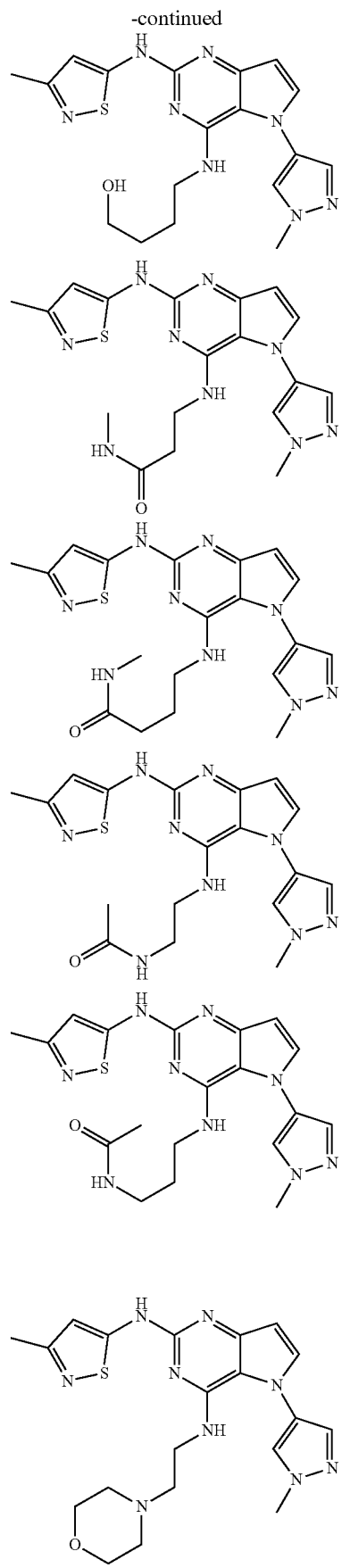

143
-continued
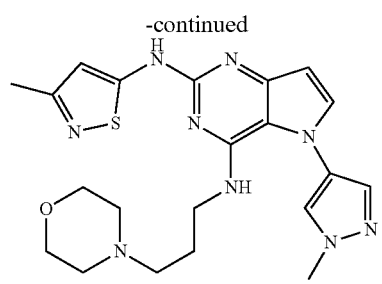
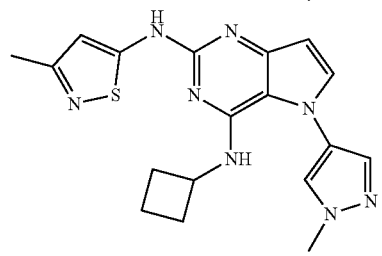
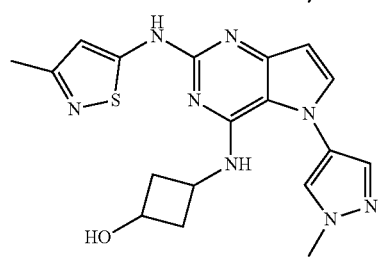
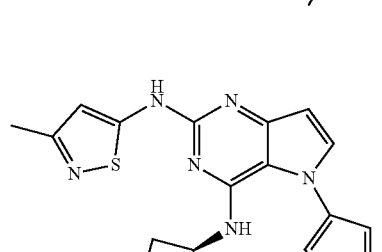
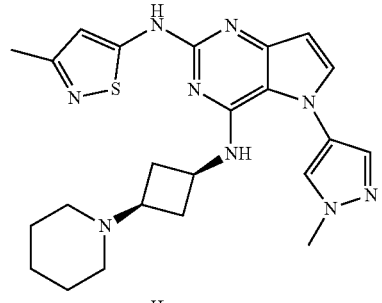
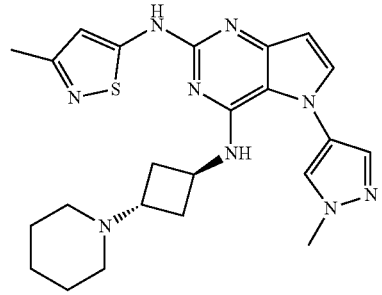
144
-continued
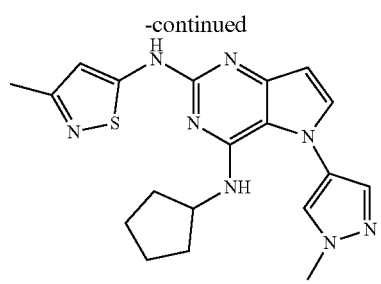
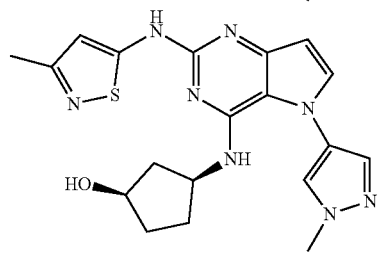
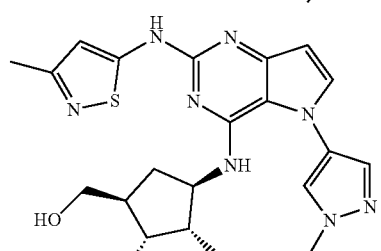
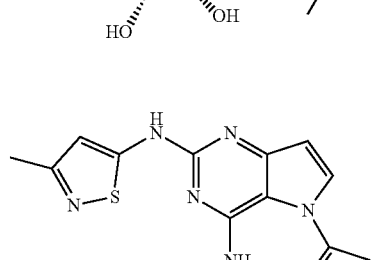
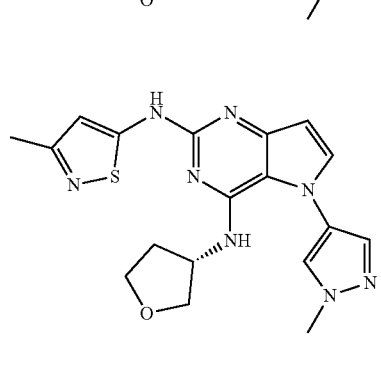
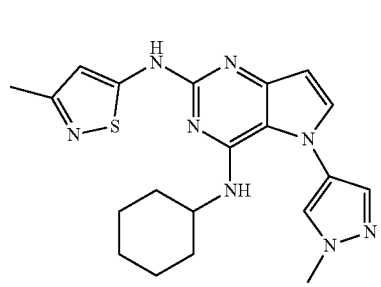

145
-continued
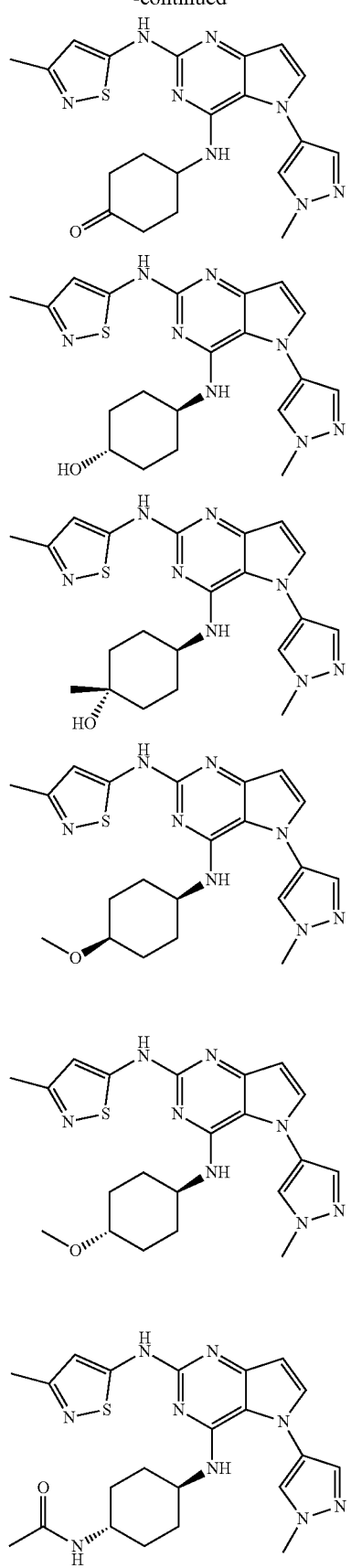
146
-continued
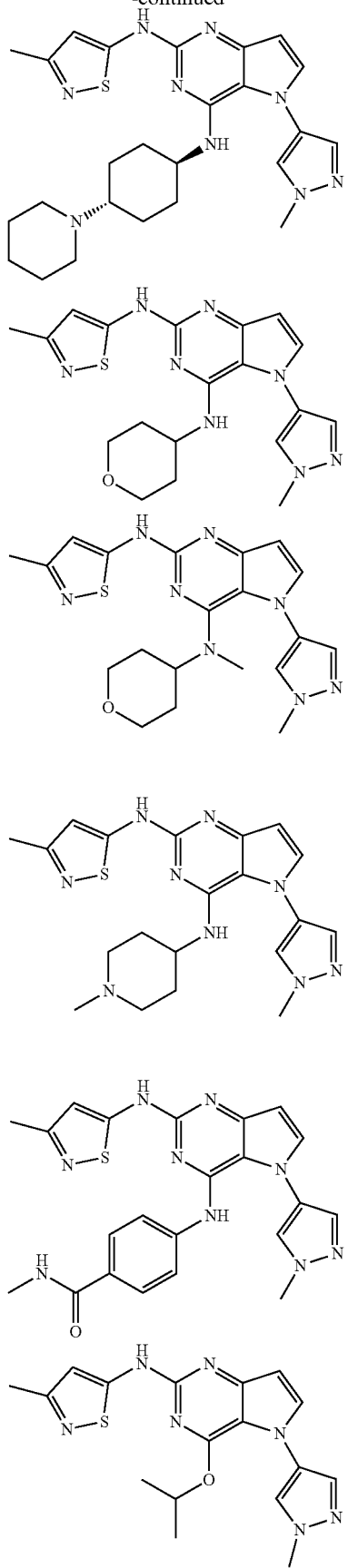

147
-continued
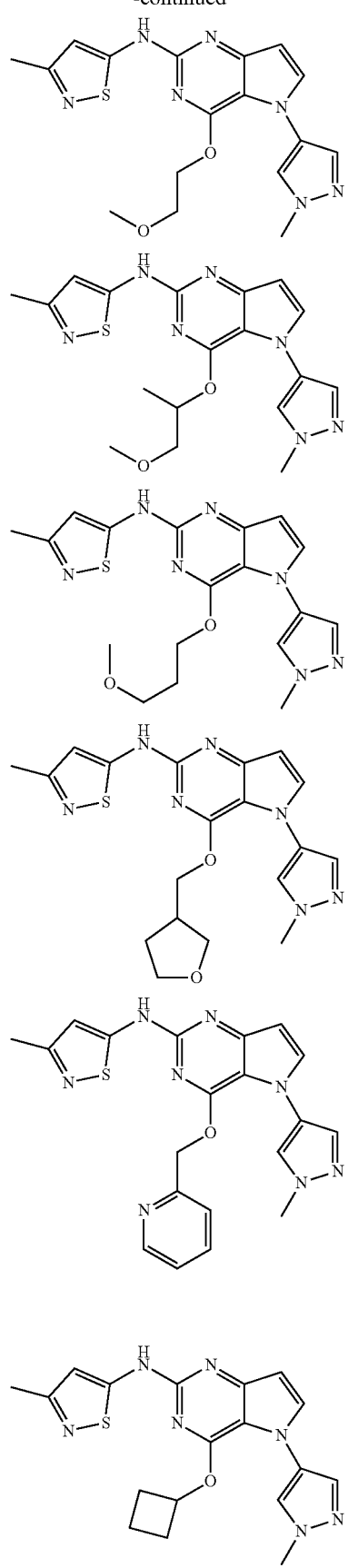
148
-continued
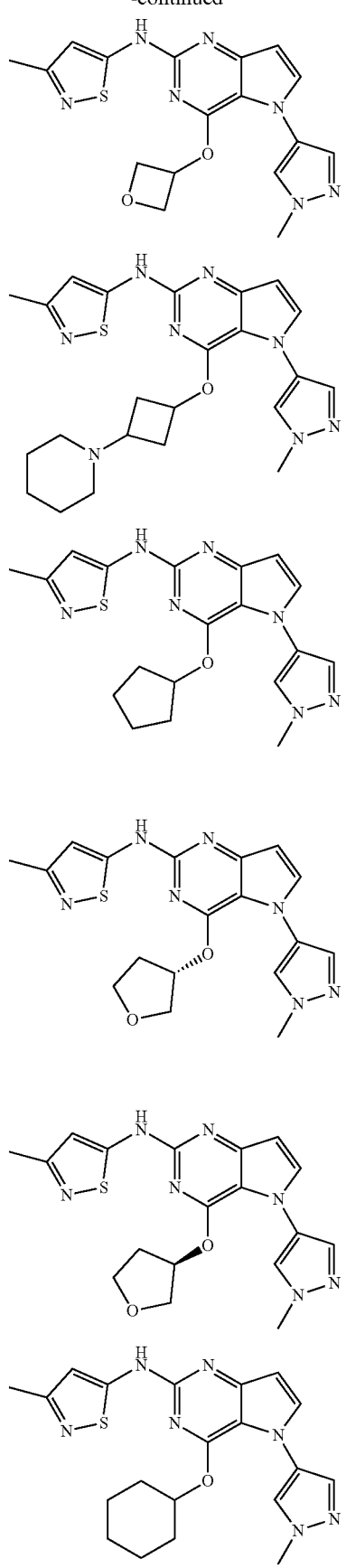

149
-continued
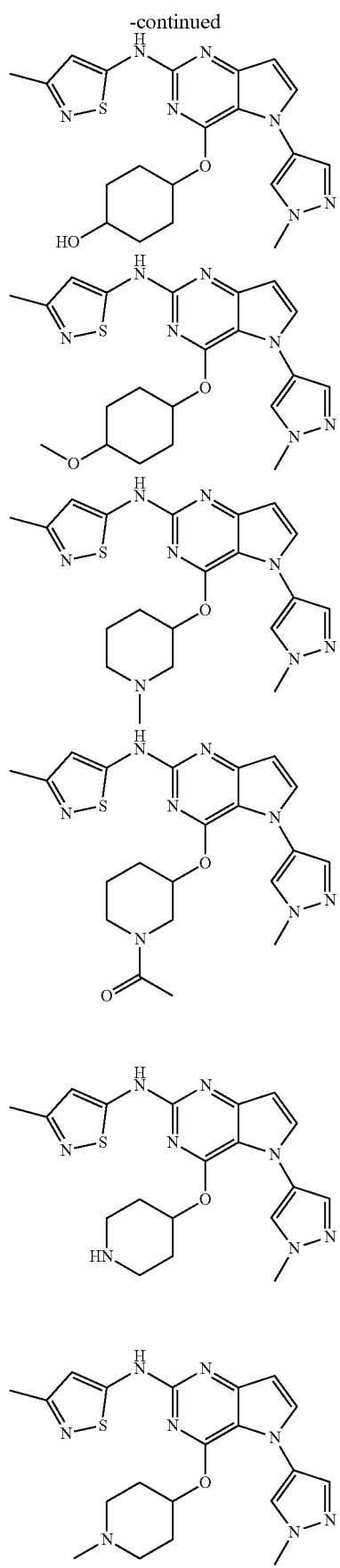
150
-continued
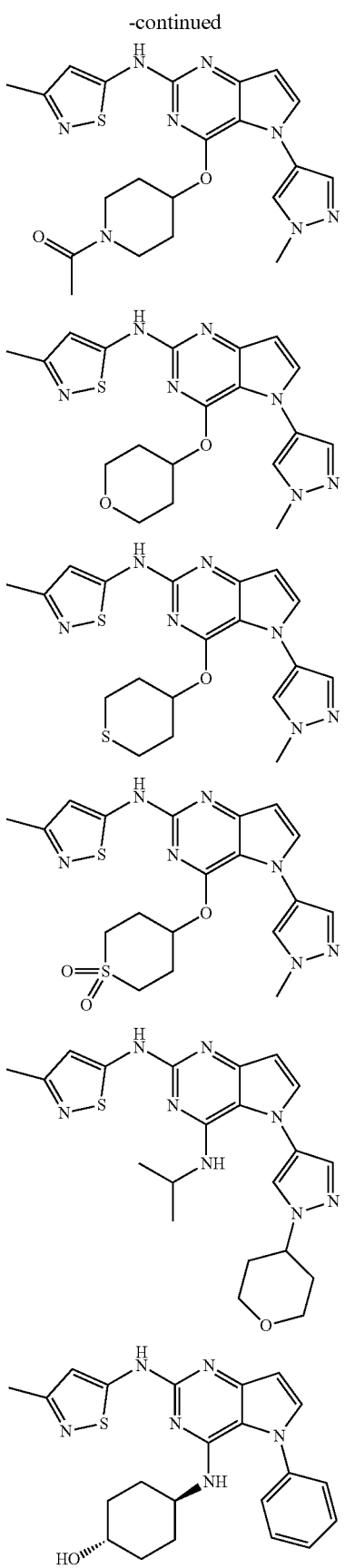

151 -continued
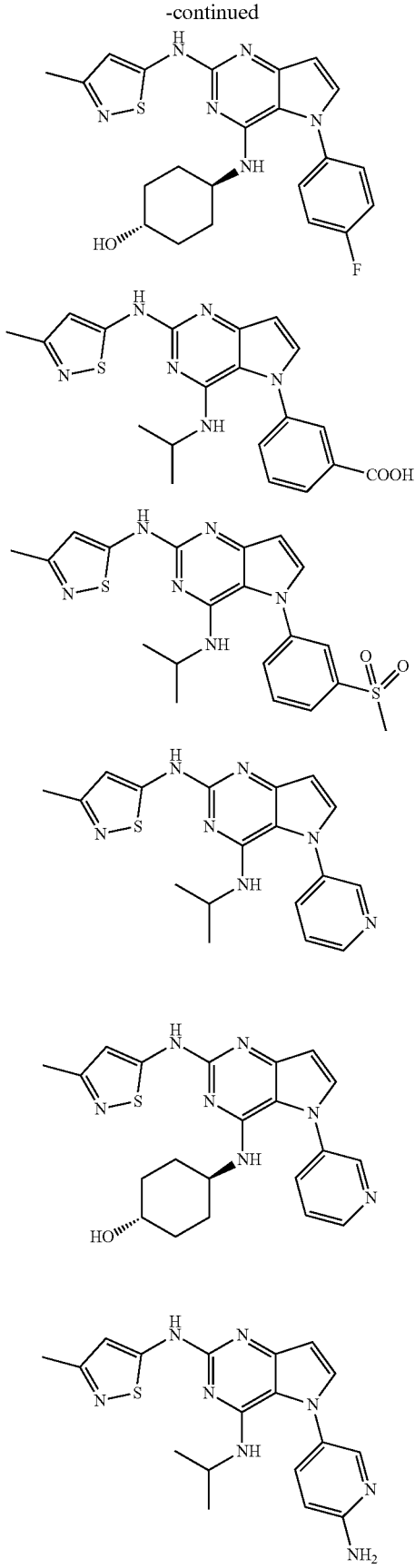
152 -continued
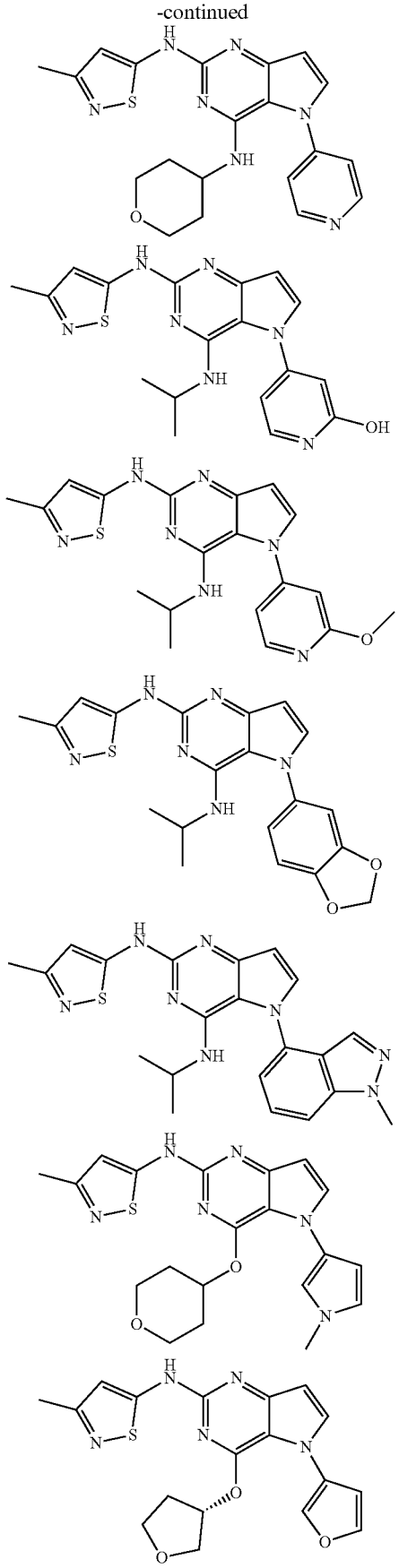

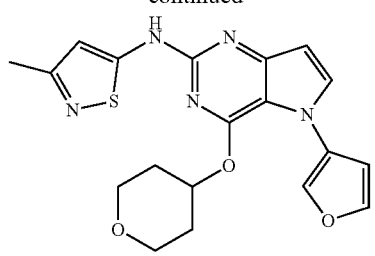
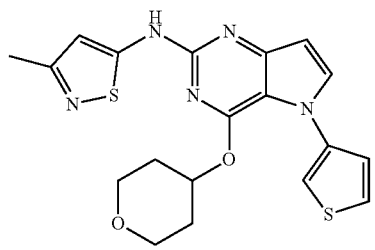
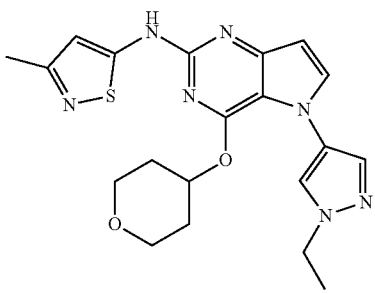
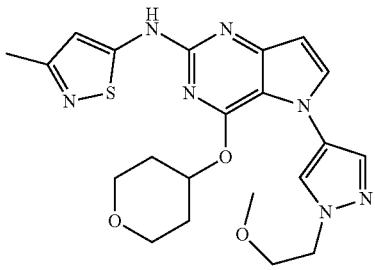
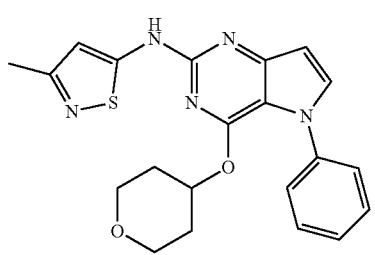
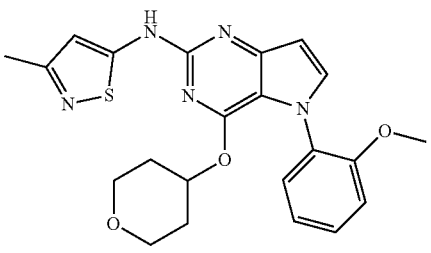
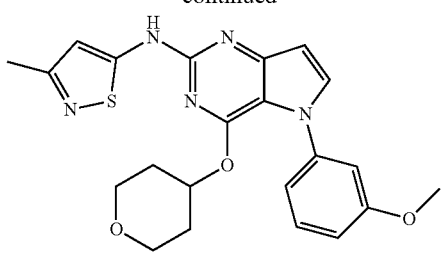
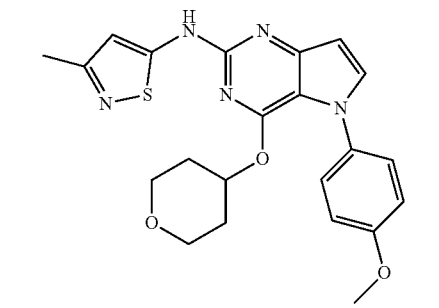
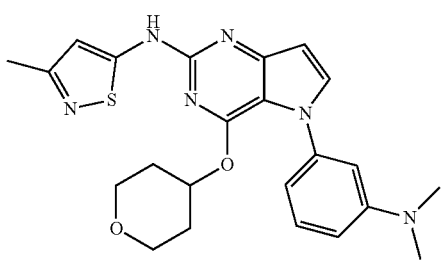
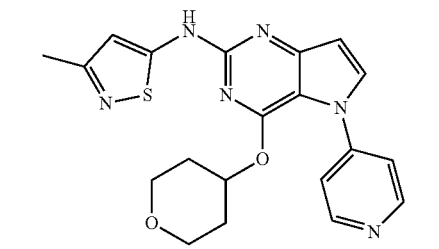
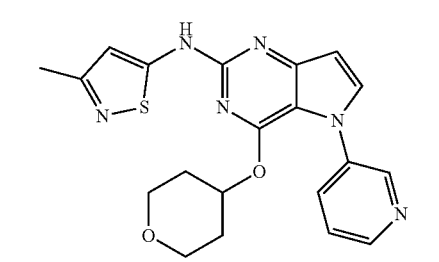
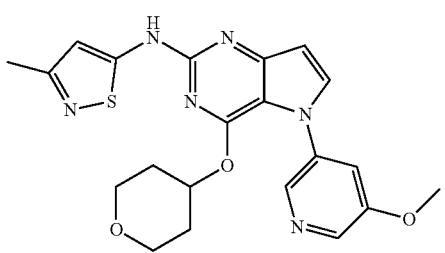

-continued
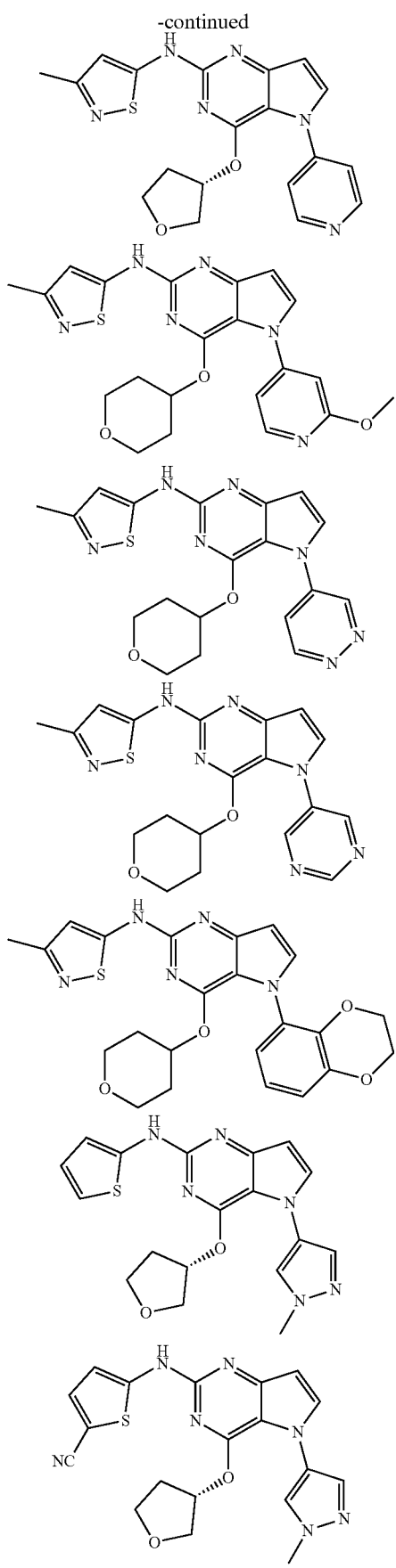
-continued
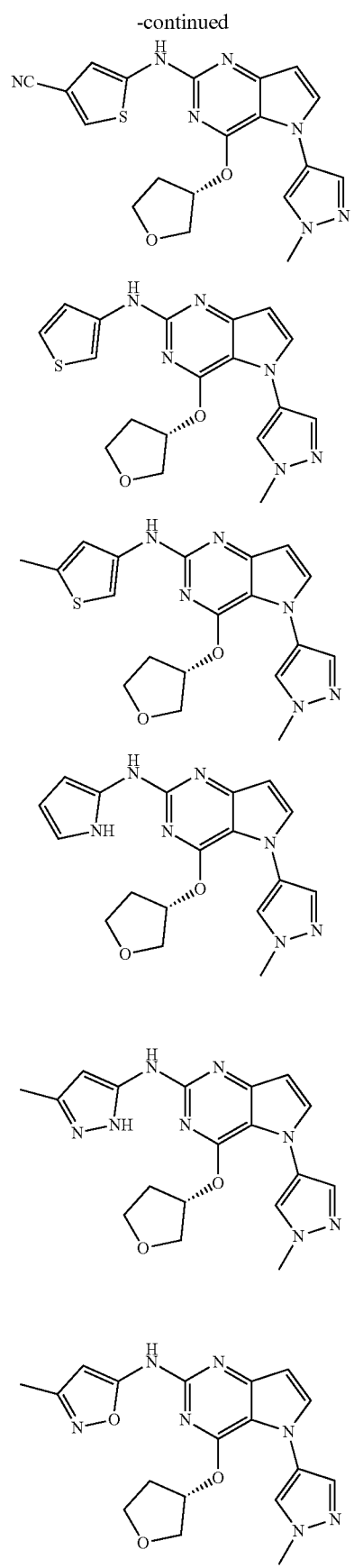

157
-continued
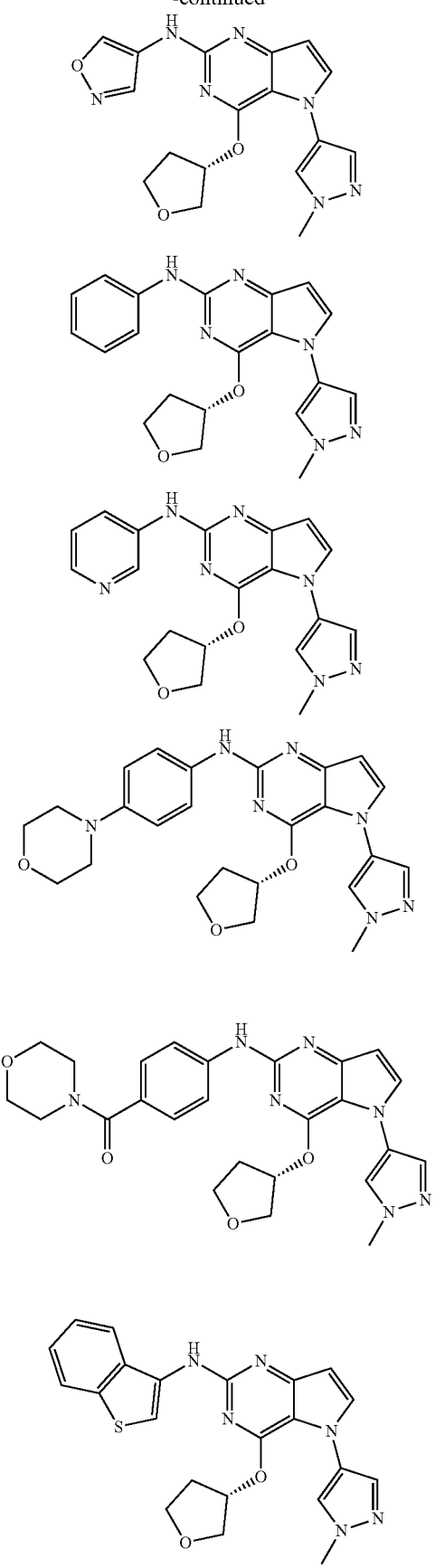
158
-continued
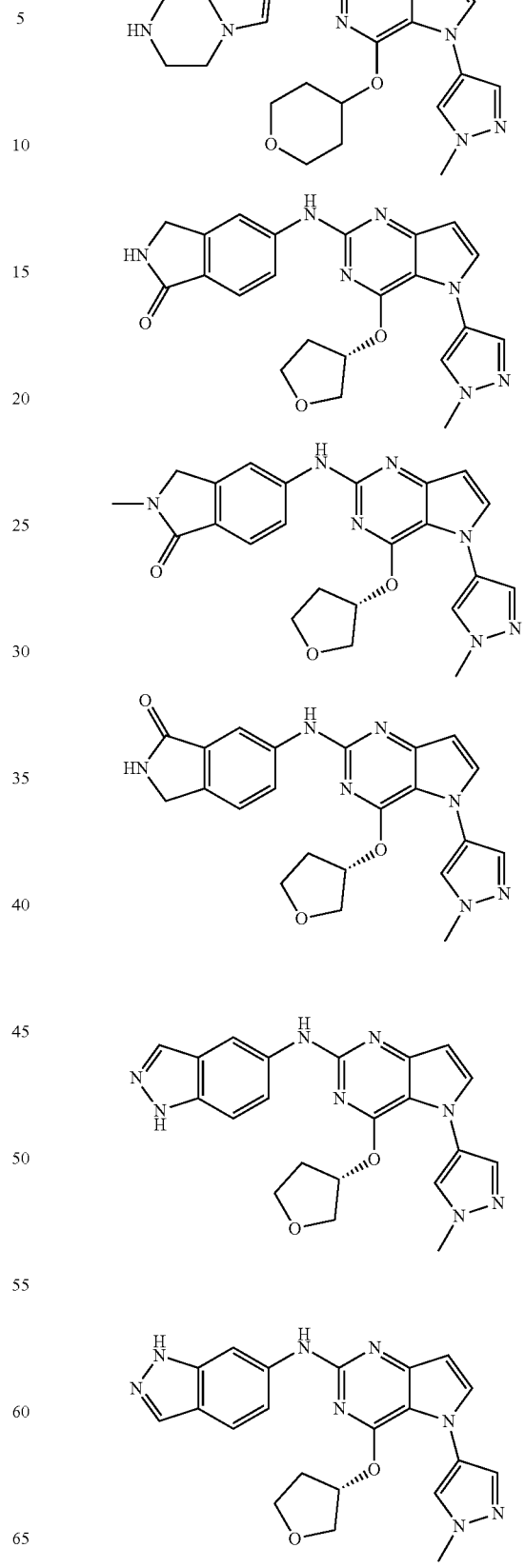

159
-continued
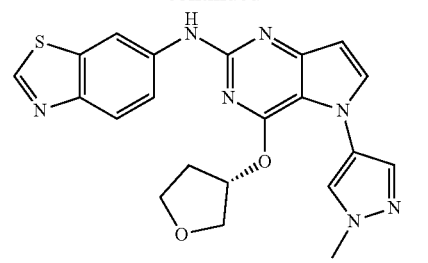
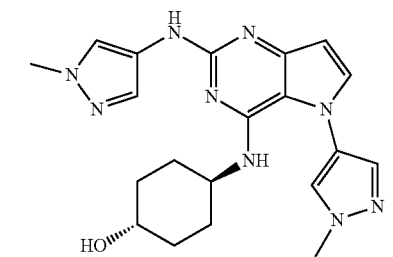
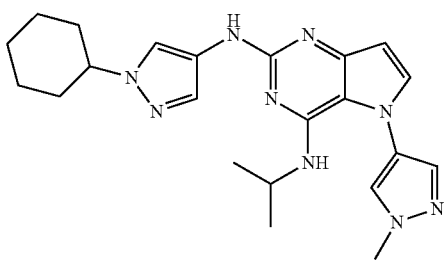
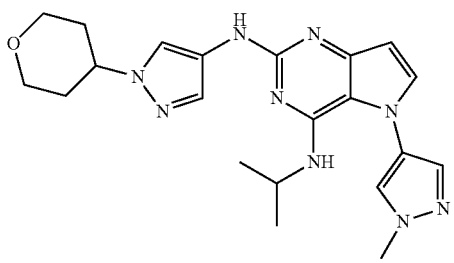
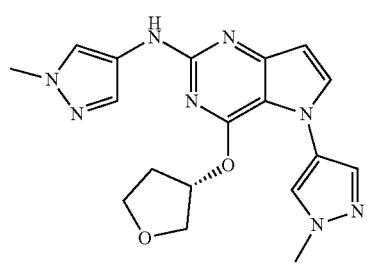
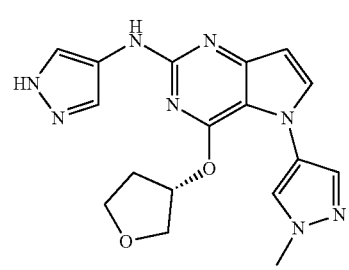
160
-continued
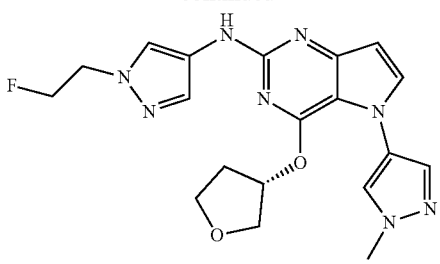
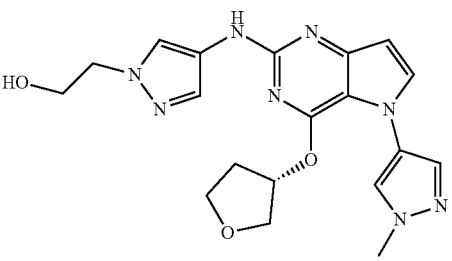
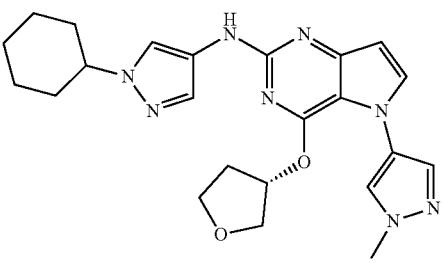
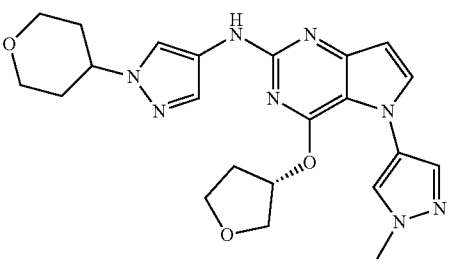
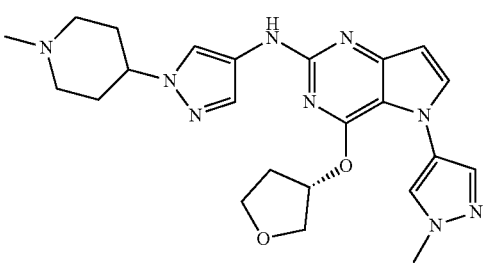
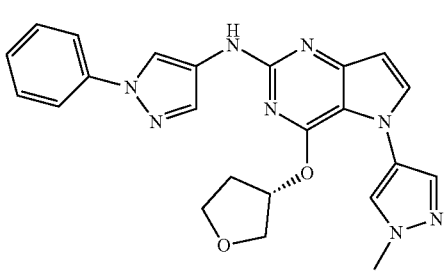

161
-continued
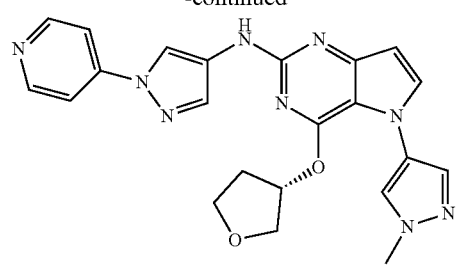
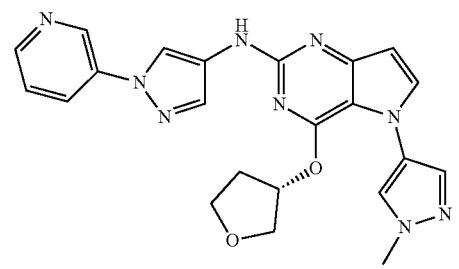
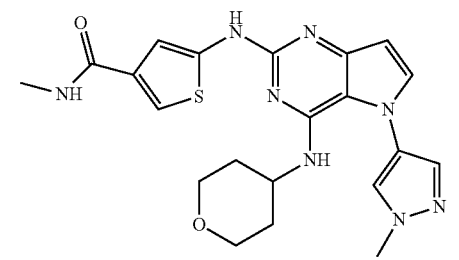
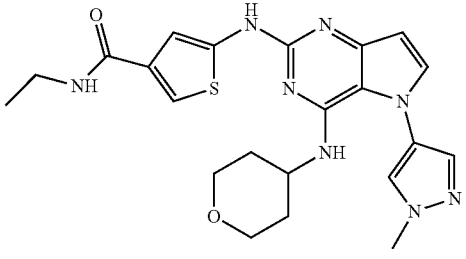
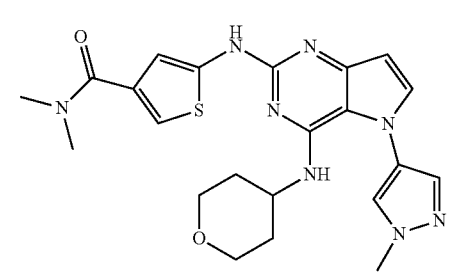
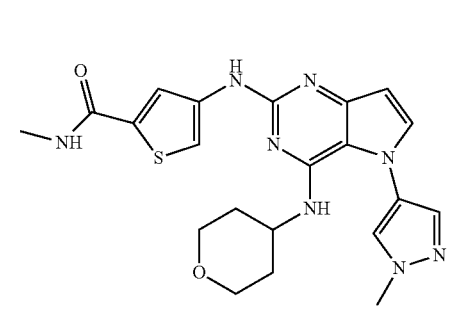
162
-continued
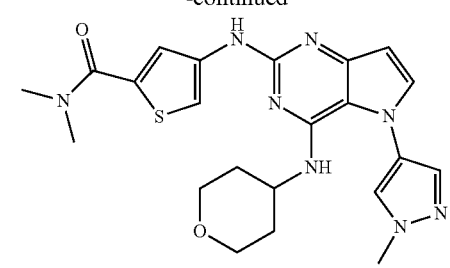
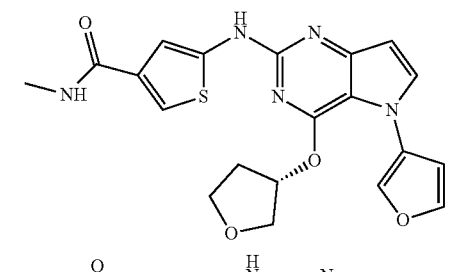
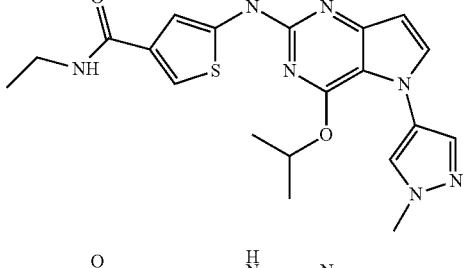
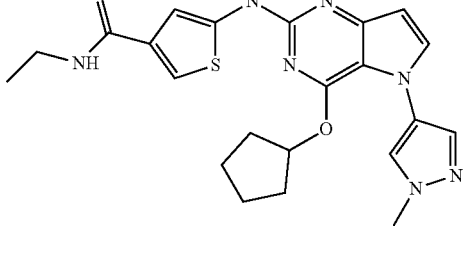
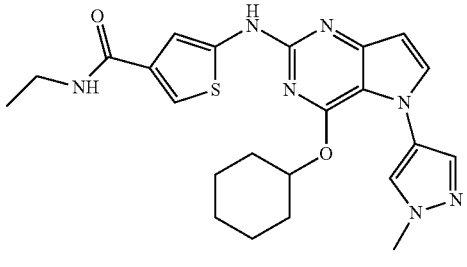
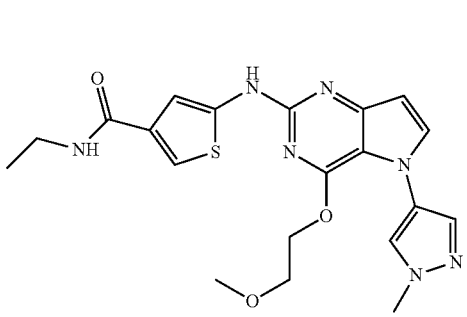

163
-continued
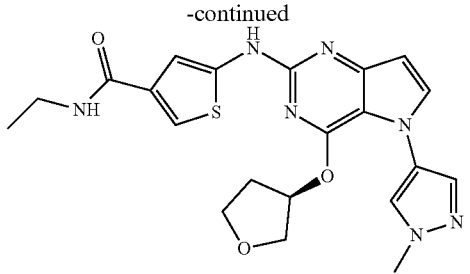
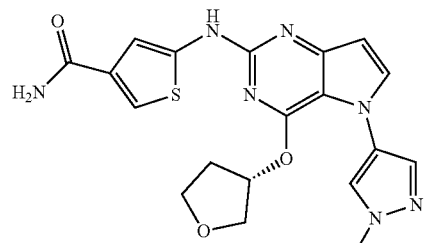
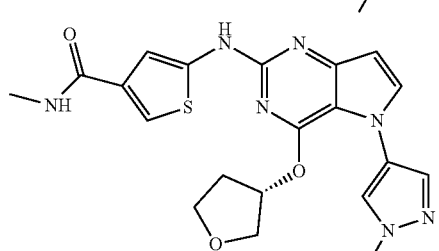
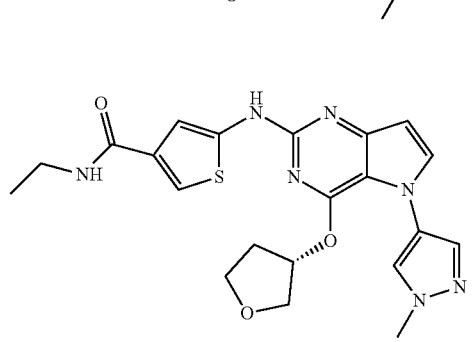
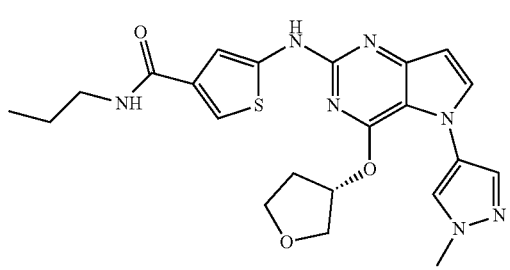
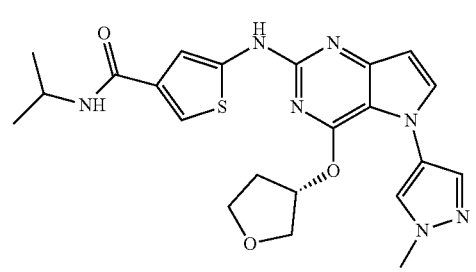
164
-continued
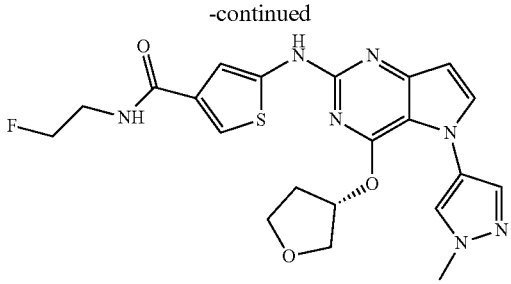
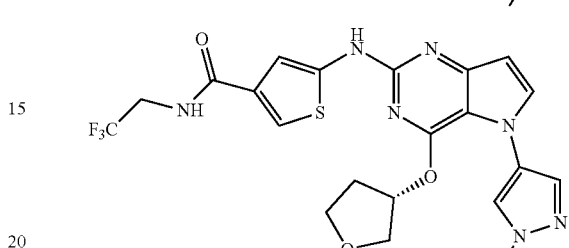
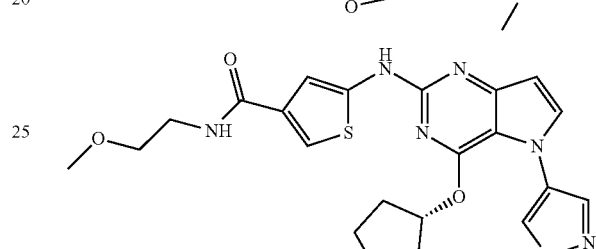
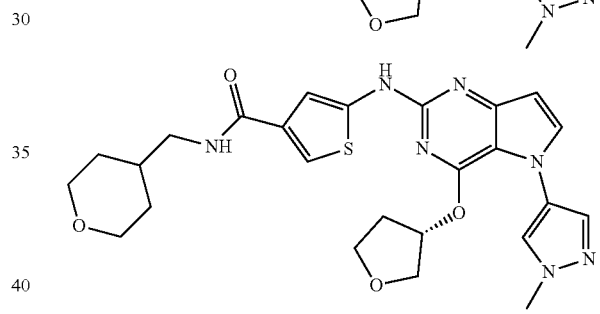
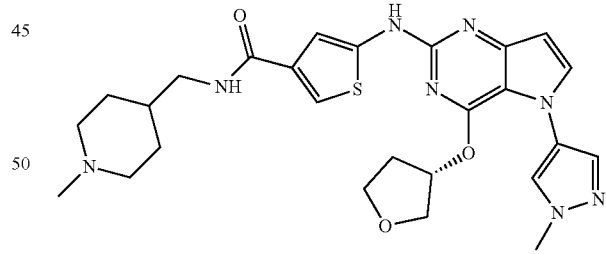
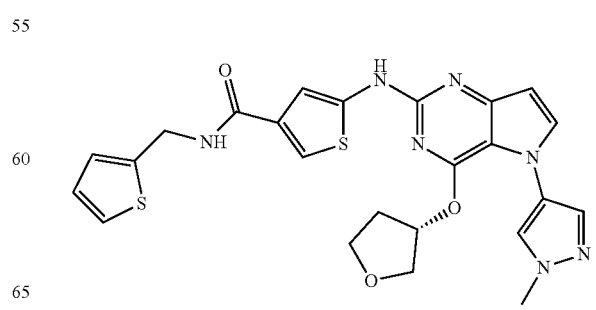

165
-continued
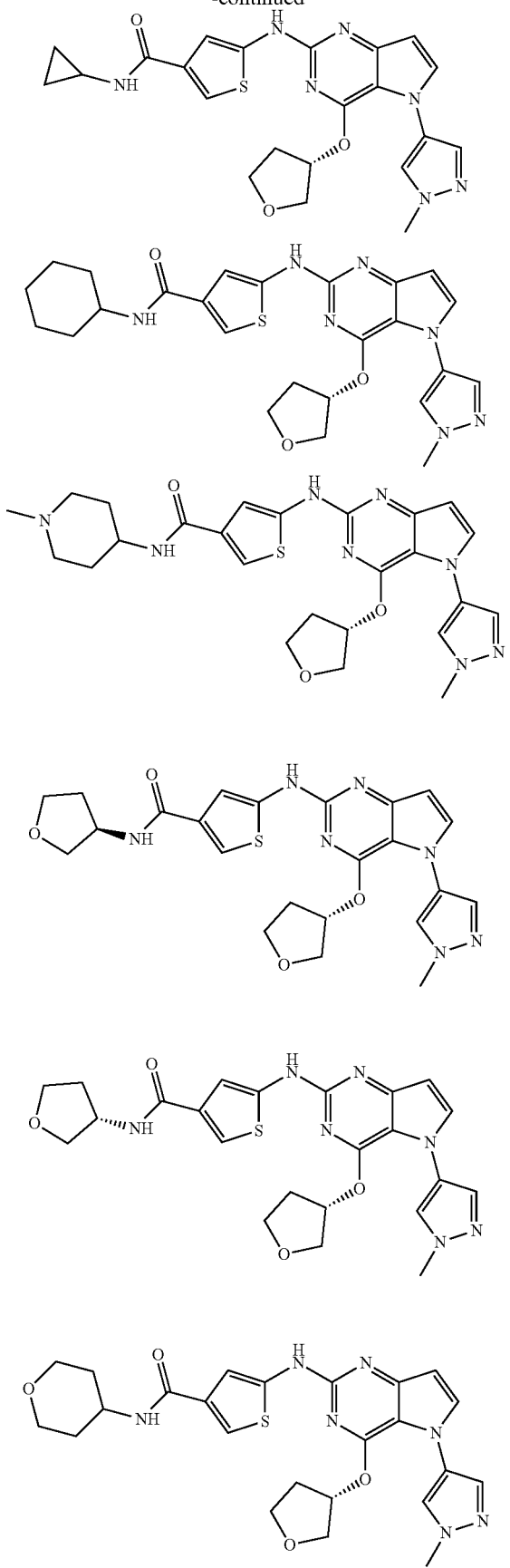
166
-continued
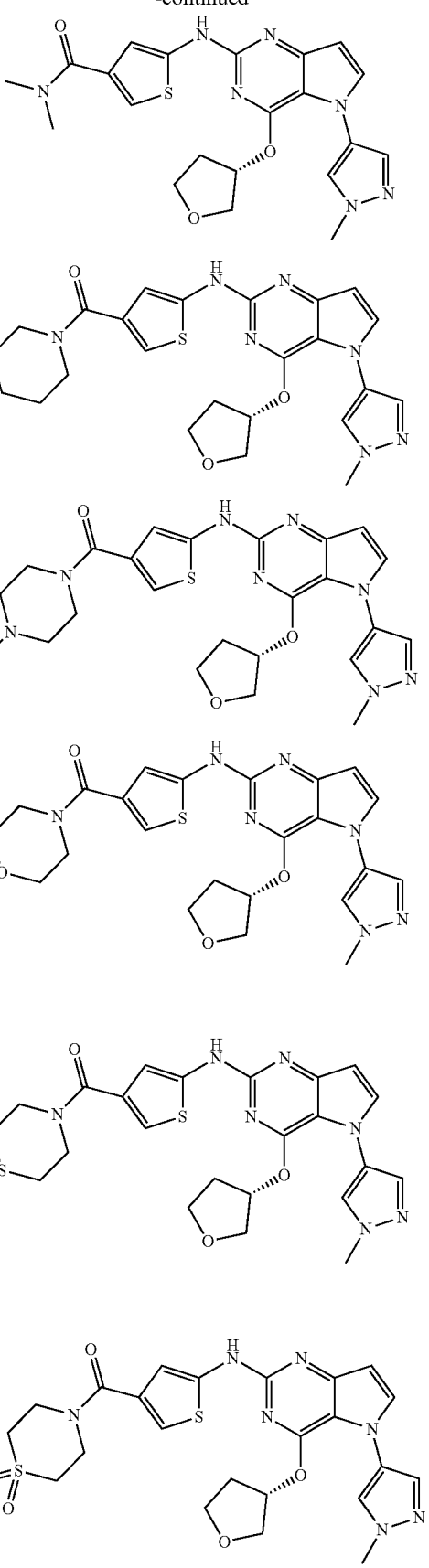

167
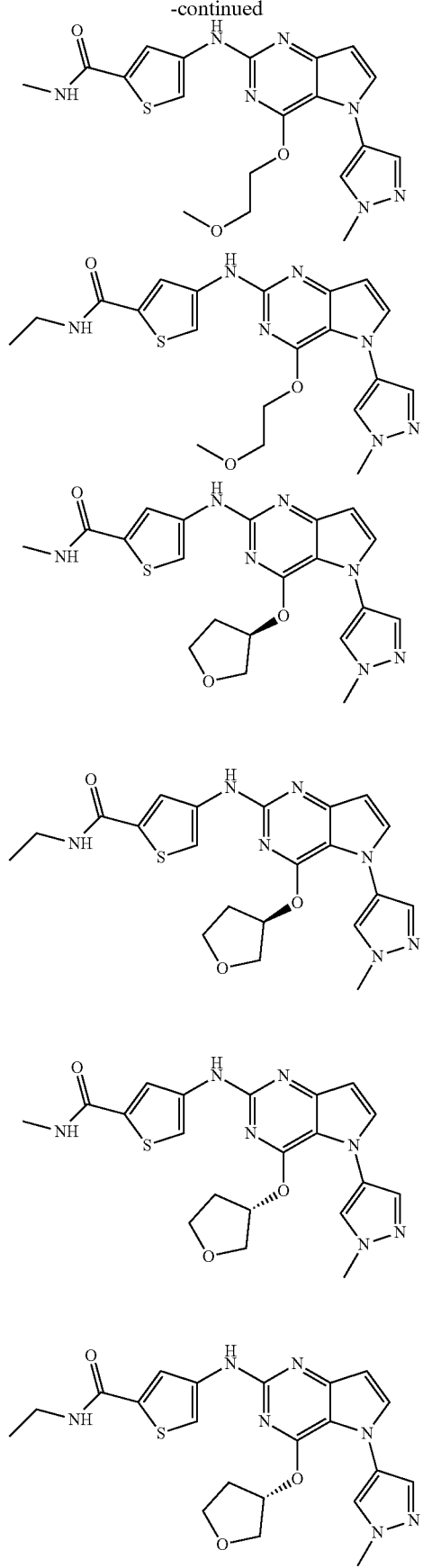
168
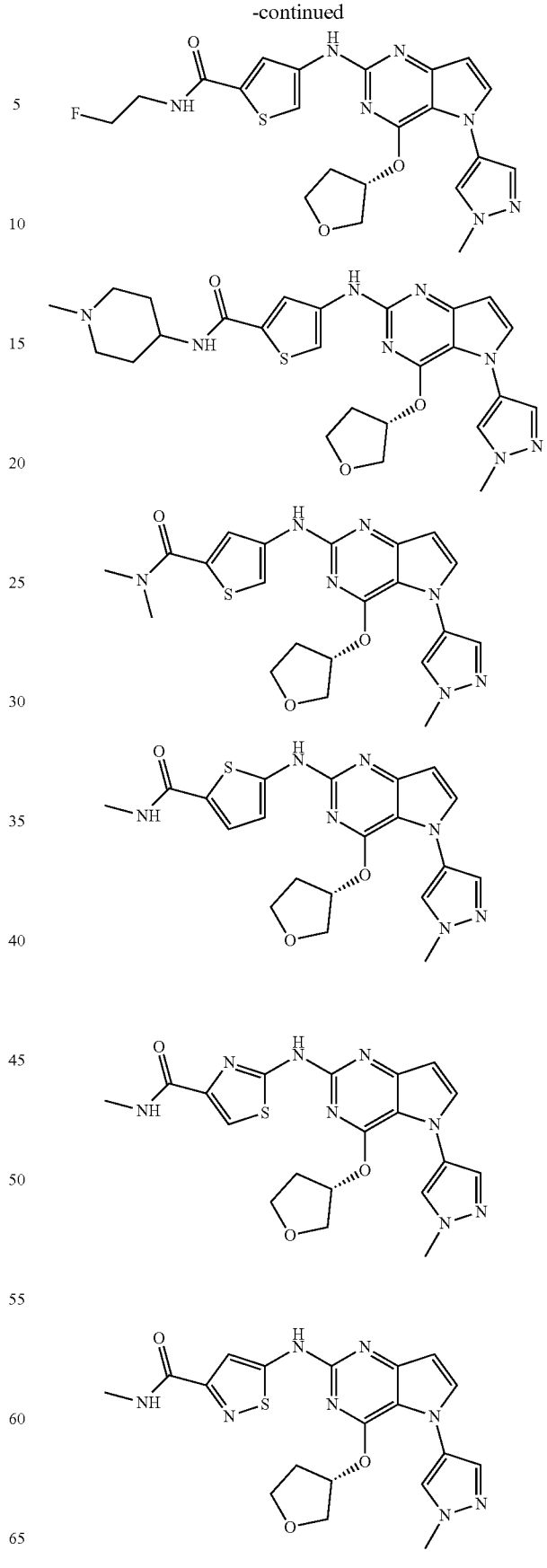

169
-continued

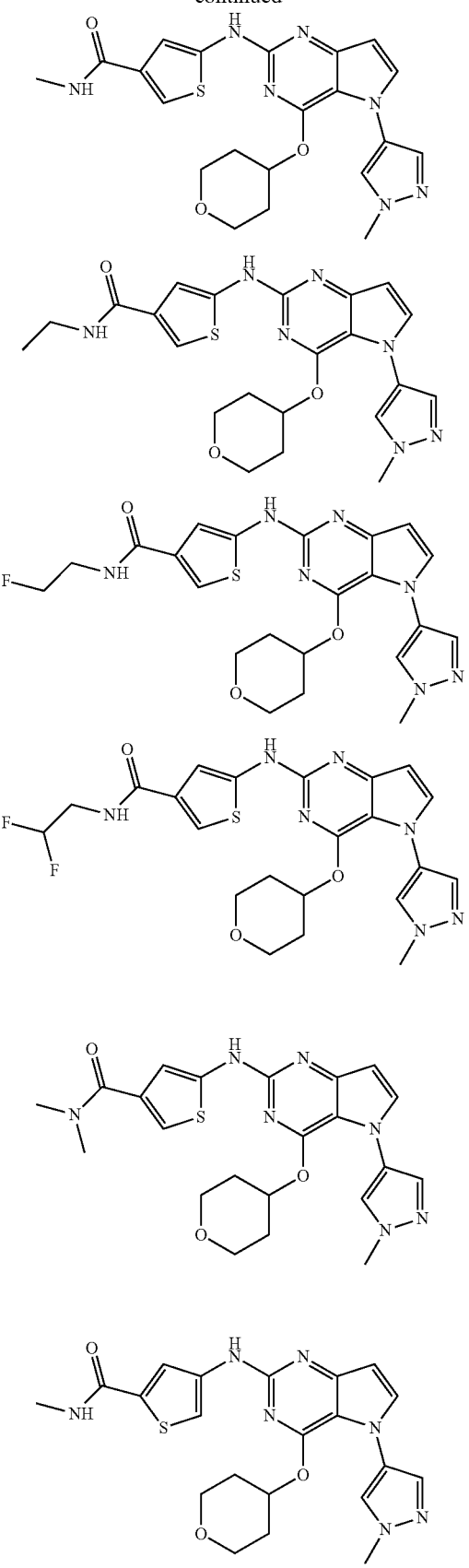

170
-continued

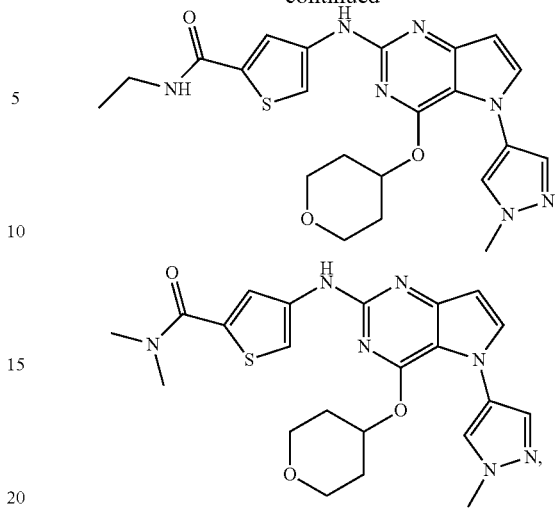

stereoisomers thereof, tautomers thereof, and pharmaceutically acceptable salts thereof.

2. A pharmaceutical composition comprising the compound of claim 1, or a stereoisomer, tautomer, or a pharmaceutically acceptable salt thereof, and a pharmaceutically acceptable excipient.

3. The pharmaceutical composition according to claim 2, further comprising one or more active agents selected from the group consisting of immunosuppressants, glucocorticoids, nonsteroidal anti-inflammatory drugs, vinca alkaloids, paclitaxel, DNA damaging agents, Bcl-2 inhibitors, BTK inhibitors, JAK inhibitors, Hsp90 inhibitors, ALK inhibitors, Flt3 inhibitors, PI3K inhibitors and SYK inhibitors, wherein said DNA damaging agents are selected from the group consisting of nitrogen mustards and nitrosoureas.

4. A method for treating IRAK4-mediated diseases, comprising administering to a subject in need thereof a therapeutically effective amount of a compound of claim 1, or a stereoisomer, tautomer, or a pharmaceutically acceptable salt thereof, wherein the IRAK4-mediated disease is selected from the group consisting of autoimmune diseases, inflammatory diseases, thromboembolic diseases and cancers, wherein the autoimmune disease and the inflammatory disease are selected from the group consisting of rheumatoid arthritis, osteoarthritis, juvenile arthritis, chronic obstructive pulmonary disease, multiple sclerosis, systemic lupus erythematosus, psoriasis, psoriatic arthritis, Crohn's disease, ulcerative colitis, and irritable bowel syndrome, and wherein the cancer is selected from the group consisting of B-cell chronic lymphocytic leukemia, acute lymphocytic leukemia, non-Hodgkin's lymphoma, Hodgkin's lymphoma, acute myeloid leukemia, diffuse large B-cell lymphoma, multiple myeloma, mantle cell lymphoma, small lymphocytic lymphoma, and Waldenstrom macroglobulinemia.

5. The pharmaceutical composition according to claim 3, wherein the nitrogen mustards are selected from the group consisting of Mechlorethamine, Cyclophosphamide and Ifosfamide.

6. The pharmaceutical composition according to claim 3, wherein the nitrosoureas are selected from the group consisting of Carmustine, Lomustine, Semustine and Nimustine.

\* \* \* \* \*